US009345245B2

(12) United States Patent
Cutler et al.

(10) Patent No.: US 9,345,245 B2
(45) Date of Patent: May 24, 2016

(54) SYNTHETIC COMPOUNDS FOR VEGETATIVE ABA RESPONSES

(71) Applicant: THE REGENTS OF THE UNIVERSITY OF CALIFORNIA, Oakland, CA (US)

(72) Inventors: Sean R. Cutler, Riverside, CA (US); Masanori Okamoto, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/385,695

(22) PCT Filed: Mar. 15, 2013

(86) PCT No.: PCT/US2013/032281
§ 371 (c)(1),
(2) Date: Sep. 16, 2014

(87) PCT Pub. No.: WO2013/148339
PCT Pub. Date: Oct. 3, 2013

(65) Prior Publication Data
US 2015/0047073 A1 Feb. 12, 2015

Related U.S. Application Data

(60) Provisional application No. 61/618,386, filed on Mar. 30, 2012.

(51) Int. Cl.
*A01N 43/42* (2006.01)
*C07D 215/227* (2006.01)

(52) U.S. Cl.
CPC ............ *A01N 43/42* (2013.01); *C07D 215/227* (2013.01)

(58) Field of Classification Search
CPC ............................ A01N 43/42; C07D 215/227
See application file for complete search history.

(56) References Cited

U.S. PATENT DOCUMENTS

| 5,498,755 | A | 3/1996 | Chandraratna et al. |
| 6,127,382 | A | 10/2000 | Beard et al. |
| 2011/0230350 | A1 | 9/2011 | Frackenpohl et al. |
| 2011/0271408 | A1 | 11/2011 | Cutler et al. |
| 2013/0045952 | A1 | 2/2013 | Xu et al. |

FOREIGN PATENT DOCUMENTS

| WO | 2010/093954 A2 | 8/2010 |
| WO | 2011/139798 A2 | 11/2011 |

OTHER PUBLICATIONS

Bartel et al., "Analyzing protein-protein interactions using two-hybrid system", *Methods Enzymol.* vol. 254, pp. 241-263 (1995).

Cutler et al., "Abscisic Acid: Emergence of a Core Signaling Network", *Annual Review of Plant Biology*, vol. 61, pp. 651-679 (2010).
Iyer et al., "Adaptations of the helix-grip fold for ligand binding and catalysis in the START domain superfamily", Protens: Structure, Function, and Bioinformatcis, vol. 43, No. 2, pp. 134-144 (2001).
Melcher et al., "Thirsty plants and beyond: structural mechanisms of abscisic acid perception and signaling", *Current Opinion in Structural Biology*, vol. 20, No. 6, pp. 722-729 (2010).
Notman, "Organic compound comes to the aid of thirsty plants", Royal Society of Chemistry (May 1, 2009) http://www.rsc.org/chemistryworld/News/2009/May/01050901.asp (downloaded on Jun. 29, 2015).
Park et al., Abscisic Acid Inhibits Type 2C Protein Phosphatases via the PYR/PYL Family of START Proteins, *Science*, vol. 324, No. 5930, pp. 1068-1071 (2009).
Ponting et al., "START: a lipid-binding domain in StAR, HD-ZIP and signalling proteins", *Trends Biochem*, vol. 24, No. 4, pp. 130-132 (1999).
Radauer, "The Bet v 1 fold: an ancient, versatile scaffold for binding of large, hydrophobic ligands", *BMC Evol*. Biol., vol. 8, pp. 286 (2008).
Rademacher W, Maisch R, Liessegang J, Jung J (1987) Water consumption and yield formation in crop plants under the influence of synthetic analogues of abscisic acid. In: Hawkins AF, Stead AD, Pinfield NJ (eds) Plant growth regulators for agricultural and amenity use. BCPC Monograph 36:53-66.
Database accession No. 1340941-81-2, Database Registry, Chemical Abstract Service, Columbus, Ohio, US (Nov. 4, 2011).
Database accession No. 1331274-04-4, Database Registry, Chemical Abstract Service, Columbus, Ohio, US (Sep. 11, 2011).
Database accession No. 1324695-29-5, Database Registry, Chemical Abstract Service, Columbus, Ohio, US (Aug. 28, 2011).
Database accession No. 1211832-29-9, Database Registry, Chemical Abstract Service, Columbus, Ohio, US (Mar. 19, 2010).
Yang et al., "Narrowing Down the Targets: Towards Successful Genetic Engineering of Drought-Tolerant Crops", *Mol. Plant*, vol. 3, No. 3, pp. 469-490 (2010).
Wang et al., "Molecular tailoring of farnesylation for plant drought tolerance and yield protection", *The Plant Journal*, vol. 43, No. 3, pp. 413-424 (2005).
Tamura et al., Mega5: Molecular Evolutionary Genetics Analysis Using maximum Likelihood, Evolutionary Distance, and Maximum Parsimony Methods, *Molecular Biology and Evolution*, vol. 28, No. 10, pp. 2731-2739 (2011).

(Continued)

*Primary Examiner* — Johann R Richter
*Assistant Examiner* — Andriae M Holt
(74) *Attorney, Agent, or Firm* — Kilpatrick Townsend & Stockton LLP

(57) ABSTRACT

The present invention provides agonist compounds that active ABA receptors, and agricultural formulations comprising the agonist compounds. The agricultural formulations are useful for inducing ABA responses in plant vegetative tissues, reducing abiotic stress in plants, and inhibiting germination of plant seeds. The compounds are also useful for inducing expression of ABA-responsive genes in cells that express endogenous or heterologous ABA receptors.

19 Claims, 27 Drawing Sheets

(56) References Cited

OTHER PUBLICATIONS

Peterson et al., "Structural basis for selective activation of ABA receptors", *Nature Structural & Molecular Biology*, vol. 17, No. 9, pp. 1109-1113 (2010).
Vidal et al., "Reverse two-hybrid and one hybrid systems to detect dissociation of protein-protein and DNA-protein interactions", *Proceeding of the national Academy of Sciences of the USA*, vol. 93, No. 19, pp. 10315-10320 (1996).
Gassner et al., "Accelerating the discovery of biologically active small molecules using a high-throughput yeast halo assay", *Journal of Natural Products*, vol. 70, No. 3, pp. 383-390 (2007).
Mosquna et al., Potent and selective activation of abscisic acid reeptors in vivo by mutational stabilization of their agonist-bound conformation, *PNAS*, vol. 108, No. 51, pp. 20838-20843 (2011).
Fujii et al., "In vitro Reconstitution of an ABA Signaling Pathway", *Nature*, vol. 462, No. 7273, pp. 660-664 (2009).
Leon-Kloosterziel et al., "Isolation and characterization of abscisic acid-deficient Arabidopsis mutants at two new loci", *Plant J*, vol. 10, No. 4, pp. 655-661 (1996).
Umezawa et al., "Type 2C protein phosphataes directly regulate abscisic acid-activated protein kinases in Arabidopsis", *Proceedings of the National Acdemy of Sciences of the USA*, vol. 106, No. 41, pp. 17588-17593 (2009).
Nambara et al., "A screen for genes that function in abscisic acid signaling in Arabidopsis thaliana", *Genetics*, vol. 161, No. 3, pp. 1247-1255 (2002).
Matsui et al., "Arabidopsis Transcriptome Analysis under Drought, Cold, High-Salinity and ABA Treatment Conditions using a Tiling Array", *Plant Cell Physiol*, vol. 49, No. 8, pp. 1135-1149 (2008).
EP13715055.3, "Office Action", Dec. 18, 2015, 4 pages.
CN201380018656.X, "Office Action", Sep. 15, 2015, 8 pages.
Liu Bulin (ed.) "Processing Technology for Pesticide Dosage Forms," Beijing: Chemical Industry Press, Oct. 1998, pp. 1Zhou, et al., "Synthesis and Plant Growth Regulation Activity of Pyrabactin", Agrochemicals, vol. 49, No. 7, Jul. 2010, pp. 484-485.
Zhou, et al., "Synthesis and Plant Growth Regulation Activity of Pyrabactin", Agrochemicals, vol. 49, No. 7, Jul. 2010, pp. 484-485.
Patent Examination Report No. 1, Australian Pat. Appln. No. 2013240193, dated Feb. 9, 2016, 4 pages.

| IC$_{50}$(nM) | Dimeric type | | | | | Monomeric type | | | | | |
|---|---|---|---|---|---|---|---|---|---|---|---|
| | PYR1 | PYL1 | PYL2 | PYL3 | PYL4 | PYL5 | PYL6 | PYL8 | PYL9 | PYL10 | PYL11 |
| ABA | 307 | 301 | 151 | 70 | 68 | 27 | 29 | 57 | 60 | 121 (*18) | 64 |
| Quina | 103 | 250 | 267 | 724 | >10uM | 649 | >10uM | >10uM | >10uM | >10uM(*>10uM) | >10uM |
| PyrA | 656 | 1197 | >10uM | >10uM | >10uM | 5174 | >10uM | >10uM | >10uM | 1892 (*206) | >10uM |

FIG. 3B

|  | ABA | Pyrabactin | Quinabactin |  |
|---|---|---|---|---|
| PYR1 | 307 | 656 | 103 | Dimeric |
| PYL1 | 301 | 1197 | 250 | |
| PYL2 | 151 | >10,000 | 267 | |
| PYL3 | 70 | >10,000 | 724 | |
| PYL4 | 68 | >10,000 | >10000 | Monomeric |
| PYL5 | 27 | 5174 | 649 | |
| PYL6 | 29 | >10,000 | >10000 | |
| PYL11 | 64 | >10,000 | >10000 | |
| PYL12 | nd | nd | nd | |
| PYL7 | nd | nd | nd | |
| PYL9 | 60 | >10,000 | >10000 | |
| PYL8 | 57 | >10,000 | >10000 | |
| PYL10 | 121 | 1892 | >10000 | |

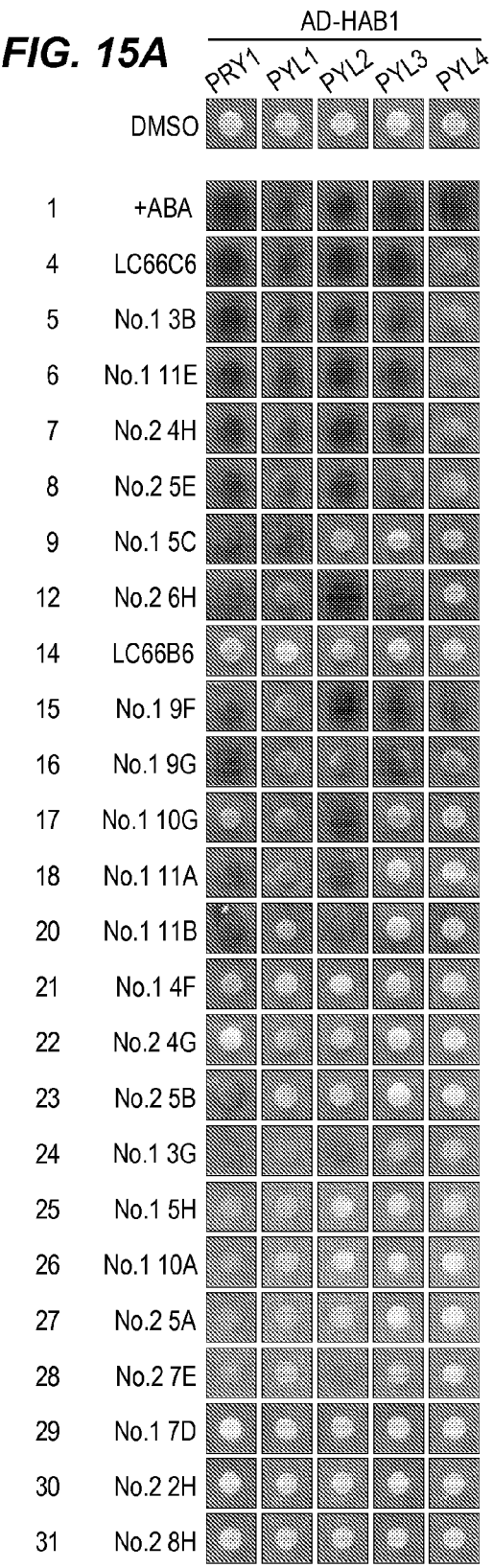
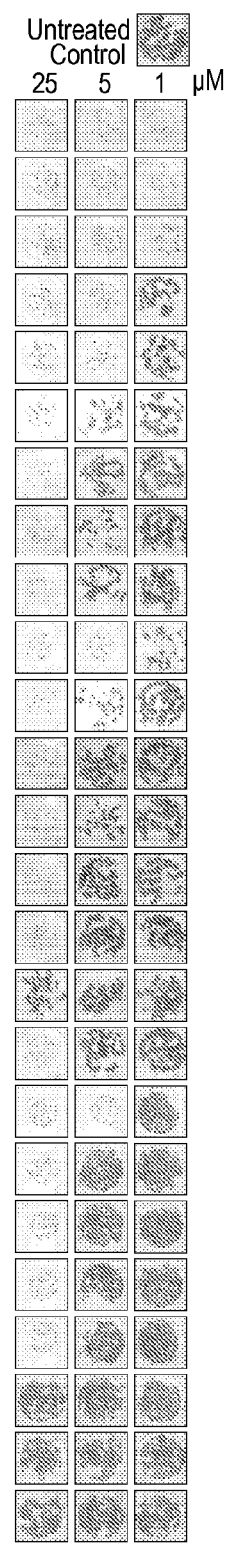
FIG. 15A  FIG. 15B  FIG. 15C

| Compound | Germination | pMAKKK18::GUS |
| --- | --- | --- |
| ABA | ++++++ | ++++++ |
| Pyrabactin | ++ | nd |
| Quinabactin | +++++ | ++++ |
| 1 | +++ | nd |
| 2 | +++ | nd |
| 3 | +++ | nd |
| 4 | + | nd |
| 5 | - | nd |
| 6 | +++++ | ++++ |
| 7 | +++++ | +++ |
| 8 | +++++ | +++++ |
| 9 | +++ | ++ |
| 10 | - | + |
| 11 | +++ | ++ |
| 12 | - | - |
| 13 | + | + |
| 14 | ++++ | +++ |
| 15 | +++ | + |
| 16 | - | - |
| 17 | +++ | ++ |
| 18 | +++ | +++ |

SYNTHETIC COMPOUNDS FOR VEGETATIVE ABA RESPONSES

CROSS-REFERENCES TO RELATED APPLICATIONS

The present application claims benefit of priority to U.S. Provisional Patent Application No. 61/618,386, filed Mar. 30, 2012, which is incorporated herein by reference in its entirety.

STATEMENT AS TO RIGHTS TO INVENTIONS MADE UNDER FEDERALLY SPONSORED RESEARCH AND DEVELOPMENT

This invention was made with Government support under Grant. No. DGE0504249 and IOS0820508, awarded by the National Science Foundation. The Government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -2094-1.TXT, created on Sep. 15, 2014, 233,472 bytes, machine format IBM-PC, MS-Windows operating system, is hereby incorporated by reference in its entirety for all purposes.

BACKGROUND OF THE INVENTION

Abscisic acid (ABA) is a plant hormone that regulates signal transduction associated with abiotic stress responses (Cutler et al., 2010, Abscisic Acid: Emergence of a Core Signaling Network. *Annual Review of Plant Biology* 61:651-679). The ABA signaling pathway has been exploited to improve plant stress response and associated yield traits via numerous approaches (Yang et al., 2010). The direct application of ABA to plants improves their water use efficiency (Raedmacher et al., 1987); for this reason, the discovery of ABA agonists (Park et al., 2009; Melcher et al., 2010, Identification and mechanism of ABA receptor antagonism. *Nature Structural & Molecular Biology* 17(9):1102-1110) has received increasing attention, as such molecules may be beneficial for improving crop yield (Notman et al., 2009). The first synthetic ABA agonist identified was the naphthalene sulfonamide named pyrabactin (Park et al., 2009), which efficiently activates ABA signaling in seeds but has limited activity in vegetative tissues, where the most critical aspects of abiotic stress tolerance occur. Sulfonamides highly similar to pyrabactin have been disclosed as ABA agonists (see US Patent Publication No. 20130045952) and abiotic stress modulating compounds (see US Patent Publication No. 20110230350); and non-sulfonamide ABA agonists have also been described (see US Patent Publication Nos. 20130045952 and 20110271408). A complementary approach to activating the ABA pathway involves increasing a plant's sensitivity to ABA via genetic methods. For example, conditional antisense of farnesyl transferase beta subunit gene, which increases a plant's ABA sensitivity, improves yield under moderate drought in both canola and *Arabidopsis* (Wang et al., 2005). Thus, the manipulation of ABA signaling to improve traits contributing to yield is now well established.

It has recently been discovered that ABA elicits many of its cellular responses by binding to a soluble family of receptors called PYR/PYL proteins. PYR/PYL proteins belong to a large family of ligand-binding proteins named the START superfamily (Iyer et al., 2001); Ponting et al., 1999). These proteins contain a conserved three-dimensional architecture consisting of seven anti-parallel beta sheets, which surround a central alpha helix to form a "helix-grip" motif; together, these structural elements form a ligand-binding pocket for binding ABA or other agonists.

BRIEF SUMMARY OF THE INVENTION

The present invention provides for small molecule ABA agonists, i.e., compounds that activate PYR/PYL proteins. In one aspect, the present invention provides for agricultural formulations comprising the ABA agonists described herein. In some embodiments, the agricultural formulation comprises a compound of Formula I:

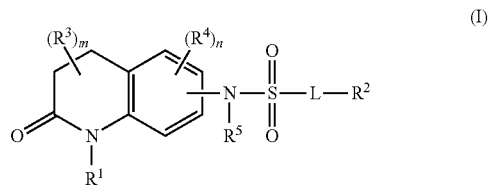

(I)

wherein
  $R^1$ is selected from the group consisting of H, $C_{1-6}$ alkyl, $C_{2-6}$ alkenyl, $C_{2-6}$ alkynyl, cycloalkyl, heterocycloalkyl, aryl and heteroaryl,
  $R^2$ is selected from the group consisting of cycloalkyl, heterocycloalkyl, aryl and heteroaryl, each optionally substituted with from 1-4 $R^{2a}$ groups,
  each $R^{2a}$ is independently selected from the group consisting of H, halogen, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, —OH, $C_{1-6}$ alkylhydroxy, —CN, —NO$_2$, —C(O)R$^{2b}$, —C(O)OR$^{2b}$, —OC(O)R$^{2b}$, —C(O)NR$^{2b}$R$^{2c}$, —NR$^{2b}$C(O)R$^{2c}$, —SO$_2$R$^{2b}$, —SO$_2$OR$^{2b}$, —SO$_2$NR$^{2b}$R$^{2c}$, and —NR$^{2b}$SO$_2$R$^{2c}$,
  each of $R^{2b}$ and $R^{2c}$ are independently selected from the group consisting of H and $C_{1-6}$ alkyl,
  each of $R^3$, $R^4$ and $R^5$ are independently selected from the group consisting of H and $C_{1-6}$ alkyl,
  L is a linker selected from the group consisting of a bond and $C_{1-6}$ alkylene,
  subscript m is an integer from 0 to 4,
  subscript n is an integer from 0 to 3,
or a salt or isomer thereof In some embodiments, the agricultural formulation further comprises an agricultural chemical that is useful for promoting plant growth, reducing weeds, or reducing pests. In some embodiments, the agricultural formulation further comprises at least one of a fungicide, an herbicide, a pesticide, a nematicide, an insecticide, a plant activator, a synergist, an herbicide safener, a plant growth regulator, an insect repellant, an acaricide, a molluscicide, or a fertilizer. In some embodiments, the agricultural formulation further comprises a surfactant. In some embodiments, the agricultural formulation further comprises a carrier.

In another aspect, the invention provides methods for increasing abiotic stress tolerance in a plant, the method comprising the step of contacting a plant with a sufficient amount of the above formulations to increase abiotic stress tolerance in the plant compared to the abiotic stress tolerance in the plant when not contacted with the formulation. In some embodiments, the plant is a monocot. In some embodiments, the plant is a dicot. In some embodiments, the abiotic stress tolerance comprises drought tolerance.

In another aspect, the invention provides a method of inhibiting seed germination in a plant, the method comprising the step of contacting a plant, a plant part, or a plant seed with a sufficient amount of the above formulations to inhibit germination.

In another aspect, the invention provides a plant or plant part in contact with the above formulations. In some embodiments, the plant is a seed.

In another aspect, the invention provides a method of activating a PYR/PYL protein. In some embodiments of the method, the PYR/PYL protein binds a type 2 protein phosphatase (PP2C) polypeptide when the PYR/PYL protein binds the agonist compound LC66C6 (also referred to herein as quinabactin). In some embodiments, the method comprises the step of contacting the PYR/PYL protein with any of the compounds described herein. In some embodiments, the PYR/PYL protein that is activated is substantially identical to any one of SEQ ID NOs:1-119. In some embodiments, the PYR/PYL protein is expressed by a cell. In some embodiments, the PYR/PYL protein is expressed by a plant cell. In some embodiments, the PYR/PYL protein is an endogenous protein. In some embodiments, the PYR/PYL protein is a heterologous protein. In some embodiments, the cell further expresses a type 2 protein phosphatase (PP2C). In some embodiments, the type 2 protein phosphatase is HAB1 (Homology to ABI1), ABI1 (Abscisic acid insensitive 1), or ABI2 (Abscisic acid insensitive 2).

BRIEF DESCRIPTION OF THE DRAWINGS

FIG. 15. The effect of ABA and agonists in yeast assays and seed germination. (A) shows the results of yeast two-hybrid assays using PYR/PYL receptors PYR1, PYL1, PYL2, PYL3, and PYL4 to test the response to each of the agonists shown in FIG. 14. (B) shows the results of testing the agonists in FIG. 14 on germination of wild-type seeds. (C) shows effects of compounds on an ABA-reporter line as measured using glucuronidase assays in a transgenic line expressing glucuronidase under the control of the ABA-inducible *Arabidopsis* gene MAPKKK18.

DEFINITIONS

Figure 1A:
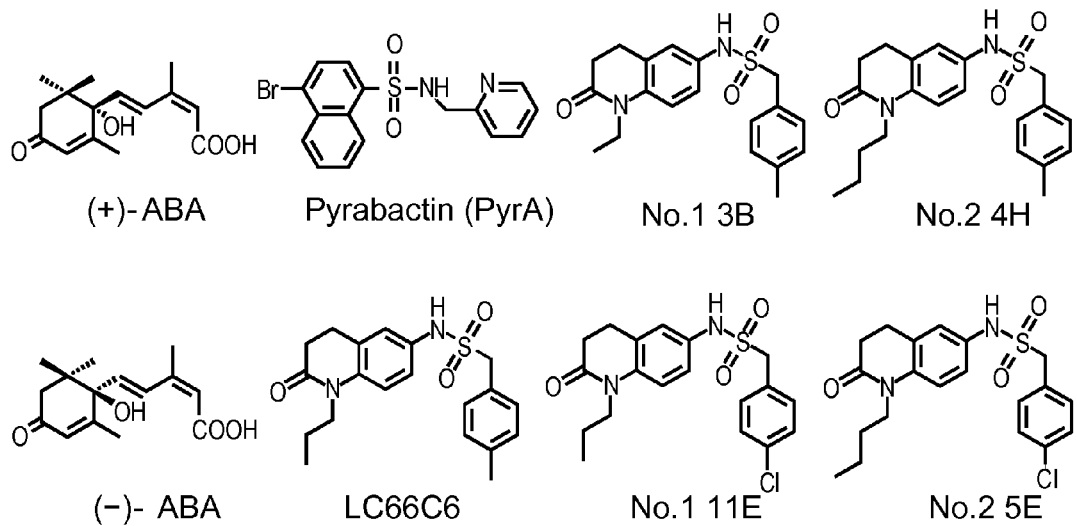
FIG. 1. Novel ABA agonists bind to multiple PYR/PYL. (A) Chemical structure of naturally occurring (+)-ABA, its (−) analog and selected ABA agonists. (B) Yeast two-hybrid agonist assays of PYR/PYL receptor sensitivity to 5 uM of test chemicals. Specific PYR/PYL Receptors and the PP2C HAB1 are expressed as Gal4 BD or AD fusion proteins respectively, as described in the text.

"Agonists" are agents that, e.g., induce or activate the expression of a described target protein or bind to, stimulate, increase, open, activate, facilitate, enhance activation, sensitize or up-regulate the activity of one or more plant PYR/PYL proteins (or encoding polynucleotide). Agonists can include naturally occurring and synthetic molecules. In some embodiments, the agonists are combined with agrichemicals to produce and agricultural formulation. Examples of suitable agrichemicals include fungicides, herbicides, pesticides, fertilizers, and/or surfactants. Assays for determining whether an agonist "agonizes" or "does not agonize" a PYR/PYL protein include, e.g., contacting putative agonists to purified PYR/PYL protein(s) and then determining the functional effects on the PYR/PYL protein activity, as described herein, or contacting putative agonists to cells expressing PYR/PYL protein(s) and then determining the functional effects on the described target protein activity, as described herein. One of skill in the art will be able to determine whether an assay is suitable for determining whether an agonist agonizes or does not agonize a PYR/PYL protein. Samples or assays comprising PYR/PYL proteins that are treated with a putative agonist are compared to control samples without the agonist to examine the extent of effect. Control samples (untreated with agonists) are assigned a relative activity value of 100%. Agonism of the PYR/PYL protein is achieved when the activity value relative to the control is 110%, optionally 150%, optionally 200, 300%, 400%, 500%, or 1000-3000% or more higher.

The term "PYR/PYL receptor polypeptide" refers to a protein characterized in part by the presence of one or more or all of a polyketide cyclase domain 2 (PF10604), a polyketide cyclase domain 1 (PF03364), and a Bet V I domain (PF03364), which in wild-type form mediates abscisic acid (ABA) and ABA analog signaling. A wide variety of PYR/PYL receptor polypeptide sequences are known in the art. In some embodiments, a PYR/PYL receptor polypeptide comprises a polypeptide that is substantially identical to any one of SEQ ID NOs:1-119. See, e.g., Published PCT Application WO 2011/139798.

The term "activity assay" refers to any assay that measures or detects the activity of a PYR/PYL receptor polypeptide. An exemplary assay to measure PYR/PYL receptor activity is a yeast two-hybrid assay that detects binding of a PYR/PYL polypeptide to a type 2 protein phosphatase (PP2C) polypeptide, as described in the Examples.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantially identical," used in the context of two nucleic acids or polypeptides, refers to a sequence that has at least 60% sequence identity with a reference sequence. Alternatively, percent identity can be any integer from 60% to 100%. Some embodiments include at least: 60%, 65%, 70%, 75%, 80%, 85%, 90%, 91%, 92%, 93%, 94% 95%, 96%, 97%, 98%, or 99%, compared to a reference sequence using the programs described herein; preferably BLAST using standard parameters, as described below. Embodiments of the present invention provide for polypeptides, and nucleic acids encoding polypeptides, that are substantially identical to any of SEQ ID NO:1-119.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. ScL USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, Proteins (1984)).

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the methods of the invention includes angiosperms (monocotyledonous and dicotyledonous plants), gymnosperms, ferns, bryophytes, and multicellular and unicellular algae. It includes plants of a variety of ploidy levels, including aneuploid, polyploid, diploid, haploid, and hemizygous.

As used herein, the term "transgenic" describes a non-naturally occurring plant that contains a genome modified by man, wherein the plant includes in its genome an exogenous nucleic acid molecule, which can be derived from the same or a different plant species. The exogenous nucleic acid molecule can be a gene regulatory element such as a promoter, enhancer, or other regulatory element, or can contain a coding sequence, which can be linked to a heterologous gene regulatory element. Transgenic plants that arise from sexual cross or by selfing are descendants of such a plant and are also considered "transgenic.".

As used herein, the term "drought-resistance" or "drought-tolerance," including any of their variations, refers to the ability of a plant to recover from periods of drought stress (i.e., little or no water for a period of days). Typically, the drought stress will be at least 5 days and can be as long as, for example, 18 to 20 days or more (e.g., at least 6, 7, 8, 9, 10, 11, 12, 13, 14, 15, 16, 17, 18, 19, 20 days), depending on, for example, the plant species.

As used herein, the terms "abiotic stress," "stress," or "stress condition" refer to the exposure of a plant, plant cell, or the like, to a non-living ("abiotic") physical or chemical agent that has an adverse effect on metabolism, growth, development, propagation, or survival of the plant (collectively, "growth"). A stress can be imposed on a plant due, for example, to an environmental factor such as water (e.g., flooding, drought, or dehydration), anaerobic conditions (e.g., a lower level of oxygen or high level of $CO_2$), abnormal osmotic conditions, salinity, or temperature (e.g., hot/heat, cold, freezing, or frost), a deficiency of nutrients or exposure to pollutants, or by a hormone, second messenger, or other molecule. Anaerobic stress, for example, is due to a reduction in oxygen levels (hypoxia or anoxia) sufficient to produce a stress response. A flooding stress can be due to prolonged or transient immersion of a plant, plant part, tissue, or isolated cell in a liquid medium such as occurs during monsoon, wet season, flash flooding, or excessive irrigation of plants, or the like. A cold stress or heat stress can occur due to a decrease or increase, respectively, in the temperature from the optimum range of growth temperatures for a particular plant species. Such optimum growth temperature ranges are readily determined or known to those skilled in the art. Dehydration stress can be induced by the loss of water, reduced turgor, or reduced water content of a cell, tissue, organ or whole plant. Drought stress can be induced by or associated with the deprivation of water or reduced supply of water to a cell, tissue, organ or organism. Salinity-induced stress (salt-stress) can be associated with or induced by a perturbation in the osmotic potential of the intracellular or extracellular environment of a cell. As used herein, the term "abiotic stress tolerance" or "stress tolerance" refers to a plant's increased resistance or tolerance to abiotic stress as compared to plants under normal conditions and the ability to perform in a relatively superior manner when under abiotic stress conditions.

A polypeptide sequence is "heterologous" to an organism or a second polypeptide sequence if it originates from a foreign species, or, if from the same species, is modified from its original form.

DETAILED DESCRIPTION OF THE INVENTION

I. Introduction

The present invention is based, in part, on the discovery of selective abscisic acid (ABA) agonists. Unlike previous ABA agonists, the agonists described herein potently activate the ABA pathway in plant vegetative tissues and induce abiotic stress tolerance. The new agonists can be used to induce stress tolerance in crop species of plants. The agonists can be used to induce stress tolerance in monocot and dicot plant species, including but not limited to broccoli, radish, alfalfa, soybean, barley, and corn (maize).

Abscisic acid is a multifunctional phytohormone involved in a variety of phyto-protective functions including bud dormancy, seed dormancy and/or maturation, abscission of leaves and fruits, and response to a wide variety of biological stresses (e.g. cold, heat, salinity, and drought). ABA is also responsible for regulating stomatal closure by a mechanism independent of $CO_2$ concentration. The PYR/PYL family of ABA receptor proteins mediate ABA signaling. Plants examined to date express more than one PYR/PYL receptor protein family member, which have at least somewhat redundant activity. PYR/PYL receptor proteins mediate ABA signaling as a positive regulator in, for example, seed germination, post-germination growth, stomatal movement and plant tolerance to stress including, but not limited to, drought.

A wide variety of wild-type (naturally occurring) PYR/PYL polypeptide sequences are known in the art. Although PYR1 was originally identified as an abscisic acid (ABA) receptor in *Arabidopsis*, in fact PYR1 is a member of a group of at least 14 proteins (PYR/PYL proteins) in the same protein family in *Arabidopsis* that also mediate ABA signaling. This protein family is also present in other plants (see, e.g., SEQUENCE LISTING) and is characterized in part by the presence of one or more or all of a polyketide cyclase domain 2 (PF10604), a polyketide cyclase domain 1 (PF03364), and a Bet V I domain (PF03364). START/Bet v 1 superfamily domain are described in, for example, Radauer, *BMC Evol. Biol.* 8:286 (2008). In some embodiments, a wild-type PYR/PYL receptor polypeptide comprises any of SEQ ID NOs:1-119. In some embodiments, a wild-type PYR/PYL receptor polypeptide is substantially identical to (e.g., at least 70%, 75%, 80%, 85%, 90%, 91%, 92%, 93%, 94% 95%, 96%, 97%, 98%, or 99% identical to) any of SEQ ID NOs:1-119. In some embodiments, a PYR/PYL receptor polypeptide is substantially identical to (e.g., at least 70%, 75%, 80%, 85%, 90%, 91%, 92%, 93%, 94% 95%, 96%, 97%, 98%, or 99% identical to) any of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, or 119.

II. ABA Agonists

The present invention provides for small molecule ABA agonists, i.e., compounds that activate PYR/PYL proteins. Exemplary ABA agonists include, e.g., a compound selected from the following:

A compound of Formula I:

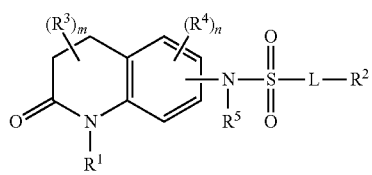

wherein
  $R^1$ is selected from the group consisting of H, $C_{1-6}$ alkyl, $C_{2-6}$ alkenyl, $C_{2-6}$ alkynyl, cycloalkyl, heterocycloalkyl, aryl and heteroaryl,
  $R^2$ is selected from the group consisting of cycloalkyl, heterocycloalkyl, aryl and heteroaryl, each optionally substituted with from 1-4 $R^{2a}$ groups,
  each $R^{2a}$ is independently selected from the group consisting of H, halogen, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, —OH, $C_{1-6}$ alkylhydroxy, —CN, —NO$_2$, —C(O)R$^{2b}$, —C(O)OR$^{2b}$, —OC(O)R$^{2b}$, —C(O)NR$^{2b}$R$^{2c}$, —NR$^{2b}$C(O)R$^{2c}$, —SO$_2$R$^{2b}$, —SO$_2$OR$^{2b}$, —SO$_2$NR$^{2b}$R$^{2c}$, and —NR$^{2b}$SO$_2$R$^{2c}$;
  each of $R^{2b}$ and $R^{2c}$ are independently selected from the group consisting of H and $C_{1-6}$ alkyl,
  each of $R^3$, $R^4$ and $R^5$ are independently selected from the group consisting of H and $C_{1-6}$ alkyl,
  L is a linker selected from the group consisting of a bond and $C_{1-6}$ alkylene,
  subscript m is an integer from 0 to 4,
  subscript n is an integer from 0 to 3,
or a salt or isomer thereof.

In some embodiments, the compound has the formula (II):

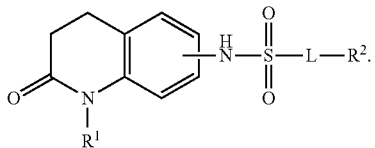

In some embodiments, the compound has the formula (III):

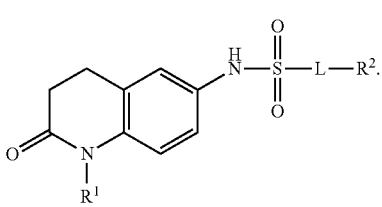

In some embodiments, $R^1$ is $C_{1-6}$ alkyl, and $R^2$ is selected from the group consisting of aryl and heteroaryl, each optionally substituted with from 1-4 $R^{2a}$ groups.

In some embodiments, each $R^{2a}$ is independently selected from the group consisting of H, halogen and $C_{1-6}$ alkyl.

In some embodiments, $R^2$ is selected from the group consisting of phenyl, naphthyl, thiophene, furan, pyrrole, and pyridyl.

In some embodiments, $R^1$ is selected from the group consisting of methyl, ethyl, propyl, isopropyl, butyl, iso-butyl, sec-butyl, tert-butyl, pentyl, isopentyl, neo-pentyl and hexyl;

$R^2$ is selected from the group consisting of phenyl and thiophene, each optionally substituted with 1 $R^{2a}$ group; each $R^{2a}$ is independently selected from the group consisting of H, F, Cl, methyl, and ethyl; and L is selected from the group consisting of a bond and methylene.

In some embodiments, the compound has the formula (IV):

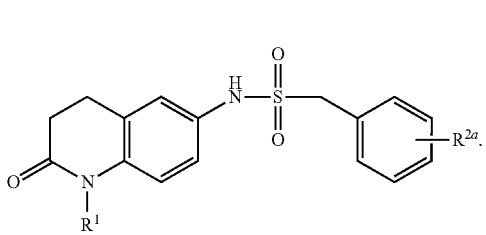

In some embodiments, the compound has the formula (V):

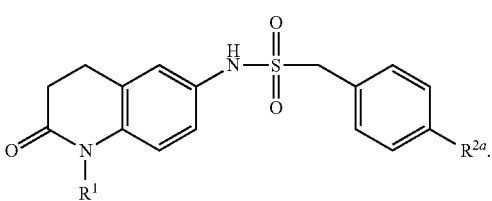

In some embodiments, the compound is one of the compounds shown in FIG. 8.

In some embodiments, the compound has the formula (VI):

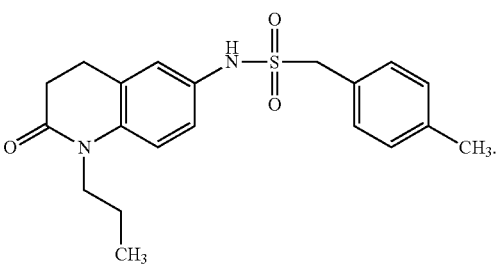

The compound having the formula (VI) is also referred to as LC66C6 or quinabactin (1-(4-methylphenyl)-N-(2-oxo-1,2,3,4-tetrahydroquinolin-6-yl)methanesulfonamide). The compounds described above were identified by screening a library of structurally diverse compounds purchased from Life Chemicals (Orange, Conn.).

In some embodiments, the compound has the formula (VII):

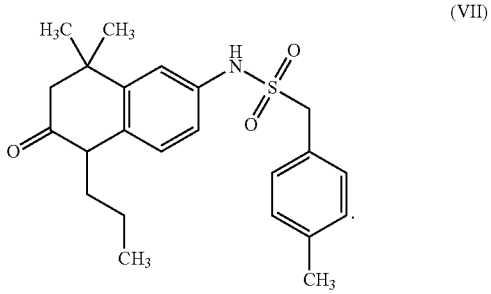 [SMILES: CCCC1C(=O)CC(C)(C)c2cc(NS(=O)(=O)Cc3ccc(C)cc3)ccc21]

The compounds described above can be synthesized using methods well known in the art. For example, compounds based on the same chemical scaffold were synthesized as described in U.S. Pat. Nos. 5,498,755 and 6,127,382, the contents of which are incorporated herein by reference in their entirety.

III. ABA Agonist Formulations

The present invention provides for agricultural chemical formulations formulated for contacting to plants, wherein the formulation comprises an ABA agonist of the present invention. In some embodiments, the plants that are contacted with the agonists comprise or express an endogenous PYR/PYL polypeptide. In some embodiments, the plants that are contacted with the agonists do not comprise or express a heterologous PYR/PYL polypeptide (e.g., the plants are not transgenic or are transgenic but express heterologous proteins other than heterologous PYR/PYL proteins). In some embodiments, the plants that are contacted with the agonists do comprise or express a heterologous PYR/PYL polypeptide as described herein.

The formulations can be suitable for treating plants or plant propagation material, such as seeds, in accordance with the present invention, e.g., in a carrier. Suitable additives include buffering agents, wetting agents, coating agents, polysaccharides, and abrading agents. Exemplary carriers include water, aqueous solutions, slurries, solids and dry powders (e.g., peat, wheat, bran, vermiculite, clay, pasteurized soil, many forms of calcium carbonate, dolomite, various grades of gypsum, bentonite and other clay minerals, rock phosphates and other phosphorous compounds, titanium dioxide, humus, talc, alginate and activated charcoal. Any agriculturally suitable carrier known to one skilled in the art would be acceptable and is contemplated for use in the present invention). Optionally, the formulations can also include at least one surfactant, herbicide, fungicide, pesticide, or fertilizer.

In some embodiments, the agricultural chemical formulation comprises at least one of a surfactant, an herbicide, a pesticide, such as but not limited to a fungicide, a bactericide, an insecticide, an acaricide, and a nematicide, a plant activator, a synergist, an herbicide safener, a plant growth regulator, an insect repellant, or a fertilizer.

In some embodiments, the agricultural chemical formulation comprises an effective amount of one or more herbicides selected from the group consisting of: paraquat (592), mesotrione (500), sulcotrione (710), clomazone (159), fentrazamide (340), mefenacet (491), oxaziclomefone (583), indanofan (450), glyphosate (407), prosulfocarb (656), molinate (542), triasulfuron (773), halosulfuron-methyl (414) and pretilachlor (632). The above herbicidal active ingredients are described, for example, in "The Pesticide Manual", Editor C. D. S. Tomlin, 12th Edition, British Crop Protection Council, 2000, under the entry numbers added in parentheses; for example, mesotrione (500) is described therein under entry number 500. The above compounds are described, for example, in U.S. Pat. No. 7,338,920, which is incorporated by reference herein in its entirety.

In some embodiments, the agricultural chemical formulation comprises an effective amount of one or more fungicides selected from the group consisting of: sedaxane, fludioxonil, penthiopyrad, prothioconazole, flutriafol, difenoconazole, azoxystrobin, captan, cyproconazole, cyprodinil, boscalid, diniconazole, epoxiconazole, fluoxastrobin, trifloxystrobin, metalaxyl, metalaxyl-M (mefenoxam), fluquinconazole, fenarimol, nuarimol, pyrifenox, pyraclostrobin, thiabendazole, tebuconazole, triadimenol, benalaxyl, benalaxyl-M, benomyl, carbendazim, carboxin, flutolanil, fuberizadole, guazatine, myclobutanil, tetraconazole, imazalil, metconazole, bitertanol, cymoxanil, ipconazole, iprodione, prochloraz, pencycuron, propamocarb, silthiofam, thiram, triazoxide, triticonazole, tolylfluanid, and a manganese compound (such as mancozeb, maneb). In some embodiments, the agricultural chemical formulation comprises an effective amount of one or more of an insecticide, an acaricide and/or nematicide selected from the group consisting of: thiamethoxam, imidacloprid, clothianidin, lamda-cyhalothrin, tefluthrin, beta-cyfluthrin, permethrin, abamectin, fipronil, and spinosad. Details (e.g., structure, chemical name, commercial names, etc) of each of the above pesticides with a common name can be found in the e-Pesticide Manual, version 3.1, 13th Edition, Ed. CDC Tomlin, British Crop Protection Council, 2004-05. The above compounds are described, for example, in U.S. Pat. No. 8,124,565, which is incorporated by reference herein in its entirety.

In some embodiments, the agricultural chemical formulation comprises an effective amount of one or more fungicides selected from the group consisting of: Cyprodinil ((4-cyclopropyl-6-methyl-pyrimidin-2-yl)-phenyl-amine) (208), Dodine (289); Chlorothalonil (142); Folpet (400); Prothioconazole (685); Boscalid (88); Proquinazid (682); Dithianon (279); Fluazinam (363); Ipconazole (468); and Metrafenone. Some of the above compounds are described, for example, in "The Pesticide Manual" [The Pesticide Manual—A World Compendium; Thirteenth Edition; Editor: C. D. S. Tomlin; The British Crop Protection Council, 2003], under the entry numbers added in parentheses. The above compounds are described, for example, in U.S. Pat. No. 8,349,345, which is incorporated by reference herein in its entirety.

In some embodiments, the agricultural chemical formulation comprises an effective amount of one or more fungicides selected from the group consisting of: fludioxonil, metalaxyl and a strobilurin fungicide, or a mixture thereof. In some embodiments, the strobilurin fungicide is azoxystrobin, picoxystrobin, kresoxim-methyl, or trifloxystorbin. In some embodiments, the agricultural chemical formulation comprises an effective amount of one or more of an insecticide selected from a phenylpyrazole and a neonicotinoid. In some embodiments, the phenylpyrazole is fipronil and the neonicotinoid is selected from thiamethoxam, imidacloprid, thiacloprid, clothianidin, nitenpyram and acetamiprid. The above compounds are described, for example, in U.S. Pat. No. 7,071,188, which is incorporated by reference herein in its entirety. In some embodiments, the agricultural chemical formulation comprises an effective amount of one or more biological pesticide, including but not limited to, *Pasteuria* spp., *Paeciliomyces*, *Pochonia chlamydosporia*, *Myrothecium* metabolites, *Muscodor volatiles*, *Tagetes* spp., *bacillus firmus*, including *bacillus firmus* CNCM 1-1582.

IV. Application to Plants

The ABA agonist formulations and compositions can be applied to plants using a variety of known methods, e.g., by spraying, atomizing, dipping, pouring, irrigating, dusting or scattering the compositions over the propagation material, or brushing or pouring or otherwise contacting the compositions over the plant or, in the event of seed, by coating, encapsulating, spraying, dipping, immersing the seed in a liquid composition, or otherwise treating the seed. In an alternative to directly treating a plant or seed before planting, the formulations of the invention can also be introduced into the soil or other media into which the seed is to be planted. For example, the formulations can be introduced into the soil by spraying, scattering, pouring, irrigating or otherwise treating the soil. In some embodiments, a carrier is also used in this embodiment. The carrier can be solid or liquid, as noted above. In some embodiments peat is suspended in water as a carrier of the ABA agonist, and this mixture is sprayed into the soil or planting media and/or over the seed as it is planted.

The types of plant that can be treated with the ABA agonists described herein include both monocotyledonous and dicotyledonous plant species including cereals such as barley, rye, sorghum, tritcale, oats, rice, wheat, soybean and corn; beets (for example sugar beet and fodder beet); cucurbits including cucumber, muskmelon, canteloupe, squash and watermelon; cale crops including broccoli, cabbage, cauliflower, bok Choi, and other leafy greens, other vegetables including tomato, pepper, lettuce, beans, pea, onion, garlic and peanut; oil crops including canola, peanut, sunflower, rape, and soybean; solanaceous plants including tobacco; tuber and root crops including potato, yam, radish, beets, carrots and sweet potatoes; fruits including strawberry; fiber crops including cotton and hemp; other plants including coffee, bedding plants, perennials, woody ornamentals, turf and cut flowers including carnation and roses; sugar cane; containerized tree crops; evergreen trees including fir and pine; deciduous trees including maple and oak; and fruit and nut trees including cherry, apple, pear, almond, peach, walnut and citrus.

It will be understood that the ABA agonists described herein mimic the function of ABA on cells. Thus, it is expected that one or more cellular responses triggered by contacting the cell with ABA will also be triggered be contacting the cell with the ABA agonists described herein. The ABA agonists described herein mimic the function of ABA and are provided in a useful formulation.

In some embodiments, application of the ABA agonists described herein increases the abiotic stress resistance of a plant.

In some embodiments, application of the ABA agonists described herein to seeds inhibits germination of the seeds.

The present invention also provides plants in contact with the ABA formulations described herein. The plant in contact with the ABA formulation can include a plant part and/or a seed.

V. Screening for New ABA Agonists and Antagonists

Embodiments of the present invention also provide for methods of screening putative chemical agonists to determine whether the putative agonist agonizes a PYR/PYL receptor polypeptide, when the putative agonist is contacted to the PYR/PYL receptor polypeptide. As used herein, an agent "agonizes" a PYR/PYL receptor protein if the presence of the agent results in activation or up-regulation of activity of the receptor, e.g., to increase downstream signaling from the PYR/PYL receptor. For the present invention, an agent agonizes a PYR/PYL receptor if, when the agent is present at a concentration no greater than 200 µM, contacting the agent to the PYR/PYL receptor results in activation or up-regulation of the activity of the PYR/PYL receptor. If an agent does not induce activation or up-regulation of a PYR/PYL receptor protein's activity when the agent is present at a concentration no greater than 200 µM, then the agent does not significantly agonize the PYR/PYL receptor. As used herein, "activation" requires a minimum threshold of activity to be induced by the agent. Determining whether this minimum threshold of activity has been met can be accomplished, e.g., by using an enzymatic phosphatase assay that sets a minimum value for the level of enzymatic activity that must be induced, or by using an enzymatic phosphatase assay in the presence of a colorimetric detection reagent (e.g., para-nitrophenylphosphate) wherein the minimum threshold of activity has been met if a color change is observed.

The present invention also provides methods of screening for ABA agonists and antagonists by screening for a molecule's ability to induce PYR/PYL-PP2C binding in the case of agonists, or to disrupt the ability of ABA and other agonists to promote PYR/PYL-PP2C binding in the case of antagonists. A number of different screening protocols can be utilized to identify agents that agonize or antagonize a PYR/PYL polypeptide.

Screening can take place using isolated, purified or partially purified reagents. In some embodiments, purified or partially purified PYR/PYL polypeptide can be used.

Alternatively, cell-based methods of screening can be used. For example, cells that naturally-express a PYR/PYL polypeptide or that recombinantly express a PYR/PYL polypeptide can be used. In some embodiments, the cells used are plant cells, animal cells, bacterial cells, fungal cells, including but not limited to yeast cells, insect cells, or mammalian cells. In general terms, the screening methods involve screening a plurality of agents to identify an agent that modulates the activity of a PYR/PYL polypeptide by, e.g., binding to PYR/PYL polypeptide, or activating a PYR/PYL polypeptide or increasing expression of a PYR/PYL polypeptide, or a transcript encoding a PYR/PYL polypeptide.

1. PYR/PYL Polypeptide Binding Assays

Optionally, preliminary screens can be conducted by screening for agents capable of binding to a PYR/PRL polypeptide, as at least some of the agents so identified are likely PYR/PYL polypeptide modulators.

Binding assays can involve contacting a PYR/PYL polypeptide with one or more test agents and allowing sufficient time for the protein and test agents to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89). Other binding assays involve the use of mass spectrometry or NMR techniques to identify molecules bound to PYR/PYL polypeptide or displacement of labeled substrates (e.g., labeled ABA). The PYR/PYL polypeptide protein utilized in such assays can be naturally expressed, cloned or synthesized.

2. Activity

PYR/PYL polypeptide agonists can be identified by screening for agents that activate or increase activity of a PYR/PYL polypeptide. Antagonists can be identified by reducing activity.

One activity assay involves testing whether a candidate agonist can induce binding of a PYR/PYL protein to a type 2 protein phosphatase (PP2C) polypeptide in an agonist-specific fashion. Mammalian or yeast two-hybrid approaches (see, e.g., Bartel, P. L. et. al. *Methods Enzymol,* 254:241 (1995)) can be used to identify polypeptides or other molecules that interact or bind when expressed together in a cell. In some embodiments, agents that agonize a PYR/PYL polypeptide are identified in a two-hybrid assay between a PYR/PYL polypeptide and a type 2 protein phosphatase (PP2C) polypeptide (e.g., ABI1 or 2 or orthologs thereof, e.g., from the group A subfamily of PP2Cs), wherein an ABA agonist is identified as an agent that activates or enables binding of the PYR/PYL polypeptide and the PP2C polypeptide. Thus, the two polypeptides bind in the presence, but not in the absence of the agent. In some embodiments, a chemical compound or agent is identified as an agonist of a PYR/PYL protein if the yeast cell turns blue in the yeast two hybrid assay, The biochemical function of PYR1, and PYR/PYL proteins in general, is to inhibit PP2C activity. This can be measured in live cells using the yeast two hybrid or other cell-based methods. It can also be measured in vitro using enzymatic phosphatase assays in the presence of a colorimetric detection reagent (for example, para-nitrophenylphosphate). The yeast-based assay used above provides an indirect indicator of ligand binding. To address this potential limitation, one can use in vitro competition assays, or cell based assays using other organisms, as alternate approaches for identifying weak binding target compounds.

3. Expression Assays

Screening for a compound that increases the expression of a PYR/PYL polypeptide is also provided. Screening methods generally involve conducting cell-based or plant-based assays in which test compounds are contacted with one or more cells expressing PYR/PYL polypeptide, and then detecting an increase in PYR/PYL expression (either transcript or translation product). Assays can be performed with cells that naturally express PYR/PYL or in cells recombinantly altered to express PYR/PYL, or in cells recombinantly altered to express a reporter gene under the control of the PYR/PYL promoter.

Various controls can be conducted to ensure that an observed activity is authentic including running parallel reactions with cells that lack the reporter construct or by not contacting a cell harboring the reporter construct with test compound.

4. Validation

Agents that are initially identified by any of the foregoing screening methods can be further tested to validate the apparent activity and/or determine other biological effects of the agent. In some cases, the identified agent is tested for the ability to effect plant stress (e.g., drought tolerance), seed germination, or another phenotype affected by ABA. A number of such assays and phenotypes are known in the art and can be employed according to the methods of the invention.

5. Solid Phase and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 or more different compounds are possible using the integrated systems of the invention. In addition, microfluidic approaches to reagent manipulation can be used.

The molecule of interest (e.g., PYR/PYL or a cell expressing a PYR/PYL polypeptide) can be bound to the solid state component, directly or indirectly, via covalent or non covalent linkage.

The invention provides in vitro assays for identifying, in a high throughput format, compounds that can modulate the expression or activity of PYR/PYL.

Abiotic stress resistance can assayed according to any of a number of well-known techniques. For example, for drought tolerance, plants can be grown under conditions in which less than optimum water is provided to the plant. Drought resistance can be determined by any of a number of standard measures including turgor pressure, growth, yield, and the like.

VI. Methods of Increasing Abiotic Stress Tolerance in Plants

The present invention also provides methods of increasing abiotic stress tolerance in a plant. Thus, in some embodiments, a plant is contacted with an ABA agonist desribed herein, or an ABA agonist formulation, in sufficient amount to increase the abiotic stress tolerance in the plant. The amount of the ABA agonist formulation applied to the plant can be sufficient to increase the abiotic stress tolerance compared to not contacting the plant with the ABA agonist formulation. The plant can be contacted with the ABA formulation using any of the methods described herein. The increase in abiotic stress tolerance can improve the plants growth and/or survival to abiotic stress conditions that adversely effect the plant's growth or survival. Abiotic stress includes physical or chemical conditions described herein.

VII. Methods of Inhibiting Seed Germination in a Plant

The present invention also provides methods of inhibiting seed germination. Thus, in some embodiments, a plant, plant part, or a seed is contacted with an ABA agonist formulation in an amount sufficient to inhibit seed germination. The seed can be contacted with the ABA formulation using any of the methods described herein. In some embodiments, the seed is directly contacted with the ABA agonist formulation. In some embodiments, the ground or soil is contacted with the ABA agonist formulation either prior to or after planting or sowing the seeds. In some embodiments, a plant is contacted with sufficient ABA agonist formulation to inhibit germination of seeds that later develop from the plant.

VIII. Methods of Activating PYR/PYL Receptor Polypeptides

The present invention also provides methods of activating a PYR/PYL receptor polypeptide. In some embodiments, a PYR/PYL polypeptide is contacted with a compound described above, and the activated PYR/PYL polypeptide binds to a PP2C polypeptide. In some embodiments, the PYR/PYL polypeptide is capable of being activated by the agonist compound LC66C6. In some embodiments, the PYR/PYL protein that is activated is substantially identical to any one of SEQ ID NOs:1-119. Examples of sequences of ABA receptors from various plants are provided in U.S. Patent Publication 2011/0271408, which is incorporated by reference herein in its entirety.

In some embodiments, the method activates a PYR/PYL receptor in a cell free in vitro assay. In some embodiments, the method activates a PYR/PYL receptor expressed in a cell. In some embodiments, the cell also expresses a PP2C polypeptide. In some embodiments, the cell is a plant cell. In some embodiments, the cell is an animal or mammalian cell. In some embodiments, the cell expresses an endogenous PYR/PYL protein. In some embodiments, the cell is engineered to express a heterologous PYR/PYL polypeptide. In some embodiments, the cell expresses a heterologous PP2C polypeptide. In some embodiments, the cell expresses a PP2C polypeptide selected from HAB1 (homology to ABI1), ABI1, or ABI2.

In some embodiments, the activated PYR/PYL polypeptide induces expression of heterologous genes. In some embodiments, the heterologous genes are ABA responsive genes. In some embodiments, the induced gene expression occurs in cells that express an endogenous PYR/PYL polypeptide. In some embodiments, the induced gene expression occurs in cells that express a heterologous PYR/PYL polypeptide.

EXAMPLES

Example 1

This example demonstrates that novel ABA agonists described herein bind to and activate multiple PYR/PYL receptors.

Methods

Chemical Screening

A previously described yeast two-hybrid system was used in high throughput screens (HTS) to identify ABA agonists (see, Peterson F C, et al. (2010) Structural basis for selective activation of ABA receptors. *Nature Structural & Molecular Biology* 17(9):1109-1111). In this system the agonist promoted receptor—PP2C interaction drives expression of a URA3 or HIS3 reporter gene and rescues uracil or histidine auxotrophy of parental strains (Peterson F C, et al. (2010); Vidal M, Brachmann R K, Fattaey A, Harlow E, & Boeke J D (1996) Reverse two-hybrid and one-hybrid systems to detect dissociation of protein-protein and DNA-protein interactions. *Proceedings of the National Academy of Sciences of the United States of America* 93(19):10315-10320). HTS were conducted using 5 different reporter strains that express binding domain (BD) fusions to PYR1, PYL1, PYL2, PYL3 or PYL4; these were co-expressed with activation domain (AD) fusions to HAB1 (pACT-HAB1); the constructs used have been described previously (Park et al. 2009). We utilized these strains in two separate screens. In the first screen ~65,000 compounds obtained from Chembridge (San Diego, USA) were assayed for agonist activity using a halo assay, essentially as described by Gassner N C, et al. (2007) (Accelerating the discovery of biologically active small molecules using a high-throughput yeast halo assay. *Journal of Natural Products* 70(3):383-390). In this method yeast strains are embedded in selective agar and compounds pin transferred from 10 mM DMSO stock solutions onto assay plates; hits are evident by increased cell density in the vicinity of active compounds. Experiments using the halo assay utilized the yeast strain PJ69-4A and media supplemented with 10 mM 3-aminotriazole to improve selections. Halo screens were set up using a Biomek FX equipped with an automated microplate hotel (Thermo Cytomat) and a 384-pin tool (V & P Scientific), which was used to spot compounds on to assay plates. Prior to each chemical transfer the pins were washed in a 1:1 mixture of DMSO/water followed by a wash with 95% ethanol. After chemical transfer, plates were incubated at 28° C. and candidate agonists evident by manual inspection.

Although the halo screening method is powerful from the perspective of throughput, we subsequently employed a more conventional screening method for a second screen of a 12,000-member library obtained from Life Chemicals (Ukraine). This change was motivated by a desire to better control the assay concentration. In our second screen, reporter constructs were expressed in the yeast strain MAV99, which enables uracil-based selections via a GAL1 promoter driven URA3 transgene (Peterson F C, et al. (2010)). Screening compounds were added to selective uracil⁻ media seeded with reporter strains in 96 well plate format at a final concentration of 25 M; yeast growth was inspected manually after ~3 days. Compounds were transferred to screening wells from 2.5 mM stock solutions using a Biomek FX liquid handler.

As a third screening approach, the Life Chemicals library was also screened for *Arabidopsis* germination inhibitors in solidified agar medium containing 0.5×MS salts, 0.5% sucrose and 25 µM test compound. Hits from the germination assay were subsequently tested in yeast two hybrid assays. Hit compounds were restocked from their original vendors and used in secondary screens and compound characterization. Quinabactin and its analogs were purchased from Life Chemicals.

PP2C Activity Assay

HAB1 and PYL proteins were expressed and purified as described previously (Park S Y, et al. (2009) Abscisic Acid Inhibits Type 2C Protein Phosphatases via the PYR/PYL Family of START Proteins. *Science* 324(5930):1068-1071), with minor modifications. To obtain GST-HAB1, -ABI1 and -ABI2 fusion proteins, the HAB1 cDNA was cloned into pGex-2T whereas ABI1 and ABI2 cDNAs were cloned into the vector pGex-4T-1. Expression was conducted in BL21 [DE3]pLysS host cells. Transformed cells were pre-cultured overnight, transferred to LB medium and cultured at 30° C. to culture $A_{600}$ of ~0.5. The culture was then cooled on ice and $MnCl_2$ added to 4 mM and IPTG added to 0.3 mM. After 16 hours incubation at 15° C., cells were harvested and recombinant proteins were purified on glutathione agarose as described previously (Park S Y, et al. (2009). To obtain 6×His-PYL receptor fusion proteins, receptor cDNAs for all 13 ABA receptors were cloned into the vector pET28 and expressed and purified as described previously (Mosquna A, et al. (2011) Potent and selective activation of abscisic acid receptors in vivo by mutational stabilization of their agonist-bound conformation. *PNAS* 108(51):20838-20843); this yielded soluble and functional protein (assessed using receptor-mediated PP2C inhibition assays) for all receptors except PYL7, PYL11 and PYL12. These three receptors were therefore alternatively expressed as maltose binding (MBP) fusion proteins using the vector pMAL-c; expression of these constructs was carried out in BL21[DE3]pLysS host strain with the same induction conditions used for GST-HAB1. Recombinant MBP-PYL fusion proteins were purified from sonicated and cleared lysate using amylose resin (New England Biolab, Inc.) using the manufacturers purification instructions. This effort yielded an active MBP-PYL11 fusion protein, but failed for PYL7 and PYL12.

PP2C activity assays using recombinant receptors and PP2Cs were carried out as follows: Purified proteins were pre-incubated in 80 0 assay buffer containing 10 mM $MnCl_2$, 3 µg bovine serum albumin and 0.1% 2-mercaptoethanol with ABA or ABA agonist for 30 minutes at 22° C. Reactions were started by adding 20 µL of a reaction solution containing 156 mM Tris-OAc, pH 7.9, 330 mM KOAc and 5 mM 4-methylumbelliferyl phosphate after which fluorescence measurements were immediately collected using an excitation filter 355 nm and an emission filter 460 nm on a Wallac plate reader. Reactions contained 50 nM PP2C and 100 nM PYR/PYL proteins, respectively.

Figure 1B:
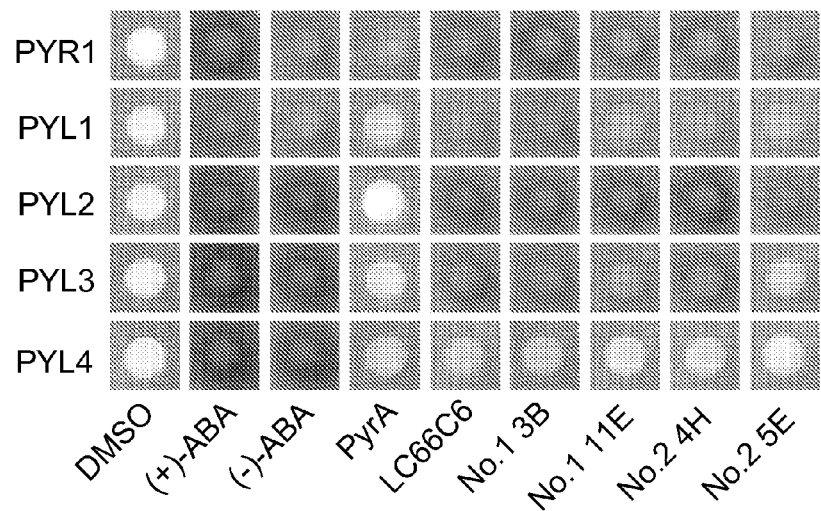
Figure 2A:
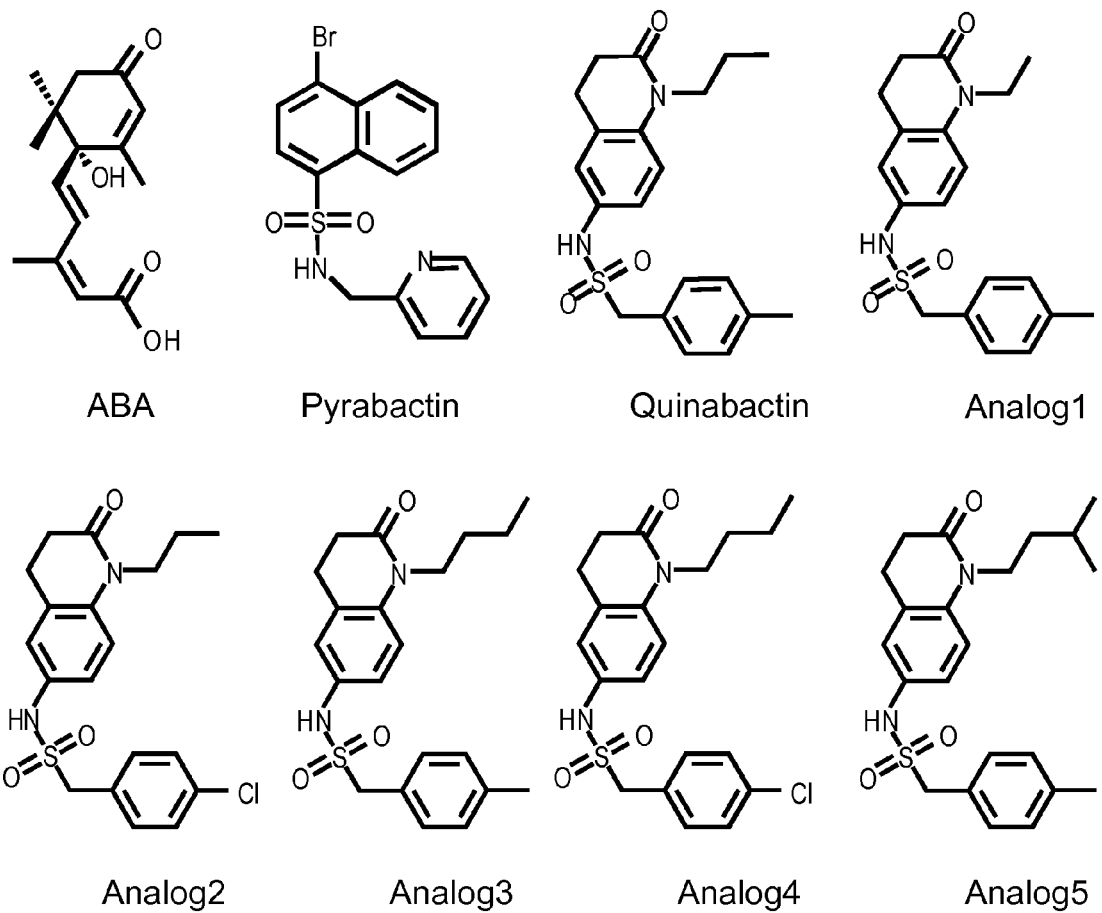
FIG. 2. Novel ABA agonists inhibit PPC2 activity through multiple PYR/PYL. (A) Chemical structure of naturally occurring (+)-ABA and selected ABA agonists. (B) and (C) HAB1, ABI1, and ABI2 PP2C enzyme activity based ABA-agonist assays for various receptors in the presence or absence of 10 μM each test chemical.
Figure 2B:
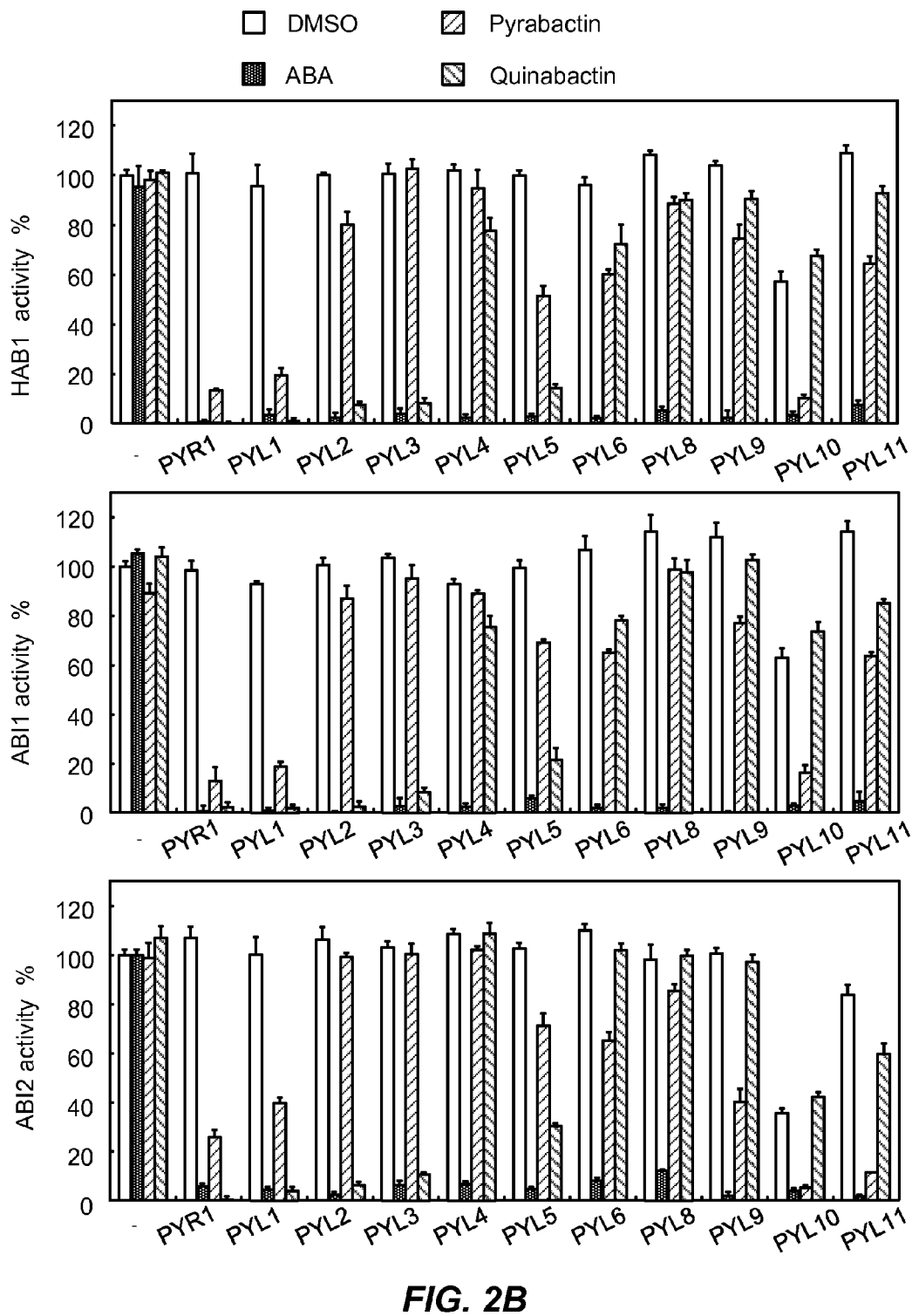
Figure 2C:
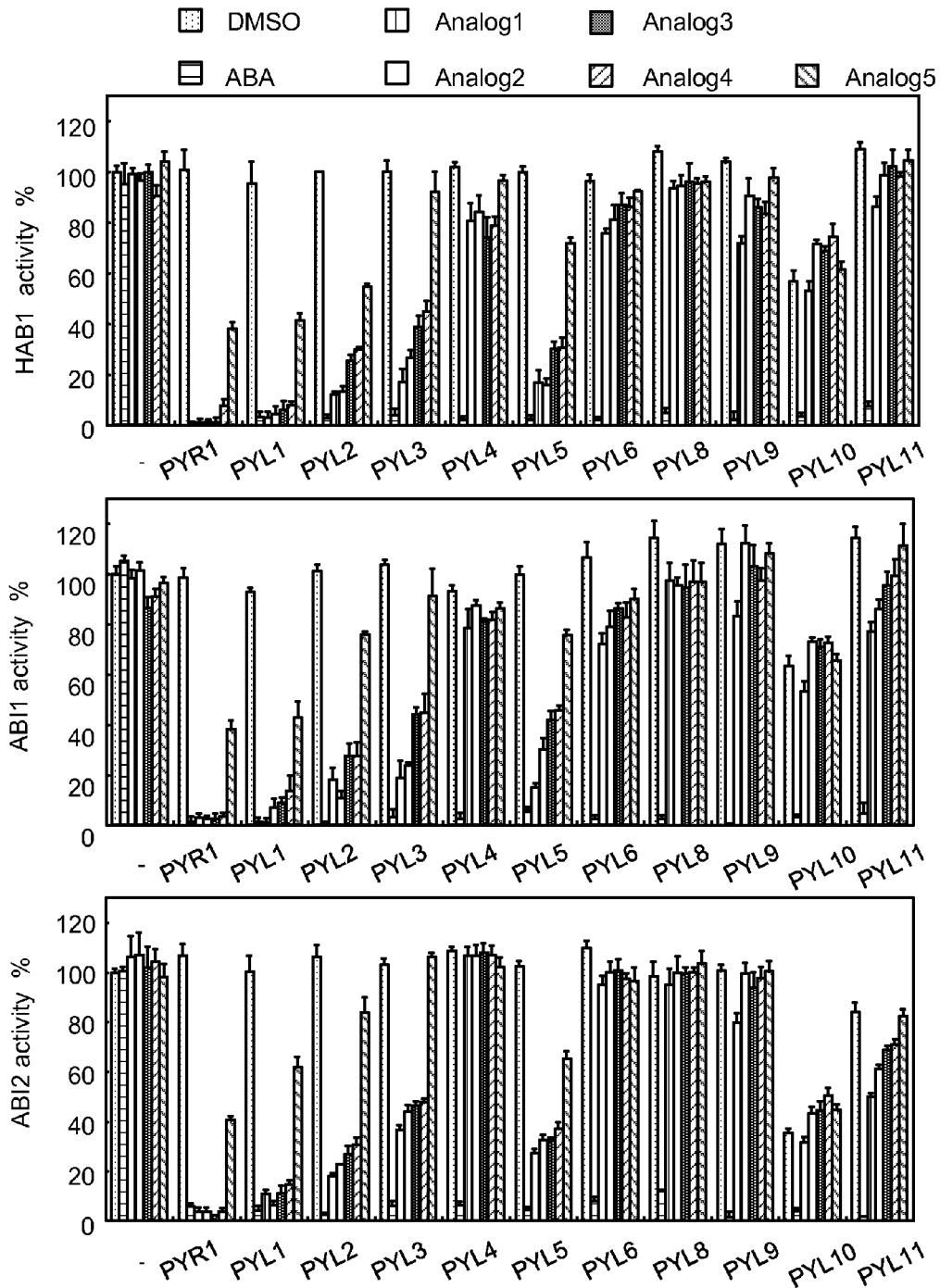

FIG. 1A shows a representative group of ABA agonists. As shown in FIG. 1B, multiple PYR/PYL receptors are activated by several agonists, including LC66C6, in a yeast two-hybrid assay. This assay reports the agonist-promoted physical interaction of PYR/PYL proteins and Glade A PP2C proteins when a specific receptor and PP2C are fused to GAL4 activation and DNA-Binding domains respectively, as previously described (Park et al. 2009). These yeast-based assays indicate that LC66C6 is an agonist of multiple PYR/PYL receptors, unlike the previously described agonist pyrabactin, which has much greater receptor selectivity than ABA or the new agonist LC66C6. As previously described, the agonist-promoted binding of a receptor to a Glade A PP2C inhibits the PP2C's phosphatase activity. In *Arabidopsis*, there are 14 PYR/PYL receptors, 13 of which can mediate ABA-responses in a protoplast-based assay system (Fujii et al. 2009). To examine LC66C6's selectivity more closely, we attempted to express and purify recombinant 6×-His-PYR/PYL proteins for all 14 members and recovered ABA-responsive receptors for all receptors except PYL7, 12 and 13, which could not be produced in active forms for technical reasons. This panel of recombinant receptors enables a near complete portrait of an ABA-agonists activity on members of the *Arabidopsis* PYR/PYL receptor family. As shown in FIG. 2, the PPC2 enzyme activity of HBA1, ABI1, and ABI2 is inhibited by >90% by 10 μM ABA in the presence of all ABA receptors tested (FIG. 2B). In response to LC66C6 (Quinabactin), >70% PP2C inhibition of HBA1, ABI1, and ABI2 was observed with the receptors PYR1, PYL1, PYL2, PYL3 and PYL5.

Figure 3A:
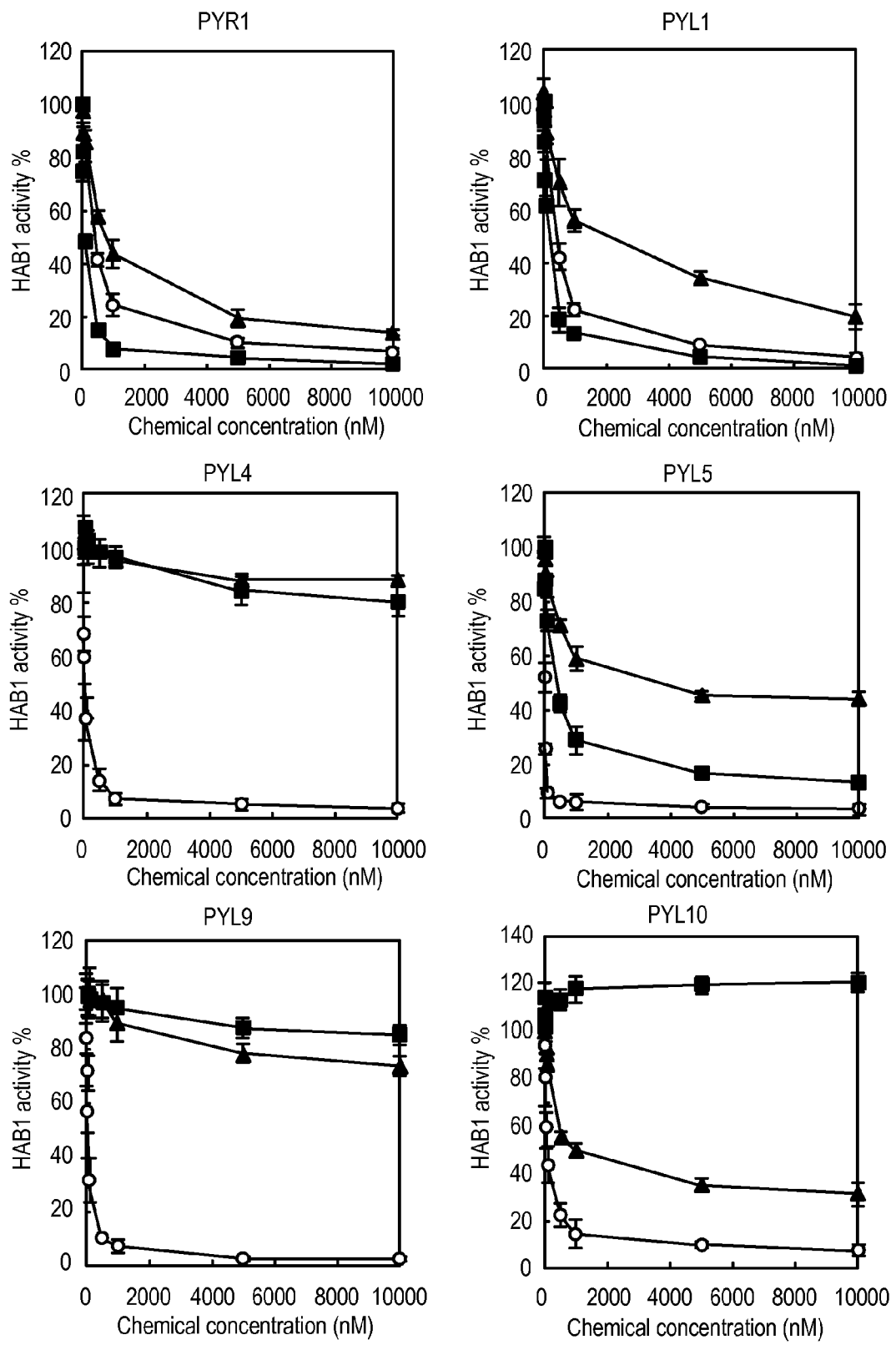
FIG. 3. (A) Receptor-mediated dose-dependent inhibition of PP2C enzyme activity by ABA agonists and analogs. (B) Observed compound $IC_{50}$ values in enzymatic HAB1 PP2C-based ABA-agonist assays.
Figure 3A:
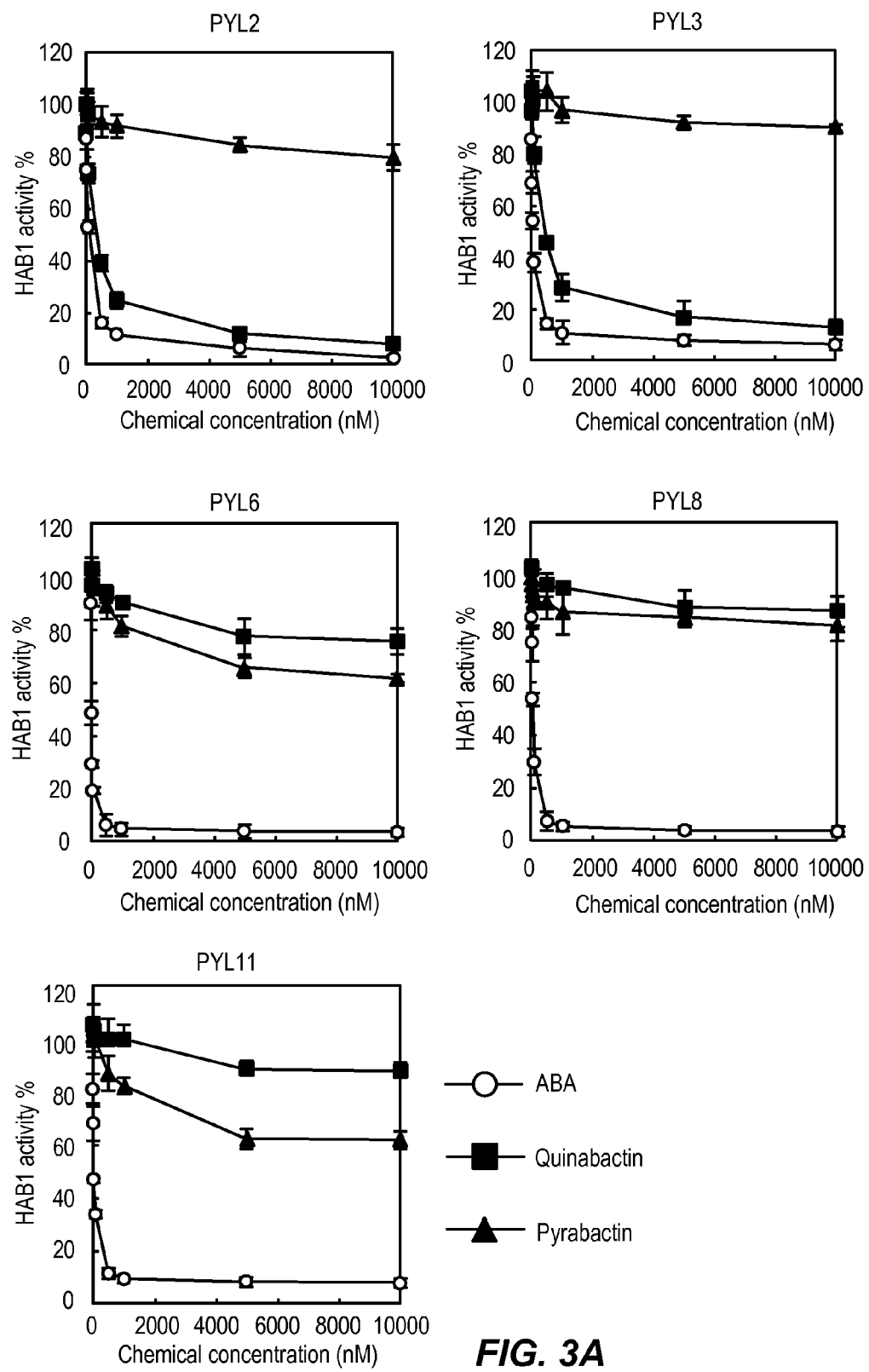
Figures 4A, 4B:
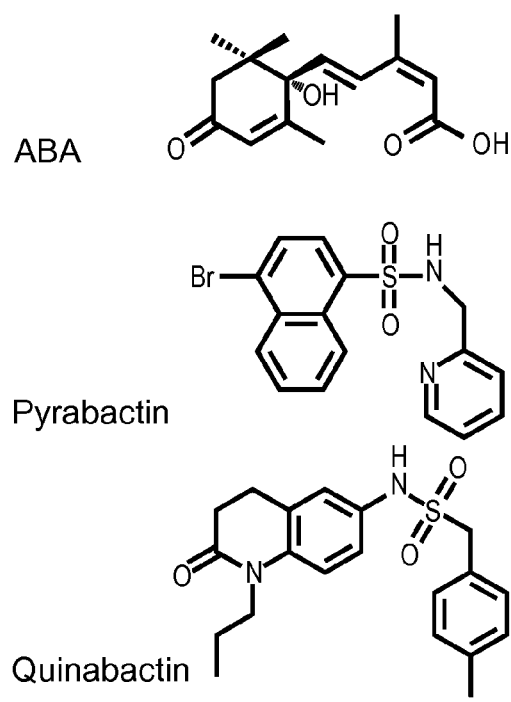
FIG. 4. Quinabactin activates multiple ABA receptors. (A) Chemical structures of ABA, pyrabactin and quinabactin. (B) Chemical-dependent inhibition of HAB1 by ABA receptors. $IC_{50}$ values (nM) were determined as described in the methods using 50 nM HAB1, 50 nM and multiple concentrations of compounds; full dose response curves are provided as in FIG. 3. (nd) correspond to receptors that were not produced as active proteins. The phylogenetic tree is a Neighbor-Joining tree made using the JTT distance matrix in MEGA5 (Tamura K, et al. (2011) MEGA5: Molecular Evolutionary Genetics Analysis Using Maximum Likelihood, Evolutionary Distance, and Maximum Parsimony Methods. *Molecular Biology and Evolution* 28(10):2731-2739).

To further characterize quinabactin's activity and define its receptor selectivity, receptor-mediated PP2C-inhibtion assays were conducted using 10 recombinant receptors in combination with the PP2Cs HAB1, ABI1 or ABI2. These experiments showed that quinabactin activates PYR1, PYLs 1-3 and PYL5 with submicromolar $IC_{50}$ values and displays substantially higher activity at dimeric receptor sites (FIGS. 2, 3 and 4). The results also show that quinabactin is a stronger PYR1 or PYL1 agonist than ABA (FIGS. 2 and 3). In addition, the maximal PP2C inhibition observed by quinabactin was higher than that observed with pyrabactin with all receptors tested. Although pyrabactin can activate PYL5 with an IC50 of 0.90 μM, it saturates at ~40% PP2C inhibition, suggesting that it is an incomplete/partial PYL5 agonist. Thus, this example demonstrates the identification of a new sulfonamide agonist with broader receptor spectrum activity and increased bioactivity relative to pyrabactin.

Example 2

This example demonstrates that novel ABA agonists inhibit germination and plant growth.

Arabidopsis germination and hypocotyl growth inhibition analysis

For *Arabidopsis* germination and hypocotyl growth inhibition analysis, seeds after-ripened about 4 weeks were surface-sterilized with a solution containing 5% NaClO and 0.05% Tween-20 for 10 minutes, and rinsed with water four times. Sterilized seeds were suspended with 0.1% agar and sowed on the 0.8% solidified agar medium containing ½ Murashige and Skoog (MS) salts (Sigma-Aldrich) in the presence of chemicals and were stored at 4° C. for 4 days, then transferred at 22° C. under the dark or light. Germination was determined after a 4-day incubation, whereas hypocotyl growth was photographed after 6-day incubation.

Plant Materials

The following alleles/mutant strains were used: aba2-1 (Leon-Kloosterziel K M, et al. (1996) Isolation and characterization of abscisic acid-deficient *Arabidopsis* mutants at two new loci. Plant J 10(4):655-661), abi1-1 (Umezawa T, et al. (2009) Type 2C protein phosphatases directly regulate abscisic acid-activated protein kinases in *Arabidopsis. Proceedings of the National Academy of Sciences of the United States of America* 106(41):17588-17593), abi3-9, abi4-11 (Nambara E, et al. (2002) A screen for genes that function in abscisic acid signaling in *Arabidopsis thaliana. Genetics* 161 (3):1247-1255), and pry1pyl1pyl2ply4 quadruple (Park S Y, et al. (2009) Abscisic Acid Inhibits Type 2C Protein Phosphatases via the PYR/PYL Family of START Proteins. *Science* 324(5930):1068-1071); all of these strains are in the Columbia background. The pry1pyl1pyl2ply4 quadruple mutant stain utilized was backcrossed to Columbia three times. Barley and soybean seeds were purchased from Living Whole Foods, Inc., whereas maize seeds were obtained W. Atlee Burpee & Co. Detail methods used for physiological experiments using these materials are provided as supporting information.

Figure 5A:
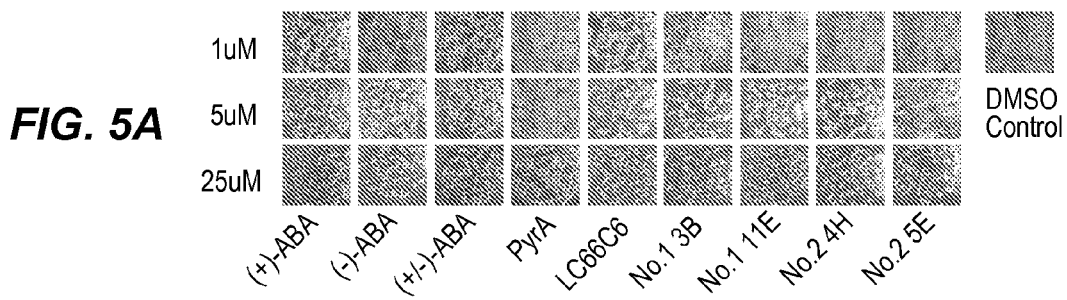
FIG. 5. Novel ABA agonists inhibit germination of *Arabidopsis* seeds more strongly than pyrabactin. (A) and (B) Comparison of seed germination inhibition by ABA agonists. (C) and (D) the effects of ABA and LC66C6 (also called quinabactin) on *Arabidopsis* ABA signaling- and biosynthesis-deficient mutants on germination (C) and seedling establishment (D). Seeds were sown on ½×MS agar plate containing chemicals, and were stored at 4° C. for 4 days, then transferred at 22±2° C. Photographs (A and C) and germination (B) or green cotyledon (D) scores were assessed after a 4-day incubation under continuous illumination. Panel C shows germination assays on 5 μM of ABA or LC66C6.
Figure 5B:
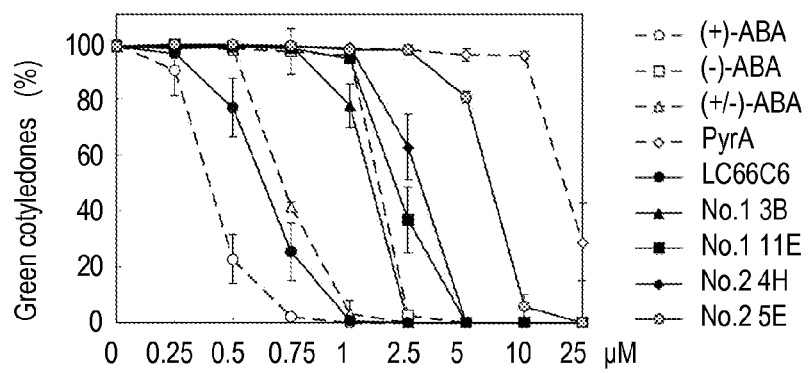

To explore the physiological consequences of LC66C's unique agonist properties, we characterized its effects on *Arabidopsis* seeds, seedlings and adult plants. As shown in FIG. 5, the ABA agonists described herein strongly inhibit seed germination in *Arabidopsis*. FIGS. 5A and 5B show that several agonists, including LC66C6, inhibit germination of seeds in a dose dependent manner. In particular, LC66C6 was nearly as effective, on a per mole basis, at inhibiting germination as (+)-ABA, and was more effective than the other agonists tested.

Figure 5C:
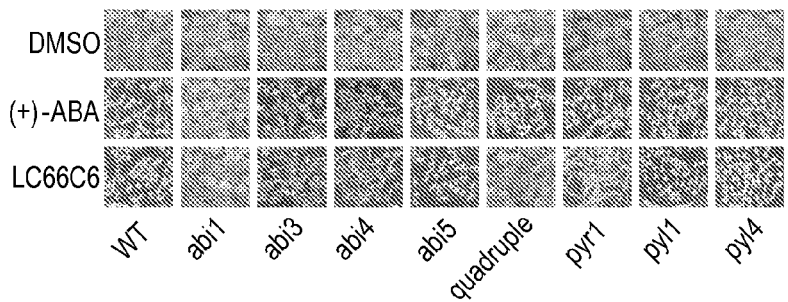
Figure 5D:
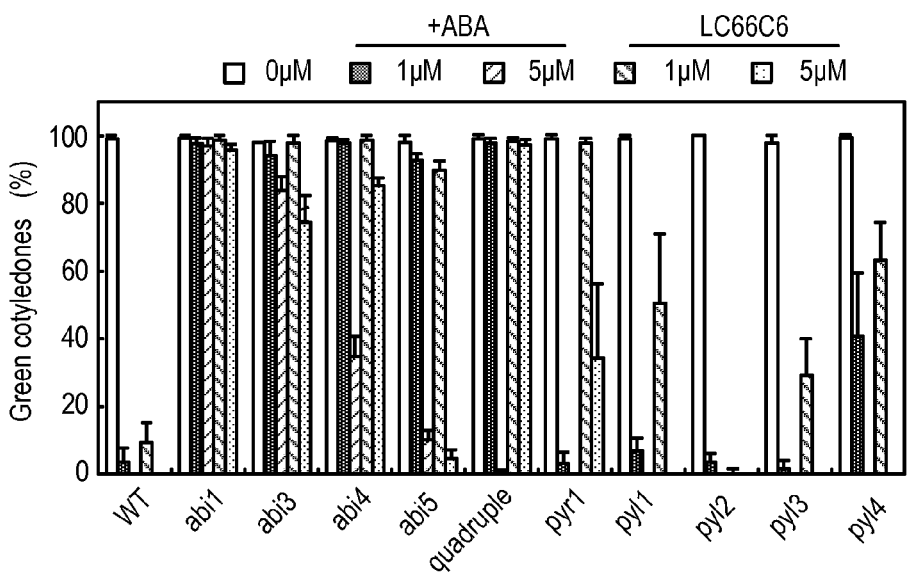

FIGS. 5C and 5D show the effect of agonists (+)-ABA and LC66C6 on inhibiting germination of seeds from various ABA-insensitive mutants. As shown in FIG. 5C, at a concentration of 5 μM, LC66C6 showed a similar pattern of inhibiting germination as (+)-ABA did for all mutants tested except for the PYR/PYL quadruple mutant (pyr1/pyl1/pyl2/pyl4) and pyr1 single mutant. Combined with the $IC_{50}$ data presented above in FIG. 4, this genetic data suggests that the germination-inhibitory activity of LC66C6 is largely explained by its ability to agonize PYR1, PYL1 and PYL2. The ability of ABA to inhibit germination in the quadruple mutant is likely explained by its agonist activity on other receptors. Our genetic data are consistent with the hypothesis that PYR1 plays an important but redundant role in seed germination in response to ABA, as the pyr1 mutant germinates in the presence of either 5 μM LC66C6 or pyrabactin (Park et al. 2009).

Figure 6A:
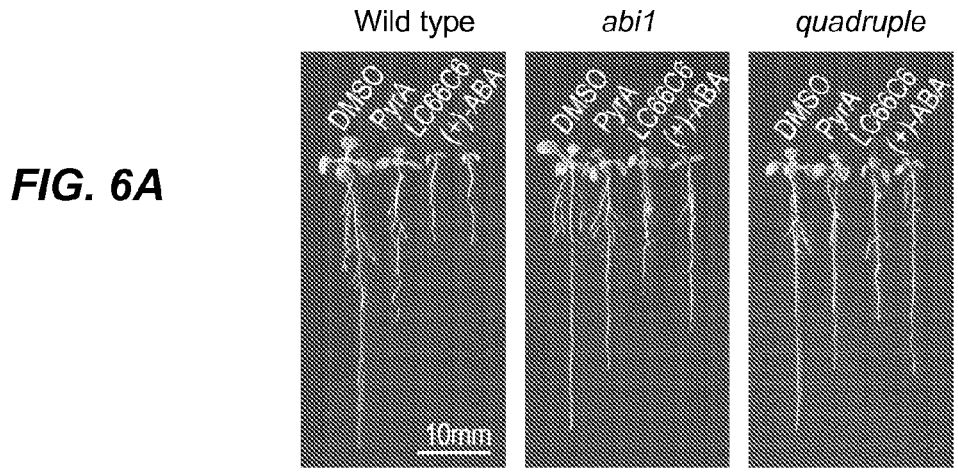
FIG. 6. LC66C6 inhibits plant growth. (A) Photographs showing the effect of ABA, Pyrabactin and LC66C6 on the wild type, abi1-1 and PYR/PYL quadruple mutant *Arabidopsis* genotypes. (B) Root growth inhibition and (C) plant growth inhibition by ABA, LC66C6 and pyrabactin. Two day old seedlings were transferred on ½×MS plate containing chemicals and phenotypes scored or photographed after a 5-day incubation on test compounds.
Figure 6B:
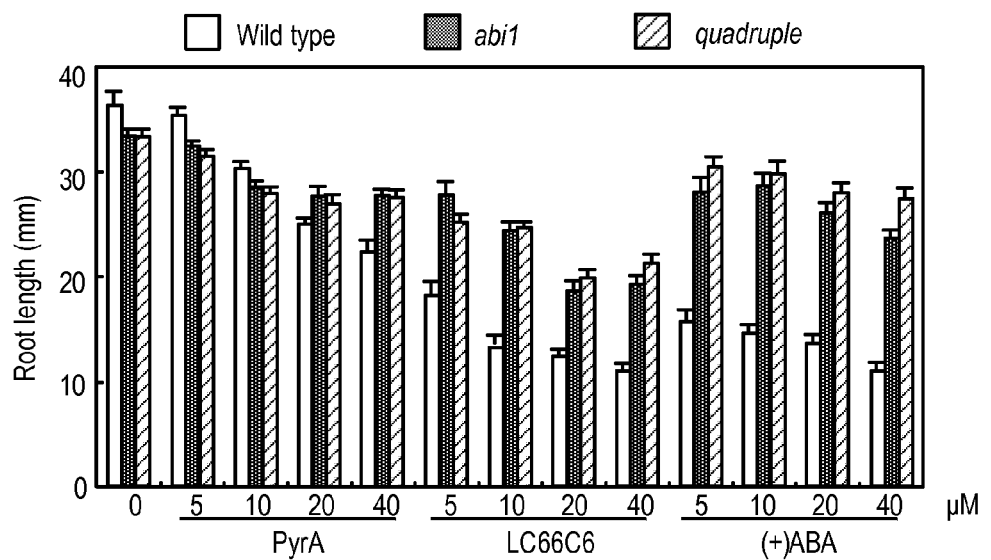
Figure 6C:
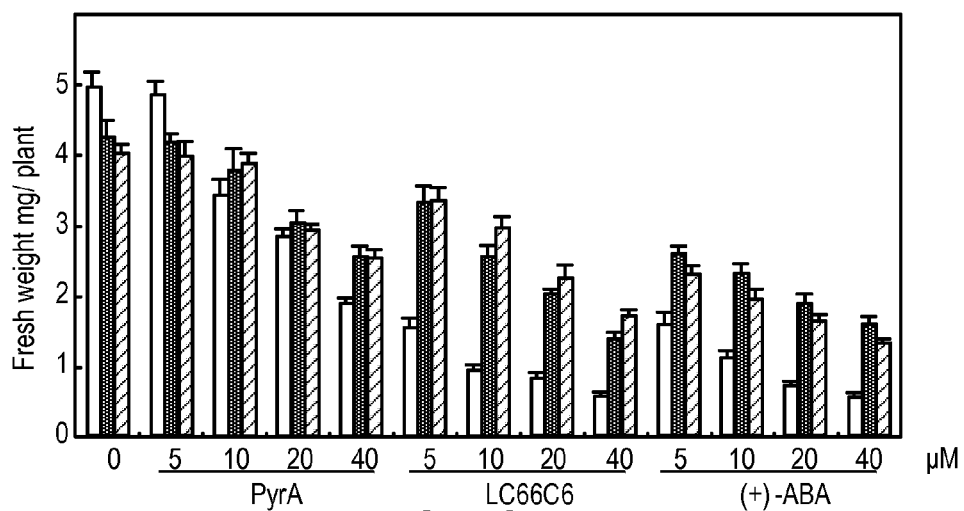
Figure 7A:
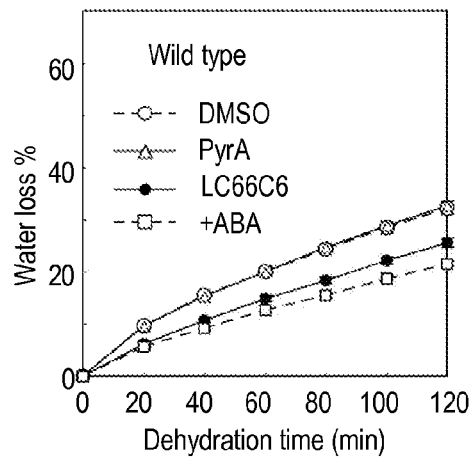
FIG. 7. LC66C6 enhances drought stress tolerance. LC66C6 represses the transpirational water loss of detached leaves in wild type (A) and the aba2 mutant genotypes (B). (C) LC66C6 cannot rescue the phenotypes of the ABA-insensitive genotype abi1-1. (D) LC66C6 induces stomatal closure in the wild type and aba2, but not abi1-1 genotypes. (E) Effects of compounds on soil water content during drought treatments in soybean. Soil water content was measured as described in the examples.
Figure 7B:
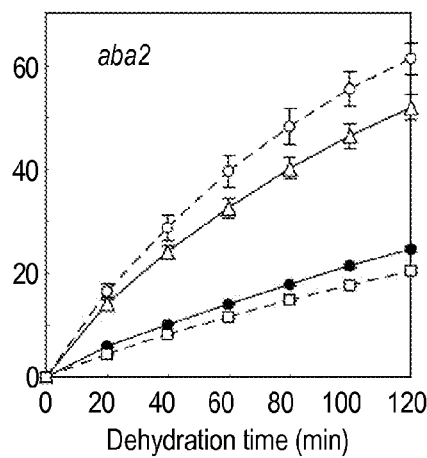
Figure 7C:
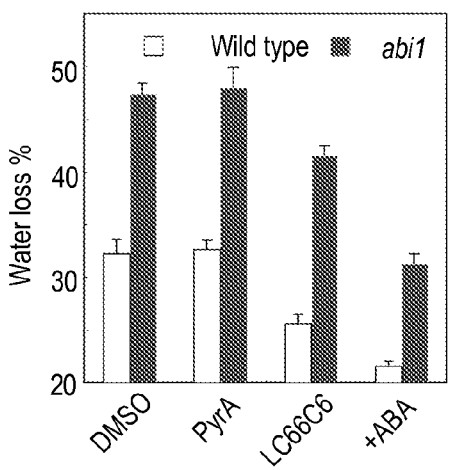
Figure 7D:
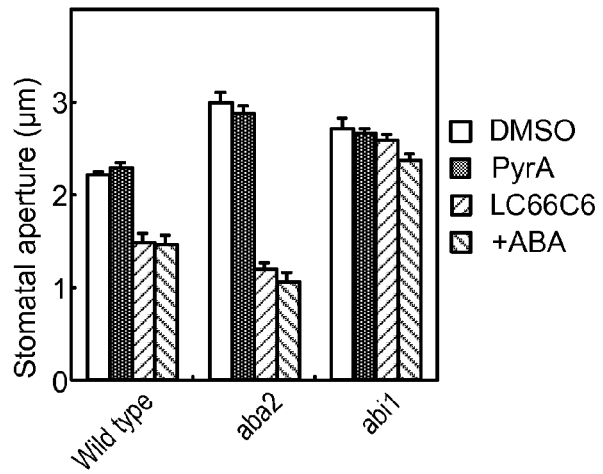
Figure 7E:
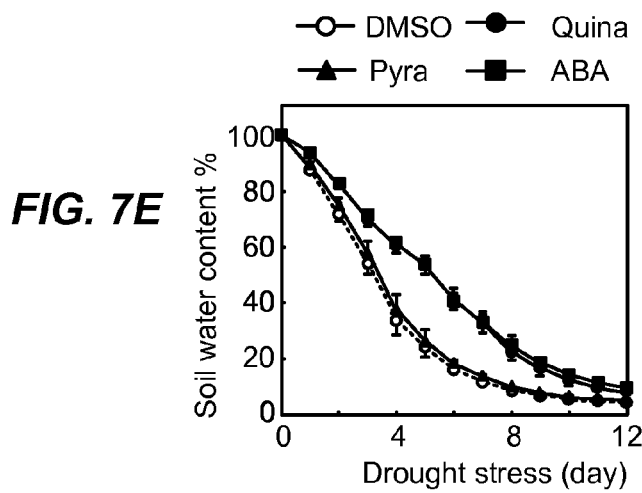

As shown in FIG. 6, LC66C6 also inhibits plant growth after germination. FIGS. 6A and 6B show that LC66C6 inhibits root elongation in wild-type, abi1, and the quadruple mutant, and is comparable to or slightly more effective than (+)-ABA in its inhibitory effects at all concentrations tested. Further, FIG. 6C demonstrates that LC66C6 inhibits growth of both wild-type and mutant plants in a concentration dependent manner. The inhibition of plant growth by LC66C6 is significantly greater than the inhibition by pyrabactin, and comparable to that of (+)-ABA.

This example demonstrates that LC66C6 is a potent inhibitor of seed germination and growth of both wild-type and ABA-insensitive mutant plants.

Example 3

This example demonstrates that agonist LC66C6 induces drought stress tolerance.

Physiological Assays

Physiological assays were performed on *Arabidopsis* plants grown at 22±2° C. and relative humidity (RH) 45±10% under a 16/8-h light/dark cycle. For transpirational water loss analyses in *Arabidopsis*, plants were pre-treated by aerosol spray of 4 ml solution containing 25 μM compound and 0.05% Tween-20. 12 4-week old plants were sprayed per compound or control analyzed. After overnight pre-treatment with compounds, the aerial portions were detached from roots, and their fresh weight measured at 20 min intervals over a 2 hour time period. To measure stomatal aperture, plants were pre-treated with compounds as described above, covered with plastic lids to maintain high RH and after overnight pre-treatment leaf epidermal impressions were obtained using Suzuki's Universal Micro-Printing (SUMP) method using SUMP impression solution with SUMP B plates (SUMP Laboratory). The leaf impressions were analyzed by light microscopy and stomatal apertures were determined from the pore widths using ImageJ 1.43v software (National Institutes of Health, USA). For *Arabidopsis* drought stress assays, approximately 1.5 ml of a 25 μM chemical solution was applied by aerosol to plants at daily intervals over a 3 day period. Plants were grown in square 6×6×5 cm pots containing 100 g soil per pot. Soybean drought stress assays were performed on plants grown at 25±2° C., 65±10% RH under a 16/8-h light/dark cycles. Approximately 20 ml of a 50 μM chemical solution containing 0.05% Tween-20 was sprayed per pot (3 plants per pot) four times each 3 days. Pots used were 250 ml size, and contained 200 g soil per pot. Pots were covered in Parafilm to so that the water loss measured was transpiration mediated. Soil water content % was determined by measuring pot weight and computed by removing dry soil weight from total weight.

Water Loss Analyses in Soybean, Barley and Maize.

For water loss analyses using soybean barley and maize, 100 μM chemical solution containing 0.05% Tween-20 was sprayed on to the aerial parts of the plants. The soybean, barley and maize plants used were approximately 4-, 2- and 2-weeks old respectively. Compounds were applied 16 hours before water loss assays were conduction. To measure water loss entire shoots were detached and their fresh weight monitored.

FIG. 7 shows the effect of LC66C6 on various parameters related to drought stress. As shown in FIGS. 7A and 7B, LC66C6 reduced the amount of transpirational water loss in detached leaves from wild-type and aba2 (ABA-deficient mutant 2) mutant plants. However, as shown in FIG. 7C, LC66C6 did not reduce transpirational water loss in detached leaves from the abi1-1 mutant. FIG. 7D shows that LC66C6 induces stomatal closure in wild-type and the aba2 mutant, but not in the abi1-1 mutant. FIG. 7E shows the effects of agonist compounds on soil water content during drought treatment of soybean plants.

Figure 8A:
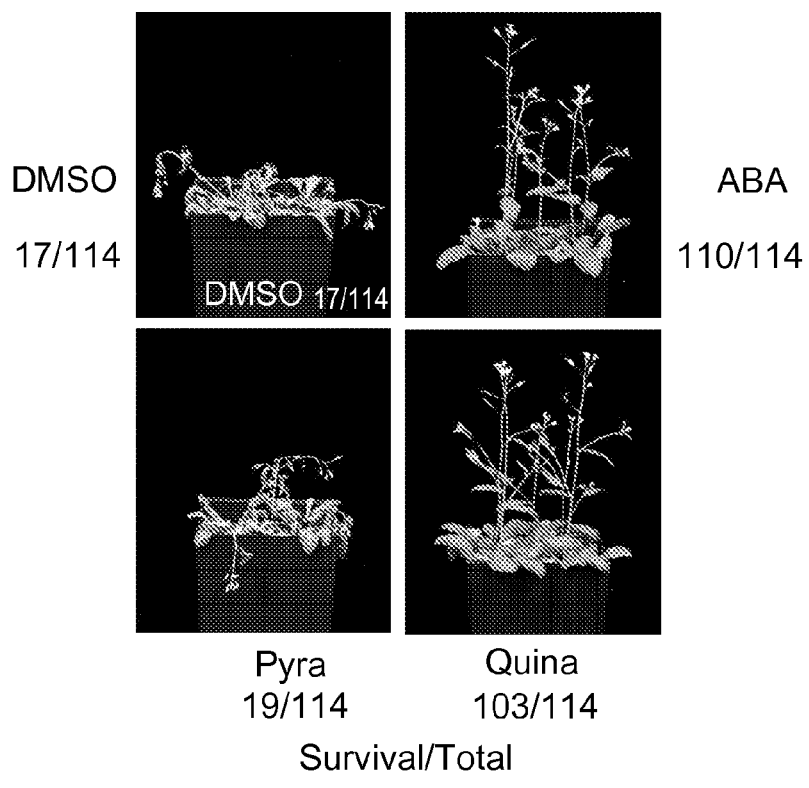
FIG. 8. Quinabactin confers drought stress tolerance to wild-type plants. (A) Effect of quinabactin on *Arabidopsis* drought tolerance. Two-week-old plants were subjected to drought stress by withholding water and were photographed after 12 days. During the drought period, plants were treated every 3 days with 25 μM compound. Plants were re-hydrated after 2 weeks drought treatment; the number of surviving plants (out of total number tested) for each treatment is shown next to each image. (B) Effects of quinabactin on soybean. Two-week-old plants were subjected to drought stress by withholding water and photographed after 8 days drought treatment. For all drought stress treatments, compounds (tested at 25 μM for *Arabidopsis* and 50 μM for soybean) were applied in solutions containing 0.05% Tween-20 and applied as aerosols every 3 days over the drought regime. Values for all experiments are means±SEM (n=6, 3 plants used per experiment).
Figure 8B:
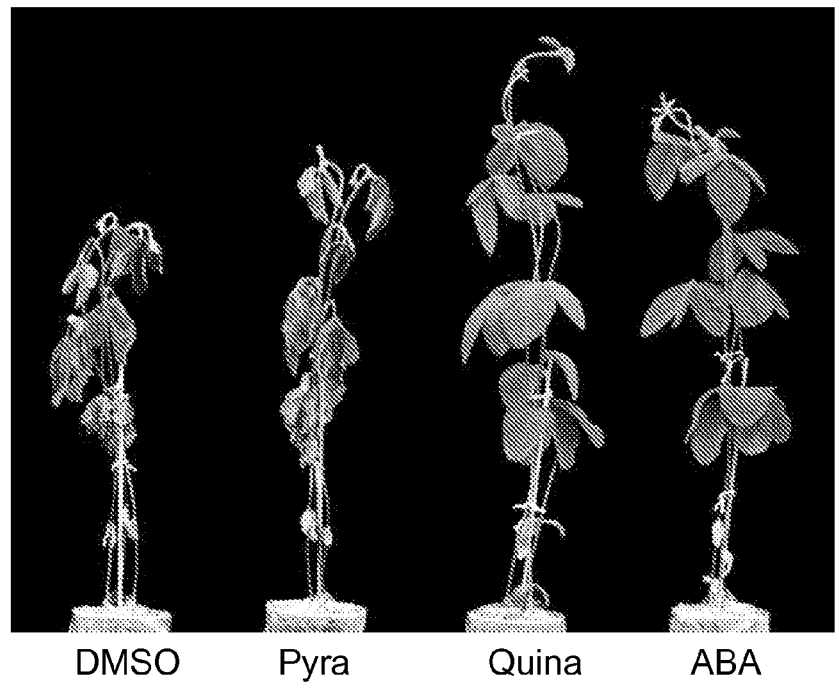

FIG. 8A shows that treatment of plants with quinabactin confers drought stress tolerance in Arabidopsis plants similar to that conferred by treatment with (+)-ABA. In this example, two-week-old plants were subjected to drought stress by withholding water and were photographed after 12 days. Plants were re-hydrated after 2 weeks drought treatment. The number of surviving plants per total number of tested plants is shown adjacent to the photographs. FIG. 8B shows that treatment of soybean plants with quinabactin confers drought stress tolerance similar to that conferred by treatment with (+)-ABA. In this example, two-week-old plants were subjected to drought stress by withholding water and photographed after 8 days of drought treatment. For all drought stress treatments, compounds (tested at 25 μM for Arabidopsis and 50 μM for soybean) were applied in solutions containing 0.05% Tween-20 and applied as aerosols every 3 days over the drought regime. Values for all experiments are means±SEM (n=6, 3 plants used per experiment).

This example shows that LC66C6 induces drought stress tolerance in wild-type and aba2 mutant Arabidopsis plants and in wild-type soybean plants similar to that conferred by (+)-ABA.

Example 4

This example demonstrates the LC66C6 induces ABA-responsive genes in a manner similar to those induced by (+)-ABA.

Microarray Analyses

Total RNA was isolated using RNAeasy Plant Mini Kit (Qiagen, USA) according to the manufacturer's instructions. cDNA synthesis, labeling and hybridization to the Arabidopsis ATH1 chips (Affymetrix, USA) were performed by the IIGB Core Instrumentation Facility of University of California at Riverside using Affymetrix protocols. Biological triplicate samples were hybridized for DMSO controls, ABA, pyrabactin and quinabactin treatments; compound were applied at 25 μM final concentration and RNA prepared from frozen tissue after 6 hours exposure to compounds or controls. Expression signals for probe sets were calculated and normalized by MASS Statistical Algorithm (Affymetrix, USA). Experimental filtering of array data was performed for the presence of signal in all experiments. Average transcript levels in each chemical treatment were compared to those in control experiments and used to compute to fold-change values. $\log_2$-transformed fold-change values were used to compute Person Correlation Coefficients between experimental conditions.

Quantitative RT-PCR Analysis

Total RNA was isolated using Plant RNA purification reagent (Invitrogen, USA) according to the manufacturer's instructions. cDNA was synthesized from 1 μg of total RNA using the QantiTec reverse transcription kit (Qiagen, USA). Real-time PCR using Maxima® SYBR Green/Fluorescein qPCR Master Mix (Fermentas) was performed with the iQ5 real-time PCR detection system (Bio-Rad, Hercules, Calif.). The relative amounts of target mRNAs were determined using the relative standard curve method and were normalized by relative amount of internal control mRNA. Biological triplicate experiments were performed. The primer sequences used in these experiments are shown in Table 1.

TABLE 1

Primer sets for quantitative RT-PCR

|  | Abbreviation | Forward primer (SEQ ID NO:) | Reverse primer (SEQ ID NO:) |
| --- | --- | --- | --- |
| Arabidopsis AGI gene code | | | |
| AT1G05100 | MAPKKK18 | AAGCGGCGCGTGGAGAGAGA (120) | GCTGTCCATCTCTCCGTCGC (121) |
| AT5G52310 | RD29A | TGAAGTGATCGATGCACCAGG (122) | GACACGACAGGAAACACCTTTG (123) |
| AT5G52300 | RD29B | TATGAATCCTCTGCCGTGAGAGGTG (124) | ACACCACTGAGATAATCCGATCCT (125) |
| AT4G34000 | ABF3F | GTTGATGGTGTGAGTGAGCAGC (126) | AACCCATTACTAGCTGTCCCAAG (127) |
| AT2G46270 | GBF3 | GACGCTTTTGAGCATCGACACT (128) | ACTGTTTCCTTCGCTCCCGTTTC (129) |
| Internal control | ACT2 | CTCATGAAGATCCTTACAG (130) | CTTTCAGGTGGTGCAACGAC (131) |
| Soybean | | | |
|  | GmNAC4 | ACGTCAGTTCCGCAAAAGAT (132) | GGACCCGTTGGTTTCTCAC (133) |
|  | GmbZIP1 | GGGAATGGGAATTTGGGTGAGAA (134) | CCTTCTGCCAGGGCTAGCATG (135) |
| Internal control | Gm18S | CCTGCGGCTTAATTTGACTCAAC (136) | TAAGAACGGCCATGCACCA (137) |

TABLE 1-continued

Primer sets for quantitative RT-PCR

| | Abbreviation | Forward primer (SEQ ID NO:) | Reverse primer (SEQ ID NO:) |
|---|---|---|---|
| Barley | | | |
| | HVA1 | AACACGCTGGGCATGGGAG (138) | CGAACGACCAAACACGACTAAA (139) |
| | HvDRF1 | CGGGCGGCGCGATTGCGAGC (140) | ACGGAATTAGGGCCATCACG (141) |
| Internal control | Hvtubulin2 | TCCATGATGGCCAAGTGTGA (142) | GACATCCCCACGGTACATGAG (143) |
| Maize | | | |
| | ZmLEA | GCAGCAGGCAGGGGAGAA (144) | GCCGAGCGAGTTCATCATC (145) |
| | ZmRAB17 | ATGAGTACGGTCAGCAGGGCAG (146) | CTCCCTCGCAGGCTGGAACTG (147) |
| Internal control | ZmUbi | TGCCGATGTGCCTGCGTCGTCTGGTGC (148) | TGAAAGACAGAACATAATGAGCACAG (149) |

ABA-Responsive Reporter Gene Assays

Existing ABA-responsive promoter-GUS fusions are, in our experience, not ideal due to either high background levels or relatively low induction levels in response to ABA. MAPKKK18 as a highly-ABA inducible gene with low background levels (Matsui A, et al., Plant Cell Physiol 49(8):1135-1149 (2008)); MAPKKK18 is also strongly induced by drought and salt stress. We therefore characterized the effects of agonists on MAPKKK18 promoter::GUS reporter transgenic plants. GUS staining was performed in a reaction buffer of the following composition: 50 mM sodium phosphate buffer pH 7.0, 0.05% Tween-20, 2.5 mM potassium ferrocyanide, 2.5 mM potassium ferricyanide, 1 mM X-gluc. The reaction buffer was vacuum infiltrated into test samples for 10 min two times and then incubated at 37° C. for 5 h. The reaction was stopped by washing the samples with 70% ethanol, and chlorophyll pigments bleached by incubation at 65° C.

FIG. 9 shows gene expression changes induced in response to pyrabactin, LC66C6, and (+)-ABA. As shown in FIG. 9A, LC66C6 induced the expression of RD29B and MAPKKK18 mRNA in a dose dependent manner in wild-type plants, whereas those induction levels impaired in both abi1-1 and PYR/PYL quadruple mutant plants. The induction of gene expression by LC66C6 is similar to that observed with (+)-ABA. In contrast to (+)-ABA and LC66C6, pyrabactin did not induce gene expression in wild-type plants, although it does induce modest ABA-related gene expression in seedings when higher concentrations are utilized in treatment (Park et al., 2009).

Figure 9A:
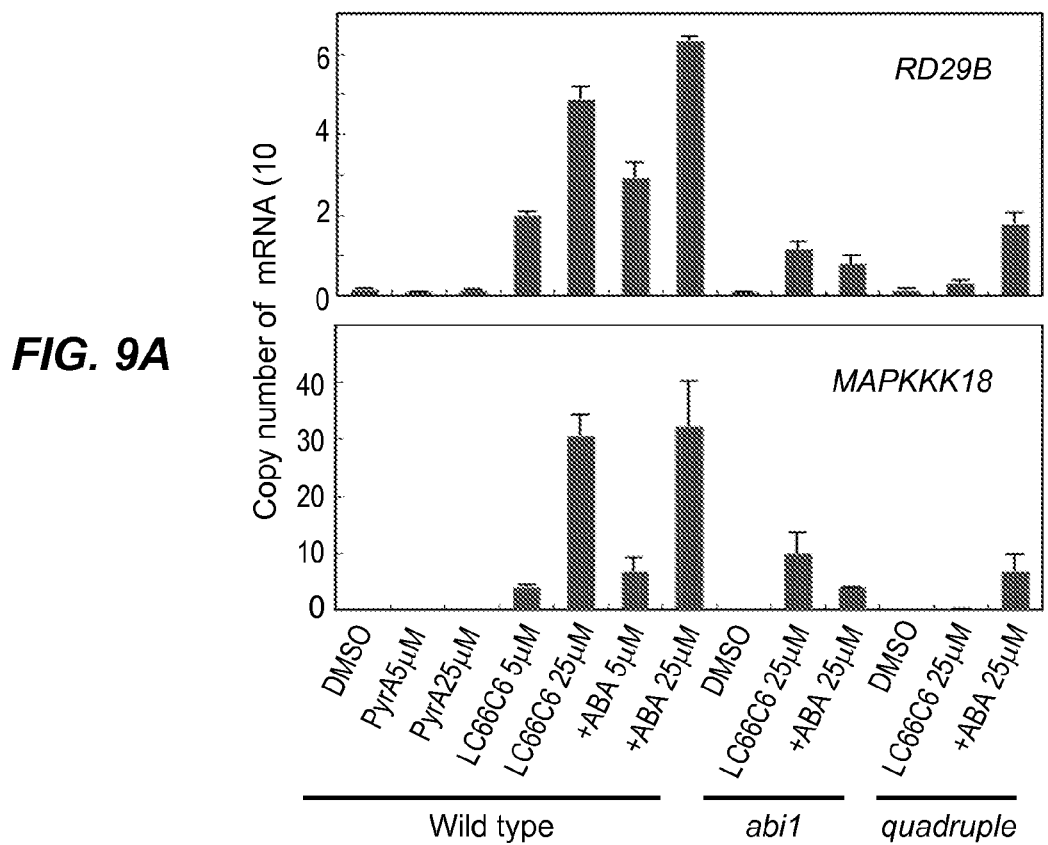
FIG. 9. LC66C6 induces numerous ABA-responsive genes. (A) Shows the chemical induced mRNA expression levels of of the ABA-responsive reporter genes RD29B and MAPKKK18 in wild-type, abi1-1, the pyr1/pyl1/pyl2/pyl4 quadruple receptor mutant genotypes of *Arabidopsis* seedlings treated with either vehicle (DMSO), pyrabactin, LC66C6, or (+)-ABA. (B) LC66C6 efficiently induces ABA-responsive genes in *Arabidopsis* seedlings, while pyrabactin does not. Ten-day old seedlings were treated with carrier solvent (DMSO) or either 25 μM ABA, pyrabactin or LC66C6 for 8 hours. Total RNA was then prepared labeled and hybridized to ATH1 microarrays. Data plotted are log 2 transformed average expression values for ~13K probes that were detectable across all experiments. Data shown are averages determined from triplicate biological replicates. (C) and (D) show the expression of a reporter gene in different plant tissues after treatment with vehicle (DMSO), pyrabactin, LC66C6, or (+)-ABA.
Figure 9B:
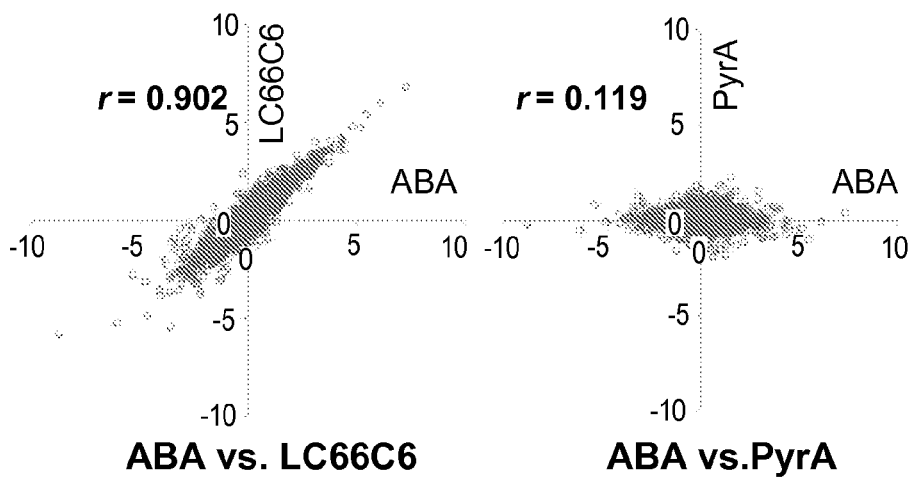

FIG. 9B shows genome-wide comparison of ABA and LC66C or pyrabactin effects, in comparison to control treatments, on the wild-type seedlings, as measured by hybridization of labeled RNAs to ATH1 microarrays. As shown in FIG. 9B, LC66C6 induces a similar set of genes to those induced by ABA in a microarray experiment. In contrast, pyrabactin did not induce an expression pattern similar to that of ABA.

Figure 9C:
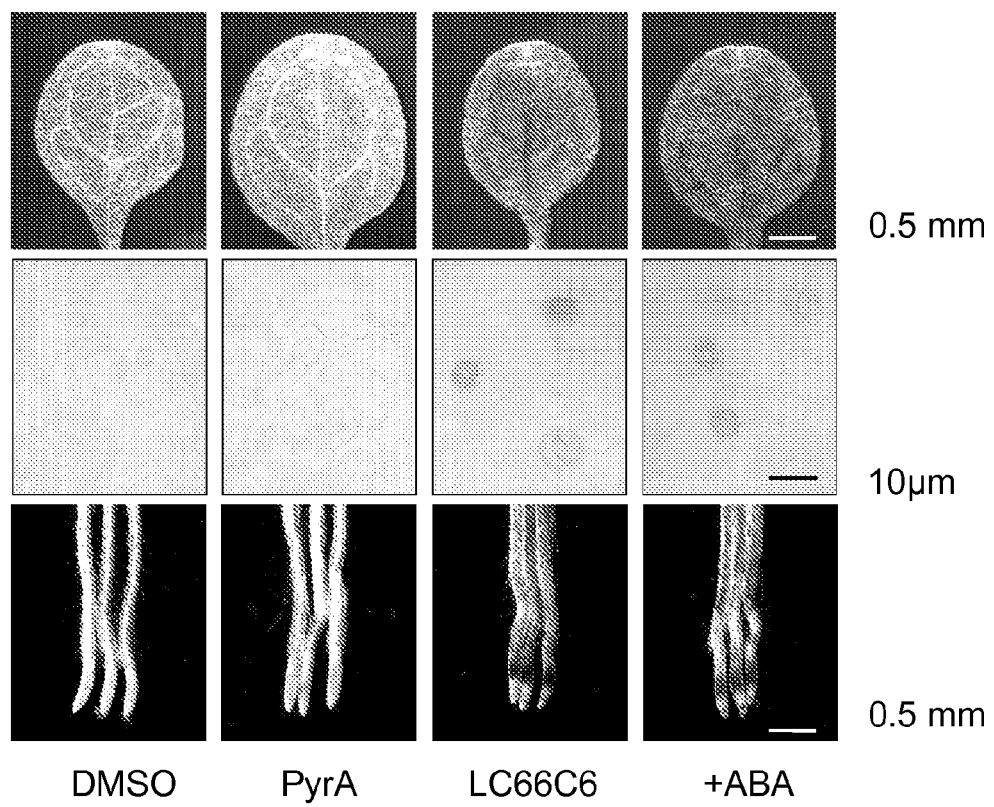
Figure 9D:
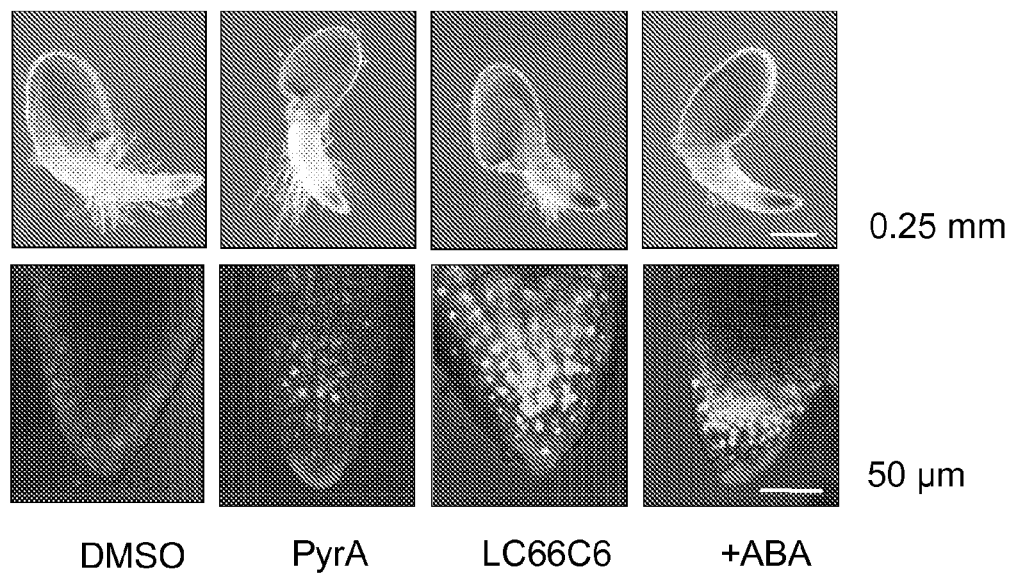

FIGS. 9C and 9D show that LC66C6 induces expression of reporter genes in the same tissues as (+)-ABA. The expression of reporter genes was observed in guard cells and vascular tissues of leaves and roots, and in radicle tips of imbibed seeds.

Figure 10:
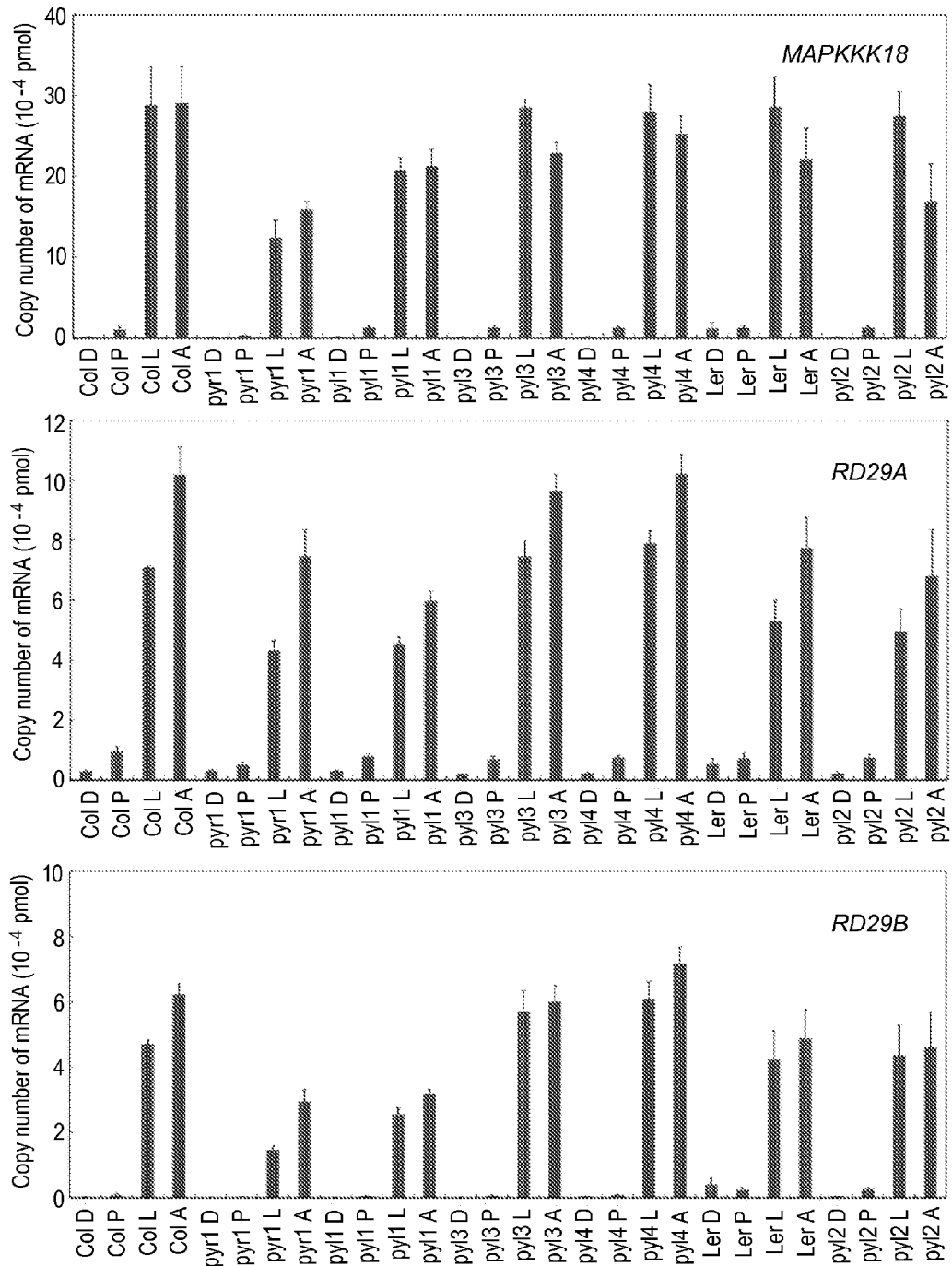
FIG. 10. ABA-responsive gene expression in PYR/PYL single mutants. The response of the ABA-responsive MAP-KKK18, RD29A, and RD29B mRNAs to LC66C6, ABA and pyrabactin were characterized in the Col and Ler ecotypes and the pyr1, pyl1, ply2, pyl3 and pyl4 single mutant genotypes.

FIG. 10 shows ABA-responsive gene expression in PYR/PYL single mutants. As shown in FIG. 10, the ABA-responsive MAPKKK18, RD29A, and RD29B mRNAs were induced by both LC66C6 and (+)-ABA in the Col and Ler ecotypes and the pyr1, pyl1, ply2, pyl3 and pyl4 single mutant genotypes. In contrast, pyrabactin did not significantly induce expression of any of the genes assayed in any of the single mutants or wild-type ecotypes.

Figure 11:
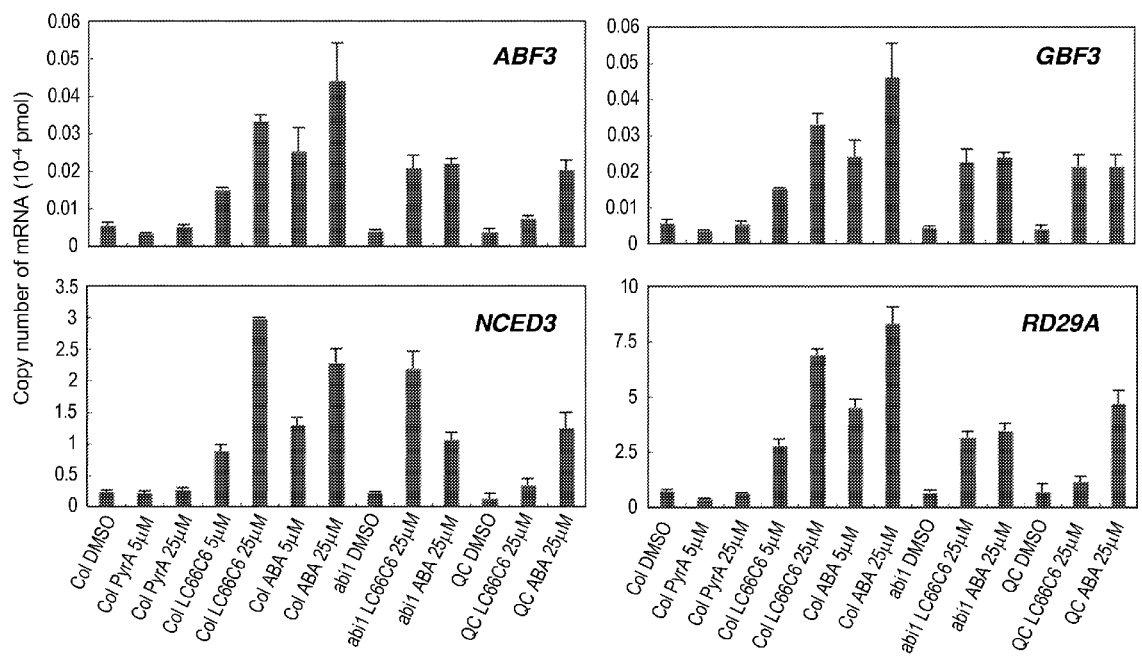
FIG. 11. LC66C6 induces ABA-responsive gene expression in wild-type plants, abi1-1 and PYR/PYL quadruple mutants. LC66C6 and (+)-ABA induced expression of ABF3, GBF3, NCED3, and RD29A in a dose dependent manner in Col wild-type plants, while pyrabactin does not.
Figure 12A:
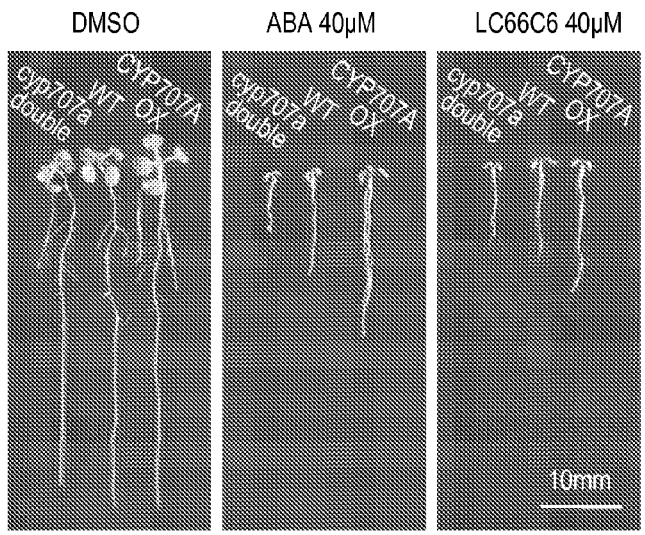
FIG. 12. LC66C6 sensitivity is not influenced by the CYP707A ABA-hydroxylating enzymes. (A) shows photographs and (B) shows quantitation of primary root length in wild-type plants, plants that overexpress CYP707A (CYP707AOX), and plants that are double mutant for cyp707a treated with DMSO, 40 µM (+)-ABA, and 40 µM LC66C6. (C) shows fresh weight and (D) shows the percent of plants with green cotyledons in the plants treated as in (A).
Figure 12B:
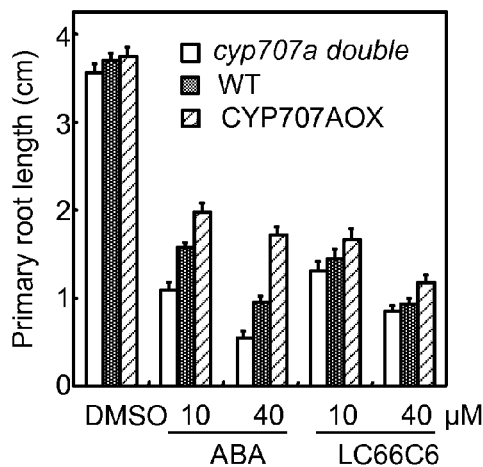
Figure 12C:
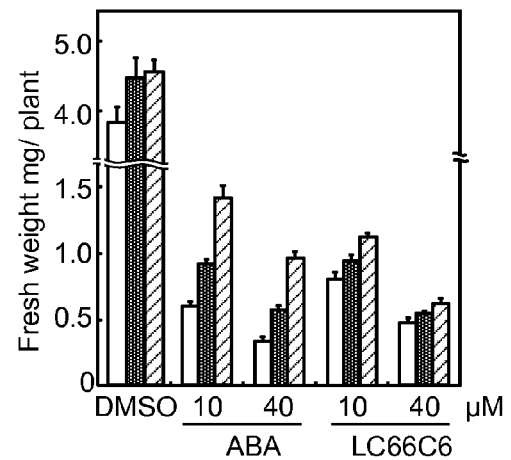
Figure 12D:
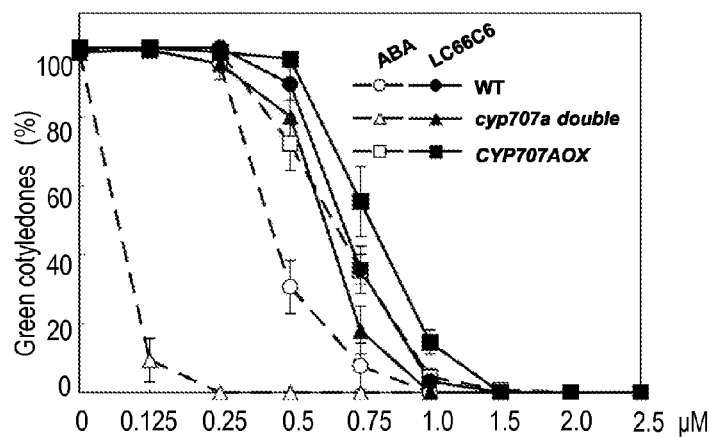

FIG. 11 shows ABA-responsive gene expression in wild-type plants, abi1-1 and PYR/PYL quadruple mutants. As shown in FIG. 11, both LC66C6 and (+)-ABA induced expression of ABF3, GBF3, NCED3, and RD29A in a dose dependent manner in Col wild-type plants, whereas the induction levels were impaired in both abi1-1 and PYR/PYL quadruple mutant plants. Consistent with the above results, pyrabactin did not induce significant expression of any genes analyzed in the wild-type plants.

Example 5

This example demonstrates that key enzymes for ABA catabolism do not affect the responses induced by LC66C6.

As shown in FIG. 12, the inhibition of plant growth and germination by ABA is enhanced in plants that are double mutant for cyp707a, a key enzyme for ABA catabolism, but is reduced in plants that overexpress CYP707A (CYP707AOX; see FIGS. 12A-D). In contrast, the effects on plant growth and germination by LC66C6 are not significantly different in plants that are double mutant for cyp707a, wild-type plants, or in plants that overexpress CYP707AOX (see FIGS. 12A-D).

This example shows that enzymes that are involved in the breakdown of ABA do not influence the phenotypes regulated by LC66C6.

Example 6

This example shows that LC66C6 is bioactive on diverse plant species, including monocots and dicots.

Figure 13A:
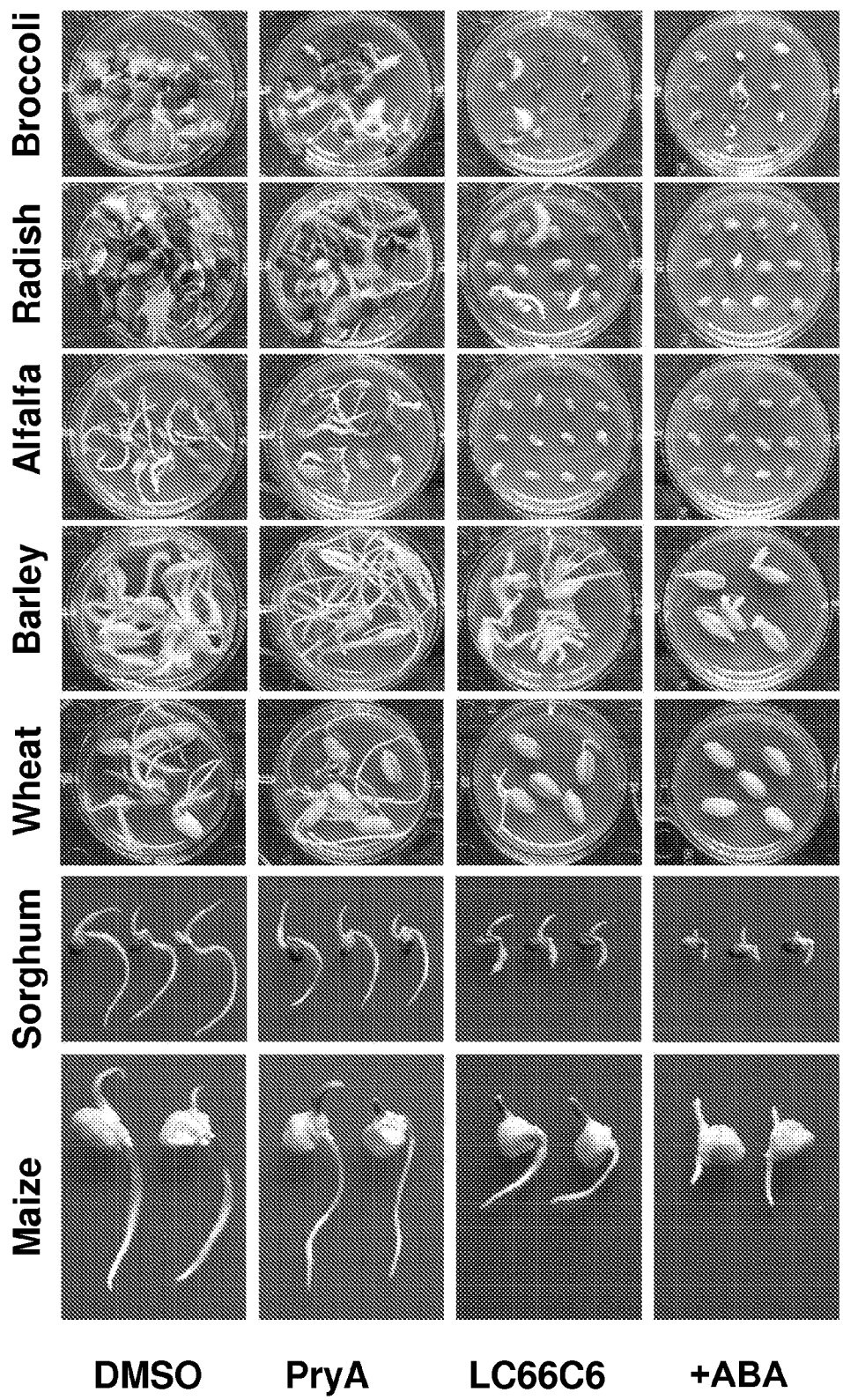
FIG. 13. LC66C6 modulates ABA responses in diverse species. Germination inhibition (A) and transpirational water loss in detached leaves 2-hours after detachment (B) in response to compounds shown. The expression of ABA-responsive marker genes in Soybean (C), Barley (D) and Maize (E) after application of chemicals. D, P, L and A indicate DMSO, pyrabactin, LC66C6 and (+)-ABA, respectively.
Figure 13B:
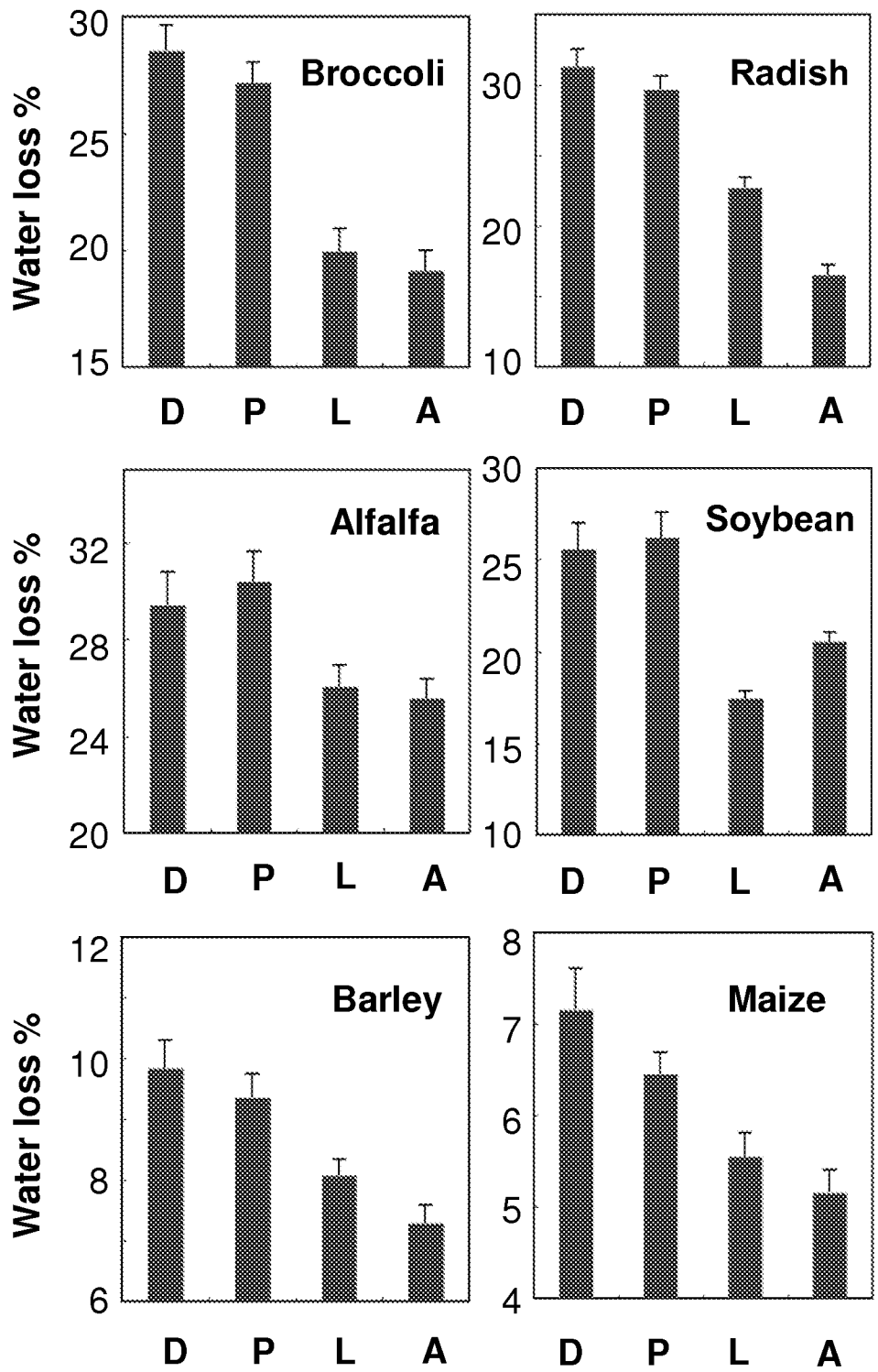
Figure 13C:
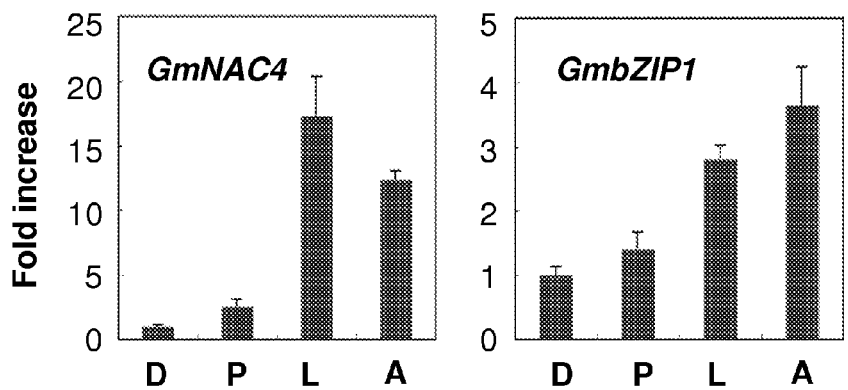
Figure 13D:
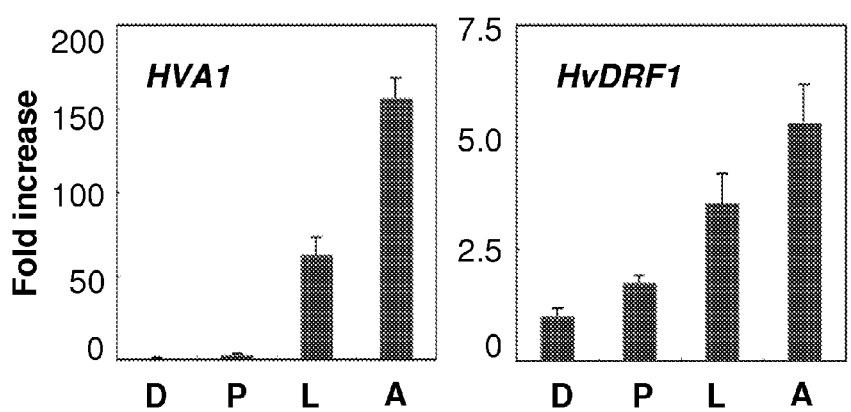
Figure 13E:
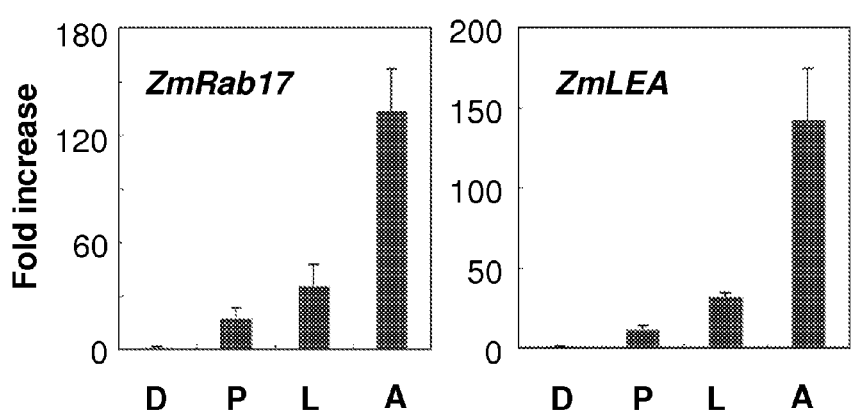

FIG. 13A shows that LC66C6 inhibits germination of broccoli, radish, alfalfa, soybean, barely, wheat, shorghum and maize seeds. The level of inhibition of germination by LC66C6 is greater than pyrabactin. As shown in FIG. 13B, LC66C6 reduces transpirational water loss over a period of 2 hours in detached leaves of the above species. Further, LC66C6 strongly induces expression of the ABA-responsive genes GmNAC4 and GmbZIP1 in soybeans (FIG. 13C), moderately induces expression of the ABA-responsive genes HVA1 and HvDRF1 in barley (FIG. 13D), and weakly induces expression of the ABA-responsive genes ZmRab17 and ZmLEA in maize (FIG. 13E).

This example demonstrates that LC66C6 inhibits germination and reduces transpirational water loss in a diverse group of agriculturally important species, indicating that LC66C6 is useful in reducing drought stress in multiple species.

Example 7

This example shows the chemical structures of ABA and the agonists described herein, and the effect of the agonists in vitro and in vivo.

Figure 14:
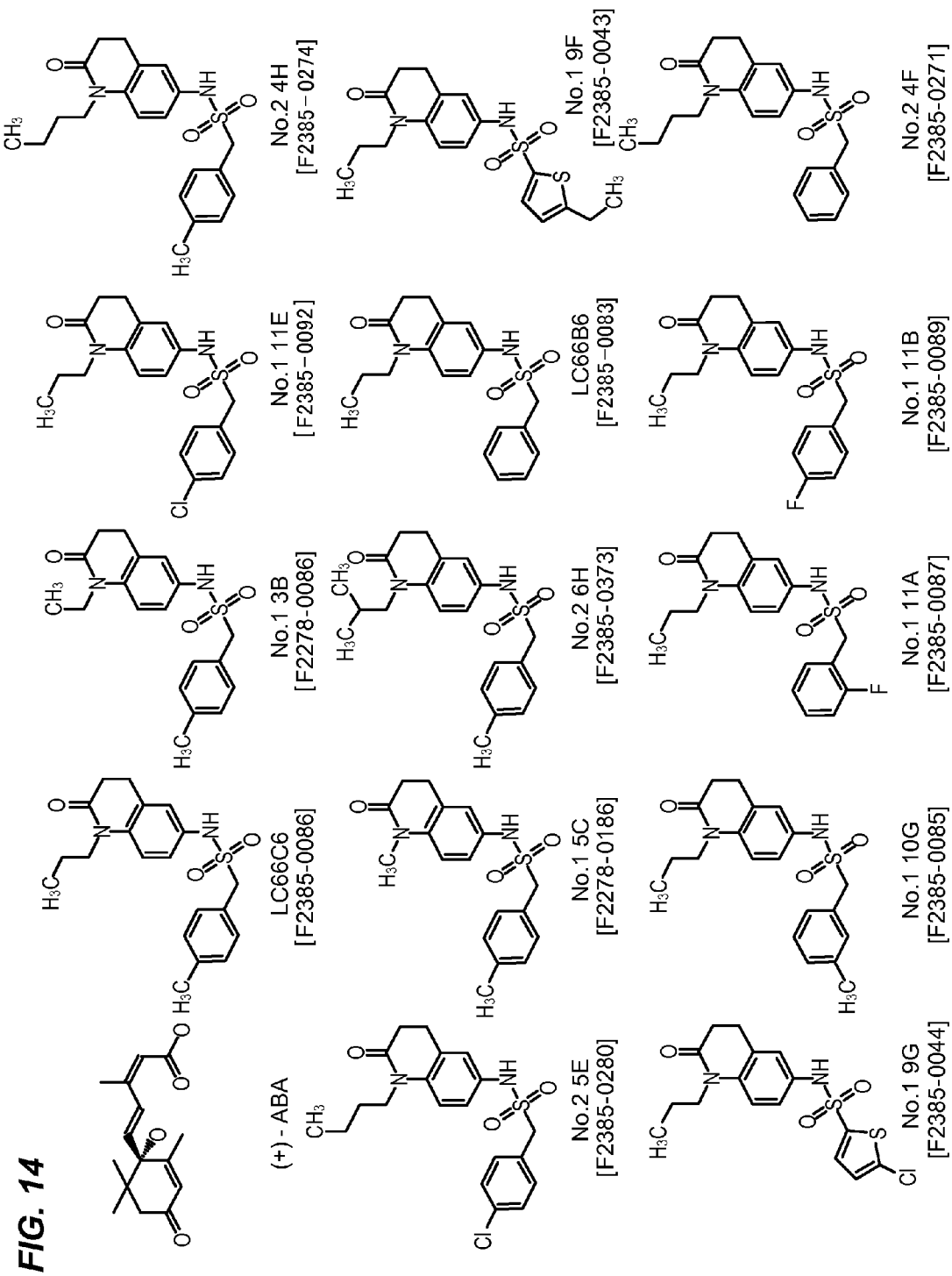
FIG. 14. Chemical structure of ABA and agonists.
Figure 14:
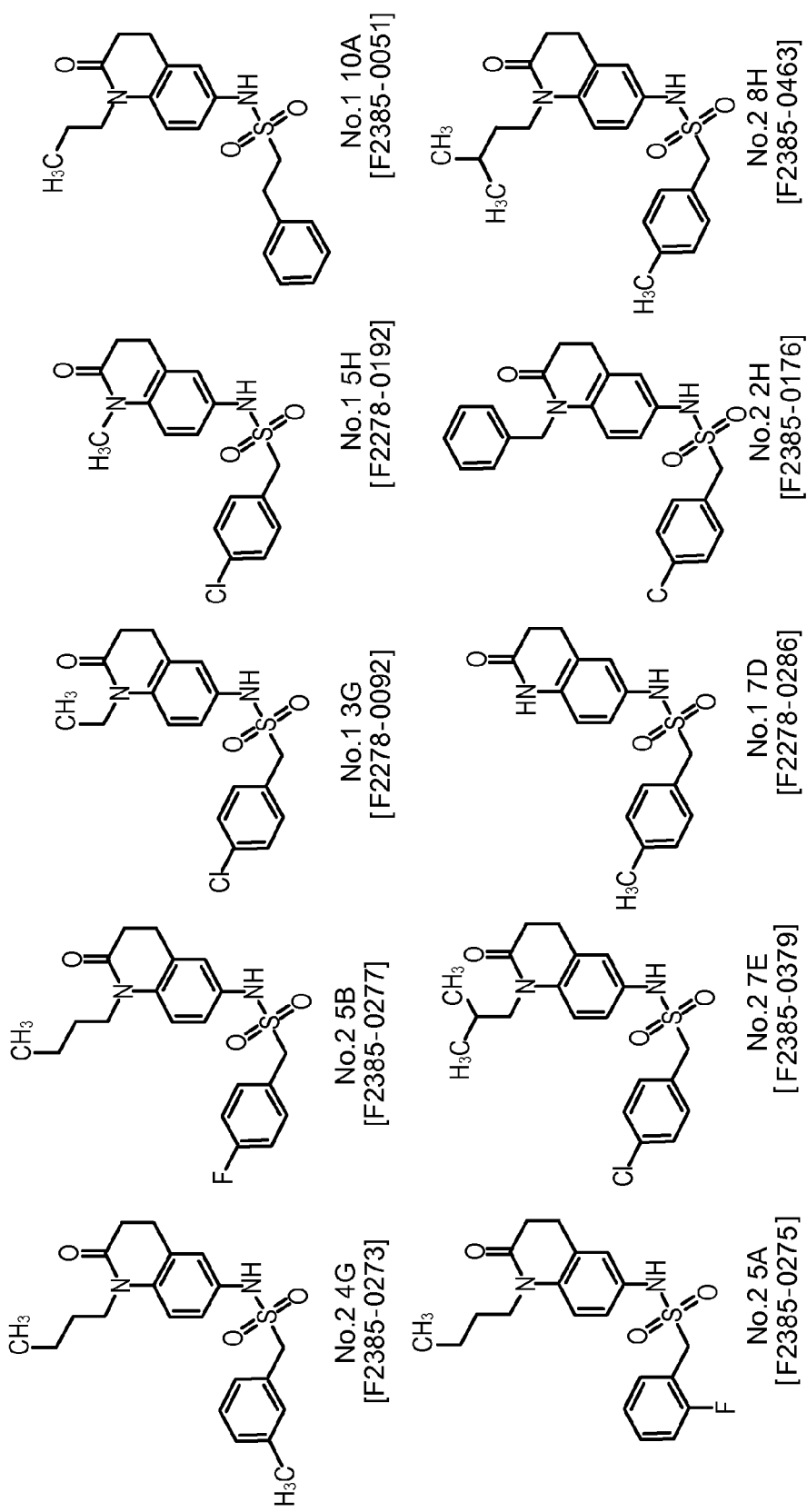
Figure 18:
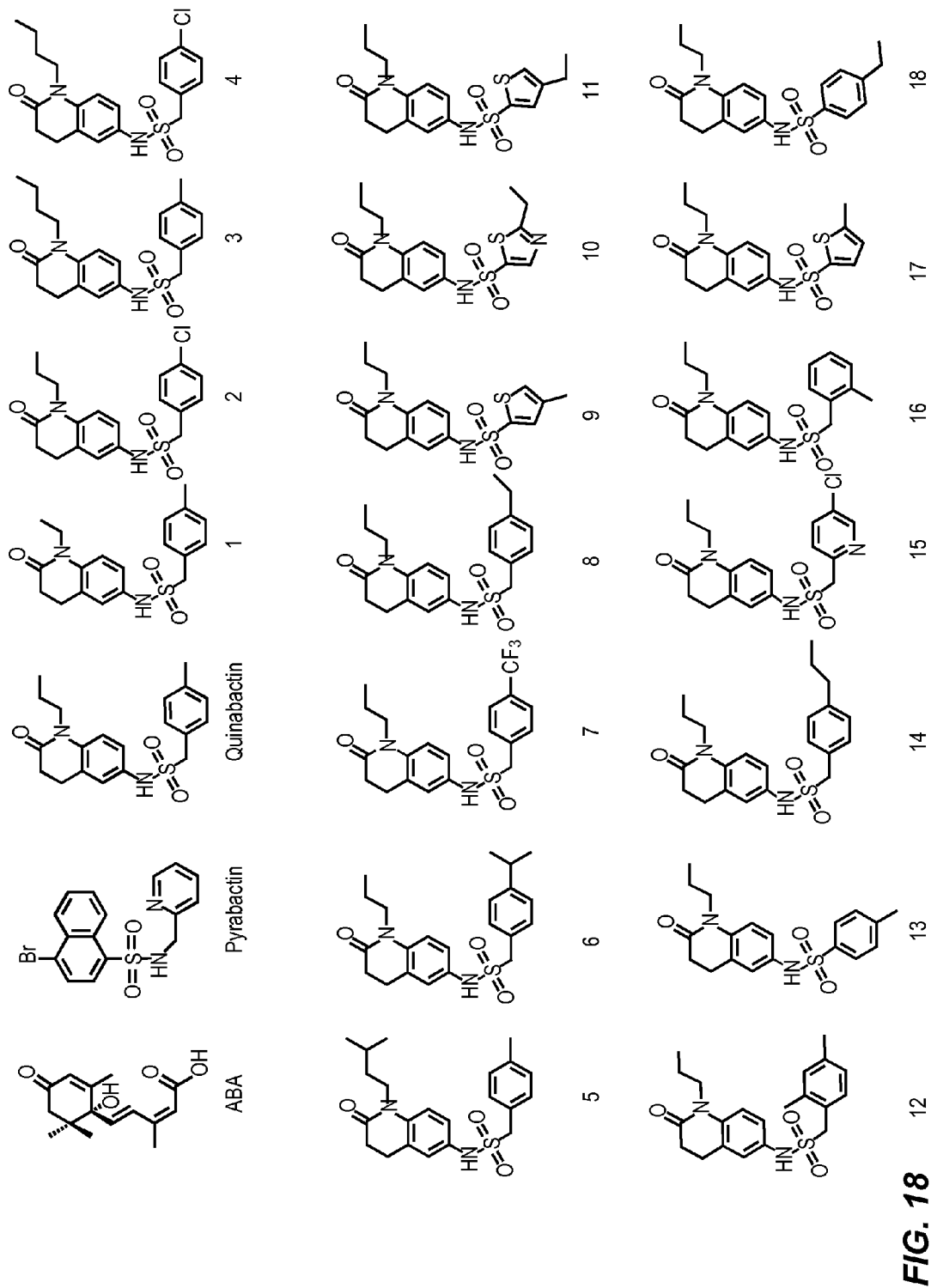
FIG. 18 shows a summary of the agonist compounds tested for their effect on inhibition of germination and pMAPKK18: Gus reporter expression. ++++++ indicates strong activity, whereas a single + indicates weak activity, a dash (-) indicates no activity, and n.d. indicates not determined.

FIGS. 14 and 18 show the chemical structures of ABA and the agonists tested. FIG. 15A shows the results of yeast two-hybrid assays using PYR/PYL receptors PYR1, PYL1, PYL2, PYL3, and PYL4 to test the response to each of the agonists shown in FIG. 14. FIG. 15B shows the results of testing the agonists in FIG. 14 on germination of wild-type seeds, and demonstrates that LC66C6 is one of the most effective agonists, after (+)-ABA, at inhibiting germination of wild-type seeds. FIG. 15C shows the effects of compounds on an ABA-reporter line as measured using glucuronidase assays in a transgenic line expressing glucuronidase under the control of the ABA-inducible Arabidopsis gene MAP-KKK18.

This example demonstrates that LC66C6 is one of the most effective agonists tested both in vitro and in vivo.

Example 8

This example shows that LC66C6 can increase the size of ABA-deficient mutant plants.

Figure 16A:
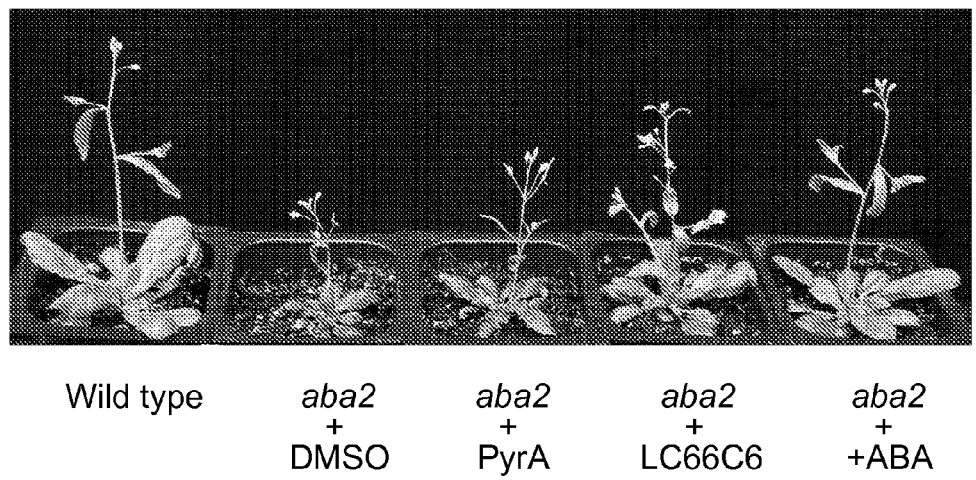
FIG. 16. Application of LC66C6 can rescue growth defects observed in the ABA-deficient mutant aba2. Chemical solution (25 µM) was sprayed on 14-day-plants two times per day for 2 weeks. The image (A) and fresh weight (B) were obtained from 4-week plants.
Figure 16B:
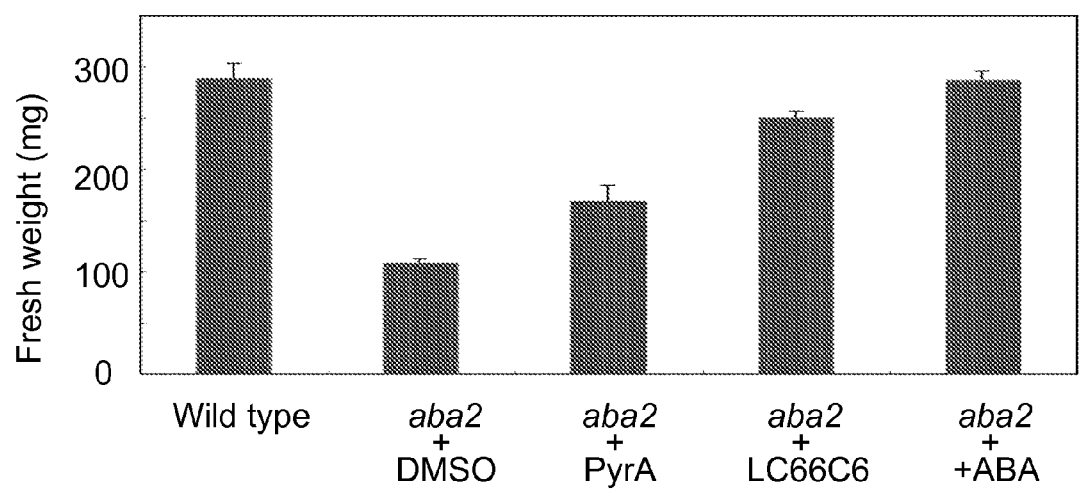

In this example, 14-day old wild-type and aba2 mutant plants were sprayed with a solution containing 25 µM of agonist two times a day for two weeks. Images and fresh weight were obtained from 4 week old plants. As shown in FIG. 16, application of LC66C6 to aba2 mutant plants significantly increased the size of the mutant plants compared to control plants treated with the carrier DMSO only.

This example demonstrates that LC66C6 can complement the growth phenotype observed in the aba2 mutation in a manner similar to that of (+)-ABA.

Example 9

This example shows that LC66C6 can weakly inhibit protonema growth in moss, but has no effect on growth of the unicellular green algae Chlamydomonas.

Figure 17A:
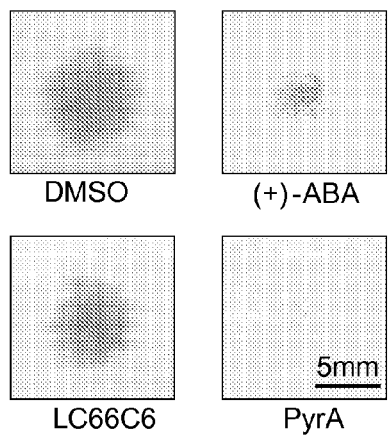
FIG. 17. The effect of ABA and its agonists in *Physcomitrella patens* and *Chlamydomonas*. Protonemal growth images (A) and quantitative analysis (B) of the effects of ABA and agonists on *Phsycomitrella patens*. Protonema were grown on 200 µM of specific test chemical for 10 days. LC66C6's effects were weak, but significantly inhibited protonema growth. Pyrabactin bleached protonema. (C) The expression of ABA-responsive genes of *Physcomitrella patens*. Protonema were treated with 200 µM chemical solutions for 3 h. (D) Colony growth of *Chlamydomonas* on the chemical with salinity stress and osmotic stress. There was no effect of ABA and LC66C6 on the *Chlamydomonas* growth with and without stresses. Pryabactin bleached *Physcomitrella patens* and *Chlamydomonas*, suggesting that this compound may have toxicity in these species unrelated to its ABA agonist activity.
Figure 17B:
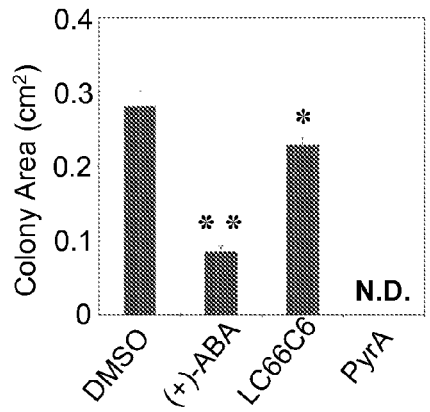

As shown in FIGS. 17A and 17B, LC66C6 showed a weak but significant inhibition on the growth of protonema of the moss Physcomitrella patens. Pyrabactin bleached the protonema, suggesting it might be toxic for this species.

Figure 17C:
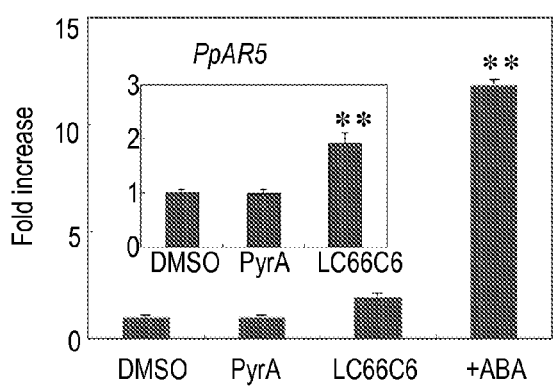

FIG. 17C shows that LC66C6 can induce the expression of ABA-responsive genes in moss. However, these induction levels were weaker than those of ABA.

Figure 17D:
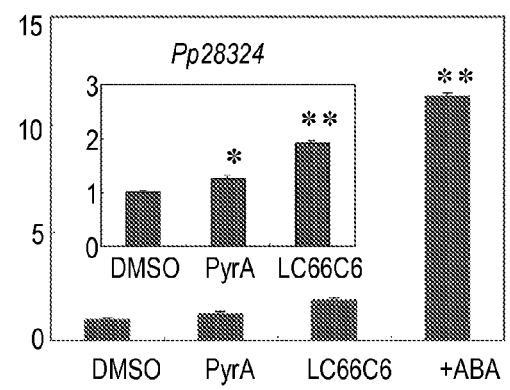
Figure 17D:
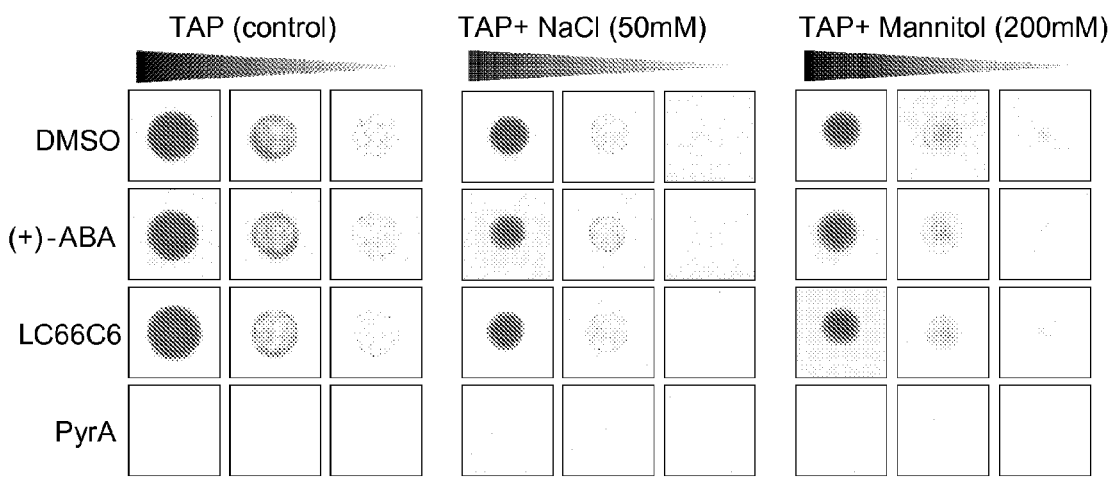

As shown in FIG. 17D, both (+)-ABA and LC66C6 had no effect on the growth of Chlamydomonas with and without salinity and osmotic stress. Again, pyrabactin bleached the Chlamydomonas, suggesting it is toxic to this species as well.

This example shows that LC66C6 can weakly inhibit protonemal growth and weakly induce ABA-responsive gene expression in the moss Physcomitrella patens, but does not effect the growth of the unicellular algae Chlamydomonas.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. An agricultural formulation, comprising a compound of Formula I:

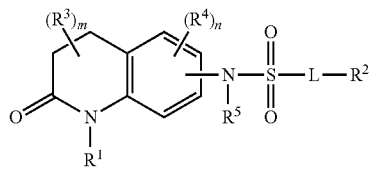

wherein
R$^1$ is selected from the group consisting of H, C$_{1-6}$ alkyl, C$_{2-6}$ alkenyl, C$_{2-6}$ alkynyl, cycloalkyl, heterocycloalkyl, aryl and heteroaryl,
R$^2$ is selected from the group consisting of cycloalkyl, heterocycloalkyl, aryl and heteroaryl, each optionally substituted with from 1-4 R$^{2a}$ groups,
each R$^{2a}$ is independently selected from the group consisting of H, halogen, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, —OH, C$_{1-6}$ alkylhydroxy, —CN, —NO$_2$, —C(O)R$^{2b}$, —C(O)OR$^{2b}$, —OC(O)R$^{2b}$, —C(O)NR$^{2b}$R$^{2c}$, —NR$^{2b}$C(O)R$^{2c}$, —SO$_2$R$^{2b}$, —SO$_2$OR$^{2b}$, —SO$_2$NR$^{2b}$R$^{2c}$, and —NR$^{2b}$SO$_2$R$^{2c}$,
each of R$^{2b}$ and R$^{2c}$ are independently selected from the group consisting of H and C$_{1-6}$ alkyl,
each of R$^3$, R$^4$ and R$^5$ are independently selected from the group consisting of H and C$_{1-6}$ alkyl,
L is a linker selected from the group consisting of a bond and C$_{1-6}$ alkylene,
subscript m is an integer from 0 to 4,
subscript n is an integer from 0 to 3,
or a salt or isomer thereof.

2. The formulation of claim 1, wherein the compound has the formula:

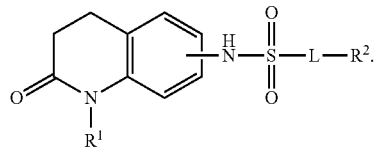

3. The formulation of claim 2, wherein the compound has the formula:

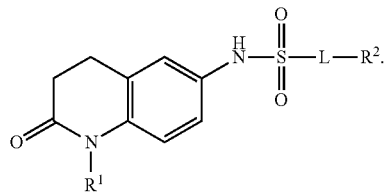

4. The formulation of claim 2, wherein
R$^1$ is C$_{1-6}$ alkyl, and
R$^2$ is selected from the group consisting of aryl and heteroaryl, each optionally substituted with from 1-4 R$^{2a}$ groups.

5. The formulation of claim 4, wherein each R$^{2a}$ is independently selected from the group consisting of H, halogen and C$_{1-6}$ alkyl.

6. The formulation of claim 4, wherein R$^2$ is selected from the group consisting of phenyl, naphthyl, thiophene, furan, pyrrole, and pyridyl.

7. The formulation of claim 4, wherein
R$^1$ is selected from the group consisting of methyl, ethyl, propyl, isopropyl, butyl, iso-butyl, sec-butyl, tert-butyl, pentyl, isopentyl, neo-pentyl and hexyl;
R$^2$ is selected from the group consisting of phenyl and thiophene, each optionally substituted with 1 R$^{2a}$ group;
each R$^{2a}$ is independently selected from the group consisting of H, F, Cl, methyl, and ethyl; and
L is selected from the group consisting of a bond and methylene.

8. The formulation of claim 7, wherein the compound has the formula:

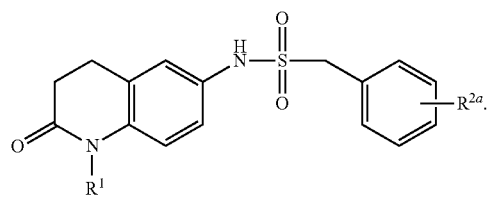

9. The formulation of claim 7, wherein the compound has the formula:

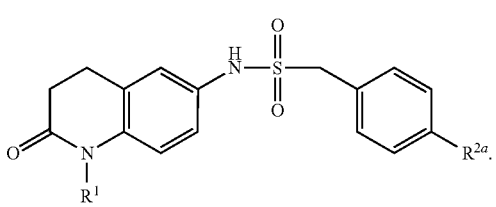

10. The formulation of claim 1, wherein the compound is one of the compounds below:

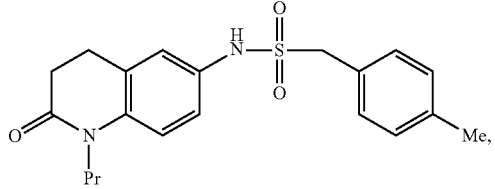

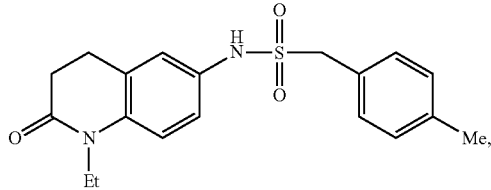

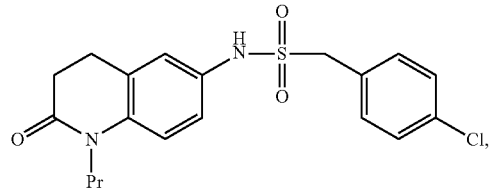

-continued
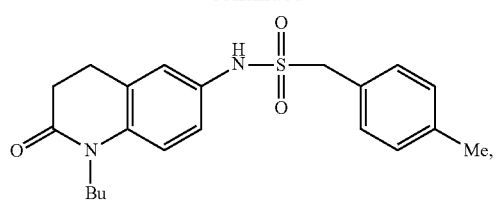
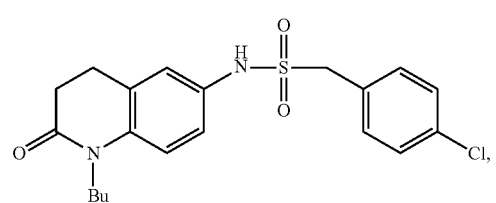
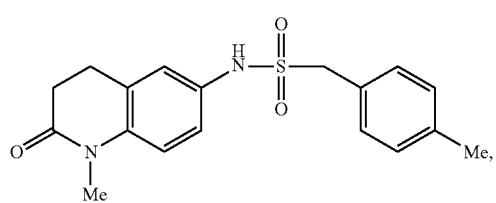
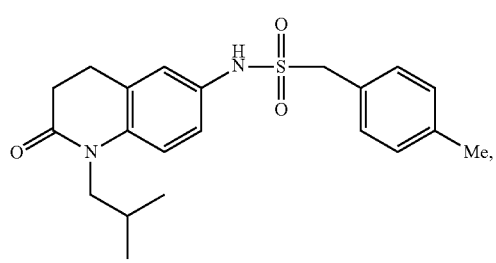
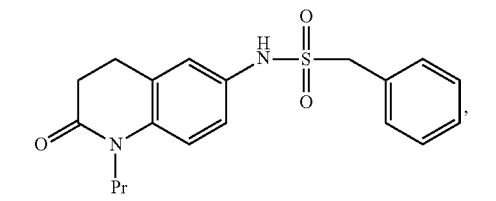
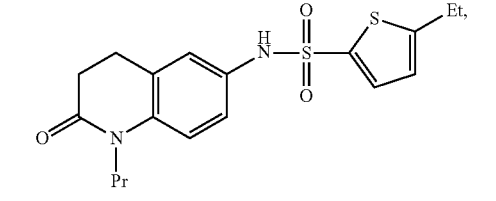
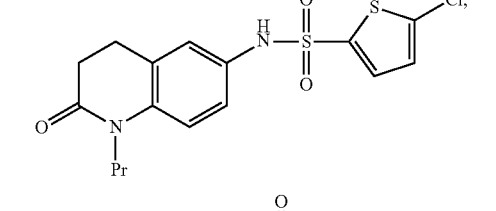
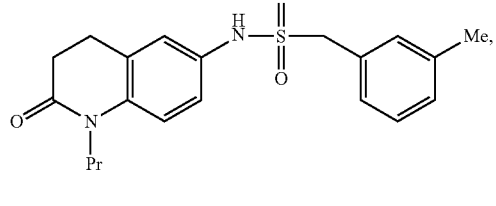
-continued
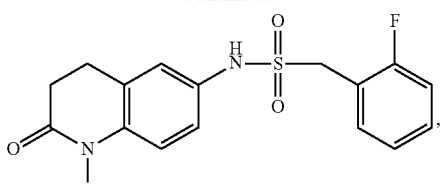
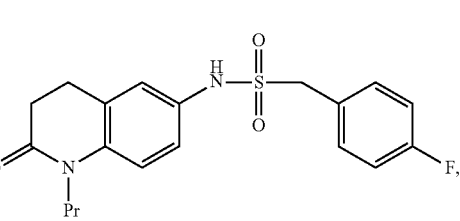
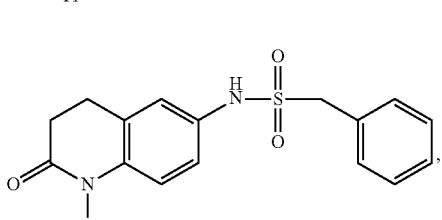
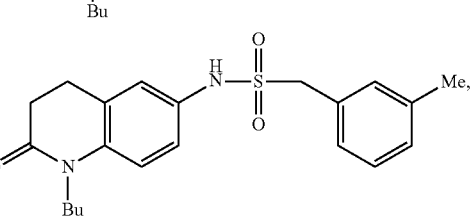
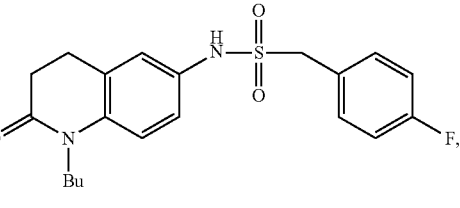
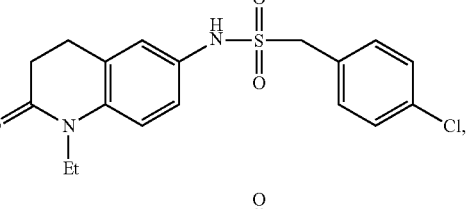
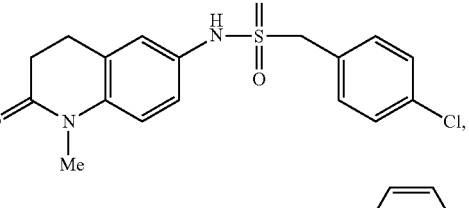
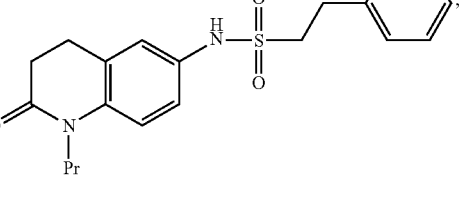

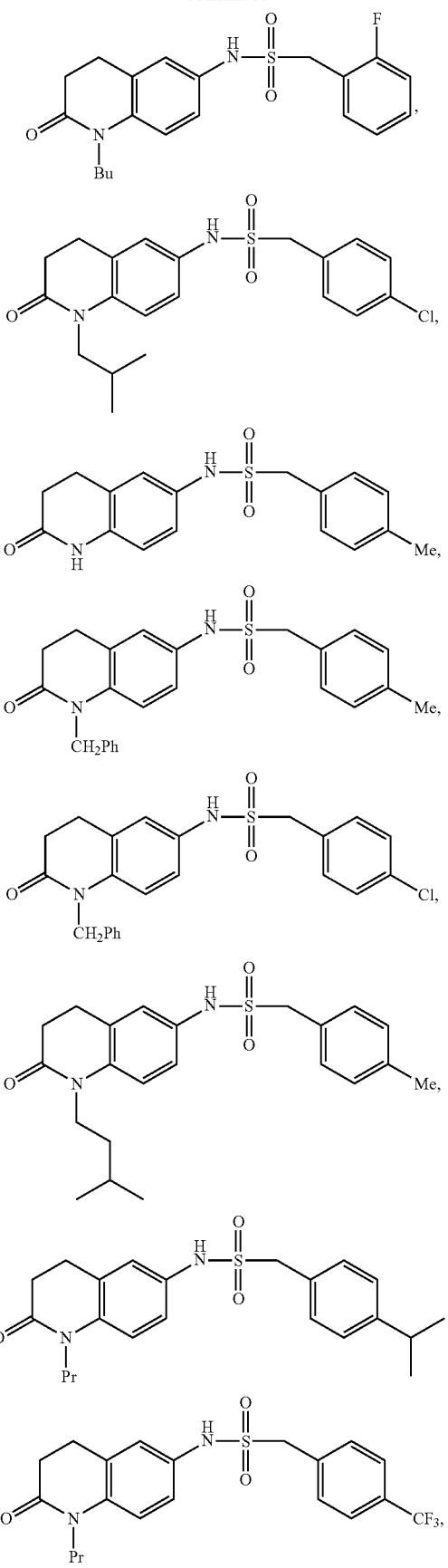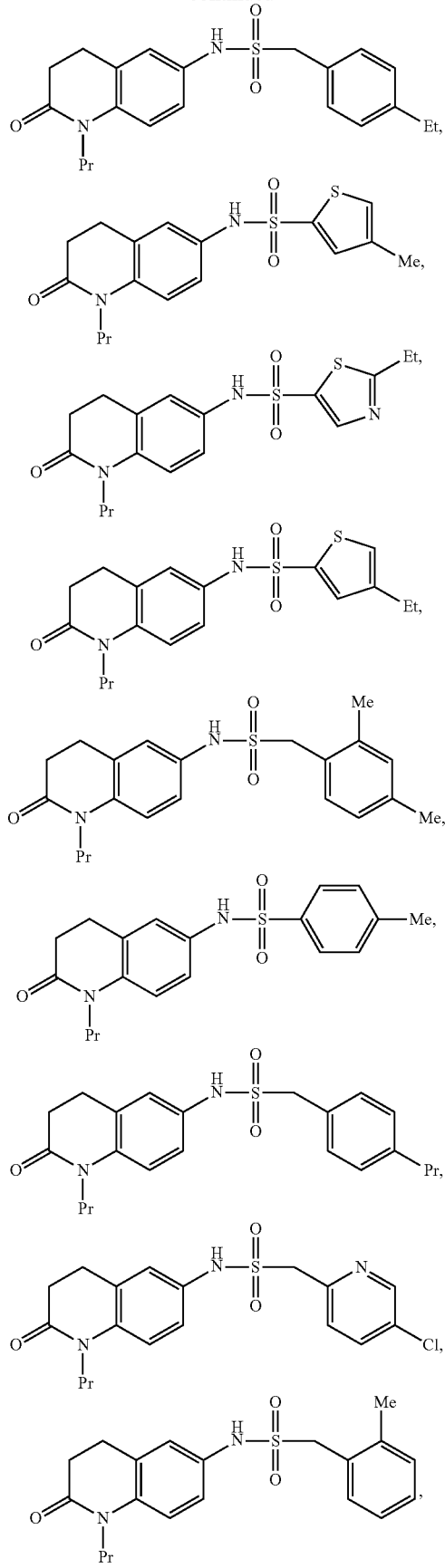

-continued

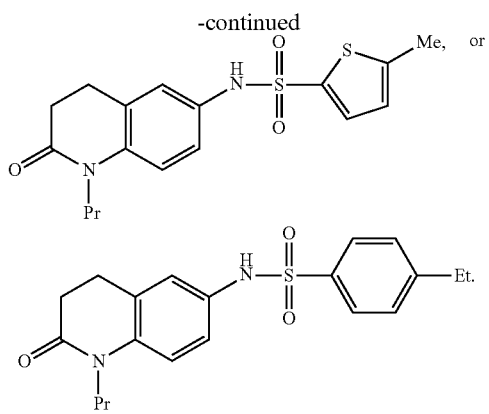

11. The formulation of claim 1, wherein the compound

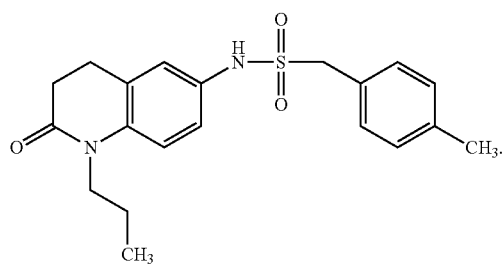 [SMILES: CCCN1C(=O)CCc2cc(NS(=O)(=O)Cc3ccc(C)cc3)ccc21]

12. The formulation of claim 1, further comprising at least one of a fungicide, an herbicide, a pesticide, a nematicide, an insecticide, a plant activator, an herbicide safener, a plant growth regulator, an insect repellant, an acaricide, a molluscicide, or a fertilizer.

13. The formulation of claim 1, further comprising a surfactant.

14. The formulation of claim 1, further comprising a carrier.

15. A method of increasing abiotic stress tolerance in a plant, the method comprising contacting a plant with a sufficient amount of the agricultural formulation according to claim 1 to increase abiotic stress tolerance in the plant compared to not contacting the plant with the formulation.

16. A method of inhibiting seed germination in a plant, the method comprising contacting a seed with a sufficient amount of the formulation according to claim 1 to inhibit germination.

17. A method of bringing a plant in contact with the agricultural formulation according to any of claims 1 to 14, comprising contacting the plant with the agricultural formulation.

18. The plant of claim 17, wherein the plant is a seed.

19. A method of activating a PYR/PYL protein, the method comprising contacting the PYR/PYL protein with an agricultural formulation according to claim 1.

* * * * *

```
                        SEQUENCE LISTING

<160> NUMBER OF SEQ ID NOS: 149

<210> SEQ ID NO 1
<211> LENGTH: 191
<212> TYPE: PRT
<213> ORGANISM: Arabidopsis thaliana
<220> FEATURE:
<223> OTHER INFORMATION: thale cress PYR/PYL receptor, Pyrabactin
      resistance 1, abscisic acid receptor PYR1 (PYR1), ABI1-binding
      protein 6 (ABIP6), regulatory components of ABA receptor 11
      (RCAR11), At4g17870, T6K21.50

<400> SEQUENCE: 1

Met Pro Ser Glu Leu Thr Pro Glu Glu Arg Ser Glu Leu Lys Asn Ser
 1               5                  10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys His Phe Ile Lys Ser
        50                  55                  60

Cys Ser Val Glu Gln Asn Phe Glu Met Arg Val Gly Cys Thr Arg Asp
 65                  70                  75                  80

Val Ile Val Ile Ser Gly Leu Pro Ala Asn Thr Ser Thr Glu Arg Leu
                85                  90                  95
```

```
Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 2
<211> LENGTH: 221
<212> TYPE: PRT
<213> ORGANISM: Arabidopsis thaliana
<220> FEATURE:
<223> OTHER INFORMATION: thale cress PYR/PYL receptor, abscisic acid
      receptor PYL1, PYR1-like protein 1 (PYL1), ABI1-binding protein 6
      (ABIP6), regulatory components of ABA receptor 9 (RCAR12),
      At5g46790, MZA15.21

<400> SEQUENCE: 2

Met Ala Asn Ser Glu Ser Ser Ser Pro Val Asn Glu Glu Asn
  1               5                  10                  15

Ser Gln Arg Ile Ser Thr Leu His His Gln Thr Met Pro Ser Asp Leu
                20                  25                  30

Thr Gln Asp Glu Phe Thr Gln Leu Ser Gln Ser Ile Ala Glu Phe His
            35                  40                  45

Thr Tyr Gln Leu Gly Asn Gly Arg Cys Ser Ser Leu Leu Ala Gln Arg
        50                  55                  60

Ile His Ala Pro Pro Glu Thr Val Trp Ser Val Val Arg Arg Phe Asp
65                  70                  75                  80

Arg Pro Gln Ile Tyr Lys His Phe Ile Lys Ser Cys Asn Val Ser Glu
                85                  90                  95

Asp Phe Glu Met Arg Val Gly Cys Thr Arg Asp Val Asn Val Ile Ser
            100                 105                 110

Gly Leu Pro Ala Asn Thr Ser Arg Glu Arg Leu Asp Leu Leu Asp Asp
        115                 120                 125

Asp Arg Arg Val Thr Gly Phe Ser Ile Thr Gly Gly Glu His Arg Leu
130                 135                 140

Arg Asn Tyr Lys Ser Val Thr Thr Val His Arg Phe Glu Lys Glu Glu
145                 150                 155                 160

Glu Glu Glu Arg Ile Trp Thr Val Val Leu Glu Ser Tyr Val Val Asp
                165                 170                 175

Val Pro Glu Gly Asn Ser Glu Glu Asp Thr Arg Leu Phe Ala Asp Thr
            180                 185                 190

Val Ile Arg Leu Asn Leu Gln Lys Leu Ala Ser Ile Thr Glu Ala Met
        195                 200                 205

Asn Arg Asn Asn Asn Asn Asn Ser Ser Gln Val Arg
    210                 215                 220

<210> SEQ ID NO 3
<211> LENGTH: 190
<212> TYPE: PRT
<213> ORGANISM: Arabidopsis thaliana
<220> FEATURE:
```

<223> OTHER INFORMATION: thale cress PYR/PYL receptor, abscisic acid
receptor PYL2, PYR1-like protein 2 (PYL2), ABI1-binding protein
6 (ABIP6), regulatory components of ABA receptor 14 (RCAR14),
Bet v I allergen family protein, At2g26040, T19L18.15

<400> SEQUENCE: 3

Met Ser Ser Ser Pro Ala Val Lys Gly Leu Thr Asp Glu Glu Gln Lys
1               5                   10                  15

Thr Leu Glu Pro Val Ile Lys Thr Tyr His Gln Phe Glu Pro Asp Pro
            20                  25                  30

Thr Thr Cys Thr Ser Leu Ile Thr Gln Arg Ile His Ala Pro Ala Ser
        35                  40                  45

Val Val Trp Pro Leu Ile Arg Arg Phe Asp Asn Pro Glu Arg Tyr Lys
    50                  55                  60

His Phe Val Lys Arg Cys Arg Leu Ile Ser Gly Asp Gly Asp Val Gly
65                  70                  75                  80

Ser Val Arg Glu Val Thr Val Ile Ser Gly Leu Pro Ala Ser Thr Ser
                85                  90                  95

Thr Glu Arg Leu Glu Phe Val Asp Asp Asp His Arg Val Leu Ser Phe
            100                 105                 110

Arg Val Val Gly Gly Glu His Arg Leu Lys Asn Tyr Lys Ser Val Thr
        115                 120                 125

Ser Val Asn Glu Phe Leu Asn Gln Asp Ser Gly Lys Val Tyr Thr Val
    130                 135                 140

Val Leu Glu Ser Tyr Thr Val Asp Ile Pro Glu Gly Asn Thr Glu Glu
145                 150                 155                 160

Asp Thr Lys Met Phe Val Asp Thr Val Val Lys Leu Asn Leu Gln Lys
                165                 170                 175

Leu Gly Val Ala Ala Thr Ser Ala Pro Met His Asp Asp Glu
            180                 185                 190

<210> SEQ ID NO 4
<211> LENGTH: 209
<212> TYPE: PRT
<213> ORGANISM: Arabidopsis thaliana
<220> FEATURE:
<223> OTHER INFORMATION: thale cress PYR/PYL receptor, abscisic acid
receptor PYL3, PYR1-like protein 3 (PYL3), regulatory components
of ABA receptor 13 (RCAR13), At1g73000, F3N23.20

<400> SEQUENCE: 4

Met Asn Leu Ala Pro Ile His Asp Pro Ser Ser Ser Thr Thr Thr Thr
1               5                   10                  15

Thr Ser Ser Ser Thr Pro Tyr Gly Leu Thr Lys Asp Glu Phe Ser Thr
            20                  25                  30

Leu Asp Ser Ile Ile Arg Thr His His Thr Phe Pro Arg Ser Pro Asn
        35                  40                  45

Thr Cys Thr Ser Leu Ile Ala His Arg Val Asp Ala Pro Ala His Ala
    50                  55                  60

Ile Trp Arg Phe Val Arg Asp Phe Ala Asn Pro Asn Lys Tyr Lys His
65                  70                  75                  80

Phe Ile Lys Ser Cys Thr Ile Arg Val Asn Gly Asn Gly Ile Lys Glu
                85                  90                  95

Ile Lys Val Gly Thr Ile Arg Glu Val Ser Val Val Ser Gly Leu Pro
            100                 105                 110

Ala Ser Thr Ser Val Glu Ile Leu Glu Val Leu Asp Glu Glu Lys Arg
        115                 120                 125

```
Ile Leu Ser Phe Arg Val Leu Gly Gly Glu His Arg Leu Asn Asn Tyr
    130                 135                 140

Arg Ser Val Thr Ser Val Asn Glu Phe Val Val Leu Glu Lys Asp Lys
145                 150                 155                 160

Lys Lys Arg Val Tyr Ser Val Val Leu Glu Ser Tyr Ile Val Asp Ile
                165                 170                 175

Pro Gln Gly Asn Thr Glu Glu Asp Thr Arg Met Phe Val Asp Thr Val
                180                 185                 190

Val Lys Ser Asn Leu Gln Asn Leu Ala Val Ile Ser Thr Ala Ser Pro
                195                 200                 205

Thr

<210> SEQ ID NO 5
<211> LENGTH: 207
<212> TYPE: PRT
<213> ORGANISM: Arabidopsis thaliana
<220> FEATURE:
<223> OTHER INFORMATION: thale cress PYR/PYL receptor, abscisic acid
      receptor PYL4, PYR1-like protein 4 (PYL4), ABI1-binding protein
      2 (ABIP2), regulatory components of ABA receptor 10 (RCAR10),
      At2g38310, T19C21.20

<400> SEQUENCE: 5

Met Leu Ala Val His Arg Pro Ser Ser Ala Val Ser Asp Gly Asp Ser
1               5                   10                  15

Val Gln Ile Pro Met Met Ile Ala Ser Phe Gln Lys Arg Phe Pro Ser
                20                  25                  30

Leu Ser Arg Asp Ser Thr Ala Ala Arg Phe His Thr His Glu Val Gly
            35                  40                  45

Pro Asn Gln Cys Cys Ser Ala Val Ile Gln Glu Ile Ser Ala Pro Ile
        50                  55                  60

Ser Thr Val Trp Ser Val Val Arg Arg Phe Asp Asn Pro Gln Ala Tyr
65                  70                  75                  80

Lys His Phe Leu Lys Ser Cys Ser Val Ile Gly Gly Asp Gly Asp Asn
                85                  90                  95

Val Gly Ser Leu Arg Gln Val His Val Val Ser Gly Leu Pro Ala Ala
            100                 105                 110

Ser Ser Thr Glu Arg Leu Asp Ile Leu Asp Asp Glu Arg His Val Ile
        115                 120                 125

Ser Phe Ser Val Val Gly Gly Asp His Arg Leu Ser Asn Tyr Arg Ser
    130                 135                 140

Val Thr Thr Leu His Pro Ser Pro Ile Ser Gly Thr Val Val Val Glu
145                 150                 155                 160

Ser Tyr Val Val Asp Val Pro Pro Gly Asn Thr Lys Glu Glu Thr Cys
                165                 170                 175

Asp Phe Val Asp Val Ile Val Arg Cys Asn Leu Gln Ser Leu Ala Lys
                180                 185                 190

Ile Ala Glu Asn Thr Ala Ala Glu Ser Lys Lys Lys Met Ser Leu
                195                 200                 205

<210> SEQ ID NO 6
<211> LENGTH: 203
<212> TYPE: PRT
<213> ORGANISM: Arabidopsis thaliana
<220> FEATURE:
<223> OTHER INFORMATION: thale cress PYR/PYL receptor, abscisic acid
      receptor PYL5, PYR1-like protein 5 (PYL5), ABI1-binding protein
      3 (ABIP3), regulatory components of ABA receptor 8 (RCAR8),
      Bet v I allergen family protein, At5g05440, K18I23.25
```

<400> SEQUENCE: 6

```
Met Arg Ser Pro Val Gln Leu Gln His Gly Ser Asp Ala Thr Asn Gly
1               5                   10                  15

Phe His Thr Leu Gln Pro His Asp Gln Thr Asp Gly Pro Ile Lys Arg
            20                  25                  30

Val Cys Leu Thr Arg Gly Met His Val Pro Glu His Val Ala Met His
        35                  40                  45

His Thr His Asp Val Gly Pro Asp Gln Cys Cys Ser Ser Val Val Gln
    50                  55                  60

Met Ile His Ala Pro Pro Glu Ser Val Trp Ala Leu Val Arg Arg Phe
65                  70                  75                  80

Asp Asn Pro Lys Val Tyr Lys Asn Phe Ile Arg Gln Cys Arg Ile Val
                85                  90                  95

Gln Gly Asp Gly Leu His Val Gly Asp Leu Arg Glu Val Met Val Val
            100                 105                 110

Ser Gly Leu Pro Ala Val Ser Ser Thr Glu Arg Leu Glu Ile Leu Asp
        115                 120                 125

Glu Glu Arg His Val Ile Ser Phe Ser Val Val Gly Gly Asp His Arg
130                 135                 140

Leu Lys Asn Tyr Arg Ser Val Thr Thr Leu His Ala Ser Asp Asp Glu
145                 150                 155                 160

Gly Thr Val Val Val Glu Ser Tyr Ile Val Asp Val Pro Pro Gly Asn
                165                 170                 175

Thr Glu Glu Thr Leu Ser Phe Val Asp Thr Ile Val Arg Cys Asn
            180                 185                 190

Leu Gln Ser Leu Ala Arg Ser Thr Asn Arg Gln
        195                 200
```

<210> SEQ ID NO 7
<211> LENGTH: 215
<212> TYPE: PRT
<213> ORGANISM: Arabidopsis thaliana
<220> FEATURE:
<223> OTHER INFORMATION: thale cress PYR/PYL receptor, abscisic acid
      receptor PYL6, PYR1-like protein 6 (PYL6), ABI1-binding protein
      5 (ABIP5), regulatory components of ABA receptor 9 (RCAR9),
      Bet v I allergen family protein, At2g40330, T7M7.15

<400> SEQUENCE: 7

```
Met Pro Thr Ser Ile Gln Phe Gln Arg Ser Ser Thr Ala Ala Glu Ala
1               5                   10                  15

Ala Asn Ala Thr Val Arg Asn Tyr Pro His His His Gln Lys Gln Val
            20                  25                  30

Gln Lys Val Ser Leu Thr Arg Gly Met Ala Asp Val Pro Glu His Val
        35                  40                  45

Glu Leu Ser His Thr His Val Val Gly Pro Ser Gln Cys Phe Ser Val
    50                  55                  60

Val Val Gln Asp Val Glu Ala Pro Val Ser Thr Val Trp Ser Ile Leu
65                  70                  75                  80

Ser Arg Phe Glu His Pro Gln Ala Tyr Lys His Phe Val Lys Ser Cys
                85                  90                  95

His Val Val Ile Gly Asp Gly Arg Glu Val Gly Ser Val Arg Glu Val
            100                 105                 110

Arg Val Val Ser Gly Leu Pro Ala Ala Phe Ser Leu Glu Arg Leu Glu
        115                 120                 125
```

```
Ile Met Asp Asp Asp Arg His Val Ile Ser Phe Val Val Gly Gly
        130                 135                 140

Asp His Arg Leu Met Asn Tyr Lys Ser Val Thr Val His Glu Ser
145                 150                 155                 160

Glu Glu Asp Ser Asp Gly Lys Lys Arg Thr Arg Val Val Glu Ser Tyr
                165                 170                 175

Val Val Asp Val Pro Ala Gly Asn Asp Lys Glu Glu Thr Cys Ser Phe
                180                 185                 190

Ala Asp Thr Ile Val Arg Cys Asn Leu Gln Ser Leu Ala Lys Leu Ala
                195                 200                 205

Glu Asn Thr Ser Lys Phe Ser
        210                 215

<210> SEQ ID NO 8
<211> LENGTH: 211
<212> TYPE: PRT
<213> ORGANISM: Arabidopsis thaliana
<220> FEATURE:
<223> OTHER INFORMATION: thale cress PYR/PYL receptor, abscisic acid
      receptor PYL7, PYR1-like protein 7 (PYL7), ABI1-binding protein
      7 (ABIP7), regulatory components of ABA receptor 2 (RCAR2),
      At4g01026

<400> SEQUENCE: 8

Met Glu Met Ile Gly Gly Asp Asp Thr Asp Thr Glu Met Tyr Gly Ala
1               5                   10                  15

Leu Val Thr Ala Gln Ser Leu Arg Leu Arg His Leu His His Cys Arg
                20                  25                  30

Glu Asn Gln Cys Thr Ser Val Leu Val Lys Tyr Ile Gln Ala Pro Val
            35                  40                  45

His Leu Val Trp Ser Leu Val Arg Arg Phe Asp Gln Pro Gln Lys Tyr
        50                  55                  60

Lys Pro Phe Ile Ser Arg Cys Thr Val Asn Gly Asp Pro Glu Ile Gly
65                  70                  75                  80

Cys Leu Arg Glu Val Asn Val Lys Ser Gly Leu Pro Ala Thr Thr Ser
                85                  90                  95

Thr Glu Arg Leu Glu Gln Leu Asp Asp Glu His Ile Leu Gly Ile
            100                 105                 110

Asn Ile Ile Gly Gly Asp His Arg Leu Lys Asn Tyr Ser Ser Ile Leu
        115                 120                 125

Thr Val His Pro Glu Met Ile Asp Gly Arg Ser Gly Thr Met Val Met
130                 135                 140

Glu Ser Phe Val Val Asp Val Pro Gln Gly Asn Thr Lys Asp Asp Thr
145                 150                 155                 160

Cys Tyr Phe Val Glu Ser Leu Ile Lys Cys Asn Leu Lys Ser Leu Ala
                165                 170                 175

Cys Val Ser Glu Arg Leu Ala Ala Gln Asp Ile Thr Asn Ser Ile Ala
                180                 185                 190

Thr Phe Cys Asn Ala Ser Asn Gly Tyr Arg Glu Lys Asn His Thr Glu
                195                 200                 205

Thr Asn Leu
    210

<210> SEQ ID NO 9
<211> LENGTH: 188
<212> TYPE: PRT
<213> ORGANISM: Arabidopsis thaliana
<220> FEATURE:
```

<223> OTHER INFORMATION: thale cress PYR/PYL receptor, abscisic acid
      receptor PYL8, PYR1-like protein 8 (PYL8), ABI1-binding protein 1
      (ABIP1), regulatory components of ABA receptor 3 (RCAR3),
      At5g53160, MFH8.10

<400> SEQUENCE: 9

```
Met Glu Ala Asn Gly Ile Glu Asn Leu Thr Asn Pro Asn Gln Glu Arg
1               5                   10                  15

Glu Phe Ile Arg Arg His His Lys His Glu Leu Val Asp Asn Gln Cys
            20                  25                  30

Ser Ser Thr Leu Val Lys His Ile Asn Ala Pro Val His Ile Val Trp
        35                  40                  45

Ser Leu Val Arg Arg Phe Asp Gln Pro Gln Lys Tyr Lys Pro Phe Ile
    50                  55                  60

Ser Arg Cys Val Val Lys Gly Asn Met Glu Ile Gly Thr Val Arg Glu
65                  70                  75                  80

Val Asp Val Lys Ser Gly Leu Pro Ala Thr Arg Ser Thr Glu Arg Leu
                85                  90                  95

Glu Leu Leu Asp Asp Asn Glu His Ile Leu Ser Ile Arg Ile Val Gly
            100                 105                 110

Gly Asp His Arg Leu Lys Asn Tyr Ser Ser Ile Ile Ser Leu His Pro
        115                 120                 125

Glu Thr Ile Glu Gly Arg Ile Gly Thr Leu Val Ile Glu Ser Phe Val
    130                 135                 140

Val Asp Val Pro Glu Gly Asn Thr Lys Asp Glu Thr Cys Tyr Phe Val
145                 150                 155                 160

Glu Ala Leu Ile Lys Cys Asn Leu Lys Ser Leu Ala Asp Ile Ser Glu
                165                 170                 175

Arg Leu Ala Val Gln Asp Thr Thr Glu Ser Arg Val
            180                 185
```

<210> SEQ ID NO 10
<211> LENGTH: 187
<212> TYPE: PRT
<213> ORGANISM: Arabidopsis thaliana
<220> FEATURE:
<223> OTHER INFORMATION: thale cress PYR/PYL receptor, abscisic acid
      receptor PYL9, PYR1-like protein 9 (PYL9), ABI1-binding protein
      4 (ABIP4), regulatory components of ABA receptor 1 (RCAR1),
      At1g01360, F6F3.16

<400> SEQUENCE: 10

```
Met Met Asp Gly Val Glu Gly Gly Thr Ala Met Tyr Gly Gly Leu Glu
1               5                   10                  15

Thr Val Gln Tyr Val Arg Thr His His Gln His Leu Cys Arg Glu Asn
            20                  25                  30

Gln Cys Thr Ser Ala Leu Val Lys His Ile Lys Ala Pro Leu His Leu
        35                  40                  45

Val Trp Ser Leu Val Arg Arg Phe Asp Gln Pro Gln Lys Tyr Lys Pro
    50                  55                  60

Phe Val Ser Arg Cys Thr Val Ile Gly Asp Pro Glu Ile Gly Ser Leu
65                  70                  75                  80

Arg Glu Val Asn Val Lys Ser Gly Leu Pro Ala Thr Thr Ser Thr Glu
                85                  90                  95

Arg Leu Glu Leu Leu Asp Asp Glu Glu His Ile Leu Gly Ile Lys Ile
            100                 105                 110

Ile Gly Gly Asp His Arg Leu Lys Asn Tyr Ser Ser Ile Leu Thr Val
        115                 120                 125
```

His Pro Glu Ile Ile Glu Gly Arg Ala Gly Thr Met Val Ile Glu Ser
            130                 135                 140

Phe Val Val Asp Val Pro Gln Gly Asn Thr Lys Asp Glu Thr Cys Tyr
145                 150                 155                 160

Phe Val Glu Ala Leu Ile Arg Cys Asn Leu Lys Ser Leu Ala Asp Val
                165                 170                 175

Ser Glu Arg Leu Ala Ser Gln Asp Ile Thr Gln
            180                 185

<210> SEQ ID NO 11
<211> LENGTH: 183
<212> TYPE: PRT
<213> ORGANISM: Arabidopsis thaliana
<220> FEATURE:
<223> OTHER INFORMATION: thale cress PYR/PYL receptor, abscisic acid
      receptor PYL10, PYR1-like protein 10 (PYL10), ABI1-binding protein
      8 (ABIP8), regulatory components of ABA receptor 4 (RCAR4),
      At4g27920, T13J8.30

<400> SEQUENCE: 11

Met Asn Gly Asp Glu Thr Lys Lys Val Glu Ser Glu Tyr Ile Lys Lys
1               5                   10                  15

His His Arg His Glu Leu Val Glu Ser Gln Cys Ser Ser Thr Leu Val
            20                  25                  30

Lys His Ile Lys Ala Pro Leu His Leu Val Trp Ser Ile Val Arg Arg
        35                  40                  45

Phe Asp Glu Pro Gln Lys Tyr Lys Pro Phe Ile Ser Arg Cys Val Val
    50                  55                  60

Gln Gly Lys Lys Leu Glu Val Gly Ser Val Arg Glu Val Asp Leu Lys
65                  70                  75                  80

Ser Gly Leu Pro Ala Thr Lys Ser Thr Glu Val Leu Glu Ile Leu Asp
                85                  90                  95

Asp Asn Glu His Ile Leu Gly Ile Arg Ile Val Gly Gly Asp His Arg
            100                 105                 110

Leu Lys Asn Tyr Ser Ser Thr Ile Ser Leu His Ser Glu Thr Ile Asp
        115                 120                 125

Gly Lys Thr Gly Thr Leu Ala Ile Glu Ser Phe Val Val Asp Val Pro
    130                 135                 140

Glu Gly Asn Thr Lys Glu Glu Thr Cys Phe Phe Val Glu Ala Leu Ile
145                 150                 155                 160

Gln Cys Asn Leu Asn Ser Leu Ala Asp Val Thr Glu Arg Leu Gln Ala
                165                 170                 175

Glu Ser Met Glu Lys Lys Ile
            180

<210> SEQ ID NO 12
<211> LENGTH: 161
<212> TYPE: PRT
<213> ORGANISM: Arabidopsis thaliana
<220> FEATURE:
<223> OTHER INFORMATION: thale cress PYR/PYL receptor, abscisic acid
      receptor PYL11, PYR1-like protein 11 (PYL11), regulatory
      components of ABA receptor 5 (RCAR5), Bet v I allergen family
      protein, At5g45860, K15I22.6

<400> SEQUENCE: 12

Met Glu Thr Ser Gln Lys Tyr His Thr Cys Gly Ser Thr Leu Val Gln
1               5                   10                  15

Thr Ile Asp Ala Pro Leu Ser Leu Val Trp Ser Ile Leu Arg Arg Phe

```
                    20                  25                  30

Asp Asn Pro Gln Ala Tyr Lys Gln Phe Val Lys Thr Cys Asn Leu Ser
            35                  40                  45

Ser Gly Asp Gly Gly Glu Gly Ser Val Arg Glu Val Thr Val Val Ser
    50                  55                  60

Gly Leu Pro Ala Glu Phe Ser Arg Glu Arg Leu Asp Glu Leu Asp Asp
65                  70                  75                  80

Glu Ser His Val Met Met Ile Ser Ile Ile Gly Gly Asp His Arg Leu
                85                  90                  95

Val Asn Tyr Arg Ser Lys Thr Met Ala Phe Val Ala Ala Asp Thr Glu
            100                 105                 110

Glu Lys Thr Val Val Val Glu Ser Tyr Val Val Asp Val Pro Glu Gly
            115                 120                 125

Asn Ser Glu Glu Glu Thr Thr Ser Phe Ala Asp Thr Ile Val Gly Phe
        130                 135                 140

Asn Leu Lys Ser Leu Ala Lys Leu Ser Glu Arg Val Ala His Leu Lys
145                 150                 155                 160

Leu
```

<210> SEQ ID NO 13
<211> LENGTH: 159
<212> TYPE: PRT
<213> ORGANISM: Arabidopsis thaliana
<220> FEATURE:
<223> OTHER INFORMATION: thale cress PYR/PYL receptor, abscisic acid
      receptor PYL12, PYR1-like protein 12 (PYL12), regulatory
      components of ABA receptor 6 (RCAR6), Bet v I allergen family
      protein, At5g45870, K15I22.7

<400> SEQUENCE: 13

```
Met Lys Thr Ser Gln Glu Gln His Val Cys Gly Ser Thr Val Val Gln
1               5                   10                  15

Thr Ile Asn Ala Pro Leu Pro Leu Val Trp Ser Ile Leu Arg Arg Phe
            20                  25                  30

Asp Asn Pro Lys Thr Phe Lys His Phe Val Lys Thr Cys Lys Leu Arg
            35                  40                  45

Ser Gly Asp Gly Gly Glu Gly Ser Val Arg Glu Val Thr Val Val Ser
    50                  55                  60

Asp Leu Pro Ala Ser Phe Ser Leu Glu Arg Leu Asp Glu Leu Asp Asp
65                  70                  75                  80

Glu Ser His Val Met Val Ile Ser Ile Ile Gly Gly Asp His Arg Leu
                85                  90                  95

Val Asn Tyr Gln Ser Lys Thr Thr Val Phe Val Ala Ala Glu Glu Glu
            100                 105                 110

Lys Thr Val Val Val Glu Ser Tyr Val Val Asp Val Pro Glu Gly Asn
            115                 120                 125

Thr Glu Glu Glu Thr Thr Leu Phe Ala Asp Thr Ile Val Gly Cys Asn
        130                 135                 140

Leu Arg Ser Leu Ala Lys Leu Ser Glu Lys Met Met Glu Leu Thr
145                 150                 155
```

<210> SEQ ID NO 14
<211> LENGTH: 164
<212> TYPE: PRT
<213> ORGANISM: Arabidopsis thaliana
<220> FEATURE:
<223> OTHER INFORMATION: thale cress PYR/PYL receptor, abscisic acid
      receptor PYL13, PYR1-like protein 13 (PYL13), regulatory -continued components of ABA receptor 7 (RCAR7), At4g18620, F28A21.30

<400> SEQUENCE: 14

Met Glu Ser Ser Lys Gln Lys Arg Cys Arg Ser Val Val Glu Thr
1               5                   10                  15

Ile Glu Ala Pro Leu Pro Leu Val Trp Ser Ile Leu Arg Ser Phe Asp
            20                  25                  30

Lys Pro Gln Ala Tyr Gln Arg Phe Val Lys Ser Cys Thr Met Arg Ser
        35                  40                  45

Gly Gly Gly Gly Gly Lys Gly Gly Glu Gly Lys Gly Ser Val Arg Asp
    50                  55                  60

Val Thr Leu Val Ser Gly Phe Pro Ala Asp Phe Ser Thr Glu Arg Leu
65                  70                  75                  80

Glu Glu Leu Asp Asp Glu Ser His Val Met Val Val Ser Ile Ile Gly
                85                  90                  95

Gly Asn His Arg Leu Val Asn Tyr Lys Ser Lys Thr Lys Val Val Ala
            100                 105                 110

Ser Pro Glu Asp Met Ala Lys Lys Thr Val Val Glu Ser Tyr Val
        115                 120                 125

Val Asp Val Pro Glu Gly Thr Ser Glu Glu Asp Thr Ile Phe Phe Val
    130                 135                 140

Asp Asn Ile Ile Arg Tyr Asn Leu Thr Ser Leu Ala Lys Leu Thr Lys
145                 150                 155                 160

Lys Met Met Lys

<210> SEQ ID NO 15
<211> LENGTH: 191
<212> TYPE: PRT
<213> ORGANISM: Brassica oleracea
<220> FEATURE:
<223> OTHER INFORMATION: wild cabbage Streptomyces cyclase/dehydrase
      family protein, locus tag 40.t00062, GenBank Accession No.
      ABD65175.1

<400> SEQUENCE: 15

Met Pro Ser Gln Leu Thr Pro Glu Glu Arg Ser Glu Leu Ala Gln Ser
1               5                   10                  15

Ile Ala Glu Phe His Thr Tyr His Leu Gly Pro Gly Ser Cys Ser Ser
            20                  25                  30

Leu His Ala Gln Arg Ile His Ala Pro Pro Glu Ile Val Trp Ser Val
        35                  40                  45

Val Arg Arg Phe Asp Lys Pro Gln Thr Tyr Lys His Phe Ile Lys Ser
    50                  55                  60

Cys Ser Val Glu Asp Gly Phe Glu Met Arg Val Gly Cys Thr Arg Ala
65                  70                  75                  80

Val Asn Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Arg Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Thr Glu

-continued

```
                165                 170                 175
Ala Met Ala Arg Asn Ala Gly Asp Gly Ser Gly Ala Gln Val Thr
            180                 185                 190

<210> SEQ ID NO 16
<211> LENGTH: 281
<212> TYPE: PRT
<213> ORGANISM: Brassica oleracea
<220> FEATURE:
<223> OTHER INFORMATION: wild cabbage Streptomyces cyclase/dehydrase
      family protein, locus tag 23.t00047, GenBank Accession No.
      ABD65631.1

<400> SEQUENCE: 16

Met Pro Ser Glu Leu Thr Gln Glu Glu Arg Ser Lys Leu Thr Gln Ser
  1               5                  10                  15

Ile Ser Glu Phe His Thr Tyr His Leu Gly Pro Gly Ser Cys Ser Ser
             20                  25                  30

Leu His Ala Gln Arg Ile His Ala Pro Pro Glu Ile Val Trp Ser Val
         35                  40                  45

Val Arg Gln Phe Asp Lys Pro Gln Thr Tyr Lys His Phe Ile Lys Ser
     50                  55                  60

Cys Ser Val Glu Glu Gly Phe Glu Met Arg Val Gly Cys Thr Arg Asp
 65                  70                  75                  80

Val Ile Val Ile Ser Gly Leu Pro Ala Asn Thr Ser Thr Glu Arg Leu
                 85                  90                  95

Asp Met Leu Asp Asp Glu Arg Arg Val Thr Gly Phe Ser Ile Ile Gly
            100                 105                 110

Gly Glu His Arg Leu Lys Asn Tyr Lys Ser Val Thr Thr Val His Arg
        115                 120                 125

Phe Glu Arg Glu Arg Arg Ile Trp Thr Val Val Leu Glu Ser Tyr Val
    130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Thr Glu
                165                 170                 175

Ala Met Ala Arg Asn Ala Gly Asp Gly Arg Gly Ser Arg Glu Thr Thr
            180                 185                 190

Cys Arg Glu Ser Phe His Leu Ile Thr Ala Phe Glu Lys Gln Arg Gln
        195                 200                 205

Ile Thr Glu Pro Thr Val Tyr Gln Asn Pro Pro Tyr His Thr Gly Met
    210                 215                 220

Thr Pro Glu Pro Arg Thr Ser Thr Val Phe Ile Glu Leu Glu Asp His
225                 230                 235                 240

Arg Thr Leu Pro Gly Asn Leu Thr Pro Thr Thr Glu Glu His Leu Gln
                245                 250                 255

Arg Met Tyr Gln Arg Phe Trp Gly Ile Arg Gln Leu Gly Arg Pro Arg
            260                 265                 270

Gln Ser Phe Gly Glu Arg Gln Ser Ile
        275                 280

<210> SEQ ID NO 17
<211> LENGTH: 453
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00015766001, GenBank Accession No.
```

CAO63410.1

<400> SEQUENCE: 17

| | | | | | | | | | | | | | | |
|---|---|---|---|---|---|---|---|---|---|---|---|---|---|---|
| Met | Gln | Met | Lys | Tyr | Leu | Glu | Gly | Lys | Gln | Asn | Leu | Met | Glu | Lys |
| 1 | | | | 5 | | | | | 10 | | | | | 15 |
| Gly | Glu | Lys | Gln | Cys | Ile | Pro | Met | Asp | Leu | Ala | Val | Arg | Glu | Ala | Gln |
| | | | 20 | | | | | 25 | | | | | 30 | | |
| Phe | Lys | Gly | Ser | Leu | Leu | Asp | Arg | Ile | Thr | Trp | Leu | Glu | Gln | Arg | Leu |
| | | | 35 | | | | | 40 | | | | | 45 | | |
| His | Lys | Leu | Ser | Leu | Gln | Leu | Glu | Thr | Arg | Ser | Lys | Gln | Gln | Pro | His |
| | 50 | | | | | 55 | | | | | 60 | | | | |
| Pro | Ser | Arg | Met | Gln | Thr | Ala | Gly | Glu | Thr | Ser | Ser | Arg | His | Gly | Pro |
| 65 | | | | | 70 | | | | | 75 | | | | | 80 |
| Lys | Lys | Glu | Leu | Ser | Cys | Ser | Phe | Pro | Val | Phe | Ser | Thr | Arg | Asn | His |
| | | | | 85 | | | | | 90 | | | | | 95 | |
| Asn | His | Gly | His | Lys | Gln | Thr | Ser | Gln | Phe | His | Val | Pro | Arg | Phe | Glu |
| | | | 100 | | | | | 105 | | | | | 110 | | |
| Tyr | Gln | Glu | Gly | Gly | Arg | Glu | Asn | Pro | Ala | Val | Val | Ile | Thr | Lys | Leu |
| | | | 115 | | | | | 120 | | | | | 125 | | |
| Thr | Pro | Phe | His | His | Pro | Lys | Ile | Ile | Thr | Ile | Leu | Phe | Pro | Ile | Ser |
| | 130 | | | | | 135 | | | | | 140 | | | | |
| Asn | Tyr | Phe | Ile | Ile | Phe | Phe | Phe | Leu | Thr | Phe | Asp | Thr | Lys | Lys | Gln |
| 145 | | | | | 150 | | | | | 155 | | | | | 160 |
| Tyr | Pro | Leu | Leu | Phe | Pro | Ile | Leu | Pro | Ser | Arg | Phe | Leu | Pro | Ile | Ser |
| | | | | 165 | | | | | 170 | | | | | 175 | |
| His | Leu | Ile | Thr | Gln | Glu | Ile | Glu | Lys | Tyr | Lys | Thr | Ser | Ser | His | Phe |
| | | | 180 | | | | | 185 | | | | | 190 | | |
| Ser | Ser | Pro | Ala | Ser | Leu | Phe | Ala | Ala | Met | Asn | Lys | Ala | Glu | Thr | Ser |
| | | | 195 | | | | | 200 | | | | | 205 | | |
| Ser | Met | Ala | Glu | Ala | Glu | Ser | Glu | Asp | Ser | Glu | Thr | Thr | Thr | Pro | Thr |
| | 210 | | | | | 215 | | | | | 220 | | | | |
| Thr | His | His | Leu | Thr | Ile | Pro | Pro | Gly | Leu | Thr | Gln | Pro | Glu | Phe | Gln |
| 225 | | | | | 230 | | | | | 235 | | | | | 240 |
| Glu | Leu | Ala | His | Ser | Ile | Ser | Glu | Phe | His | Thr | Tyr | Gln | Val | Gly | Pro |
| | | | | 245 | | | | | 250 | | | | | 255 | |
| Gly | Gln | Cys | Ser | Ser | Leu | Leu | Ala | Gln | Arg | Val | His | Ala | Pro | Leu | Pro |
| | | | 260 | | | | | 265 | | | | | 270 | | |
| Thr | Val | Trp | Ser | Val | Val | Arg | Arg | Phe | Asp | Lys | Pro | Gln | Thr | Tyr | Lys |
| | | | 275 | | | | | 280 | | | | | 285 | | |
| His | Phe | Ile | Lys | Ser | Cys | His | Val | Glu | Asp | Gly | Phe | Glu | Met | Arg | Val |
| | 290 | | | | | 295 | | | | | 300 | | | | |
| Gly | Cys | Leu | Arg | Asp | Val | Asn | Val | Ile | Ser | Gly | Leu | Pro | Ala | Glu | Thr |
| 305 | | | | | 310 | | | | | 315 | | | | | 320 |
| Ser | Thr | Glu | Arg | Leu | Asp | Ile | Leu | Asp | Asp | Glu | Arg | His | Val | Thr | Gly |
| | | | | 325 | | | | | 330 | | | | | 335 | |
| Phe | Ser | Ile | Ile | Gly | Gly | Glu | His | Arg | Leu | Arg | Asn | Tyr | Arg | Ser | Val |
| | | | 340 | | | | | 345 | | | | | 350 | | |
| Thr | Thr | Asn | His | Gly | Gly | Glu | Ile | Trp | Thr | Val | Val | Leu | Glu | Ser | Tyr |
| | | | 355 | | | | | 360 | | | | | 365 | | |
| Val | Val | Asp | Met | Pro | Glu | Gly | Asn | Thr | Glu | Glu | Asp | Thr | Arg | Leu | Phe |
| | 370 | | | | | 375 | | | | | 380 | | | | |
| Ala | Asp | Thr | Val | Val | Lys | Leu | Asn | Leu | Gln | Lys | Leu | Ala | Ser | Val | Thr |
| 385 | | | | | 390 | | | | | 395 | | | | | 400 |

```
Glu Val Ser Gln Ser Cys Asn Tyr Pro Cys Gln Phe His Ile Ile Glu
                405                 410                 415

Asn Glu Asp Ile Gln Pro Glu Met Asn Leu Gly Val Leu Thr Thr
            420                 425                 430

Ser Ile Glu Glu Gln Arg Lys Lys Arg Val Val Ala Met Lys Asp
        435                 440                 445

Gly Ser Thr Ser Ser
        450

<210> SEQ ID NO 18
<211> LENGTH: 195
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_033963, GenBank
      Accession No. CAN64657.1
<220> FEATURE:
<221> NAME/KEY: VARIANT
<222> LOCATION: (193)...(193)
<223> OTHER INFORMATION: Xaa = any amino acid

<400> SEQUENCE: 18

Met Ala Glu Ala Glu Ser Glu Asp Ser Glu Thr Thr Thr Pro Thr Thr
1               5                   10                  15

His His Leu Thr Ile Pro Pro Gly Leu Thr Gln Pro Glu Phe Gln Glu
            20                  25                  30

Leu Ala His Ser Ile Ser Glu Phe His Thr Tyr Gln Val Gly Pro Gly
        35                  40                  45

Gln Cys Ser Ser Leu Leu Ala Gln Arg Val His Ala Pro Leu Pro Thr
    50                  55                  60

Val Trp Ser Val Val Arg Arg Phe Asp Lys Pro Gln Thr Tyr Lys His
65                  70                  75                  80

Phe Ile Lys Ser Cys His Val Glu Asp Gly Phe Glu Met Arg Val Gly
                85                  90                  95

Cys Leu Arg Asp Val Asn Val Ile Ser Gly Leu Pro Ala Glu Thr Ser
            100                 105                 110

Thr Glu Arg Leu Asp Ile Leu Asp Asp Glu Arg His Val Thr Gly Phe
        115                 120                 125

Ser Ile Ile Gly Gly Glu His Arg Leu Arg Asn Tyr Arg Ser Val Thr
    130                 135                 140

Thr Val His Glu Tyr Gln Asn His Gly Gly Glu Ile Trp Thr Val Val
145                 150                 155                 160

Leu Glu Ser Tyr Val Val Asp Met Pro Glu Gly Asn Thr Glu Glu Asp
                165                 170                 175

Thr Arg Leu Phe Ala Asp Thr Val Lys Leu Asn Leu Ser Glu Ala
            180                 185                 190

Xaa Arg Arg
        195

<210> SEQ ID NO 19
<211> LENGTH: 217
<212> TYPE: PRT
<213> ORGANISM: Medicago truncatula
<220> FEATURE:
<223> OTHER INFORMATION: barrel medic unknown protein, clone
      MTYFD_FE_FF_FG1G-N-24, GenBank Accession No. ACJ85026.1

<400> SEQUENCE: 19

Met Glu Lys Ala Glu Ser Ser Thr Ala Ser Thr Ser Asp Gln Asp Ser
```

```
                1               5                  10                 15
Asp Glu Asn His Arg Thr Gln His His Leu Thr Leu Pro Ser Gly Leu
                20                 25                 30

Arg Gln His Glu Phe Asp Ser Leu Ile Pro Phe Ile Asn Ser His His
                35                 40                 45

Thr Tyr Leu Ile Gly Pro Asn Gln Cys Ser Thr Leu Leu Ala Gln Arg
    50                 55                 60

Ile His Ala Pro Pro Gln Thr Val Trp Ser Val Val Arg Ser Phe Asp
65                  70                 75                  80

Lys Pro Gln Ile Tyr Lys His Ile Ile Lys Ser Cys Ser Leu Lys Glu
                85                 90                 95

Gly Phe Gln Met Lys Val Gly Cys Thr Arg Asp Val Asn Val Ile Ser
                100                105                110

Gly Leu Pro Ala Ala Thr Ser Thr Glu Arg Leu Asp Val Leu Asp Asp
                115                120                125

Glu Arg Arg Val Thr Gly Phe Ser Ile Ile Gly Gly Glu His Arg Leu
                130                135                140

Lys Asn Tyr Arg Ser Val Thr Ser Val His Gly Phe Gly Asp Gly Asp
145                 150                155                 160

Asn Gly Gly Glu Ile Trp Thr Val Val Leu Glu Ser Tyr Val Val Asp
                165                170                175

Val Pro Glu Gly Asn Thr Glu Glu Asp Thr Arg Leu Phe Ala Asp Thr
                180                185                190

Val Val Lys Leu Asn Leu Gln Lys Leu Ala Ser Val Thr Glu Gly Lys
                195                200                205

Asn Arg Asp Gly Asp Gly Lys Ser His
                210                215

<210> SEQ ID NO 20
<211> LENGTH: 212
<212> TYPE: PRT
<213> ORGANISM: Oryza sativa
<220> FEATURE:
<223> OTHER INFORMATION: rice Japonica Group, cultivar Nipponbare,
      conserved hypothetical protein Os10g0573400, GenBank Accession No.
      NP_00106570.1

<400> SEQUENCE: 20

Met Glu Gln Gln Glu Glu Val Pro Pro Pro Ala Gly Leu Gly Leu
1               5                  10                 15

Thr Ala Glu Glu Tyr Ala Gln Val Arg Ala Thr Val Glu Ala His His
                20                 25                 30

Arg Tyr Ala Val Gly Pro Gly Gln Cys Ser Ser Leu Leu Ala Gln Arg
                35                 40                 45

Ile His Ala Pro Pro Ala Val Trp Ala Val Val Arg Arg Phe Asp
    50                 55                 60

Cys Pro Gln Val Tyr Lys His Phe Ile Arg Ser Cys Val Leu Arg Pro
65                  70                 75                  80

Asp Pro His His Asp Asp Asn Gly Asn Asp Leu Arg Pro Gly Arg Leu
                85                 90                 95

Arg Glu Val Ser Val Ile Ser Gly Leu Pro Ala Ser Thr Ser Thr Glu
                100                105                110

Arg Leu Asp Leu Leu Asp Asp Ala His Arg Val Phe Gly Phe Thr Ile
                115                120                125

Thr Gly Gly Glu His Arg Leu Arg Asn Tyr Arg Ser Val Thr Thr Val
                130                135                140
```

```
Ser Gln Leu Asp Glu Ile Cys Thr Leu Val Leu Glu Ser Tyr Ile Val
145                 150                 155                 160

Asp Val Pro Asp Gly Asn Thr Glu Asp Asp Thr Arg Leu Phe Ala Asp
                165                 170                 175

Thr Val Ile Arg Leu Asn Leu Gln Lys Leu Lys Ser Val Ser Glu Ala
            180                 185                 190

Asn Ala Asn Ala Ala Ala Ala Ala Ala Pro Pro Pro Pro Pro
        195                 200                 205

Ala Ala Ala Glu
    210
```

<210> SEQ ID NO 21
<211> LENGTH: 212
<212> TYPE: PRT
<213> ORGANISM: Zea mays
<220> FEATURE:
<223> OTHER INFORMATION: maize cyclase/dehydrase family protein, clone 306819, GenBank Accession No. ACG40002.1

<400> SEQUENCE: 21

```
Met Asp Gln Gln Gly Ala Gly Gly Asp Ala Glu Val Pro Ala Gly Leu
1               5                   10                  15

Gly Leu Thr Ala Ala Glu Tyr Glu Gln Leu Arg Ser Thr Val Asp Ala
            20                  25                  30

His His Arg Tyr Ala Val Gly Glu Gly Gln Cys Ser Ser Leu Leu Ala
        35                  40                  45

Gln Arg Ile His Ala Pro Pro Glu Ala Val Trp Ala Val Val Arg Arg
50                  55                  60

Phe Asp Cys Pro Gln Val Tyr Lys His Phe Ile Arg Ser Cys Ala Leu
65                  70                  75                  80

Arg Pro Asp Pro Glu Ala Gly Asp Ala Leu Cys Pro Gly Arg Leu Arg
                85                  90                  95

Glu Val Ser Val Ile Ser Gly Leu Pro Ala Ser Thr Ser Thr Glu Arg
            100                 105                 110

Leu Asp Leu Leu Asp Asp Ala Ala Arg Val Phe Gly Phe Ser Ile Thr
        115                 120                 125

Gly Gly Glu His Arg Leu Arg Asn Tyr Arg Ser Val Thr Thr Val Ser
130                 135                 140

Glu Leu Ala Val Pro Ala Ile Cys Thr Val Val Leu Glu Ser Tyr Val
145                 150                 155                 160

Val Asp Val Pro Asp Gly Asn Thr Glu Asp Asp Thr Arg Leu Phe Ala
                165                 170                 175

Asp Thr Val Ile Arg Leu Asn Leu Gln Lys Leu Lys Ser Val Ala Glu
            180                 185                 190

Ala Asn Ala Ala Glu Ala Ala Ala Thr Thr Asn Ser Val Leu Leu Pro
        195                 200                 205

Arg Pro Ala Glu
    210
```

<210> SEQ ID NO 22
<211> LENGTH: 212
<212> TYPE: PRT
<213> ORGANISM: Zea mays
<220> FEATURE:
<223> OTHER INFORMATION: maize cyclase/dehydrase family protein, clone 241996, GenBank Accession No. ACG34473.1
<220> FEATURE:
<221> NAME/KEY: VARIANT

```
<222> LOCATION: (11)...(11)
<223> OTHER INFORMATION: Xaa = any amino acid

<400> SEQUENCE: 22

Met Asp Gln Gln Gly Ala Gly Asp Ala Xaa Val Pro Ala Gly Leu
1               5                   10                  15

Gly Leu Thr Ala Ala Glu Tyr Glu Gln Leu Arg Ser Thr Val Asp Ala
            20                  25                  30

His His Arg Tyr Ala Val Gly Glu Gly Gln Cys Ser Ser Leu Leu Ala
            35                  40                  45

Gln Arg Ile His Ala Pro Pro Glu Ala Val Trp Ala Val Arg Arg
50                  55                  60

Phe Asp Cys Pro Gln Val Tyr Lys His Phe Ile Arg Ser Cys Ala Leu
65                  70                  75                  80

Arg Pro Asp Pro Glu Ala Gly Asp Ala Leu Cys Pro Gly Arg Leu Arg
                85                  90                  95

Glu Val Ser Val Ile Ser Gly Leu Pro Ala Ser Thr Ser Thr Glu Arg
            100                 105                 110

Leu Asp Leu Leu Asp Asp Ala Ala Arg Val Phe Gly Phe Ser Ile Thr
            115                 120                 125

Gly Gly Glu His Arg Leu Arg Asn Tyr Arg Ser Val Thr Val Ser
130                 135                 140

Glu Leu Ala Asp Pro Ala Ile Cys Thr Val Val Leu Glu Ser Tyr Val
145                 150                 155                 160

Val Asp Val Pro Asp Gly Asn Thr Glu Asp Thr Arg Leu Phe Ala
                165                 170                 175

Asp Thr Val Ile Arg Leu Asn Leu Gln Lys Leu Lys Ser Val Thr Glu
            180                 185                 190

Ala Asn Ala Ala Glu Ala Ala Thr Thr Asn Ser Val Leu Leu Pro
            195                 200                 205

Arg Pro Ala Glu
    210

<210> SEQ ID NO 23
<211> LENGTH: 233
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00032173001, GenBank Accession No.
      CAO43790.1

<400> SEQUENCE: 23

Met Asp Pro His His His His Gly Leu Thr Glu Glu Glu Phe Arg Ala
1               5                   10                  15

Leu Glu Pro Ile Ile Gln Asn Tyr His Thr Phe Glu Pro Ser Pro Asn
            20                  25                  30

Thr Cys Thr Ser Leu Ile Thr Gln Lys Ile Asp Ala Pro Ala Gln Val
            35                  40                  45

Val Trp Pro Phe Val Arg Ser Phe Glu Asn Pro Gln Lys Tyr Lys His
50                  55                  60

Phe Ile Lys Asp Cys Thr Met Arg Gly Asp Gly Gly Val Gly Ser Ile
65                  70                  75                  80

Arg Glu Val Thr Val Val Ser Gly Leu Pro Ala Ser Thr Ser Thr Glu
                85                  90                  95

Arg Leu Glu Ile Leu Asp Asp Glu Lys His Ile Leu Ser Phe Arg Val
            100                 105                 110
```

```
Val Gly Gly Glu His Arg Leu Asn Asn Tyr Arg Ser Val Thr Ser Val
        115                 120                 125

Asn Asp Phe Ser Lys Glu Gly Lys Asp Tyr Thr Ile Val Leu Glu Ser
130                 135                 140

Tyr Ile Val Asp Ile Pro Glu Gly Asn Thr Gly Glu Asp Thr Lys Met
145                 150                 155                 160

Phe Val Asp Thr Val Val Lys Leu Asn Leu Gln Lys Leu Ala Val Val
                165                 170                 175

Ala Ile Thr Ser Leu His Glu Asn Glu Glu Ile Ala Asp Asn Glu Gly
                180                 185                 190

Pro Ser Arg Glu Ile Ser Leu Gln Ser Glu Thr Glu Ser Ala Glu Arg
            195                 200                 205

Gly Asp Glu Arg Arg Asp Gly Asp Gly Pro Ser Lys Ala Cys Asn Arg
210                 215                 220

Asn Glu Trp His Cys Thr Thr Lys Glu
225                 230
```

<210> SEQ ID NO 24
<211> LENGTH: 207
<212> TYPE: PRT
<213> ORGANISM: Oryza sativa
<220> FEATURE:
<223> OTHER INFORMATION: rice Japonica Group, cultivar Nipponbare,
      Bet v I allergen-like protein, clone P0495C02.29, GenBank
      Accession No. BAD25659.1

<400> SEQUENCE: 24

```
Met Glu Pro His Met Glu Arg Ala Leu Arg Ala Val Ala Ser Glu
1               5                   10                  15

Ala Glu Arg Arg Glu Leu Glu Gly Val Val Arg Ala His His Thr Phe
            20                  25                  30

Pro Ala Ala Glu Arg Ala Ala Gly Pro Gly Arg Arg Pro Thr Cys Thr
            35                  40                  45

Ser Leu Val Ala Gln Arg Val Asp Ala Pro Leu Ala Ala Val Trp Pro
50                  55                  60

Ile Val Arg Gly Phe Ala Asn Pro Gln Arg Tyr Lys His Phe Ile Lys
65                  70                  75                  80

Ser Cys Glu Leu Ala Ala Gly Asp Gly Ala Thr Val Gly Ser Val Arg
                85                  90                  95

Glu Val Ala Val Val Ser Gly Leu Pro Ala Ser Thr Ser Thr Glu Arg
            100                 105                 110

Leu Glu Ile Leu Asp Asp Asp Arg His Val Leu Ser Phe Arg Val Val
            115                 120                 125

Gly Gly Asp His Arg Leu Arg Asn Tyr Arg Ser Val Thr Ser Val Thr
130                 135                 140

Glu Phe Ser Ser Pro Ser Ser Pro Arg Pro Tyr Cys Val Val Val
145                 150                 155                 160

Glu Ser Tyr Val Val Asp Val Pro Glu Gly Asn Thr Glu Glu Asp Thr
                165                 170                 175

Arg Met Phe Thr Asp Thr Val Val Lys Leu Asn Leu Gln Lys Leu Ala
            180                 185                 190

Ala Val Ala Thr Ser Ser Ser Pro Ala Ala Gly Asn His His
            195                 200                 205
```

<210> SEQ ID NO 25
<211> LENGTH: 210

```
<212> TYPE: PRT
<213> ORGANISM: Oryza sativa
<220> FEATURE:
<223> OTHER INFORMATION: rice Indica Group, cultivar 93-11,
      hypothetical protein OsI_06433, GenBank Accession No. EAY85077.1

<400> SEQUENCE: 25

Met Glu Pro His Met Glu Arg Ala Leu Arg Glu Ala Val Ala Ser Glu
 1               5                  10                  15

Ala Glu Arg Arg Glu Leu Glu Gly Val Val Arg Ala His His Thr Phe
            20                  25                  30

Pro Ala Ala Glu Arg Ala Ala Gly Pro Gly Arg Arg Pro Thr Cys Thr
        35                  40                  45

Ser Leu Val Ala Gln Arg Val Asp Ala Pro Leu Ala Ala Val Trp Pro
    50                  55                  60

Ile Val Arg Gly Phe Ala Asn Pro Gln Arg Tyr Lys His Phe Ile Lys
65                  70                  75                  80

Ser Cys Glu Leu Ala Ala Gly Asp Gly Ala Thr Val Gly Ser Val Arg
                85                  90                  95

Glu Val Ala Val Val Ser Gly Leu Pro Ala Ser Thr Ser Thr Glu Arg
            100                 105                 110

Leu Glu Ile Leu Asp Asp Asp Arg His Val Leu Ser Phe Arg Val Val
        115                 120                 125

Gly Gly Asp His Arg Leu Arg Asn Tyr Arg Ser Val Thr Ser Val Thr
    130                 135                 140

Glu Phe Ser Ser Pro Ser Ser Pro Pro Ser Pro Arg Pro Tyr Cys
145                 150                 155                 160

Val Val Val Glu Ser Tyr Val Val Asp Val Pro Glu Gly Asn Thr Glu
                165                 170                 175

Glu Asp Thr Arg Met Phe Thr Asp Thr Val Val Lys Leu Asn Leu Gln
            180                 185                 190

Lys Leu Ala Ala Val Ala Thr Ser Ser Ser Pro Pro Ala Ala Gly Asn
        195                 200                 205

His His
    210

<210> SEQ ID NO 26
<211> LENGTH: 200
<212> TYPE: PRT
<213> ORGANISM: Zea mays
<220> FEATURE:
<223> OTHER INFORMATION: maize strain B73 unknown protein, clone
      ZM_BFb0151H07, GenBank Accession No. ACF82013.1

<400> SEQUENCE: 26

Met Pro Tyr Thr Ala Pro Arg Pro Ser Pro Gln Gln His Ser Arg Val
 1               5                  10                  15

Leu Ser Gly Gly Gly Ala Lys Ala Ala Ser His Gly Ala Ser Cys Ala
            20                  25                  30

Ala Val Pro Ala Glu Val Ala Arg His His Glu His Ala Ala Arg Ala
        35                  40                  45

Gly Gln Cys Cys Ser Ala Val Val Gln Ala Ile Ala Ala Pro Val Gly
    50                  55                  60

Ala Val Trp Ser Val Val Arg Arg Phe Asp Arg Pro Gln Ala Tyr Lys
65                  70                  75                  80

His Phe Ile Arg Ser Cys Arg Leu Val Gly Gly Asp Val Ala Val
                85                  90                  95
```

```
Gly Ser Val Arg Glu Val Arg Val Val Ser Gly Leu Pro Ala Thr Ser
                100                 105                 110

Ser Arg Glu Arg Leu Glu Ile Leu Asp Asp Glu Arg Val Leu Ser
        115                 120                 125

Phe Arg Val Val Gly Glu His Arg Leu Ala Asn Tyr Arg Ser Val
    130                 135                 140

Thr Thr Val His Glu Ala Gly Ala Gly Ala Gly Thr Gly Thr Val Val
145                 150                 155                 160

Val Glu Ser Tyr Val Asp Val Pro His Gly Asn Thr Ala Asp Glu
                165                 170                 175

Thr Arg Val Phe Val Asp Thr Ile Val Arg Cys Asn Leu Gln Ser Leu
        180                 185                 190

Ala Arg Thr Ala Glu Arg Leu Ala
        195                 200

<210> SEQ ID NO 27
<211> LENGTH: 215
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00037390001, GenBank Accession No.
      CAO48777.1

<400> SEQUENCE: 27

Met Pro Ser Asn Pro Lys Ser Ser Leu Val Val His Arg Ile Asn
 1               5                  10                  15

Ser Pro Asn Ser Ile Thr Thr Ala Thr Thr Ala Ser Ala Ala Asn
            20                  25                  30

Asn His Asn Thr Ser Thr Met Pro Pro His Lys Gln Val Pro Asp Ala
        35                  40                  45

Val Ser Arg His His Thr His Val Gly Pro Asn Gln Cys Cys Ser
 50                 55                  60

Ala Val Val Gln Gln Ile Ala Ala Pro Val Ser Thr Val Trp Ser Val
65                  70                  75                  80

Val Arg Arg Phe Asp Asn Pro Gln Ala Tyr Lys His Phe Val Lys Ser
                85                  90                  95

Cys His Val Val Val Gly Asp Gly Asp Val Gly Thr Leu Arg Glu Val
            100                 105                 110

His Val Ile Ser Gly Leu Pro Ala Ala Asn Ser Thr Glu Arg Leu Glu
        115                 120                 125

Ile Leu Asp Asp Glu Arg His Val Leu Ser Phe Ser Val Ile Gly Gly
    130                 135                 140

Asp His Arg Leu Ser Asn Tyr Arg Ser Val Thr Thr Leu His Pro Ser
145                 150                 155                 160

Pro Ser Ser Thr Gly Thr Val Val Leu Glu Ser Tyr Val Val Asp Ile
                165                 170                 175

Pro Pro Gly Asn Thr Lys Glu Asp Thr Cys Val Phe Val Asp Thr Ile
            180                 185                 190

Val Arg Cys Asn Leu Gln Ser Leu Ala Gln Ile Ala Glu Asn Ala Ala
        195                 200                 205

Gly Cys Lys Arg Ser Ser Ser
    210                 215

<210> SEQ ID NO 28
<211> LENGTH: 213
<212> TYPE: PRT
```

<213> ORGANISM: Nicotiana tabacum
<220> FEATURE:
<223> OTHER INFORMATION: tobacco hypothetical protein, gene c17, GenBank
      Accession No. CAI84653.1

<400> SEQUENCE: 28

```
Met Pro Pro Ser Ser Pro Asp Ser Ser Val Leu Leu Gln Arg Ile Ser
 1               5                   10                  15

Ser Asn Thr Thr Pro Asp Phe Ala Cys Lys Gln Ser Gln Gln Leu Gln
            20                  25                  30

Arg Arg Thr Met Pro Ile Pro Cys Thr Thr Gln Val Pro Asp Ser Val
        35                  40                  45

Val Arg Phe His Thr His Pro Val Gly Pro Asn Gln Cys Cys Ser Ala
 50                  55                  60

Val Ile Gln Arg Ile Ser Ala Pro Val Ser Thr Val Trp Ser Val Val
 65                  70                  75                  80

Arg Arg Phe Asp Asn Pro Gln Ala Tyr Lys His Phe Val Lys Ser Cys
                85                  90                  95

His Val Ile Val Gly Asp Gly Asp Val Gly Thr Leu Arg Glu Val Arg
            100                 105                 110

Val Ile Ser Gly Leu Pro Ala Ala Ser Ser Thr Glu Arg Leu Glu Ile
        115                 120                 125

Leu Asp Asp Glu Arg His Val Ile Ser Phe Ser Val Val Gly Gly Asp
130                 135                 140

His Arg Leu Ala Asn Tyr Arg Ser Val Thr Thr Leu His Pro Glu Pro
145                 150                 155                 160

Ser Gly Asp Gly Thr Thr Ile Val Val Glu Ser Tyr Val Val Asp Val
                165                 170                 175

Pro Pro Gly Asn Thr Arg Asp Glu Thr Cys Val Phe Val Asp Thr Ile
            180                 185                 190

Val Lys Cys Asn Leu Thr Ser Leu Ser Gln Ile Ala Val Asn Val Asn
        195                 200                 205

Arg Arg Lys Asp Ser
    210
```

<210> SEQ ID NO 29
<211> LENGTH: 208
<212> TYPE: PRT
<213> ORGANISM: Oryza sativa
<220> FEATURE:
<223> OTHER INFORMATION: rice Indica Group, cultivar 93-11,
      hypothetical protein OsI_04285, GenBank Accession No. EAY76350.1

<400> SEQUENCE: 29

```
Met Pro Tyr Ala Ala Val Arg Pro Ser Pro Pro Gln Leu Ser Arg
 1               5                   10                  15

Pro Ile Gly Ser Gly Ala Gly Gly Lys Ala Cys Pro Ala Val Pro
            20                  25                  30

Cys Glu Val Ala Arg Tyr His Glu His Ala Val Gly Ala Gly Gln Cys
        35                  40                  45

Cys Ser Thr Val Val Gln Ala Ile Ala Ala Pro Ala Asp Ala Val Trp
 50                  55                  60

Ser Val Val Arg Arg Phe Asp Arg Pro Gln Ala Tyr Lys Lys Phe Ile
 65                  70                  75                  80

Lys Ser Cys Arg Leu Val Asp Gly Asp Gly Gly Glu Val Gly Ser Val
                85                  90                  95

Arg Glu Val Arg Val Val Ser Gly Leu Pro Ala Thr Ser Ser Arg Glu
```

```
                100                 105                 110
Arg Leu Glu Val Leu Asp Asp Arg Arg Val Leu Ser Phe Arg Ile
            115                 120                 125

Val Gly Gly Glu His Arg Leu Ala Asn Tyr Arg Ser Val Thr Thr Val
        130                 135                 140

His Glu Ala Ala Ala Pro Ala Met Ala Val Val Glu Ser Tyr Val
145                 150                 155                 160

Val Asp Val Pro Pro Gly Asn Thr Trp Glu Glu Thr Arg Val Phe Val
                165                 170                 175

Asp Thr Ile Val Arg Cys Asn Leu Gln Ser Leu Ala Arg Thr Val Glu
            180                 185                 190

Arg Leu Ala Pro Glu Ala Pro Arg Ala Asn Gly Ser Ile Asp His Ala
        195                 200                 205

<210> SEQ ID NO 30
<211> LENGTH: 208
<212> TYPE: PRT
<213> ORGANISM: Oryza sativa
<220> FEATURE:
<223> OTHER INFORMATION: rice Japonica Group, cultivar Nipponbare,
      Bet v I allergen-like protein, gene B1088C09.11, clone B1088C09,
      GenBank Accession No. BAB68102.1

<400> SEQUENCE: 30

Met Pro Tyr Ala Ala Val Arg Pro Ser Pro Pro Gln Leu Ser Arg
1               5                   10                  15

Pro Ile Gly Ser Gly Ala Gly Gly Lys Ala Cys Pro Ala Val Pro
            20                  25                  30

Cys Glu Val Ala Arg Tyr His Glu His Ala Val Gly Ala Gly Gln Cys
        35                  40                  45

Phe Ser Thr Val Val Gln Ala Ile Ala Ala Pro Ala Asp Ala Val Trp
    50                  55                  60

Ser Val Val Arg Arg Phe Asp Arg Pro Gln Ala Tyr Lys Lys Phe Ile
65                  70                  75                  80

Lys Ser Cys Arg Leu Val Asp Gly Asp Gly Gly Glu Val Gly Ser Val
                85                  90                  95

Arg Glu Val Arg Val Val Ser Gly Leu Pro Ala Thr Ser Ser Arg Glu
            100                 105                 110

Arg Leu Glu Val Leu Asp Asp Arg Arg Val Leu Ser Phe Arg Ile
            115                 120                 125

Val Gly Gly Glu His Arg Leu Ala Asn Tyr Arg Ser Val Thr Thr Val
        130                 135                 140

His Glu Ala Ala Ala Pro Ala Met Ala Val Val Glu Ser Tyr Val
145                 150                 155                 160

Val Asp Val Pro Pro Gly Asn Thr Trp Glu Glu Thr Arg Val Phe Val
                165                 170                 175

Asp Thr Ile Val Arg Cys Asn Leu Gln Ser Leu Ala Arg Thr Val Glu
            180                 185                 190

Arg Leu Ala Pro Glu Ala Pro Arg Ala Asn Gly Ser Ile Asp His Ala
        195                 200                 205

<210> SEQ ID NO 31
<211> LENGTH: 213
<212> TYPE: PRT
<213> ORGANISM: Picea sitchensis
<220> FEATURE:
<223> OTHER INFORMATION: Sitka spruce cultivar FB3-425, unknown protein,
      clone WS0276_P02, GenBank Accession No. ABK22940.1
```

<400> SEQUENCE: 31

```
Met Asp Ile Ile Ala Gly Phe Asp Gln Leu Ser Phe Arg Leu Ser Gly
  1               5                  10                  15

Ala Ser Lys Gln Ile Thr Lys Thr Gly Ala Val Gln Tyr Leu Lys Gly
             20                  25                  30

Glu Glu Gly Tyr Gly Glu Trp Leu Lys Glu Val Met Gly Arg Tyr His
         35                  40                  45

Tyr His Ser His Asp Gly Ala Arg Glu Cys Arg Cys Ser Ser Val Val
     50                  55                  60

Val Gln Gln Val Glu Ala Pro Val Ser Val Val Trp Ser Leu Val Arg
 65                  70                  75                  80

Arg Phe Asp Gln Pro Gln Val Tyr Lys His Phe Val Ser Asn Cys Phe
                 85                  90                  95

Met Arg Gly Asp Leu Lys Val Gly Cys Leu Arg Glu Val Arg Val Val
            100                 105                 110

Ser Gly Leu Pro Ala Ala Thr Ser Thr Glu Arg Leu Asp Ile Leu Asp
        115                 120                 125

Glu Glu Arg His Ile Leu Ser Phe Ser Ile Val Gly Gly Asp His Arg
    130                 135                 140

Leu Asn Asn Tyr Arg Ser Ile Thr Thr Leu His Glu Thr Leu Ile Asn
145                 150                 155                 160

Gly Lys Pro Gly Thr Ile Val Ile Glu Ser Tyr Val Leu Asp Val Pro
                165                 170                 175

His Gly Asn Thr Lys Glu Glu Thr Cys Leu Phe Val Asp Thr Ile Val
            180                 185                 190

Lys Cys Asn Leu Gln Ser Leu Ala His Val Ser Asn His Leu Asn Ser
        195                 200                 205

Thr His Arg Cys Leu
        210
```

<210> SEQ ID NO 32
<211> LENGTH: 207
<212> TYPE: PRT
<213> ORGANISM: Oryza sativa
<220> FEATURE:
<223> OTHER INFORMATION: rice Japonica Group, cultivar Nipponbare,
      hypothetical protein Os06g0562200, Bet v I allergen family
      protein, GenBank Accession No. NP_001057874.1

<400> SEQUENCE: 32

```
Met Glu Ala His Val Glu Arg Ala Leu Arg Glu Gly Leu Thr Glu Glu
  1               5                  10                  15

Glu Arg Ala Ala Leu Glu Pro Ala Val Met Ala His His Thr Phe Pro
             20                  25                  30

Pro Ser Thr Thr Thr Ala Thr Thr Ala Ala Thr Cys Thr Ser Leu
         35                  40                  45

Val Thr Gln Arg Val Ala Ala Pro Val Arg Ala Val Trp Pro Ile Val
 50                  55                  60

Arg Ser Phe Gly Asn Pro Gln Arg Tyr Lys His Phe Val Arg Thr Cys
 65                  70                  75                  80

Ala Leu Ala Ala Gly Asp Gly Ala Ser Val Gly Ser Val Arg Glu Val
                 85                  90                  95

Thr Val Val Ser Gly Leu Pro Ala Ser Thr Ser Thr Glu Arg Leu Glu
            100                 105                 110

Met Leu Asp Asp Asp Arg His Ile Ile Ser Phe Arg Val Val Gly Gly
```

```
              115                 120                 125
Gln His Arg Leu Arg Asn Tyr Arg Ser Val Thr Ser Val Thr Glu Phe
        130                 135                 140

Gln Pro Pro Ala Ala Gly Pro Gly Pro Ala Pro Pro Tyr Cys Val Val
145                 150                 155                 160

Val Glu Ser Tyr Val Asp Val Pro Asp Gly Asn Thr Ala Glu Asp
                165                 170                 175

Thr Arg Met Phe Thr Asp Thr Val Lys Leu Asn Leu Gln Met Leu
            180                 185                 190

Ala Ala Val Ala Glu Asp Ser Ser Ala Ser Arg Arg Arg Asp
        195                 200                 205

<210> SEQ ID NO 33
<211> LENGTH: 216
<212> TYPE: PRT
<213> ORGANISM: Oryza sativa
<220> FEATURE:
<223> OTHER INFORMATION: rice Japonica Group, cultivar Nipponbare,
      hypothetical protein Os05g0473000, Streptomyces cyclase/dehydrase
      family protein, GenBank Accession No. NP_001055819.1

<400> SEQUENCE: 33

Met Pro Tyr Thr Ala Pro Arg Pro Ser Pro Pro Gln His Ser Arg Ile
1               5                   10                  15

Gly Gly Cys Gly Gly Gly Val Leu Lys Ala Ala Gly Ala Ala Gly
            20                  25                  30

His Ala Ala Ser Cys Val Ala Val Pro Ala Glu Val Ala Arg His His
        35                  40                  45

Glu His Ala Ala Gly Val Gly Gln Cys Cys Ser Ala Val Val Gln Ala
    50                  55                  60

Ile Ala Ala Pro Val Asp Ala Val Trp Ser Val Val Arg Arg Phe Asp
65                  70                  75                  80

Arg Pro Gln Ala Tyr Lys His Phe Ile Arg Ser Cys Arg Leu Leu Asp
                85                  90                  95

Gly Asp Gly Asp Gly Gly Ala Val Ala Val Gly Ser Val Arg Glu Val
            100                 105                 110

Arg Val Val Ser Gly Leu Pro Ala Thr Ser Ser Arg Glu Arg Leu Glu
        115                 120                 125

Ile Leu Asp Asp Glu Arg Arg Val Leu Ser Phe Arg Val Val Gly Gly
    130                 135                 140

Glu His Arg Leu Ser Asn Tyr Arg Ser Val Thr Thr Val His Glu Thr
145                 150                 155                 160

Ala Ala Gly Ala Ala Ala Val Val Val Glu Ser Tyr Val Val Asp
                165                 170                 175

Val Pro His Gly Asn Thr Ala Asp Glu Thr Arg Met Phe Val Asp Thr
            180                 185                 190

Ile Val Arg Cys Asn Leu Gln Ser Leu Ala Arg Thr Ala Glu Gln Leu
        195                 200                 205

Ala Leu Ala Ala Pro Arg Ala Ala
    210                 215

<210> SEQ ID NO 34
<211> LENGTH: 212
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00029365001, GenBank Accession No.
```

CAO41436.1

<400> SEQUENCE: 34

```
Met Pro Ser Ser Leu Gln Leu His Arg Ile Asn Asn Ile Asp Pro Thr
 1               5                  10                  15

Thr Val Ala Val Ala Ala Thr Ala Ala Val Asn Cys His Lys Gln Ser
            20                  25                  30

Arg Thr Pro Leu Arg Cys Ala Thr Pro Val Pro Asp Ala Val Ala Ser
        35                  40                  45

Tyr His Ala His Ala Val Gly Pro His Gln Cys Cys Ser Met Val Val
    50                  55                  60

Gln Thr Thr Ala Ala Ala Leu Pro Thr Val Trp Ser Val Val Arg Arg
65                  70                  75                  80

Phe Asp Asn Pro Gln Ala Tyr Lys His Phe Leu Lys Ser Cys His Val
                85                  90                  95

Ile Phe Gly Asp Gly Asp Ile Gly Thr Leu Arg Glu Val His Val Val
            100                 105                 110

Ser Gly Leu Pro Ala Glu Ser Ser Thr Glu Arg Leu Glu Ile Leu Asp
        115                 120                 125

Asp Glu Arg His Val Leu Ser Phe Ser Val Val Gly Gly Asp His Arg
    130                 135                 140

Leu Cys Asn Tyr Arg Ser Val Thr Thr Leu His Pro Ser Pro Thr Gly
145                 150                 155                 160

Thr Gly Thr Val Val Val Glu Ser Tyr Val Val Asp Ile Pro Pro Gly
                165                 170                 175

Asn Thr Lys Glu Asp Thr Cys Val Phe Val Asp Thr Ile Val Lys Cys
            180                 185                 190

Asn Leu Gln Ser Leu Ala Gln Met Ser Glu Lys Leu Thr Asn Asn Asn
        195                 200                 205

Arg Asn Ser Ser
    210
```

<210> SEQ ID NO 35
<211> LENGTH: 218
<212> TYPE: PRT
<213> ORGANISM: Zea mays
<220> FEATURE:
<223> OTHER INFORMATION: maize cyclase/dehydrase family protein, clone
      1678999, GenBank Accession No. ACG30334.1

<400> SEQUENCE: 35

```
Met Pro Cys Leu Gln Ala Ser Ser Pro Gly Ser Met Pro Tyr Gln His
 1               5                  10                  15

His Gly Arg Gly Val Gly Cys Ala Ala Glu Ala Gly Ala Ala Val Gly
            20                  25                  30

Ala Ser Ala Gly Thr Gly Thr Arg Cys Gly Ala His Asp Gly Glu Val
        35                  40                  45

Pro Ala Glu Ala Ala Arg His His Glu His Ala Ala Pro Gly Pro Gly
    50                  55                  60

Arg Cys Cys Ser Ala Val Val Gln Arg Val Ala Ala Pro Ala Glu Ala
65                  70                  75                  80

Val Trp Ser Val Val Arg Arg Phe Asp Gln Pro Gln Ala Tyr Lys Arg
                85                  90                  95

Phe Val Arg Ser Cys Ala Leu Leu Ala Gly Asp Gly Gly Val Gly Thr
            100                 105                 110

Leu Arg Glu Val Arg Val Val Ser Gly Leu Pro Ala Ala Ser Ser Arg
```

```
              115                 120                 125
Glu Arg Leu Glu Val Leu Asp Asp Glu Ser His Val Leu Ser Phe Arg
        130                 135                 140

Val Val Gly Gly Glu His Arg Leu Gln Asn Tyr Leu Ser Val Thr Thr
145                 150                 155                 160

Val His Pro Ser Pro Ala Ala Pro Asp Ala Thr Val Val Val Glu
                165                 170                 175

Ser Tyr Val Val Asp Val Pro Pro Gly Asn Thr Pro Glu Asp Thr Arg
            180                 185                 190

Val Phe Val Asp Thr Ile Val Lys Cys Asn Leu Gln Ser Leu Ala Thr
                195                 200                 205

Thr Ala Glu Lys Leu Ala Leu Ala Ala Val
            210                 215
```

<210> SEQ ID NO 36
<211> LENGTH: 179
<212> TYPE: PRT
<213> ORGANISM: Physcomitrella patens
<220> FEATURE:
<223> OTHER INFORMATION: Physcomitrella patens subsp. patens moss,
      ecotype Gransden 2004, hypothetical protein, predicted protein,
      locus tag PHYPADRAFT_222359, GenBank Accession No. XP_001778048.1

<400> SEQUENCE: 36

```
Met Gln Thr Lys Gly Arg Gln Ala Asp Phe Gln Thr Leu Leu Glu Gly
 1               5                  10                  15

Gln Gln Asp Leu Ile Cys Arg Phe His Arg His Glu Leu Gln Pro His
            20                  25                  30

Gln Cys Gly Ser Ile Leu Leu Gln Leu Ile Lys Ala Pro Val Glu Thr
        35                  40                  45

Val Trp Ser Val Ala Arg Ser Phe Asp Lys Pro Gln Val Tyr Lys Arg
    50                  55                  60

Phe Ile Gln Thr Cys Glu Ile Ile Glu Gly Asp Gly Val Gly Ser
65                  70                  75                  80

Ile Arg Glu Val Arg Leu Val Ser Ser Ile Pro Ala Thr Ser Ser Ile
                85                  90                  95

Glu Arg Leu Glu Ile Leu Asp Asp Glu His Ile Ile Ser Phe Arg
            100                 105                 110

Val Leu Gly Gly His Arg Leu Gln Asn Tyr Trp Ser Val Thr Ser
        115                 120                 125

Leu His Ser His Glu Ile Asp Gly Gln Met Gly Thr Leu Val Leu Glu
130                 135                 140

Ser Tyr Val Val Asp Ile Pro Glu Gly Asn Thr Arg Glu Glu Thr His
145                 150                 155                 160

Met Phe Val Asp Thr Val Val Arg Cys Asn Leu Lys Ala Leu Ala Gln
                165                 170                 175

Val Ser Glu
```

<210> SEQ ID NO 37
<211> LENGTH: 229
<212> TYPE: PRT
<213> ORGANISM: Oryza sativa
<220> FEATURE:
<223> OTHER INFORMATION: rice Indica Group, cultivar 93-11, hypothetical
      protein OsI_11160, GenBank Accession No. EAY89631.1

<400> SEQUENCE: 37

Met Pro Cys Ile Pro Ala Ser Ser Pro Gly Ile Pro His Gln His Gln

```
            1               5                  10                 15
His Gln His His Arg Ala Leu Ala Gly Val Gly Met Ala Val Gly Cys
                20                 25                 30

Ala Ala Glu Ala Ala Val Ala Ala Ala Gly Val Ala Gly Thr Arg Cys
                35                 40                 45

Gly Ala His Asp Gly Glu Val Pro Met Glu Val Ala Arg His His Glu
            50                 55                 60

His Ala Glu Pro Gly Ser Gly Arg Cys Cys Ser Ala Val Val Gln His
65                  70                 75                 80

Val Ala Ala Pro Ala Pro Ala Val Trp Ser Val Val Arg Arg Phe Asp
                85                 90                 95

Gln Pro Gln Ala Tyr Lys Arg Phe Val Arg Ser Cys Ala Leu Leu Ala
                100                105                110

Gly Asp Gly Gly Val Gly Thr Leu Arg Glu Val Arg Val Val Ser Gly
                115                120                125

Leu Pro Ala Ala Ser Ser Arg Glu Arg Leu Glu Ile Leu Asp Asp Glu
            130                135                140

Ser His Val Leu Ser Phe Arg Val Val Gly Gly Glu His Arg Leu Lys
145                 150                155                160

Asn Tyr Leu Ser Val Thr Thr Val His Pro Ser Pro Ser Ala Pro Thr
                165                170                175

Ala Ala Thr Val Val Val Glu Ser Tyr Val Val Asp Val Pro Pro Gly
                180                185                190

Asn Thr Pro Glu Asp Thr Arg Val Phe Val Asp Thr Ile Val Lys Cys
                195                200                205

Asn Leu Gln Ser Leu Ala Lys Thr Ala Glu Lys Leu Ala Ala Gly Ala
            210                215                220

Arg Ala Ala Gly Ser
225

<210> SEQ ID NO 38
<211> LENGTH: 229
<212> TYPE: PRT
<213> ORGANISM: Oryza sativa
<220> FEATURE:
<223> OTHER INFORMATION: rice Japonica Group, cultivar Nipponbare,
      hypothetical protein Os03g0297600, Streptomyces cyclase/dehydrase
      family protein, GenBank Accession No. NP_001049838.1

<400> SEQUENCE: 38

Met Pro Cys Ile Pro Ala Ser Ser Pro Gly Ile Pro His Gln His Gln
1               5                  10                 15

His Gln His His Arg Ala Leu Ala Gly Val Gly Met Ala Val Gly Cys
                20                 25                 30

Ala Ala Glu Ala Ala Val Ala Ala Ala Gly Val Ala Gly Thr Arg Cys
                35                 40                 45

Gly Ala His Asp Gly Glu Val Pro Met Glu Val Ala Arg His His Glu
            50                 55                 60

His Ala Glu Pro Gly Ser Gly Arg Cys Cys Ser Ala Val Val Gln His
65                  70                 75                 80

Val Ala Ala Pro Ala Ala Ala Val Trp Ser Val Val Arg Arg Phe Asp
                85                 90                 95

Gln Pro Gln Ala Tyr Lys Arg Phe Val Arg Ser Cys Ala Leu Leu Ala
                100                105                110

Gly Asp Gly Gly Val Gly Thr Leu Arg Glu Val Arg Val Val Ser Gly
                115                120                125
```

-continued

Leu Pro Ala Ala Ser Ser Arg Glu Arg Leu Glu Ile Leu Asp Asp Glu
    130                 135                 140

Ser His Val Leu Ser Phe Arg Val Val Gly Gly Glu His Arg Leu Lys
145                 150                 155                 160

Asn Tyr Leu Ser Val Thr Thr Val His Pro Ser Pro Ser Ala Pro Thr
                165                 170                 175

Ala Ala Thr Val Val Val Glu Ser Tyr Val Val Asp Val Pro Pro Gly
            180                 185                 190

Asn Thr Pro Glu Asp Thr Arg Val Phe Val Asp Thr Ile Val Lys Cys
        195                 200                 205

Asn Leu Gln Ser Leu Ala Lys Thr Ala Glu Lys Leu Ala Ala Gly Ala
    210                 215                 220

Arg Ala Ala Gly Ser
225

<210> SEQ ID NO 39
<211> LENGTH: 205
<212> TYPE: PRT
<213> ORGANISM: Medicago truncatula
<220> FEATURE:
<223> OTHER INFORMATION: barrel medic unknown protein, clone
      MTYFP_FQ_FR_FS1G-H-19, GenBank Accession No. ACJ85898.1

<400> SEQUENCE: 39

Met Pro Ser Pro Val Gln Phe Gln Arg Phe Asp Ser Asn Thr Ala Ile
1               5                   10                  15

Thr Asn Gly Val Asn Cys Pro Lys Gln Ile Gln Ala Cys Arg Tyr Ala
            20                  25                  30

Leu Ser Ser Leu Lys Pro Thr Val Ser Val Pro Glu Thr Val Val Asp
        35                  40                  45

His His Met His Val Val Gly Gln Asn Gln Cys Tyr Ser Val Val Ile
    50                  55                  60

Gln Thr Ile Asn Ala Ser Val Ser Thr Val Trp Ser Val Val Arg Arg
65                  70                  75                  80

Phe Asp Tyr Pro Gln Gly Tyr Lys His Phe Val Lys Ser Cys Asn Val
                85                  90                  95

Val Ala Ser Gly Asp Gly Ile Arg Val Gly Ala Leu Arg Glu Val Arg
            100                 105                 110

Leu Val Ser Gly Leu Pro Ala Val Ser Ser Thr Glu Arg Leu Asp Ile
        115                 120                 125

Leu Asp Glu Glu Arg His Val Ile Ser Phe Ser Val Val Gly Gly Val
    130                 135                 140

His Arg Cys Arg Asn Tyr Arg Ser Val Thr Thr Leu His Gly Asp Gly
145                 150                 155                 160

Asn Gly Gly Thr Val Val Ile Glu Ser Tyr Val Val Asp Val Pro Gln
                165                 170                 175

Gly Asn Thr Lys Glu Gly Thr Cys Ser Phe Ala Asp Thr Ile Val Arg
            180                 185                 190

Cys Asn Leu Gln Ser Leu Val Gln Ile Ala Glu Lys Leu
        195                 200                 205

<210> SEQ ID NO 40
<211> LENGTH: 212
<212> TYPE: PRT
<213> ORGANISM: Zea mays
<220> FEATURE:
<223> OTHER INFORMATION: maize AT-rich element binding factor 3, clone 1458362, GenBank Accession No. ACG26321.1

<400> SEQUENCE: 40

Met Pro Phe Ala Ala Ser Arg Thr Ser Gln Gln His Ser Arg Val
1               5                   10                  15

Ala Thr Asn Gly Arg Ala Val Ala Val Cys Ala Gly His Ala Gly Val
            20                  25                  30

Pro Asp Glu Val Ala Arg His His Glu His Ala Val Ala Ala Gly Gln
            35                  40                  45

Cys Cys Ala Ala Met Val Gln Ser Ile Ala Ala Pro Val Asp Ala Val
    50                  55                  60

Trp Ser Leu Val Arg Arg Phe Asp Gln Pro Gln Arg Tyr Lys Arg Phe
65                  70                  75                  80

Ile Arg Ser Cys His Leu Val Asp Gly Asp Gly Ala Glu Val Gly Ser
                85                  90                  95

Val Arg Glu Leu Leu Leu Val Ser Gly Leu Pro Ala Glu Ser Ser Arg
                100                 105                 110

Glu Arg Leu Glu Ile Arg Asp Asp Glu Arg Arg Val Ile Ser Phe Arg
            115                 120                 125

Val Leu Gly Gly Asp His Arg Leu Ala Asn Tyr Arg Ser Val Thr Thr
    130                 135                 140

Val His Glu Ala Ala Pro Ser Gln Asp Gly Arg Pro Leu Thr Met Val
145                 150                 155                 160

Val Glu Ser Tyr Val Val Asp Val Pro Pro Gly Asn Thr Val Glu Glu
                165                 170                 175

Thr Arg Ile Phe Val Asp Thr Ile Val Arg Cys Asn Leu Gln Ser Leu
            180                 185                 190

Glu Gly Thr Val Ile Arg Gln Leu Glu Ile Ala Ala Met Pro His Asp
        195                 200                 205

Asp Asn Gln Asn
    210

<210> SEQ ID NO 41
<211> LENGTH: 233
<212> TYPE: PRT
<213> ORGANISM: Zea mays
<220> FEATURE:
<223> OTHER INFORMATION: maize strain B73 unknown protein, clone
      ZM_BFb0105O18, GenBank Accession No. ACF87013.1

<400> SEQUENCE: 41

Met Arg Glu Arg Asn Ser Ser Ile Asp Gln Glu His Gln Arg Gly Ser
1               5                   10                  15

Ser Ser Arg Ser Thr Met Pro Phe Ala Ala Ser Arg Thr Ser Gln Gln
            20                  25                  30

Gln His Ser Arg Val Ala Thr Asn Gly Arg Ala Val Ala Val Cys Ala
            35                  40                  45

Gly His Ala Gly Val Pro Asp Glu Val Ala Arg His His Glu His Ala
    50                  55                  60

Val Ala Ala Gly Gln Cys Cys Ala Ala Met Val Gln Ser Ile Ala Ala
65                  70                  75                  80

Pro Val Asp Ala Val Trp Ser Leu Val Arg Arg Phe Asp Gln Pro Gln
                85                  90                  95

Arg Tyr Lys Arg Phe Ile Arg Ser Cys His Leu Val Asp Gly Asp Gly
                100                 105                 110

Ala Glu Val Gly Ser Val Arg Glu Leu Leu Leu Val Ser Gly Leu Pro

```
                    115                 120                 125
Ala Glu Ser Ser Arg Glu Arg Leu Glu Ile Arg Asp Asp Glu Arg Arg
        130                 135                 140

Val Ile Ser Phe Arg Val Leu Gly Gly Asp His Arg Leu Ala Asn Tyr
145                 150                 155                 160

Arg Ser Val Thr Thr Val His Glu Ala Ala Pro Ser Gln Asp Gly Arg
                165                 170                 175

Pro Leu Thr Met Val Val Glu Ser Tyr Val Val Asp Val Pro Pro Gly
            180                 185                 190

Asn Thr Val Glu Glu Thr Arg Ile Phe Val Asp Thr Ile Val Arg Cys
        195                 200                 205

Asn Leu Gln Ser Leu Glu Gly Thr Val Ile Arg Gln Leu Glu Ile Ala
    210                 215                 220

Ala Met Pro His Asp Asp Asn Gln Asn
225                 230

<210> SEQ ID NO 42
<211> LENGTH: 194
<212> TYPE: PRT
<213> ORGANISM: Physcomitrella patens
<220> FEATURE:
<223> OTHER INFORMATION: Physcomitrella patens subsp. patens moss,
      ecotype Gransden 2004, hypothetical protein, predicted protein,
      locus tag PHYPADRAFT_209242, GenBank Accession No. XP_001762113.1

<400> SEQUENCE: 42

Met Met Gln Glu Lys Gln Gly Arg Pro Asp Phe Gln Phe Leu Leu Glu
1               5                   10                  15

Gly Gln Gln Asp Leu Ile Cys Arg Phe His Lys His Glu Leu Leu Pro
            20                  25                  30

His Gln Cys Gly Ser Ile Leu Leu Gln Gln Ile Lys Ala Pro Val Gln
        35                  40                  45

Thr Val Trp Leu Ile Val Arg Arg Phe Asp Glu Pro Gln Val Tyr Lys
    50                  55                  60

Arg Phe Ile Gln Arg Cys Asp Ile Val Glu Gly Asp Gly Val Val Gly
65                  70                  75                  80

Ser Ile Arg Glu Val Gln Leu Val Ser Ser Ile Pro Ala Thr Ser Ser
                85                  90                  95

Ile Glu Arg Leu Glu Ile Leu Asp Asp Glu His Ile Ile Ser Phe
            100                 105                 110

Arg Val Leu Gly Gly Gly His Arg Leu Gln Asn Tyr Trp Ser Val Thr
        115                 120                 125

Ser Leu His Arg His Glu Ile Gln Gly Gln Met Gly Thr Leu Val Leu
    130                 135                 140

Glu Ser Tyr Val Val Asp Ile Pro Asp Gly Asn Thr Arg Glu Glu Thr
145                 150                 155                 160

His Thr Phe Val Asp Thr Val Val Arg Cys Asn Leu Lys Ala Leu Ala
                165                 170                 175

Gln Val Ser Glu Gln Lys His Leu Leu Asn Ser Asn Glu Lys Pro Ala
            180                 185                 190

Ala Pro

<210> SEQ ID NO 43
<211> LENGTH: 191
<212> TYPE: PRT
<213> ORGANISM: Vitis vinifera
<220> FEATURE:
```

<223> OTHER INFORMATION: wine grape cultivar PN40024 unnamed protein product, locus tag GSVIVT00035869001, GenBank Accession No. CAO48052.1

<400> SEQUENCE: 43

```
Met Lys Val Tyr Ser Pro Ser Gln Ile Leu Ala Glu Arg Gly Pro Arg
1               5                   10                  15

Ala Gln Ala Met Gly Asn Leu Tyr His Thr His Leu Leu Pro Asn
            20                  25                  30

Gln Cys Ser Ser Leu Val Val Gln Thr Thr Asp Ala Pro Leu Pro Gln
        35                  40                  45

Val Trp Ser Met Val Arg Arg Phe Asp Arg Pro Gln Ser Tyr Lys Arg
50                  55                  60

Phe Val Arg Gly Cys Thr Leu Arg Arg Gly Lys Gly Val Gly Ser
65                  70                  75                  80

Val Arg Glu Val Asn Ile Val Ser Gly Leu Pro Ala Glu Ile Ser Leu
                85                  90                  95

Glu Arg Leu Asp Lys Leu Asp Asp Leu His Val Met Arg Phe Thr
            100                 105                 110

Val Ile Gly Gly Asp His Arg Leu Ala Asn Tyr His Ser Thr Leu Thr
        115                 120                 125

Leu His Glu Asp Glu Asp Gly Val Arg Lys Thr Val Val Met Glu
    130                 135                 140

Ser Tyr Val Val Asp Val Pro Gly Gly Asn Ser Ala Gly Glu Thr Cys
145                 150                 155                 160

Tyr Phe Ala Asn Thr Ile Ile Gly Phe Asn Leu Lys Ala Leu Ala Ala
                165                 170                 175

Val Thr Glu Thr Met Ala Leu Lys Ala Asn Ile Pro Ser Gly Phe
            180                 185                 190
```

<210> SEQ ID NO 44
<211> LENGTH: 217
<212> TYPE: PRT
<213> ORGANISM: Physcomitrella patens
<220> FEATURE:
<223> OTHER INFORMATION: Physcomitrella patens subsp. patens moss, ecotype Gransden 2004, hypothetical protein, predicted protein, locus tag PHYPADRAFT_132509, GenBank Accession No. XP_001767821.1

<400> SEQUENCE: 44

```
Met Gln Gln Val Lys Gly Arg Gln Asp Phe Gln Arg Leu Leu Glu Ala
1               5                   10                  15

Gln Gln Asp Leu Ile Cys Arg Tyr His Thr His Glu Leu Lys Ala His
            20                  25                  30

Gln Cys Gly Ser Ile Leu Leu Gln Gln Ile Lys Val Pro Leu Pro Ile
        35                  40                  45

Val Trp Ala Ile Val Arg Ser Phe Asp Lys Pro Gln Val Tyr Lys Arg
50                  55                  60

Phe Ile Gln Thr Cys Lys Ile Thr Glu Gly Asp Gly Val Gly Ser
65                  70                  75                  80

Ile Arg Glu Val His Leu Val Ser Ser Val Pro Ala Thr Cys Ser Ile
                85                  90                  95

Glu Arg Leu Glu Ile Leu Asp Asp Glu Lys His Ile Ile Ser Phe Arg
            100                 105                 110

Val Leu Gly Gly Gly His Arg Leu Gln Asn Tyr Ser Ser Val Ser Ser
        115                 120                 125

Leu His Glu Leu Glu Val Glu Gly His Pro Cys Thr Leu Val Leu Glu
```

| | | | | | 130 | | | | | 135 | | | | | 140 | |

Ser Tyr Met Val Asp Ile Pro Asp Gly Asn Thr Arg Glu Glu Thr His
145                 150                 155                 160

Met Phe Val Asp Thr Val Val Arg Cys Asn Leu Lys Ser Leu Ala Gln
            165                 170                 175

Ile Ser Glu Gln Gln Tyr Asn Lys Asp Cys Leu Gln Gln Lys Gln His
        180                 185                 190

Asp Gln Gln Gln Met Tyr Gln Gln Arg His Pro Pro Leu Pro Pro Ile
    195                 200                 205

Pro Ile Thr Asp Lys Asn Met Glu Arg
    210                 215

<210> SEQ ID NO 45
<211> LENGTH: 195
<212> TYPE: PRT
<213> ORGANISM: Physcomitrella patens
<220> FEATURE:
<223> OTHER INFORMATION: Physcomitrella patens subsp. patens moss,
      ecotype Gransden 2004, hypothetical protein, predicted protein,
      locus tag PHYPADRAFT_213389, GenBank Accession No. XP_001767012.1

<400> SEQUENCE: 45

Met Arg Phe Asp Ile Gly His Asn Asp Val Arg Gly Phe Phe Thr Cys
1               5                   10                  15

Glu Glu Glu His Ala Tyr Ala Leu His Ser Gln Thr Val Glu Leu Asn
            20                  25                  30

Gln Cys Gly Ser Ile Leu Met Gln Gln Ile His Ala Pro Ile Glu Val
        35                  40                  45

Val Trp Ser Ile Val Arg Ser Phe Gly Ser Pro Gln Ile Tyr Lys Lys
    50                  55                  60

Phe Ile Gln Ala Cys Ile Leu Thr Val Gly Asp Gly Gly Val Gly Ser
65                  70                  75                  80

Ile Arg Glu Val Phe Leu Val Ser Gly Val Pro Ala Thr Ser Ser Ile
                85                  90                  95

Glu Arg Leu Glu Ile Leu Asp Asp Glu Lys His Val Phe Ser Phe Arg
            100                 105                 110

Val Leu Lys Gly Gly His Arg Leu Gln Asn Tyr Arg Ser Val Thr Thr
        115                 120                 125

Leu His Glu Gln Glu Val Asn Gly Arg Gln Thr Thr Thr Val Leu Glu
    130                 135                 140

Ser Tyr Val Val Asp Val Pro Asp Gly Asn Thr Arg Glu Glu Thr His
145                 150                 155                 160

Met Phe Ala Asp Thr Val Val Met Cys Asn Leu Lys Ser Leu Ala Gln
            165                 170                 175

Val Ala Glu Trp Arg Ala Met Gln Gly Ile Thr Gln Gln Leu Ser Thr
        180                 185                 190

Ser Ser Leu
    195

<210> SEQ ID NO 46
<211> LENGTH: 172
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_004947, GenBank
      Accession No. CAN72620.1

<400> SEQUENCE: 46

```
Met Gly Asn Leu Tyr His Thr His His Leu Leu Pro Asn Gln Cys Ser
 1               5                  10                  15

Ser Leu Val Val Gln Thr Thr Asp Ala Pro Leu Pro Gln Val Trp Ser
                20                  25                  30

Met Val Arg Arg Phe Asp Arg Pro Gln Ser Tyr Lys Arg Phe Val Arg
                35                  40                  45

Gly Cys Thr Leu Arg Arg Gly Lys Gly Gly Val Gly Ser Val Arg Glu
 50                  55                  60

Val Asn Ile Val Ser Gly Leu Pro Ala Glu Ile Ser Leu Glu Arg Leu
 65                  70                  75                  80

Asp Lys Leu Asp Asp Leu His Val Met Arg Phe Thr Val Ile Gly
                85                  90                  95

Gly Asp His Arg Leu Ala Asn Tyr His Ser Thr Leu Thr Leu His Glu
                100                 105                 110

Asp Glu Glu Asp Gly Val Arg Lys Thr Val Val Met Glu Ser Tyr Val
                115                 120                 125

Val Asp Val Pro Gly Gly Asn Ser Ala Gly Glu Thr Cys Tyr Phe Ala
 130                 135                 140

Asn Thr Ile Ile Gly Phe Asn Leu Lys Ala Leu Ala Ala Val Thr Glu
 145                 150                 155                 160

Thr Met Ala Leu Lys Ala Asn Ile Pro Ser Gly Phe
                165                 170
```

<210> SEQ ID NO 47
<211> LENGTH: 196
<212> TYPE: PRT
<213> ORGANISM: Picea sitchensis
<220> FEATURE:
<223> OTHER INFORMATION: Sitka spruce cultivar FB3-425, unknown protein,
      clone WS0281_I24, GenBank Accession No. ABK23752.1

<400> SEQUENCE: 47

```
Met Glu Asp Leu Ser Ser Trp Arg Glu Gly Arg Ala Met Trp Leu Gly
 1               5                  10                  15

Asn Pro Pro Ser Glu Ser Glu Leu Val Cys Arg His His Arg His Glu
                20                  25                  30

Leu Gln Gly Asn Gln Cys Ser Ser Phe Leu Val Lys His Ile Arg Ala
                35                  40                  45

Pro Val His Leu Val Trp Ser Ile Val Arg Thr Phe Asp Gln Pro Gln
 50                  55                  60

Lys Tyr Lys Pro Phe Val His Ser Cys Ser Val Arg Gly Gly Ile Thr
 65                  70                  75                  80

Val Gly Ser Ile Arg Asn Val Asn Val Lys Ser Gly Leu Pro Ala Thr
                85                  90                  95

Ala Ser Glu Glu Arg Leu Glu Ile Leu Asp Asp Asn Glu His Val Phe
                100                 105                 110

Ser Ile Lys Ile Leu Gly Gly Asp His Arg Leu Gln Asn Tyr Ser Ser
                115                 120                 125

Ile Ile Thr Val His Pro Glu Ile Ile Asp Gly Arg Pro Gly Thr Leu
 130                 135                 140

Val Ile Glu Ser Tyr Val Val Asp Val Pro Glu Gly Asn Thr Arg Glu
 145                 150                 155                 160

Glu Thr Arg Phe Phe Val Glu Ala Leu Val Lys Cys Asn Leu Lys Ser
                165                 170                 175

Leu Ala Asp Val Ser Glu Arg Leu Ala Ser Gln His His Thr Glu Leu
```

```
            180                 185                 190

Leu Glu Arg Thr
        195

<210> SEQ ID NO 48
<211> LENGTH: 185
<212> TYPE: PRT
<213> ORGANISM: Solanum tuberosum
<220> FEATURE:
<223> OTHER INFORMATION: potato cultivar Kuras, CAPIP1-like protein,
      clone 153D02, similar to Casicum annuum CAPIP1, GenBank Accession
      No. ABB29920.1

<400> SEQUENCE: 48

Met Asn Ala Asn Gly Phe Cys Gly Val Glu Lys Glu Tyr Ile Arg Lys
1               5                   10                  15

His His Leu His Glu Pro Lys Glu Asn Gln Cys Ser Ser Phe Leu Val
            20                  25                  30

Lys His Ile Arg Ala Pro Val His Leu Val Trp Ser Leu Val Arg Arg
        35                  40                  45

Phe Asp Gln Pro Gln Lys Tyr Lys Pro Phe Ile Ser Arg Cys Ile Val
    50                  55                  60

Gln Gly Asp Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                85                  90                  95

Glu Glu His Ile Leu Ser Val Arg Ile Val Gly Gly Asp His Arg Leu
            100                 105                 110

Arg Asn Tyr Ser Ser Val Ile Ser Val His Pro Glu Val Ile Asp Gly
        115                 120                 125

Arg Pro Gly Thr Val Val Leu Glu Ser Phe Val Val Asp Val Pro Glu
    130                 135                 140

Gly Asn Thr Lys Asp Glu Thr Cys Tyr Phe Val Glu Ala Leu Ile Asn
145                 150                 155                 160

Cys Asn Leu Lys Ser Leu Ala Asp Ile Ser Glu Arg Val Ala Val Gln
                165                 170                 175

Asp Arg Thr Glu Pro Ile Asp Gln Val
            180                 185

<210> SEQ ID NO 49
<211> LENGTH: 190
<212> TYPE: PRT
<213> ORGANISM: Medicago truncatula
<220> FEATURE:
<223> OTHER INFORMATION: barrel medic unknown protein, clone
      MTYFP_FQ_FR_FS1G-E-17, GenBank Accession No. ACJ85952.1

<400> SEQUENCE: 49

Met Asn Asn Gly Cys Glu Gln Gln Gln Tyr Ser Val Ile Glu Thr Gln
1               5                   10                  15

Tyr Ile Arg Arg His His Lys His Asp Leu Arg Asp Asn Gln Cys Ser
            20                  25                  30

Ser Ala Leu Val Lys His Ile Lys Ala Pro Val His Leu Val Trp Ser
        35                  40                  45

Leu Val Arg Arg Phe Asp Gln Pro Gln Lys Tyr Lys Pro Phe Ile Ser
    50                  55                  60

Arg Cys Ile Met Gln Gly Asp Leu Ser Ile Gly Ser Val Arg Glu Val
65                  70                  75                  80
```

-continued

```
Asn Val Lys Ser Gly Leu Pro Ala Thr Thr Ser Thr Glu Arg Leu Glu
             85                  90                  95

Gln Leu Asp Asp Glu Glu His Ile Leu Gly Ile Arg Ile Val Gly Gly
            100                 105                 110

Asp His Arg Leu Arg Asn Tyr Ser Ser Ile Ile Thr Val His Pro Gly
        115                 120                 125

Val Ile Asp Gly Arg Pro Gly Thr Met Val Ile Glu Ser Phe Val Val
    130                 135                 140

Asp Val Pro Glu Gly Asn Thr Lys Asp Glu Thr Cys Tyr Phe Val Glu
145                 150                 155                 160

Ala Leu Ile Arg Tyr Asn Leu Ser Ser Leu Ala Asp Val Ser Glu Arg
                165                 170                 175

Met Ala Val Gln Gly Arg Thr Asp Pro Ile Asn Ile Asn Pro
            180                 185                 190

<210> SEQ ID NO 50
<211> LENGTH: 185
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00002440001, GenBank Accession No.
      CAO65816.1

<400> SEQUENCE: 50

Met Ser Gly Tyr Gly Cys Ile Lys Met Glu Asp Glu Tyr Ile Arg Arg
 1               5                  10                  15

His His Arg His Glu Ile Arg Asp Asn Gln Cys Ser Ser Ser Leu Val
            20                  25                  30

Lys His Ile Lys Ala Pro Val His Leu Val Trp Ser Leu Val Arg Ser
        35                  40                  45

Phe Asp Gln Pro Gln Lys Tyr Lys Pro Phe Val Ser Arg Cys Ile Val
    50                  55                  60

Gln Gly Asp Leu Glu Ile Gly Ser Val Arg Glu Val Asn Val Lys Ser
65                  70                  75                  80

Gly Leu Pro Ala Thr Thr Ser Thr Glu Arg Leu Glu Leu Leu Asp Asp
                85                  90                  95

Glu Glu His Ile Phe Gly Met Arg Ile Val Gly Gly Asp His Arg Leu
            100                 105                 110

Lys Asn Tyr Ser Ser Ile Val Thr Val His Pro Glu Ile Ile Asp Gly
        115                 120                 125

Arg Pro Gly Thr Leu Val Ile Glu Ser Phe Val Val Asp Val Pro Asp
    130                 135                 140

Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Ile Gln
                165                 170                 175

Asp Arg Thr Glu Pro Ile Asp Arg Met
            180                 185

<210> SEQ ID NO 51
<211> LENGTH: 185
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00006507001, GenBank Accession No.
      CAO69376.1
```

```
<400> SEQUENCE: 51

Met Asn Gly Asn Gly Leu Ser Ser Met Glu Ser Glu Tyr Ile Arg Arg
1               5                   10                  15

His His Arg His Glu Pro Ala Glu Asn Gln Cys Ser Ser Ala Leu Val
            20                  25                  30

Lys His Ile Lys Ala Pro Val Pro Leu Val Trp Ser Leu Val Arg Arg
        35                  40                  45

Phe Asp Gln Pro Gln Lys Tyr Lys Pro Phe Ile Ser Arg Cys Val Val
    50                  55                  60

Gln Gly Asn Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                85                  90                  95

Asp Glu His Ile Leu Ser Met Arg Ile Ile Gly Gly Asp His Arg Leu
            100                 105                 110

Arg Asn Tyr Ser Ser Ile Ile Ser Leu His Pro Glu Ile Ile Asp Gly
        115                 120                 125

Arg Pro Gly Thr Met Val Ile Glu Ser Tyr Val Val Asp Val Pro Glu
    130                 135                 140

Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Arg Met
            180                 185

<210> SEQ ID NO 52
<211> LENGTH: 208
<212> TYPE: PRT
<213> ORGANISM: Oryza sativa
<220> FEATURE:
<223> OTHER INFORMATION: rice Japonica Group, cultivar Nipponbare,
      hypothetical protein OsJ_21703, GenBank Accession No. EAZ37364.1

<400> SEQUENCE: 52

Met Glu Ala His Val Glu Arg Ala Leu Arg Gly Leu Thr Glu Glu
1               5                   10                  15

Glu Arg Ala Ala Leu Glu Pro Ala Val Met Ala His His Thr Phe Pro
            20                  25                  30

Pro Ser Thr Thr Thr Ala Thr Thr Ala Ala Ala Thr Cys Thr Ser Leu
        35                  40                  45

Val Thr Gln Arg Val Ala Ala Pro Val Arg Ala Val Trp Pro Ile Val
    50                  55                  60

Arg Ser Phe Gly Asn Pro Gln Arg Tyr Lys His Phe Val Arg Thr Cys
65                  70                  75                  80

Ala Leu Ala Ala Gly Asn Gly Pro Ser Phe Gly Ser Val Arg Glu Val
                85                  90                  95

Thr Val Val Ser Gly Pro Ser Arg Leu Pro Pro Gly Thr Glu Arg Leu
            100                 105                 110

Glu Met Leu Asp Asp Asp Arg His Ile Ile Ser Phe Arg Val Val Gly
        115                 120                 125

Gly Gln His Arg Leu Arg Asn Tyr Arg Ser Val Thr Ser Val Thr Glu
    130                 135                 140

Phe Gln Pro Pro Ala Ala Gly Pro Gly Pro Ala Pro Tyr Cys Val
145                 150                 155                 160
```

Val Val Glu Ser Tyr Val Asp Val Pro Asp Gly Asn Thr Ala Glu
            165                 170                 175

Asp Thr Arg Met Phe Thr Asp Thr Val Val Lys Leu Asn Leu Gln Met
            180                 185                 190

Leu Ala Ala Val Ala Glu Asp Ser Ser Ala Ser Arg Arg Arg Asp
        195                 200                 205

<210> SEQ ID NO 53
<211> LENGTH: 186
<212> TYPE: PRT
<213> ORGANISM: Capsicum annuum
<220> FEATURE:
<223> OTHER INFORMATION: pepper cultivar hanbyul, CAPIP1 protein,
      GenBank Accession No. AAT35532.1

<400> SEQUENCE: 53

Met Met Asn Ala Asn Gly Phe Ser Gly Val Glu Lys Glu Tyr Ile Arg
1               5                   10                  15

Lys His His Leu His Gln Pro Lys Glu Asn Gln Cys Ser Ser Phe Leu
            20                  25                  30

Val Lys His Ile Arg Ala Pro Val His Leu Val Trp Ser Leu Val Arg
        35                  40                  45

Arg Phe Asp Gln Pro Gln Lys Tyr Lys Pro Phe Val Ser Arg Cys Ile
    50                  55                  60

Ala Gln Gly Asp Leu Glu Ile Gly Ser Leu Arg Glu Val Asp Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Ser Phe Arg Ile Ile Gly Gly Asp His Arg
            100                 105                 110

Leu Arg Asn Tyr Ser Ser Ile Ile Ser Leu His Pro Gly Val Ile Asp
        115                 120                 125

Gly Arg Pro Gly Thr Leu Val Ile Glu Ser Phe Val Val Asp Val Pro
    130                 135                 140

Gln Gly Asn Thr Lys Asp Glu Thr Cys Tyr Phe Val Glu Ala Leu Ile
145                 150                 155                 160

Asn Cys Asn Leu Lys Ser Leu Ala Asp Val Ser Glu Arg Leu Ala Val
                165                 170                 175

Gln Asp Arg Thr Glu Pro Ile Asp Gln Val
            180                 185

<210> SEQ ID NO 54
<211> LENGTH: 186
<212> TYPE: PRT
<213> ORGANISM: Populus trichocarpa
<220> FEATURE:
<223> OTHER INFORMATION: California poplar (Western balsam poplar,
      black cottonwood) cultivar 383-2499 (Nisqually-1), unknown
      protein, clone PX0011_1113, GenBank Accession No. ABK92491.1

<400> SEQUENCE: 54

Met Asn Gly Ser Asp Ala Tyr Ser Ala Thr Glu Ala Gln Tyr Val Arg
1               5                   10                  15

Arg His His Lys His Glu Pro Arg Glu Asn Gln Cys Thr Ser Ala Leu
            20                  25                  30

Val Lys His Ile Lys Ala Pro Ala His Leu Val Trp Ser Leu Val Arg
        35                  40                  45

Arg Phe Asp Gln Pro Gln Arg Tyr Lys Pro Phe Val Ser Arg Cys Val
    50                  55                  60

```
Met Asn Gly Glu Leu Gly Ile Gly Ser Val Arg Glu Val Asn Val Lys
 65                  70                  75                  80

Ser Gly Leu Pro Ala Thr Thr Ser Thr Glu Arg Leu Glu Leu Leu Asp
                 85                  90                  95

Asp Glu Glu His Ile Leu Gly Val Gln Ile Val Gly Gly Asp His Arg
                100                 105                 110

Leu Lys Asn Tyr Ser Ser Ile Met Thr Val His Pro Glu Phe Ile Asp
            115                 120                 125

Gly Arg Pro Gly Thr Leu Val Ile Glu Ser Phe Ile Val Asp Val Pro
130                 135                 140

Asp Gly Asn Thr Lys Asp Glu Thr Cys Tyr Phe Val Glu Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
                180                 185

<210> SEQ ID NO 55
<211> LENGTH: 185
<212> TYPE: PRT
<213> ORGANISM: Capsicum annuum
<220> FEATURE:
<223> OTHER INFORMATION: pepper cultivar hanbyul, PIP1 protein, GenBank
      Accession No. ABF72432.1

<400> SEQUENCE: 55

Met Asn Ala Asn Gly Phe Ser Gly Val Glu Lys Glu Tyr Ile Arg Lys
  1               5                  10                  15

His His Leu His Gln Pro Lys Glu Asn Gln Cys Ser Ser Phe Leu Val
             20                  25                  30

Lys His Ile Arg Ala Pro Val His Leu Val Trp Ser Leu Val Arg Arg
         35                  40                  45

Phe Asp Gln Pro Gln Lys Tyr Lys Pro Phe Val Ser Arg Cys Ile Ala
 50                  55                  60

Gln Gly Asp Leu Glu Ile Gly Ser Leu Arg Glu Val Asp Val Lys Ser
 65                  70                  75                  80

Gly Leu Pro Ala Thr Thr Ser Thr Glu Arg Leu Glu Leu Leu Asp Asp
                 85                  90                  95

Glu Glu His Ile Leu Ser Phe Arg Ile Ile Gly Gly Asp His Arg Leu
                100                 105                 110

Arg Asn Tyr Ser Ser Ile Ile Ser Leu His Pro Glu Val Ile Asp Gly
            115                 120                 125

Arg Pro Gly Thr Leu Val Ile Glu Ser Phe Val Val Asp Val Pro Gln
130                 135                 140

Gly Asn Thr Lys Asp Glu Thr Cys Tyr Phe Val Glu Ala Leu Ile Asn
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Gln Val
                180                 185

<210> SEQ ID NO 56
<211> LENGTH: 186
<212> TYPE: PRT
<213> ORGANISM: Populus trichocarpa x Populus deltoides
<220> FEATURE:
<223> OTHER INFORMATION: California poplar (Western balsam poplar,
``` black cottonwood) x Eastern cottonwood, cultivar H11-11, unknown
protein, clone WS0133_I04, GenBank Accession No. ABK96505.1

<400> SEQUENCE: 56

Met Asn Gly Ser Asp Ala Tyr Ser Ala Thr Glu Ala Gln Tyr Val Arg
1               5                   10                  15

Arg His His Lys His Glu Pro Arg Glu Asn Gln Cys Thr Ser Ala Leu
            20                  25                  30

Val Lys His Ile Lys Ala Pro Ala His Leu Val Trp Ser Leu Val Arg
        35                  40                  45

Arg Phe Asp Gln Pro Gln Arg Tyr Lys Pro Phe Val Ser Arg Cys Val
    50                  55                  60

Met Asn Gly Glu Leu Gly Ile Gly Ser Val Arg Glu Val Asn Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Gly Val Gln Ile Val Gly Gly Asp His Arg
            100                 105                 110

Leu Lys Asn Tyr Ser Ser Ile Met Thr Val His Pro Glu Phe Ile Asp
        115                 120                 125

Gly Arg Pro Gly Thr Leu Val Ile Glu Ser Phe Ile Val Asp Val Pro
    130                 135                 140

Asp Gly Asn Thr Lys Asp Glu Thr Cys Tyr Phe Val Lys Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
            180                 185

<210> SEQ ID NO 57
<211> LENGTH: 188
<212> TYPE: PRT
<213> ORGANISM: Pisum sativum
<220> FEATURE:
<223> OTHER INFORMATION: pea AT-rich element binding factor 3 (PsATF,
      ATF3), potential transcription factor, GenBank Accession No.
      AAV85853.1

<400> SEQUENCE: 57

Met Asn Asn Gly Gly Glu Gln Tyr Ser Ala Ile Glu Thr Gln Tyr Ile
1               5                   10                  15

Arg Arg Arg His Lys His Asp Leu Arg Asp Asn Gln Cys Ser Ser Ala
            20                  25                  30

Leu Val Lys His Ile Lys Ala Pro Val His Leu Val Trp Ser Leu Val
        35                  40                  45

Arg Arg Phe Asp Gln Pro Gln Lys Tyr Lys Pro Phe Val Ser Arg Cys
    50                  55                  60

Ile Met Gln Gly Asp Leu Gly Ile Gly Ser Val Arg Glu Val Asn Val
65                  70                  75                  80

Lys Ser Gly Leu Pro Ala Thr Thr Ser Thr Glu Arg Leu Glu Gln Leu
                85                  90                  95

Asp Asp Glu Glu His Ile Leu Gly Ile Arg Ile Val Gly Gly Asp His
            100                 105                 110

Arg Leu Arg Asn Tyr Ser Ser Val Ile Thr Val His Pro Glu Val Ile
        115                 120                 125

Asp Gly Arg Pro Gly Thr Met Val Ile Glu Ser Phe Val Val Asp Val
    130                 135                 140

-continued

Pro Glu Gly Asn Thr Arg Asp Glu Thr Cys Tyr Phe Val Glu Ala Leu
145                 150                 155                 160

Ile Arg Gly Asn Leu Ser Ser Leu Ala Asp Val Ser Glu Arg Met Ala
                165                 170                 175

Val Gln Gly Arg Thr Asp Pro Ile Asn Val Asn Pro
            180                 185

<210> SEQ ID NO 58
<211> LENGTH: 177
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00027009001, GenBank Accession No.
      CAO39744.1

<400> SEQUENCE: 58

Met Glu Ala Gln Val Ile Cys Arg His His Ala His Glu Pro Arg Glu
1               5                   10                  15

Asn Gln Cys Ser Ser Val Leu Val Arg His Val Lys Ala Pro Ala Asn
                20                  25                  30

Leu Val Trp Ser Leu Val Arg Arg Phe Asp Gln Pro Gln Lys Tyr Lys
            35                  40                  45

Pro Phe Val Ser Arg Cys Val Val Gln Gly Asp Leu Arg Ile Gly Ser
    50                  55                  60

Val Arg Glu Val Asn Val Lys Thr Gly Leu Pro Ala Thr Thr Ser Thr
65                  70                  75                  80

Glu Arg Leu Glu Leu Phe Asp Asp Asp Glu His Val Leu Gly Ile Lys
                85                  90                  95

Ile Leu Asp Gly Asp His Arg Leu Arg Asn Tyr Ser Ser Val Ile Thr
            100                 105                 110

Val His Pro Glu Ile Ile Asp Gly Arg Pro Gly Thr Leu Val Ile Glu
        115                 120                 125

Ser Phe Val Val Asp Val Pro Glu Gly Asn Thr Lys Asp Asp Thr Cys
    130                 135                 140

Tyr Phe Val Arg Ala Leu Ile Asn Cys Asn Leu Lys Cys Leu Ala Glu
145                 150                 155                 160

Val Ser Glu Arg Met Ala Met Leu Gly Arg Val Glu Pro Ala Asn Ala
                165                 170                 175

Val

<210> SEQ ID NO 59
<211> LENGTH: 178
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_004915, GenBank
      Accession No. CAN82501.1

<400> SEQUENCE: 59

Met Met Glu Ala Gln Val Ile Cys Arg His His Ala His Glu Pro Arg
1               5                   10                  15

Glu Asn Gln Cys Ser Ser Val Leu Val Arg His Val Lys Ala Pro Ala
                20                  25                  30

Asn Leu Val Trp Ser Leu Val Arg Arg Phe Asp Gln Pro Gln Lys Tyr
            35                  40                  45

Lys Pro Phe Val Ser Arg Cys Val Val Gln Gly Asp Leu Arg Ile Gly

```
                    50                 55                 60
Ser Val Arg Glu Val Asn Val Lys Thr Gly Leu Pro Ala Thr Thr Ser
 65                 70                 75                 80

Thr Glu Arg Leu Glu Leu Phe Asp Asp Glu His Val Leu Gly Ile
                 85                 90                 95

Lys Ile Leu Asp Gly Asp His Arg Leu Arg Asn Tyr Ser Ser Val Ile
                100                105                110

Thr Val His Pro Glu Ile Ile Asp Gly Arg Pro Gly Thr Leu Val Ile
                115                120                125

Glu Ser Phe Val Val Asp Val Pro Glu Gly Asn Thr Lys Asp Asp Thr
                130                135                140

Cys Tyr Phe Val Arg Ala Leu Ile Asn Cys Asn Leu Lys Cys Leu Ala
145                150                155                160

Glu Val Ser Glu Arg Met Ala Met Leu Gly Arg Val Glu Pro Ala Asn
                165                170                175

Ala Val
```

<210> SEQ ID NO 60
<211> LENGTH: 193
<212> TYPE: PRT
<213> ORGANISM: Arachis hypogaea
<220> FEATURE:
<223> OTHER INFORMATION: peanut pathogenesis-induced protein (PIP), GenBank Accession No. ACG76109.1
<220> FEATURE:
<221> NAME/KEY: VARIANT
<222> LOCATION: (162)...(162)
<223> OTHER INFORMATION: Xaa = any amino acid

<400> SEQUENCE: 60

```
Met Met Asn Gly Ser Cys Gly Gly Gly Gly Gly Glu Ala Tyr Gly
  1               5                  10                 15

Ala Ile Glu Ala Gln Tyr Ile Arg Arg His His Arg His Glu Pro Arg
                 20                 25                 30

Asp Asn Gln Cys Thr Ser Ala Leu Val Lys His Ile Arg Ala Pro Val
                 35                 40                 45

His Leu Val Trp Ser Leu Val Arg Arg Phe Asp Gln Pro Gln Lys Tyr
                 50                 55                 60

Lys Pro Phe Val Ser Arg Cys Ile Met Gln Gly Asp Leu Gly Ile Gly
 65                 70                 75                 80

Ser Val Arg Glu Val Asn Val Lys Ser Gly Leu Pro Ala Thr Thr Ser
                 85                 90                 95

Thr Glu Arg Leu Glu Gln Leu Asp Asp Glu His Ile Leu Gly Ile
                100                105                110

Arg Ile Val Gly Gly Asp His Arg Leu Arg Asn Tyr Ser Ser Ile Ile
                115                120                125

Thr Val His Pro Glu Val Ile Glu Gly Arg Pro Gly Thr Met Val Ile
                130                135                140

Glu Ser Phe Val Val Asp Val Pro Asp Gly Asn Thr Lys Asp Glu Thr
145                150                155                160

Cys Xaa Phe Val Glu Ala Leu Ile Arg Cys Asn Leu Ser Ser Leu Ala
                165                170                175

Asp Val Ser Glu Arg Met Ala Val Gln Gly Arg Thr Asp Pro Ile Asn
                180                185                190

Gln
```

```
<210> SEQ ID NO 61
<211> LENGTH: 217
<212> TYPE: PRT
<213> ORGANISM: Zea mays
<220> FEATURE:
<223> OTHER INFORMATION: maize AT-rich element binding factor 3,
      clone 300908, GenBank Accession No. ACG39386.1

<400> SEQUENCE: 61

Met Val Val Glu Met Asp Gly Gly Val Gly Val Ala Ala Gly Gly Gly
  1               5                  10                  15

Gly Gly Ala Gln Thr Pro Ala Pro Pro Pro Arg Arg Trp Arg Leu
                 20                  25                  30

Ala Asp Glu Arg Cys Asp Leu Arg Ala Met Glu Thr Asp Tyr Val Arg
             35                  40                  45

Arg Phe His Arg His Glu Pro Arg Asp His Gln Cys Ser Ser Ala Val
         50                  55                  60

Ala Lys His Ile Lys Ala Pro Val His Leu Val Trp Ser Leu Val Arg
 65                  70                  75                  80

Arg Phe Asp Gln Pro Gln Leu Phe Lys Pro Phe Val Ser Arg Cys Glu
                 85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
        115                 120                 125

Asp Asp Glu Arg Ile Leu Ser Val Arg Phe Val Gly Gly Asp His Arg
    130                 135                 140

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Val Asp Val Pro
                165                 170                 175

Asp Gly Asn Thr Lys Asp Glu Thr Cys Tyr Phe Val Glu Ala Leu Leu
            180                 185                 190

Lys Cys Asn Leu Arg Ser Leu Ala Glu Val Ser Glu Gly Gln Val Ile
        195                 200                 205

Met Asp Gln Thr Glu Pro Leu Asp Arg
    210                 215

<210> SEQ ID NO 62
<211> LENGTH: 217
<212> TYPE: PRT
<213> ORGANISM: Zea mays
<220> FEATURE:
<223> OTHER INFORMATION: maize strain B73, unknown protein, clone
      ZM_BFb0036A01, GenBank Accession No. ACF80077.1

<400> SEQUENCE: 62

Met Val Val Glu Met Asp Gly Gly Val Gly Val Ala Ala Ala Gly Gly
  1               5                  10                  15

Gly Gly Ala Gln Thr Pro Ala Pro Pro Pro Arg Arg Trp Arg Leu
                 20                  25                  30

Ala Asp Glu Arg Cys Asp Leu Arg Ala Met Glu Thr Asp Tyr Val Arg
             35                  40                  45

Arg Phe His Arg His Glu Pro Arg Asp His Gln Cys Ser Ser Ala Val
         50                  55                  60

Ala Lys His Ile Lys Ala Pro Val His Leu Val Trp Ser Leu Val Arg
 65                  70                  75                  80

Arg Phe Asp Gln Pro Gln Leu Phe Lys Pro Phe Val Ser Arg Cys Glu
```

```
            85                  90                  95
Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
            115                 120                 125

Asp Asp Glu Arg Ile Leu Ser Val Arg Phe Val Gly Asp His Arg
            130                 135                 140

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Asp Val Pro
                165                 170                 175

Asp Gly Asn Thr Lys Asp Glu Thr Cys Tyr Phe Val Glu Ala Leu Leu
            180                 185                 190

Lys Cys Asn Leu Arg Ser Leu Ala Glu Val Ser Glu Gly Gln Val Ile
            195                 200                 205

Met Asp Gln Thr Glu Pro Leu Asp Arg
            210                 215

<210> SEQ ID NO 63
<211> LENGTH: 206
<212> TYPE: PRT
<213> ORGANISM: Oryza sativa
<220> FEATURE:
<223> OTHER INFORMATION: rice Japonica Group, cultivar Nipponbare,
      hypothetical protein Os06g0528300, GenBank Accession No.
      NP_001057772.1

<400> SEQUENCE: 63

Met Asn Gly Val Gly Gly Ala Gly Gly Ala Ala Ala Gly Lys Leu Pro
1               5                   10                  15

Met Val Ser His Arg Arg Val Gln Trp Arg Leu Ala Asp Glu Arg Cys
            20                  25                  30

Glu Leu Arg Glu Glu Glu Met Glu Tyr Ile Arg Arg Phe His Arg His
            35                  40                  45

Glu Pro Ser Ser Asn Gln Cys Thr Ser Phe Ala Ala Lys His Ile Lys
        50                  55                  60

Ala Pro Leu His Thr Val Trp Ser Leu Val Arg Arg Phe Asp Gln Pro
65              70                  75                  80

Gln Leu Phe Lys Pro Phe Val Arg Asn Cys Val Met Arg Glu Asn Ile
            85                  90                  95

Ile Ala Thr Gly Cys Ile Arg Glu Val Asn Val Gln Ser Gly Leu Pro
            100                 105                 110

Ala Thr Arg Ser Thr Glu Arg Leu Glu Leu Leu Asp Asp Asn Glu His
            115                 120                 125

Ile Leu Lys Val Asn Phe Ile Gly Gly Asp His Met Leu Lys Asn Tyr
            130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Pro Glu Gly Asn Thr
                165                 170                 175

Lys Asp Asp Ile Ser Tyr Phe Ile Glu Asn Val Leu Arg Cys Asn Leu
            180                 185                 190

Arg Thr Leu Ala Asp Val Ser Glu Glu Arg Leu Ala Asn Pro
            195                 200                 205

<210> SEQ ID NO 64
```

```
<211> LENGTH: 206
<212> TYPE: PRT
<213> ORGANISM: Oryza sativa
<220> FEATURE:
<223> OTHER INFORMATION: rice Indica Group, cultivar 93-11,
      hypothetical protein OsI_23215, GenBank Accession No. EAZ01188.1

<400> SEQUENCE: 64

Met Asn Gly Ala Gly Gly Ala Gly Gly Ala Ala Ala Gly Lys Leu Pro
 1               5                  10                  15

Met Val Ser His Arg Gln Val Gln Trp Arg Leu Ala Asp Glu Arg Cys
                20                  25                  30

Glu Leu Arg Glu Glu Met Glu Tyr Ile Arg Gln Phe His Arg His
            35                  40                  45

Glu Pro Ser Ser Asn Gln Cys Thr Ser Phe Val Ala Lys His Ile Lys
        50                  55                  60

Ala Pro Leu Gln Thr Val Trp Ser Leu Val Arg Arg Phe Asp Gln Pro
 65                  70                  75                  80

Gln Leu Phe Lys Pro Phe Val Arg Lys Cys Val Met Arg Glu Asn Ile
                85                  90                  95

Ile Ala Thr Gly Cys Val Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

Ile Leu Lys Val Lys Phe Ile Gly Gly Asp His Met Leu Lys Asn Tyr
130                 135                 140

Ser Ser Ile Leu Thr Ile His Ser Glu Val Ile Asp Gly Gln Leu Gly
145                 150                 155                 160

Thr Leu Val Val Glu Ser Phe Val Val Asp Ile Pro Glu Gly Asn Thr
                165                 170                 175

Lys Asp Asp Ile Cys Tyr Phe Ile Glu Asn Ile Leu Arg Cys Asn Leu
            180                 185                 190

Met Thr Leu Ala Asp Val Ser Glu Glu Arg Leu Ala Asn Pro
        195                 200                 205

<210> SEQ ID NO 65
<211> LENGTH: 205
<212> TYPE: PRT
<213> ORGANISM: Oryza sativa
<220> FEATURE:
<223> OTHER INFORMATION: rice Japonica Group, cultivar Nipponbare,
      hypothetical protein OsJ_06125, GenBank Accession No. EAZ22456.1

<400> SEQUENCE: 65

Met Val Glu Val Gly Gly Gly Ala Ala Glu Ala Ala Ala Gly Arg Arg
 1               5                  10                  15

Trp Arg Leu Ala Asp Glu Arg Cys Asp Leu Arg Ala Ala Glu Thr Glu
                20                  25                  30

Tyr Val Arg Arg Phe His Arg His Glu Pro Arg Asp His Gln Cys Ser
            35                  40                  45

Ser Ala Val Ala Lys His Ile Lys Ala Pro Val His Leu Val Trp Ser
        50                  55                  60

Leu Val Arg Arg Phe Asp Gln Pro Gln Leu Phe Lys Pro Phe Val Ser
 65                  70                  75                  80

Arg Cys Glu Met Lys Gly Asn Ile Glu Ile Gly Ser Val Arg Glu Val
                85                  90                  95

Asn Val Lys Ser Gly Leu Pro Ala Thr Arg Ser Thr Glu Arg Leu Glu
            100                 105                 110
```

```
Leu Leu Asp Asp Asn Glu His Ile Leu Ser Val Arg Phe Val Gly Gly
            115                 120                 125

Asp His Arg Leu Lys Asn Tyr Ser Ser Ile Leu Thr Val His Pro Glu
    130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
            180                 185                 190

Leu Val Cys Gln Gly Pro Asn Arg Ala Pro Ser Thr Arg
        195                 200                 205

<210> SEQ ID NO 66
<211> LENGTH: 204
<212> TYPE: PRT
<213> ORGANISM: Oryza sativa
<220> FEATURE:
<223> OTHER INFORMATION: rice Japonica Group, cultivar Nipponbare,
      hypothetical protein Os02g0255500, similar to extensin (fragment),
      GenBank Accession No. NP_001046464.1

<400> SEQUENCE: 66

Met Val Glu Val Gly Gly Gly Ala Ala Glu Ala Ala Gly Arg Arg
1               5                   10                  15

Trp Arg Leu Ala Asp Glu Arg Cys Asp Leu Arg Ala Ala Glu Thr Glu
            20                  25                  30

Tyr Val Arg Arg Phe His Arg His Glu Pro Arg Asp His Gln Cys Ser
        35                  40                  45

Ser Ala Val Ala Lys His Ile Lys Ala Pro Val His Leu Val Trp Ser
    50                  55                  60

Leu Val Arg Arg Phe Asp Gln Pro Gln Leu Phe Lys Pro Phe Val Ser
65                  70                  75                  80

Arg Cys Glu Met Lys Gly Asn Ile Glu Ile Gly Ser Val Arg Glu Val
                85                  90                  95

Asn Val Lys Ser Gly Leu Pro Ala Thr Arg Ser Thr Glu Arg Leu Glu
            100                 105                 110

Leu Leu Asp Asp Asn Glu His Ile Leu Ser Val Arg Phe Val Gly Gly
        115                 120                 125

Asp His Arg Leu Lys Asn Tyr Ser Ser Ile Leu Thr Val His Pro Glu
    130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
            180                 185                 190

Leu Val Val Lys Asp Gln Thr Glu Pro Leu Asp Arg
        195                 200

<210> SEQ ID NO 67
<211> LENGTH: 199
<212> TYPE: PRT
<213> ORGANISM: Medicago truncatula
<220> FEATURE:
<223> OTHER INFORMATION: barrel medic unknown protein, clone
      MTYFP_FQ_FR_FS1G-G-11, GenBank Accession No. ACJ86004.1
```

```
<400> SEQUENCE: 67

Met Glu Lys Met Asn Gly Thr Glu Asn Gly Val Phe Asn Ser Thr
  1               5                  10                  15

Glu Met Glu Tyr Ile Arg Arg His His Asn Gln Gln Pro Gly Glu Asn
                 20                  25                  30

Gln Cys Ser Ser Ala Leu Val Lys His Ile Arg Ala Pro Val Pro Leu
             35                  40                  45

Val Trp Ser Leu Val Arg Arg Phe Asp Gln Pro Gln Lys Tyr Lys Pro
         50                  55                  60

Phe Val Ser Arg Cys Val Val Arg Gly Asn Leu Glu Ile Gly Ser Leu
 65                  70                  75                  80

Arg Glu Val Asp Val Lys Ser Gly Leu Pro Ala Thr Thr Ser Thr Glu
                 85                  90                  95

Arg Leu Glu Val Leu Asp Asp Asn Glu His Ile Leu Ser Ile Arg Ile
                100                 105                 110

Ile Gly Gly Asp His Arg Leu Arg Asn Tyr Ser Ser Ile Met Ser Leu
            115                 120                 125

His Pro Glu Ile Ile Asp Gly Arg Pro Gly Thr Leu Val Ile Glu Ser
        130                 135                 140

Phe Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
                165                 170                 175

Ser Glu Gly His Ala Val Gln Asp Leu Thr Glu Pro Leu Asp Arg Val
            180                 185                 190

His Glu Leu Leu Ile Ser Gly
            195

<210> SEQ ID NO 68
<211> LENGTH: 199
<212> TYPE: PRT
<213> ORGANISM: Medicago truncatula
<220> FEATURE:
<223> OTHER INFORMATION: barrel medic unknown protein, clone
      MTYF1_F2_F3_FY1G-K-4, GenBank Accession No. ACJ83958.1

<400> SEQUENCE: 68

Met Glu Lys Met Asn Gly Thr Glu Asn Gly Val Phe Asn Ser Thr
  1               5                  10                  15

Glu Met Glu Tyr Ile Arg Arg His His Asn Gln Gln Pro Gly Glu Asn
                 20                  25                  30

Gln Cys Ser Ser Ala Leu Val Lys His Ile Arg Ala Pro Val Pro Leu
             35                  40                  45

Val Trp Ser Leu Val Arg Arg Phe Asp Gln Pro Gln Lys Tyr Lys Pro
         50                  55                  60

Phe Val Ser Arg Cys Val Val Arg Gly Asn Leu Glu Ile Gly Ser Leu
 65                  70                  75                  80

Arg Glu Val Asp Val Lys Ser Gly Leu Pro Ala Thr Thr Ser Thr Glu
                 85                  90                  95

Arg Leu Glu Val Leu Asp Asp Asn Glu His Ile Leu Ser Ile Arg Ile
                100                 105                 110

Ile Gly Gly Asp His Arg Leu Arg Asn Tyr Ser Ser Ile Met Ser Leu
            115                 120                 125

His Pro Glu Ile Ile Asp Gly Arg Pro Gly Thr Leu Val Ile Glu Ser
        130                 135                 140
```

```
Phe Val Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
            165                 170                 175

Ser Glu Gly His Ala Ala Gln Asp Leu Thr Glu Pro Leu Asp Arg Met
            180                 185                 190

His Glu Leu Leu Ile Ser Gly
            195
```

<210> SEQ ID NO 69
<211> LENGTH: 197
<212> TYPE: PRT
<213> ORGANISM: Zea mays
<220> FEATURE:
<223> OTHER INFORMATION: maize CAPIP1 protein, clone 244179, GenBank
      Accession No. ACG34726.1

<400> SEQUENCE: 69

```
Met Val Gly Leu Val Gly Gly Ser Thr Ala Arg Ala Glu His Val Val
1               5                   10                  15

Ala Asn Ala Gly Gly Glu Ala Glu Tyr Val Arg Arg Met His Arg His
            20                  25                  30

Ala Pro Thr Glu His Gln Cys Thr Ser Thr Leu Val Lys His Ile Lys
        35                  40                  45

Ala Pro Val His Leu Val Trp Gln Leu Val Arg Arg Phe Asp Gln Pro
    50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
        115                 120                 125

Ser Ser Ile Ile Thr Val His Pro Glu Ser Ile Asp Gly Arg Pro Gly
    130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Asn Ser Leu Ala Glu Val Ser Glu Gln Leu Ala Val Leu Ser Pro Thr
            180                 185                 190

Ser Leu Ile Asp Gln
        195
```

<210> SEQ ID NO 70
<211> LENGTH: 197
<212> TYPE: PRT
<213> ORGANISM: Zea mays
<220> FEATURE:
<223> OTHER INFORMATION: maize CAPIP1 protein, clone 1448906, GenBank
      Accession No. ACG26022.1

<400> SEQUENCE: 70

```
Met Val Gly Leu Val Gly Gly Ser Thr Ala Arg Ala Glu His Val Val
1               5                   10                  15

Ala Asn Ala Gly Gly Glu Ala Glu Tyr Val Arg Arg Met His Arg His
            20                  25                  30
```

```
Ala Pro Thr Glu His Gln Cys Thr Ser Thr Leu Val Lys His Ile Lys
            35                  40                  45

Ala Pro Val His Leu Val Trp Glu Leu Val Arg Arg Phe Asp Gln Pro
 50                  55                  60

Gln Arg Tyr Lys Pro Phe Val Arg Asn Cys Val Val Arg Gly Asp Gln
 65                  70                  75                  80

Leu Glu Val Gly Ser Leu Arg Asp Val Asn Val Lys Thr Gly Leu Pro
                 85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
            115                 120                 125

Ser Ser Ile Ile Thr Val His Pro Glu Ser Ile Asp Gly Arg Pro Gly
130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Asn Ser Leu Ala Glu Val Ser Glu Gln Leu Ala Val Glu Ser Pro Thr
            180                 185                 190

Ser Leu Ile Asp Gln
            195

<210> SEQ ID NO 71
<211> LENGTH: 212
<212> TYPE: PRT
<213> ORGANISM: Zea mays
<220> FEATURE:
<223> OTHER INFORMATION: maize strain B73 unknown protein, clone
      ZM_BFc0183D21, GenBank Accession No. ACF86162.1

<400> SEQUENCE: 71

Met Val Met Val Glu Met Asp Gly Gly Val Gly Gly Gly Gly Gly Gly
 1               5                  10                  15

Gly Gln Thr Pro Ala Pro Arg Arg Trp Arg Leu Ala Asp Glu Arg Cys
            20                  25                  30

Asp Leu Arg Ala Met Glu Thr Asp Tyr Val Arg Arg Phe His Arg His
            35                  40                  45

Glu Pro Arg Glu His Gln Cys Ser Ser Ala Val Ala Lys His Ile Lys
 50                  55                  60

Ala Pro Val His Leu Val Trp Ser Leu Val Arg Arg Phe Asp Gln Pro
 65                  70                  75                  80

Gln Leu Phe Lys Pro Phe Val Ser Arg Cys Glu Met Lys Gly Asn Ile
                 85                  90                  95

Glu Ile Gly Ser Val Arg Glu Val Asn Val Lys Ser Gly Leu Pro Ala
            100                 105                 110

Thr Arg Ser Thr Glu Arg Leu Glu Leu Leu Asp Asp Asn Glu His Ile
            115                 120                 125

Leu Ser Val Arg Phe Val Gly Gly Asp His Arg Leu Gln Asn Tyr Ser
130                 135                 140

Ser Ile Leu Thr Val His Pro Glu Val Ile Asp Gly Arg Pro Gly Thr
145                 150                 155                 160

Leu Val Ile Glu Ser Phe Val Val Asp Val Pro Asp Gly Asn Thr Lys
                165                 170                 175

Asp Glu Thr Cys Tyr Phe Val Glu Ala Leu Leu Lys Cys Asn Leu Lys
            180                 185                 190
```

```
Ser Leu Ala Glu Val Ser Glu Arg Gln Val Val Lys Asp Gln Thr Glu
        195                 200                 205

Pro Leu Asp Arg
    210

<210> SEQ ID NO 72
<211> LENGTH: 205
<212> TYPE: PRT
<213> ORGANISM: Oryza sativa
<220> FEATURE:
<223> OTHER INFORMATION: rice Japonica Group, cultivar Nipponbare,
      conserved hypothetical protein Os06g0527800, GenBank Accession No.
      NP_001057771.1

<400> SEQUENCE: 72

Met Asn Gly Ala Gly Gly Ala Gly Ala Ala Gly Lys Leu Pro
 1               5                  10                  15

Met Val Ser His Arg Arg Val Gln Cys Arg Leu Ala Asp Lys Arg Cys
             20                  25                  30

Glu Leu Arg Glu Glu Glu Met Glu Tyr Ile Arg Gln Phe His Arg His
         35                  40                  45

Glu Pro Ser Ser Asn Gln Cys Thr Ser Phe Val Ala Lys His Ile Lys
     50                  55                  60

Ala Pro Leu Gln Thr Val Trp Ser Leu Val Arg Arg Phe Asp Gln Pro
 65                  70                  75                  80

Gln Leu Phe Lys Pro Phe Val Arg Lys Cys Val Met Arg Glu Asn Ile
                 85                  90                  95

Ile Val Thr Gly Cys Val Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

Ile Leu Lys Val Lys Phe Ile Gly Gly Asp His Met Leu Lys Asn Tyr
    130                 135                 140

Ser Ser Ile Leu Thr Ile His Ser Glu Val Ile Asp Gly Gln Leu Gly
145                 150                 155                 160

Thr Leu Val Val Glu Ser Phe Val Val Asp Ile Pro Asp Gly Asn Thr
                165                 170                 175

Lys Asp Asp Ile Cys Tyr Phe Ile Glu Asn Val Leu Arg Cys Asn Leu
            180                 185                 190

Met Thr Leu Ala Asp Val Ser Glu Glu Arg Leu Ala Asn
        195                 200                 205

<210> SEQ ID NO 73
<211> LENGTH: 197
<212> TYPE: PRT
<213> ORGANISM: Zea mays
<220> FEATURE:
<223> OTHER INFORMATION: maize strain B73 unknown protein, clone
      ZM_BFc0063E17, GenBank Accession No. ACF85073.1

<400> SEQUENCE: 73

Met Val Gly Leu Val Gly Gly Ser Thr Ala Arg Ala Glu His Val Val
 1               5                  10                  15

Ala Asn Ala Gly Gly Glu Thr Glu Tyr Val Arg Arg Leu His Arg His
             20                  25                  30

Ala Pro Ala Glu His Gln Cys Thr Ser Thr Leu Val Lys His Ile Lys
         35                  40                  45

Ala Pro Val His Leu Val Trp Glu Leu Val Arg Ser Phe Asp Gln Pro
```

```
                   50                  55                  60

Gln Arg Tyr Lys Pro Phe Val Arg Asn Cys Val Val Arg Gly Asp Gln
 65                  70                  75                  80

Leu Glu Val Gly Ser Leu Arg Asp Val Asn Val Lys Thr Gly Leu Pro
                     85                  90                  95

Ala Thr Thr Ser Thr Glu Arg Leu Glu Gln Leu Asp Asp Asp Leu His
                100                 105                 110

Ile Leu Gly Val Lys Phe Val Gly Gly Asp His Arg Leu Gln Asn Tyr
            115                 120                 125

Ser Ser Ile Ile Thr Val His Pro Glu Ser Ile Asp Gly Arg Pro Gly
        130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Lys Ser Leu Ala Glu Val Ser Glu Gln Leu Ala Val Glu Ser Pro Thr
            180                 185                 190

Ser Pro Ile Asp Gln
        195

<210> SEQ ID NO 74
<211> LENGTH: 206
<212> TYPE: PRT
<213> ORGANISM: Oryza sativa
<220> FEATURE:
<223> OTHER INFORMATION: rice Indica Group, cultivar 93-11,
      hypothetical protein OsI_23218, GenBank Accession No. EAZ01191.1

<400> SEQUENCE: 74

Met Asn Gly Val Gly Gly Ala Gly Gly Ala Ala Gly Lys Leu Pro
  1               5                  10                  15

Met Val Ser His Arg Arg Val Gln Trp Arg Leu Ala Asp Glu Arg Cys
                 20                  25                  30

Glu Leu Arg Glu Glu Met Glu Tyr Ile Arg Arg Phe His Arg His
             35                  40                  45

Glu Pro Ser Ser Asn Gln Cys Thr Ser Phe Ala Ala Lys His Ile Lys
         50                  55                  60

Ala Pro Leu His Thr Val Trp Ser Leu Val Arg Arg Phe Asp Gln Pro
 65                  70                  75                  80

Gln Leu Phe Lys Pro Phe Val Arg Asn Cys Val Met Arg Glu Asn Ile
                 85                  90                  95

Ile Ala Thr Gly Cys Ile Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

Ile Leu Lys Val Lys Phe Ile Gly Gly Asp His Met Leu Lys Asn Tyr
    130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Leu Glu Gly Asn Thr
                165                 170                 175

Lys Asp Asp Ile Ser Tyr Phe Ile Glu Asn Val Leu Arg Cys Asn Leu
            180                 185                 190

Arg Thr Leu Ala Asp Val Ser Glu Glu Arg Leu Ala Asn Pro
        195                 200                 205
```

```
<210> SEQ ID NO 75
<211> LENGTH: 209
<212> TYPE: PRT
<213> ORGANISM: Oryza sativa
<220> FEATURE:
<223> OTHER INFORMATION: rice Japonica Group, cultivar Nipponbare,
      conserved hypothetical protein Os05g0213500, GenBank Accession No.
      NP_001054923.1

<400> SEQUENCE: 75

Met Val Gly Leu Val Gly Gly Gly Trp Arg Val Gly Asp Asp Ala
 1               5                  10                  15

Ala Gly Gly Gly Gly Gly Ala Val Ala Ala Gly Ala Ala Ala Ala
            20                  25                  30

Ala Glu Ala Glu His Met Arg Arg Leu His Ser His Ala Pro Gly Glu
        35                  40                  45

His Gln Cys Ser Ser Ala Leu Val Lys His Ile Lys Ala Pro Val His
    50                  55                  60

Leu Val Trp Ser Leu Val Arg Ser Phe Asp Gln Pro Gln Arg Tyr Lys
65                  70                  75                  80

Pro Phe Val Ser Arg Cys Val Val Arg Gly Gly Asp Leu Glu Ile Gly
                85                  90                  95

Ser Val Arg Glu Val Asn Val Lys Thr Gly Leu Pro Ala Thr Thr Ser
            100                 105                 110

Thr Glu Arg Leu Glu Leu Leu Asp Asp Glu His Ile Leu Ser Val
        115                 120                 125

Lys Phe Val Gly Gly Asp His Arg Leu Arg Asn Tyr Ser Ser Ile Val
130                 135                 140

Thr Val His Pro Glu Ser Ile Asp Gly Arg Pro Gly Thr Leu Val Ile
145                 150                 155                 160

Glu Ser Phe Val Val Asp Val Pro Asp Gly Asn Thr Lys Asp Glu Thr
                165                 170                 175

Cys Tyr Phe Val Glu Ala Val Ile Lys Cys Asn Leu Thr Ser Leu Ala
            180                 185                 190

Glu Val Ser Glu Arg Leu Ala Val Gln Ser Pro Thr Ser Pro Leu Glu
        195                 200                 205

Gln

<210> SEQ ID NO 76
<211> LENGTH: 180
<212> TYPE: PRT
<213> ORGANISM: Oryza sativa
<220> FEATURE:
<223> OTHER INFORMATION: rice Japonica Group, cultivar Nipponbare,
      Bet v I allergen-like protein, clone OSJNBa0052K15, gene
      OSJNBa0052K15.17, GenBank Accession No. BAD29692.1

<400> SEQUENCE: 76

Met Val Glu Met Asp Ala Gly Gly Arg Pro Glu Pro Ser Pro Ser
 1               5                  10                  15

Gly Gln Cys Ser Ser Ala Val Thr Met Arg Ile Asn Ala Pro Val His
            20                  25                  30

Leu Val Trp Ser Ile Val Arg Arg Phe Glu Pro His Ile Phe Gln
        35                  40                  45

Pro Phe Val Arg Gly Cys Thr Met Arg Gly Ser Thr Ser Leu Ala Val
    50                  55                  60

Gly Cys Val Arg Glu Val Asp Phe Lys Ser Gly Phe Pro Ala Lys Ser
65                  70                  75                  80
```

Ser Val Glu Arg Leu Glu Ile Leu Asp Asp Lys Glu His Val Phe Gly
            85                  90                  95

Val Arg Ile Ile Gly Gly Asp His Arg Leu Lys Asn Tyr Ser Ser Val
            100                 105                 110

Leu Thr Ala Lys Pro Glu Val Ile Asp Gly Glu Pro Ala Thr Leu Val
            115                 120                 125

Ser Glu Ser Phe Val Val Asp Val Pro Glu Gly Asn Thr Ala Asp Glu
            130                 135                 140

Thr Arg His Phe Val Glu Phe Leu Ile Arg Cys Asn Leu Arg Ser Leu
145                 150                 155                 160

Ala Met Val Ser Gln Arg Leu Leu Leu Ala Gln Gly Asp Leu Ala Glu
            165                 170                 175

Pro Pro Ala Gln
            180

<210> SEQ ID NO 77
<211> LENGTH: 176
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_029498, GenBank
      Accession No. CAN64668.1

<400> SEQUENCE: 77

Met Asn Gly Asn Gly Leu Ser Ser Met Glu Ser Glu Tyr Ile Arg Arg
1               5                   10                  15

His His Arg His Glu Pro Ala Glu Asn Gln Cys Ser Ser Ala Leu Val
            20                  25                  30

Lys His Ile Lys Ala Pro Val Pro Leu Val Trp Ser Leu Val Arg Arg
            35                  40                  45

Phe Asp Gln Pro Gln Lys Tyr Lys Pro Phe Ile Ser Arg Cys Val Val
        50                  55                  60

Gln Gly Asn Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
            85                  90                  95

Asp Glu His Ile Leu Ser Met Arg Ile Ile Gly Gly Asp His Arg Leu
            100                 105                 110

Arg Asn Tyr Ser Ser Ile Ile Ser Leu His Pro Glu Ile Ile Asp Gly
            115                 120                 125

Arg Pro Gly Thr Met Val Ile Glu Ser Tyr Val Val Asp Val Pro Glu
            130                 135                 140

Gly Asn Thr Lys Asp Glu Thr Cys Tyr Phe Ser Leu Ala Asp Val Ser
145                 150                 155                 160

Glu Arg Leu Ala Val Ala Gly Thr Val Thr Glu Pro Ile Asp Arg Met
            165                 170                 175

<210> SEQ ID NO 78
<211> LENGTH: 180
<212> TYPE: PRT
<213> ORGANISM: Oryza sativa
<220> FEATURE:
<223> OTHER INFORMATION: rice Indica Group, cultivar 93-11, hypothetical
      protein, locus tag OsI_06615, GenBank Accession No. EEC72859.1

<400> SEQUENCE: 78

Met Val Glu Met Asp Ala Gly Gly Arg Pro Glu Pro Ser Pro Pro Ser

```
                1               5                  10                 15
Gly Gln Cys Ser Ser Ala Val Thr Met Arg Ile Asn Ala Pro Val His
                20                 25                 30

Leu Val Trp Ser Ile Val Arg Arg Phe Glu Glu Pro His Ile Phe Gln
                35                 40                 45

Pro Phe Val Arg Gly Cys Thr Met Arg Gly Ser Thr Ser Leu Ala Val
 50                 55                 60

Gly Cys Val Arg Glu Val Asp Phe Lys Ser Gly Phe Ser Ala Lys Ser
 65                 70                 75                 80

Ser Val Glu Arg Leu Glu Ile Leu Asp Asp Lys Glu His Val Phe Gly
                85                 90                 95

Val Arg Ile Ile Gly Gly Asp His Arg Leu Lys Asn Tyr Ser Ser Val
                100                105                110

Leu Thr Ala Lys Pro Glu Val Ile Asp Gly Pro Ala Thr Leu Val
                115                120                125

Ser Glu Ser Phe Val Ile Asp Val Pro Glu Gly Asn Thr Ala Asp Glu
                130                135                140

Thr Arg His Phe Val Glu Phe Leu Ile Arg Cys Asn Leu Arg Ser Leu
145                 150                155                160

Ala Met Val Ser Gln Arg Leu Leu Leu Ala Gln Gly Asp Leu Ala Glu
                165                170                175

Pro Pro Ala Gln
                180

<210> SEQ ID NO 79
<211> LENGTH: 215
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_10498, GenBank Accession No.
      EAZ26598.1

<400> SEQUENCE: 79

Met Pro Cys Ile Pro Ala Ser Ser Pro Gly Ile Pro His Gln His Gln
 1               5                 10                 15

His Gln His His Arg Ala Leu Ala Gly Val Gly Met Ala Val Gly Cys
                20                 25                 30

Ala Ala Glu Ala Ala Val Ala Ala Ala Gly Val Ala Gly Thr Arg Cys
                35                 40                 45

Gly Ala His Asp Gly Glu Val Pro Met Glu Val Ala Arg His His Glu
 50                 55                 60

His Ala Glu Pro Gly Ser Gly Arg Cys Cys Ser Ala Val Val Gln His
 65                 70                 75                 80

Val Ala Ala Pro Ala Ala Val Trp Ser Val Val Arg Arg Phe Asp
                85                 90                 95

Gln Pro Gln Ala Tyr Lys Arg Phe Val Arg Ser Cys Ala Leu Leu Ala
                100                105                110

Gly Asp Gly Gly Leu Gly Lys Val Arg Glu Arg Leu Glu Ile Leu Asp
                115                120                125

Asp Glu Ser His Val Leu Ser Phe Arg Val Val Gly Gly Glu His Arg
                130                135                140

Leu Lys Asn Tyr Leu Ser Val Thr Thr Val His Pro Ser Pro Ser Ala
145                 150                155                160

Pro Thr Ala Ala Thr Val Val Val Glu Ser Tyr Val Val Asp Val Pro
                165                170                175
```

```
Pro Gly Asn Thr Pro Glu Asp Thr Arg Val Phe Val Asp Thr Ile Val
            180                 185                 190

Lys Cys Asn Leu Gln Ser Leu Ala Lys Thr Ala Glu Lys Leu Ala Ala
        195                 200                 205

Gly Ala Arg Ala Ala Gly Ser
    210                 215

<210> SEQ ID NO 80
<211> LENGTH: 186
<212> TYPE: PRT
<213> ORGANISM: Rheum australe
<220> FEATURE:
<223> OTHER INFORMATION: Himalayan rhubarb pathogen-induced protein-like
      protein, GenBank Accession No. ACH63237.1

<400> SEQUENCE: 80

Met Asn Gly Asp Gly Tyr Gly Gly Ser Glu Glu Phe Val Lys Arg
 1               5                  10                  15

Tyr His Glu His Val Leu Ala Asp His Gln Cys Ser Ser Val Leu Val
            20                  25                  30

Glu His Ile Asn Ala Pro Leu His Leu Val Trp Ser Leu Val Arg Ser
        35                  40                  45

Phe Asp Gln Pro Gln Lys Tyr Lys Pro Phe Val Ser Arg Cys Val Val
 50                  55                  60

Gln Gly Gly Asp Leu Glu Ile Gly Ser Val Arg Glu Val Asp Val Lys
 65                  70                  75                  80

Ser Gly Leu Pro Ala Thr Thr Ser Met Glu Glu Leu Glu Leu Leu Asp
                85                  90                  95

Asp Lys Glu His Val Leu Arg Val Lys Phe Val Gly Asp His Arg
            100                 105                 110

Leu Lys Asn Tyr Ser Ser Ile Val Ser Leu His Pro Glu Ile Ile Gly
        115                 120                 125

Gly Arg Ser Gly Thr Met Val Ile Glu Ser Phe Ile Val Asp Ile Ala
    130                 135                 140

Asp Gly Asn Thr Lys Glu Glu Thr Cys Tyr Phe Ile Glu Ser Leu Ile
145                 150                 155                 160

Asn Cys Asn Leu Lys Ser Leu Ser Cys Val Ser Glu Arg Leu Ala Val
                165                 170                 175

Glu Asp Ile Ala Glu Arg Ile Ala Gln Met
            180                 185

<210> SEQ ID NO 81
<211> LENGTH: 254
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_016770, GenBank Accession No.
      EAZ33287.1

<400> SEQUENCE: 81

Met Val Gly Leu Val Gly Gly Gly Gly Trp Arg Val Gly Asp Asp Ala
 1               5                  10                  15

Ala Gly Gly Gly Gly Gly Gly Ala Val Ala Ala Gly Ala Ala Ala Ala
            20                  25                  30

Ala Glu Ala Glu His Met Arg Arg Leu His Ser Gln Gly Pro Arg Arg
        35                  40                  45

Ala Pro Val Gln Leu Arg Ala Arg Gln Ala His Gln Gly Ser Cys Ser
```

```
             50                  55                  60
Pro Pro Arg Ile Glu Cys Ala Asn Phe Ala Val Phe Leu Ala Ala Arg
 65                  70                  75                  80

Asp Pro Lys Ile Val Trp Ser Leu Val Arg Ser Phe Asp Gln Pro Gln
                 85                  90                  95

Arg Tyr Lys Pro Phe Val Ser Arg Cys Val Val Arg Gly Gly Asp Leu
                100                 105                 110

Glu Ile Gly Ser Val Arg Glu Val Asn Val Lys Thr Gly Leu Pro Ala
            115                 120                 125

Thr Thr Ser Thr Glu Arg Leu Glu Leu Leu Asp Asp Asp Glu His Ile
        130                 135                 140

Leu Ser Val Lys Phe Val Gly Gly Asp His Arg Leu Arg Asn Tyr Ser
145                 150                 155                 160

Ser Ile Val Thr Val His Pro Glu Ser Ile Asp Gly Arg Pro Gly Thr
                165                 170                 175

Leu Val Ile Glu Ser Phe Val Val Asp Val Pro Asp Gly Asn Thr Lys
            180                 185                 190

Asp Glu Thr Cys Tyr Phe Val Glu Ala Val Ile Lys Cys Asn Leu Thr
        195                 200                 205

Ser Leu Ala Glu Met Val Arg Met Ile Ser Leu Val Leu Pro Phe Met
210                 215                 220

Leu Val Asp Arg Met Ser Gly Ile Thr Cys Glu Ser His Leu Glu Thr
225                 230                 235                 240

Thr Leu Val Arg Cys Gly Glu Tyr Ala Val Leu Ala His Val
                245                 250

<210> SEQ ID NO 82
<211> LENGTH: 186
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_005784, GenBank Accession No.
      EAZ22301.1

<400> SEQUENCE: 82

Met Glu Pro His Met Glu Arg Ala Leu Arg Glu Ala Val Ala Ser Glu
  1               5                  10                  15

Ala Glu Arg Arg Glu Leu Glu Gly Val Val Arg Ala His His Thr Gly
             20                  25                  30

Trp Asn Ala Pro Leu Ala Ala Val Trp Pro His Arg Ala Arg Val Arg
         35                  40                  45

Pro Thr Arg Ser Gly Thr Ser Thr Ser Ser Arg Ala Ser Ser Pro
 50                  55                  60

Pro Gly Asp Gly Ala Thr Val Gly Ser Val Arg Glu Val Ala Val Val
 65                  70                  75                  80

Ser Gly Leu Pro Ala Ser Thr Ser Thr Glu Arg Leu Glu Ile Leu Asp
                 85                  90                  95

Asp Asp Arg His Val Leu Ser Phe Arg Val Gly Gly Asp His Arg
                100                 105                 110

Leu Arg Asn Tyr Arg Ser Val Thr Ser Val Thr Glu Phe Ser Ser Pro
            115                 120                 125

Ser Ser Pro Pro Arg Pro Tyr Cys Val Val Val Glu Ser Tyr Val Val
        130                 135                 140

Asp Val Pro Glu Gly Asn Thr Glu Glu Asp Thr Arg Met Phe Thr Asp
145                 150                 155                 160
```

```
Thr Val Val Lys Leu Asn Leu Gln Lys Leu Ala Ala Val Ala Thr Ser
            165                 170                 175

Ser Ser Pro Pro Ala Ala Gly Asn His His
            180                 185

<210> SEQ ID NO 83
<211> LENGTH: 150
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_005938, GenBank Accession No.
      EAZ22455.1

<400> SEQUENCE: 83

Met Glu Val Val Trp Ser Ile Val Arg Arg Phe Glu Glu Pro His Ile
 1               5                  10                  15

Phe Gln Pro Phe Val Arg Gly Cys Thr Met Arg Gly Ser Thr Ser Leu
                20                  25                  30

Ala Val Gly Cys Val Arg Glu Val Asp Phe Lys Ser Gly Phe Pro Ala
            35                  40                  45

Lys Ser Ser Val Glu Arg Leu Glu Ile Leu Asp Asp Lys Glu His Val
 50                  55                  60

Phe Gly Val Arg Ile Ile Gly Gly Asp His Arg Leu Lys Asn Tyr Ser
 65                  70                  75                  80

Ser Val Leu Thr Ala Lys Pro Glu Val Ile Asp Gly Glu Pro Ala Thr
                85                  90                  95

Leu Val Ser Glu Ser Phe Val Val Asp Val Pro Glu Gly Asn Thr Ala
            100                 105                 110

Asp Glu Thr Arg His Phe Val Glu Phe Leu Ile Arg Cys Asn Leu Arg
            115                 120                 125

Ser Leu Ala Met Val Ser Gln Arg Leu Leu Leu Ala Gln Gly Asp Leu
        130                 135                 140

Ala Glu Pro Pro Gly Gln
145                 150

<210> SEQ ID NO 84
<211> LENGTH: 206
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_018129, GenBank Accession No.
      EAZ34646.1

<400> SEQUENCE: 84

Met Pro Tyr Thr Ala Pro Arg Pro Ser Pro Pro Gln His Ser Arg Ile
 1               5                  10                  15

Gly Gly Cys Gly Gly Gly Gly Val Leu Lys Ala Ala Gly Ala Ala Gly
                20                  25                  30

His Ala Ala Ser Cys Val Ala Val Pro Ala Glu Val Ala Arg His His
            35                  40                  45

Glu His Ala Ala Gly Val Gly Gln Cys Cys Ser Ala Val Val Gln Ala
 50                  55                  60

Ile Ala Ala Pro Val Asp Ala Val Trp Arg Thr Ser Thr Ser Ser Gly
 65                  70                  75                  80

Ala Ala Ala Ser Trp Thr Ala Thr Ala Thr Ala Gly Pro Leu Pro Val
                85                  90                  95
```

```
Gly Ser Val Arg Glu Phe Arg Val Leu Ser Gly Leu Pro Gly Thr Ser
            100                 105                 110

Ser Arg Glu Arg Leu Glu Ile Leu Asp Asp Glu Arg Val Leu Ser
        115                 120                 125

Phe Arg Val Val Gly Glu His Arg Leu Ser Asn Tyr Arg Ser Val
    130                 135                 140

Thr Thr Val His Glu Thr Ala Ala Gly Ala Ala Ala Val Val Val
145                 150                 155                 160

Glu Ser Tyr Val Val Asp Val Pro His Gly Asn Thr Ala Asp Glu Thr
                165                 170                 175

Arg Met Phe Val Asp Thr Ile Val Arg Cys Asn Leu Gln Ser Leu Ala
                180                 185                 190

Arg Thr Ala Glu Gln Leu Ala Leu Ala Ala Pro Arg Ala Ala
        195                 200                 205

<210> SEQ ID NO 85
<211> LENGTH: 396
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_001710, GenBank
      Accession No. CAN76441.1
<220> FEATURE:
<221> NAME/KEY: VARIANT
<222> LOCATION: (1)...(396)
<223> OTHER INFORMATION: Xaa = any amino acid

<400> SEQUENCE: 85

Met Pro Ile Ser Ser Leu Pro Phe Ser Leu Tyr Thr Val Thr Pro Asn
 1               5                  10                  15

Pro Leu Lys Leu Ile Thr Thr His Ala His Ala Phe Thr Pro His Thr
            20                  25                  30

His Ile Phe Thr Leu Lys Phe Met Ser His Thr Tyr Cys Pro His Ile
        35                  40                  45

His His Ile Thr Ser Ile His Tyr Thr His Leu Leu Xaa Pro Ile Pro
    50                  55                  60

His Met Pro Leu Gln Pro Pro Leu Pro His Pro Ile Leu Pro Ser
65                  70                  75                  80

Met Pro Ala Phe Gln His Leu Tyr Ser Thr Asn Gln His Leu Gln Val
                85                  90                  95

Ala Leu Phe Ser Ala Arg Gly Pro Asn Ile Arg Asp Phe Asn Phe Gln
            100                 105                 110

Asp Ala Asp Leu Leu Lys Leu Asp Ile Leu Ala Pro Gly Ser Leu Ile
        115                 120                 125

Trp Ala Ala Trp Ser Pro Asn Gly Thr Asp Glu Ala Asn Tyr Val Gly
    130                 135                 140

Glu Gly Ser Pro Thr Val Ala Met Ile Ala Lys Arg Gly Pro Arg His
145                 150                 155                 160

Gly Lys Tyr Met Ala Phe Cys Xaa Met Tyr Arg Asp Asn Val Ala Pro
                165                 170                 175

Lys Gly Val Asn Xaa Ala Val Ala Thr Val Lys Thr Lys Arg Thr Ile
            180                 185                 190

Gln Leu Lys Thr Ser Leu Glu Ile Ala Cys His Tyr Ala Gly Ile Asn
        195                 200                 205

Ile Ser Gly Ile Asn Gly Glu Val Met Pro Gly Gln Trp Glu Tyr Gln
    210                 215                 220
```

-continued

Val Gly Pro Gly Gln Cys Ser Ser Leu Leu Ala Gln Arg Val His Val
225                 230                 235                 240

Pro Leu Ser Ala Val Gly Ser Val Val His Arg Phe Asp Lys Pro Gln
            245                 250                 255

Arg Tyr Gln His Val Ile Lys Ser Cys Arg Ile Glu Asp Gly Phe Glu
            260                 265                 270

Met Arg Met Gly Xaa Leu Arg Asp Val Asn Ile Ile Ser Gly Leu Pro
        275                 280                 285

Thr Ala Thr Asn Thr Gly Arg Leu Asp Met Gln Asp Glu Arg His
    290                 295                 300

Val Thr Arg Cys Pro His Gln Arg Gln Ser Glu Ser Lys Tyr Thr Glu
305                 310                 315                 320

Asn Asn Asn Ser Asp Ala Ser Ser Ile Lys Ser Pro Ile Asn Gly Pro
                325                 330                 335

Ser Glu His Leu Lys Thr Ala Ala Ser Pro Lys Thr Glu Ser Ile Ile
            340                 345                 350

Val Ile Asp Thr Ser Lys Phe Leu Asn Glu Glu Asp Phe Glu Gly Lys
            355                 360                 365

Asp Glu Thr Ser Ser Ser Asn Gln Val Gln Ile Glu Asp Glu Asn Trp
        370                 375                 380

Glu Thr Arg Phe Pro Asn Thr Asp Ala Gly Ile Trp
385                 390                 395

<210> SEQ ID NO 86
<211> LENGTH: 443
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_014403, GenBank
      Accession No. CAN9881.1
<220> FEATURE:
<221> NAME/KEY: VARIANT
<222> LOCATION: (1)...(443)
<223> OTHER INFORMATION: Xaa = any amino acid

<400> SEQUENCE: 86

Met Pro Ser Ala Xaa Lys Ser Ser Thr Val Pro Leu Ser Leu Xaa Gln
1               5                   10                  15

Phe Lys Leu Gly Leu Arg His Gly His Arg Val Ile Pro Trp Gly Asp
            20                  25                  30

Leu Asp Ser Leu Ala Met Leu Gln Arg Gln Leu Asp Val Asp Ile Leu
        35                  40                  45

Val Thr Gly His Thr His Arg Phe Thr Ala Tyr Lys His Glu Gly Gly
    50                  55                  60

Val Val Ile Asn Pro Gly Ser Ala Thr Gly Ala Phe Gly Ser Ile Thr
65                  70                  75                  80

Tyr Asp Val Asn Pro Ser Phe Val Leu Met Asp Ile Asp Gly Leu Arg
                85                  90                  95

Val Val Val Cys Val Tyr Glu Leu Ile Asp Glu Thr Ala Asn Ile Ile
            100                 105                 110

Lys Glu Leu His Ala Arg Lys Ile Ser Phe Gly Thr Lys Ser Met Ile
        115                 120                 125

Xaa Cys Leu Leu Leu Lys Arg Arg Ser Thr Pro Lys Phe Arg Arg Lys
    130                 135                 140

Lys Leu Phe Leu Phe Gln Cys Arg Val Gln Met Thr Leu Thr Leu Thr
145                 150                 155                 160

```
Asn Leu Ala Val Ser Gly Ile Ala Gln Thr Leu Gln Val Asp Gln Trp
                165                 170                 175
Thr Val Cys Ala Leu Ile Phe Met Thr Arg Arg Asp Ile His Leu Asp
            180                 185                 190
Lys Ala Arg Phe Leu Asp Phe Lys Asp Met Gly Lys Leu Leu Ala Asp
        195                 200                 205
Ala Ser Gly Leu Arg Lys Ala Leu Ser Gly Gly Xaa Val Thr Ala Gly
    210                 215                 220
Met Ala Ile Phe Asp Thr Met Arg His Ile Arg Pro Asp Val Pro Thr
225                 230                 235                 240
Val Cys Val Gly Leu Ala Ala Val Ala Met Ile Ala Lys Arg Gly Pro
                245                 250                 255
Arg His Gly Lys Tyr Met Ala Phe Cys Pro Met Tyr Arg Asp Asn Val
            260                 265                 270
Ala Pro Lys Gly Val Asn Val Ala Val Val Thr Val Lys Thr Lys Arg
        275                 280                 285
Thr Ile Gln Leu Lys Thr Ser Leu Glu Ile Ala Cys His Tyr Ala Gly
    290                 295                 300
Ile Asn Ile Ser Gly Ile Asn Gly Glu Val Met Pro Gly Gln Trp Glu
305                 310                 315                 320
Tyr Gln Val Gly Pro Gly Gln Cys Ser Ser Leu Leu Ala Gln Arg Val
                325                 330                 335
His Val Pro Leu Ser Ala Val Gly Ser Val Val His Arg Phe Asp Lys
            340                 345                 350
Pro Gln Arg Tyr Gln His Val Ile Lys Ser Cys Arg Ile Glu Asp Gly
        355                 360                 365
Phe Glu Met Arg Met Gly Arg Leu Arg Asp Val Asn Ile Ile Ser Gly
    370                 375                 380
Leu Pro Thr Ala Thr Asn Thr Gly Arg Leu Asp Met Gln Asp Asp Glu
385                 390                 395                 400
Xaa His Val Thr Arg Cys Pro His Gln Arg Gln Ser Glu Ser Lys Tyr
                405                 410                 415
Thr Glu Asn Asn Asn Ser Asp Ala Ser Ser Val Lys Ser Pro Ile Asn
            420                 425                 430
Gly Pro Ser Glu His Leu Lys Thr Ala Ala Xaa
        435                 440

<210> SEQ ID NO 87
<211> LENGTH: 95
<212> TYPE: PRT
<213> ORGANISM: Oryza sativa
<220> FEATURE:
<223> OTHER INFORMATION: rice Indica Group, cultivar Pokkali, capip1
      protein, clone OSR-385-428-D5, GenBank Accession No. ABR25904.1

<400> SEQUENCE: 87

Glu Ile Gly Ser Val Arg Glu Val Asn Val Lys Thr Gly Leu Pro Ala
1               5                   10                  15
Thr Thr Ser Thr Glu Arg Leu Glu Leu Leu Asp Asp Asp Glu His Ile
            20                  25                  30
Leu Ser Val Lys Phe Val Gly Gly Asp His Arg Leu Arg Asn Tyr Ser
        35                  40                  45
Ser Ile Val Thr Val His Pro Glu Ser Ile Asp Gly Arg Pro Gly Thr
    50                  55                  60
Leu Val Ile Glu Ser Phe Val Val Asp Val Pro Asp Gly Asn Thr Lys
65                  70                  75                  80
```

Asp Glu Thr Cys Tyr Phe Val Glu Ala Val Ile Lys Cys Asn Leu
                85                  90                  95

<210> SEQ ID NO 88
<211> LENGTH: 191
<212> TYPE: PRT
<213> ORGANISM: Zea mays
<220> FEATURE:
<223> OTHER INFORMATION: maize strain B73 unknown protein, clone
      ZM_BFc0034007, GenBank Accession No. ACF84624.1

<400> SEQUENCE: 88

Met Val Val Glu Met Asp Gly Val Gly Val Ala Ala Ala Gly Gly
 1               5                  10                  15

Gly Gly Ala Gln Thr Pro Ala Pro Pro Pro Arg Arg Trp Arg Leu
                20                  25                  30

Ala Asp Glu Arg Cys Asp Leu Arg Ala Met Glu Thr Asp Tyr Val Arg
                35                  40                  45

Arg Phe His Arg His Glu Pro Arg Asp His Gln Cys Ser Ser Ala Val
50                  55                  60

Ala Lys His Ile Lys Ala Pro Val His Leu Val Trp Ser Leu Val Arg
65                  70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
                100                 105                 110

Ser Gly Leu Pro Ala Thr Arg Ser Thr Glu Arg Leu Glu Leu Leu Asp
                115                 120                 125

Asp Asp Glu Arg Ile Leu Ser Val Arg Phe Val Gly Gly Asp His Arg
130                 135                 140

Leu Gln Val Cys Ser Val Leu His Leu Ser Ile Phe Cys Ala Ala His
145                 150                 155                 160

Ala Arg Tyr Phe Ala His His Leu Lys Cys Val Leu Glu Phe Leu Cys
                165                 170                 175

Gln Met His Leu Asp Val Leu Pro Cys Asp Asp Ala Ile Leu Glu
                180                 185                 190

<210> SEQ ID NO 89
<211> LENGTH: 239
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_020681, GenBank Accession No.
      EAZ37198.1

<400> SEQUENCE: 89

Met Asn Gly Cys Thr Gly Gly Ala Gly Gly Val Ala Ala Gly Arg Leu
 1               5                  10                  15

Pro Ala Val Ser Leu Gln Gln Ala Gln Trp Lys Leu Val Asp Glu Arg
                20                  25                  30

Cys Glu Leu Arg Glu Glu Glu Met Glu Tyr Val Arg Arg Phe His Arg
                35                  40                  45

His Glu Ile Gly Ser Asn Gln Cys Asn Ser Phe Ile Ala Lys His Val
                50                  55                  60

Arg Ala Pro Leu Gln Asn Val Trp Ser Leu Val Arg Arg Phe Asp Gln
65                  70                  75                  80

Pro Gln Ile Tyr Lys Pro Phe Val Arg Lys Cys Val Met Arg Gly Asn

```
                85                  90                  95
Val Glu Thr Gly Ser Val Arg Glu Ile Ile Val Gln Ser Gly Leu Pro
            100                 105                 110

Ala Thr Arg Ser Ile Glu Arg Leu Glu Phe Leu Asp Asp Asn Glu Tyr
            115                 120                 125

Ile Leu Arg Val Lys Phe Ile Gly Gly Asp His Met Leu Lys Lys Arg
        130                 135                 140

Ile Pro Lys Lys Thr Tyr Ala Ile Ser Ser Arg Thr Cys Ser Asp Ser
145                 150                 155                 160

Ala Ile Ile Ala Val Gly Gln Ser Asn Cys Ala Pro Glu Ile Thr Ala
                165                 170                 175

Met Asn Gly Gly Val Ser Ile Gln Pro Trp Leu Ile Leu Leu Ala Phe
            180                 185                 190

Phe Ser Ser Pro Ser Asn Gln Thr Asn Pro Asp Ser Leu Arg Asp Met
            195                 200                 205

His Pro Gly Ser Trp Phe Gln Ile Leu Leu Val Leu Ala Met Phe Thr
        210                 215                 220

Cys Ser Lys Gly Ser Val Leu Pro Pro Ser Glu Lys Val Asn Val
225                 230                 235

<210> SEQ ID NO 90
<211> LENGTH: 188
<212> TYPE: PRT
<213> ORGANISM: Zea mays
<220> FEATURE:
<223> OTHER INFORMATION: maize GRMZM2G154987_P01 protein

<400> SEQUENCE: 90

Met Glu Pro His Met Glu Ser Ala Leu Arg Gln Gly Leu Ser Glu Ala
  1               5                  10                  15

Glu Gln Arg Glu Leu Glu Gly Val Val Arg Ala His His Thr Phe Pro
             20                  25                  30

Gly Arg Ala Pro Gly Thr Cys Thr Ser Leu Val Thr Gln Arg Val Asp
         35                  40                  45

Ala Pro Leu Ala Ala Val Trp Pro Ile Val Arg Gly Phe Gly Ser Pro
     50                  55                  60

Gln Arg Tyr Lys His Phe Ile Lys Ser Cys Asp Leu Lys Ala Gly Asp
 65                  70                  75                  80

Gly Ala Thr Val Gly Ser Val Arg Glu Val Thr Val Val Ser Gly Leu
                 85                  90                  95

Pro Ala Ser Thr Ser Thr Glu Arg Leu Glu Ile Leu Asp Asp His Arg
            100                 105                 110

His Ile Leu Ser Phe Arg Val Val Gly Gly Asp His Arg Leu Arg Asn
        115                 120                 125

Tyr Arg Ser Val Thr Ser Val Thr Glu Phe Gln Pro Gly Pro Tyr Cys
    130                 135                 140

Val Val Leu Glu Ser Tyr Val Val Asp Val Pro Asp Gly Asn Thr Glu
145                 150                 155                 160

Glu Asp Thr Arg Met Phe Thr Asp Thr Val Val Lys Leu Asn Leu Gln
                165                 170                 175

Lys Leu Ala Ala Ile Ala Thr Ser Ser Ser Ala Asn
            180                 185

<210> SEQ ID NO 91
<211> LENGTH: 205
<212> TYPE: PRT
```

<213> ORGANISM: Zea mays
<220> FEATURE:
<223> OTHER INFORMATION: maize GRMZM2G134731_P01 protein

<400> SEQUENCE: 91

```
Met Asp Gln Gln Gly Ala Gly Gly Asp Val Glu Val Pro Ala Gly Leu
1               5                  10                  15

Gly Leu Thr Ala Ala Glu Tyr Glu Gln Leu Arg Pro Thr Val Asp Ala
            20                  25                  30

His His Arg Tyr Ala Val Gly Glu Gly Gln Cys Ser Ser Leu Leu Ala
        35                  40                  45

Gln Arg Ile His Ala Pro Pro Ala Ala Val Trp Ala Ile Val Arg Arg
50                  55                  60

Phe Asp Cys Pro Gln Val Tyr Lys His Phe Ile Arg Ser Cys Ala Val
65                  70                  75                  80

Arg Pro Asp Pro Asp Ala Gly Asp Ala Leu Arg Pro Gly Arg Leu Arg
                85                  90                  95

Glu Val Cys Val Ile Ser Gly Leu Pro Ala Ser Thr Ser Thr Glu Arg
            100                 105                 110

Leu Asp His Leu Asp Asp Ala Ala Arg Val Phe Gly Phe Ser Ile Thr
        115                 120                 125

Gly Gly Glu His Arg Leu Arg Asn Tyr Arg Ser Val Thr Thr Val Ser
130                 135                 140

Glu Leu Ala Gly Pro Gly Ile Cys Thr Val Val Leu Glu Ser Tyr Ala
145                 150                 155                 160

Val Asp Val Pro Asp Gly Asn Thr Glu Asp Asp Thr Arg Leu Phe Ala
                165                 170                 175

Asp Thr Val Ile Arg Leu Asn Leu Gln Lys Leu Lys Ser Val Ala Glu
            180                 185                 190

Ala Ser Thr Ser Ser Ser Ala Pro Pro Pro Ser Glu
        195                 200                 205
```

<210> SEQ ID NO 92
<211> LENGTH: 220
<212> TYPE: PRT
<213> ORGANISM: Zea mays
<220> FEATURE:
<223> OTHER INFORMATION: maize GRMZM2G144224_P01 protein

<400> SEQUENCE: 92

```
Met Pro Cys Ile Gln Ala Ser Ser Pro Gly Gly Met Pro His Gln His
1               5                  10                  15

Gly Arg Gly Arg Val Leu Gly Gly Val Gly Cys Ala Ala Glu Val
            20                  25                  30

Ala Ala Ala Val Ala Ala Ser Ala Gly Gly Met Arg Cys Gly Ala His
        35                  40                  45

Asp Gly Glu Val Pro Ala Glu Ala Ala Arg His His Glu His Ala Ala
50                  55                  60

Ala Gly Pro Gly Arg Cys Cys Ser Ala Val Val Gln His Val Ala Ala
65                  70                  75                  80

Pro Ala Ala Ala Val Trp Ser Val Val Arg Arg Phe Asp Gln Pro Gln
                85                  90                  95

Val Tyr Lys Arg Phe Val Arg Ser Cys Ala Leu Leu Ala Gly Asp Gly
            100                 105                 110

Gly Val Gly Thr Leu Arg Glu Val Arg Val Val Ser Gly Leu Pro Ala
        115                 120                 125
```

```
Ala Ser Ser Arg Glu Arg Leu Glu Val Leu Asp Asp Glu Ser His Val
    130                 135                 140

Leu Ser Phe Arg Val Val Gly Gly Glu His Arg Leu Arg Asn Tyr Leu
145                 150                 155                 160

Ser Val Thr Thr Val His Pro Ser Pro Ala Ala Pro Asp Ala Ala Thr
                165                 170                 175

Val Val Val Glu Ser Tyr Val Val Asp Val Pro Pro Gly Asn Thr Pro
            180                 185                 190

Glu Asp Thr Arg Val Phe Val Asp Thr Ile Val Lys Cys Asn Leu Gln
            195                 200                 205

Ser Leu Ala Thr Thr Ala Glu Lys Leu Ala Ala Val
    210                 215                 220
```

<210> SEQ ID NO 93
<211> LENGTH: 221
<212> TYPE: PRT
<213> ORGANISM: Glycine max
<220> FEATURE:
<223> OTHER INFORMATION: soybean Glyma01g02290.1 protein

<400> SEQUENCE: 93

```
Met Glu Lys Ala Glu Ser Ser Ala Ser Thr Ser Glu Pro Asp Ser Asp
  1               5                  10                  15

Glu Asn His His Arg His Pro Thr Asn His His Ile Asn Pro Pro Ser
                 20                  25                  30

Gly Leu Thr Pro Leu Glu Phe Ala Ser Leu Ile Pro Ser Val Ala Glu
             35                  40                  45

His His Ser Tyr Leu Val Gly Ser Gly Gln Cys Ser Ser Leu Leu Ala
         50                  55                  60

Gln Arg Val Gln Ala Pro Pro Asp Ala Val Trp Ser Val Val Arg Arg
 65                  70                  75                  80

Phe Asp Lys Pro Gln Thr Tyr Lys His Phe Ile Lys Ser Cys Ala Val
                 85                  90                  95

Lys Glu Pro Phe His Met Ala Val Gly Val Thr Arg Asp Val Asn Val
                100                 105                 110

Ile Ser Gly Leu Pro Ala Ala Thr Ser Thr Glu Arg Leu Asp Leu Leu
            115                 120                 125

Asp Asp Ile Arg Cys Val Thr Gly Phe Ser Ile Ile Gly Gly Glu His
    130                 135                 140

Arg Leu Arg Asn Tyr Arg Ser Val Thr Thr Val His Ser Phe Glu Asp
145                 150                 155                 160

Asp Ala Asp Asp Gly Lys Ile Tyr Thr Val Val Leu Glu Ser Tyr Val
                165                 170                 175

Val Asp Val Pro Asp Gly Asn Thr Glu Glu Asp Thr Arg Leu Phe Ala
            180                 185                 190

Asp Thr Val Val Lys Leu Asn Leu Gln Lys Leu Ala Ser Val Thr Glu
    195                 200                 205

Gly Thr Asn Arg Asp Gly Asp Gly Lys Ser His Ser Arg
210                 215                 220
```

<210> SEQ ID NO 94
<211> LENGTH: 214
<212> TYPE: PRT
<213> ORGANISM: Glycine max
<220> FEATURE:
<223> OTHER INFORMATION: soybean Glyma01g12970.1 protein

<400> SEQUENCE: 94

Met Glu Lys Thr His Ser Ser Ala Glu Glu Gln Asp Pro Thr Arg
1               5                   10                  15

Arg His Leu Asp Pro Pro Gly Leu Thr Ala Glu Glu Phe Glu Asp
            20                  25                  30

Leu Lys Pro Ser Val Leu Glu His His Thr Tyr Ser Val Thr Pro Thr
        35                  40                  45

Arg Gln Ser Ser Leu Leu Ala Gln Arg Ile His Ala Pro Pro His
        50                  55                  60

Ala Val Trp Ser Val Val Arg Cys Phe Asp Asn Pro Gln Ala Tyr Lys
65              70                  75                  80

His Phe Ile Lys Ser Cys His Val Lys Glu Gly Phe Gln Leu Ala Val
                85                  90                  95

Gly Ser Thr Arg Asp Val His Val Ile Ser Gly Leu Pro Ala Ala Thr
            100                 105                 110

Ser Thr Glu Arg Leu Asp Leu Leu Asp Asp Asp Arg His Val Ile Gly
        115                 120                 125

Phe Thr Ile Val Gly Gly Asp His Arg Leu Arg Asn Tyr Arg Ser Val
130                 135                 140

Thr Ser Val His Gly Phe Glu Cys Asp Gly Lys Ile Trp Thr Val Val
145                 150                 155                 160

Leu Glu Ser Tyr Val Val Asp Val Pro Glu Gly Asn Thr Glu Asp
            165                 170                 175

Thr Arg Leu Phe Ala Asp Thr Val Val Lys Leu Asn Leu Gln Lys Leu
        180                 185                 190

Ala Ser Val Ser Glu Gly Met Cys Gly Asp Gly Asp Gly Asp Gly Asp
        195                 200                 205

Gly Lys Gly Asn Lys Ser
        210

<210> SEQ ID NO 95
<211> LENGTH: 216
<212> TYPE: PRT
<213> ORGANISM: Glycine max
<220> FEATURE:
<223> OTHER INFORMATION: soybean Glyma01g31320.1 protein

<400> SEQUENCE: 95

Met Leu Gln Asn Ser Ser Met Ser Leu Leu Leu His Arg Ile Asn
1               5                   10                  15

Gly Gly Gly Gly Ala Thr Thr Ala Thr Asn Cys His Asp Thr Val Phe
            20                  25                  30

Met Thr Val Pro Asp Gly Val Ala Arg Tyr His Thr His Ala Val Ala
        35                  40                  45

Pro Asn Gln Cys Cys Ser Ser Val Ala Gln Glu Ile Gly Ala Ser Val
        50                  55                  60

Ala Thr Val Trp Ser Val Leu Arg Arg Phe Asp Asn Pro Gln Ala Tyr
65              70                  75                  80

Lys His Phe Val Lys Ser Cys His Val Ile Gly Gly Asp Gly Asp Val
                85                  90                  95

Gly Thr Leu Arg Glu Val His Val Ile Ser Gly Leu Pro Ala Ala Arg
            100                 105                 110

Ser Thr Glu Arg Leu Glu Ile Leu Asp Asp Glu Arg His Val Ile Ser
        115                 120                 125

Phe Ser Val Val Gly Gly Asp His Arg Leu Ala Asn Tyr Arg Ser Val
130                 135                 140

Thr Thr Leu His Pro Thr Ala Ser Ser Ala Ser Gly Gly Cys Ser Gly
145                 150                 155                 160

Thr Val Val Val Glu Ser Tyr Val Val Asp Val Pro Pro Gly Asn Thr
                165                 170                 175

Arg Glu Asp Thr Arg Val Phe Val Asp Thr Ile Val Lys Cys Asn Leu
            180                 185                 190

Gln Ser Leu Ala Gln Thr Ala Glu Asn Leu Thr Leu Arg Lys Asn Asn
        195                 200                 205

Asn Asn Asp Tyr Lys Cys Cys Ser
    210                 215

<210> SEQ ID NO 96
<211> LENGTH: 208
<212> TYPE: PRT
<213> ORGANISM: Glycine max
<220> FEATURE:
<223> OTHER INFORMATION: soybean Glyma02g42990.1 protein

<400> SEQUENCE: 96

Met Thr Ser Leu Gln Phe His Arg Phe Asn Pro Ala Thr Asp Thr Ser
1               5                   10                  15

Thr Ala Ile Ala Asn Gly Val Asn Cys Pro Lys Pro Ser Thr Leu
            20                  25                  30

Arg Leu Leu Ala Lys Val Ser Leu Ser Val Pro Glu Thr Val Ala Arg
        35                  40                  45

His His Ala His Pro Val Gly Pro Asn Gln Cys Cys Ser Val Val Ile
    50                  55                  60

Gln Ala Ile Asp Ala Pro Val Ser Ala Val Trp Pro Val Val Arg Arg
65                  70                  75                  80

Phe Asp Asn Pro Gln Ala Tyr Lys His Phe Val Lys Ser Cys His Val
                85                  90                  95

Val Ala Ala Ala Gly Gly Gly Glu Asp Gly Ile Arg Val Gly Ala Leu
            100                 105                 110

Arg Glu Val Arg Val Val Ser Gly Leu Pro Ala Val Ser Ser Thr Glu
        115                 120                 125

Arg Leu Glu Ile Leu Asp Asp Glu Arg His Val Met Ser Phe Ser Val
    130                 135                 140

Val Gly Gly Asp His Arg Leu Arg Asn Tyr Arg Ser Val Thr Thr Leu
145                 150                 155                 160

His Gly Asp Gly Asn Gly Gly Thr Val Val Ile Glu Ser Tyr Val Val
                165                 170                 175

Asp Val Pro Pro Gly Asn Thr Lys Glu Glu Thr Cys Val Phe Val Asp
            180                 185                 190

Thr Ile Val Arg Cys Asn Leu Gln Ser Leu Ala Gln Ile Ala Glu Thr
        195                 200                 205

<210> SEQ ID NO 97
<211> LENGTH: 176
<212> TYPE: PRT
<213> ORGANISM: Glycine max
<220> FEATURE:
<223> OTHER INFORMATION: soybean Glyma04g05380.1 protein

<400> SEQUENCE: 97

Ala Tyr Pro Val Leu Gly Leu Thr Pro Glu Glu Phe Ser Glu Leu Glu
1               5                   10                  15

Ser Ile Ile Asn Thr His His Lys Phe Glu Pro Ser Pro Glu Ile Cys

```
                20                  25                  30
Ser Ser Ile Ile Ala Gln Arg Ile Asp Ala Pro Ala His Thr Val Trp
            35                  40                  45

Pro Leu Val Arg Ser Phe Glu Asn Pro Gln Lys Tyr Lys His Phe Val
        50                  55                  60

Lys Ser Cys Asn Met Arg Ser Gly Asp Gly Val Gly Ser Ile Arg
 65                  70                  75                  80

Glu Val Thr Val Val Ser Gly Leu Pro Ala Ser Thr Ser Thr Glu Arg
                 85                  90                  95

Leu Glu Ile Leu Asp Asp Asp Lys His Leu Leu Ser Phe Arg Val Val
            100                 105                 110

Gly Gly Glu His Arg Leu His Asn Tyr Arg Ser Val Thr Ser Val Asn
        115                 120                 125

Glu Phe Lys Asn Pro Asp Asn Gly Lys Val Tyr Thr Ile Val Leu Glu
    130                 135                 140

Ser Tyr Val Val Asp Ile Pro Glu Gly Asn Thr Gly Val Asp Thr Lys
145                 150                 155                 160

Met Phe Val Asp Thr Val Val Lys Leu Asn Leu Gln Lys Leu Gly Glu
                165                 170                 175

<210> SEQ ID NO 98
<211> LENGTH: 172
<212> TYPE: PRT
<213> ORGANISM: Glycine max
<220> FEATURE:
<223> OTHER INFORMATION: soybean Glyma06g05440.1 protein

<400> SEQUENCE: 98

Glu Phe Thr Glu Leu Glu Ser Thr Ile Asn Thr His His Lys Phe Glu
 1               5                  10                  15

Ala Ser Pro Glu Ile Cys Ser Ser Ile Ile Ala Gln Arg Ile Asp Ala
            20                  25                  30

Pro Ala His Thr Val Trp Pro Leu Val Arg Ser Phe Glu Asn Pro Gln
        35                  40                  45

Lys Tyr Lys His Phe Val Lys Ser Cys Asn Met Arg Ser Gly Asp Gly
    50                  55                  60

Gly Val Gly Ser Ile Arg Glu Val Thr Val Val Ser Gly Leu Pro Ala
 65                  70                  75                  80

Ser Thr Ser Thr Glu Arg Leu Glu Ile Leu Asp Asp Asn His Leu
                 85                  90                  95

Leu Ser Phe Arg Val Val Gly Gly Glu His Arg Leu His Asn Tyr Arg
            100                 105                 110

Ser Val Thr Ser Val Asn Glu Phe Lys Arg Pro Asp Asn Gly Lys Val
        115                 120                 125

Tyr Thr Ile Val Leu Glu Ser Tyr Val Val Asp Ile Pro Glu Gly Asn
    130                 135                 140

Thr Gly Val Asp Thr Lys Met Phe Val Asp Thr Val Val Lys Leu Asn
145                 150                 155                 160

Leu Gln Lys Leu Gly Glu Val Ala Met Ala Thr Asn
                165                 170

<210> SEQ ID NO 99
<211> LENGTH: 191
<212> TYPE: PRT
<213> ORGANISM: Glycine max
<220> FEATURE:
<223> OTHER INFORMATION: soybean Glyma06g13150.1 protein
```

-continued

<400> SEQUENCE: 99

```
Met Thr Glu Leu Ser Ser Arg Glu Val Glu Tyr Ile Arg Arg His His
  1               5                  10                  15

Ser Lys Ala Ala Glu Asp Asn Gln Cys Ala Ser Ala Leu Val Lys His
             20                  25                  30

Ile Arg Ala Pro Leu Pro Leu Val Trp Ser Leu Val Arg Arg Phe Asp
         35                  40                  45

Glu Pro Gln Lys Tyr Lys Pro Phe Val Ser Arg Cys Val Val Arg Gly
     50                  55                  60

Asn Leu Glu Ile Gly Ser Leu Arg Glu Val Asp Val Lys Ser Gly Leu
 65                  70                  75                  80

Pro Ala Thr Thr Ser Thr Glu Arg Leu Glu Ile Leu Asp Asp Asn His
                 85                  90                  95

His Ile Leu Ser Val Arg Ile Ile Gly Gly Asp His Arg Leu Arg Asn
            100                 105                 110

Tyr Ser Ser Ile Met Ser Leu His Pro Glu Ile Val Asp Gly Arg Pro
        115                 120                 125

Gly Thr Leu Val Ile Glu Ser Phe Val Val Asp Ile Pro Glu Gly Asn
    130                 135                 140

Thr Lys Asp Glu Thr Cys Tyr Phe Val Glu Ala Leu Ile Lys Cys Asn
145                 150                 155                 160

Leu Lys Ser Leu Ala Asp Val Ser Glu Gly Leu Thr Leu Gln Asp His
                165                 170                 175

Thr Glu Pro Ile Asp Arg Lys Tyr Glu Leu Leu Ile Thr Arg Gly
            180                 185                 190
```

<210> SEQ ID NO 100
<211> LENGTH: 185
<212> TYPE: PRT
<213> ORGANISM: Glycine max
<220> FEATURE:
<223> OTHER INFORMATION: soybean Glyma07g06270.1 protein

<400> SEQUENCE: 100

```
Met Asn Gly Gly Glu Ser Tyr Gly Ala Ile Glu Thr Gln Tyr Ile Arg
  1               5                  10                  15

Arg His His Lys His Glu Pro Arg Glu Asn Gln Cys Thr Ser Ala Leu
             20                  25                  30

Val Lys His Ile Arg Ala Pro Val His Leu Val Trp Ser Leu Val Arg
         35                  40                  45

Arg Phe Asp Gln Pro Gln Lys Tyr Lys Pro Phe Val Ser Arg Cys Ile
     50                  55                  60

Met Gln Gly Asp Leu Gly Ile Gly Ser Val Arg Glu Val Asn Val Lys
 65                  70                  75                  80

Ser Gly Leu Pro Ala Thr Thr Ser Thr Glu Arg Leu Glu Gln Leu Asp
                 85                  90                  95

Asp Glu Glu His Ile Leu Gly Ile Arg Ile Val Gly Gly Asp His Arg
            100                 105                 110

Leu Arg Asn Tyr Ser Ser Ile Ile Thr Val His Pro Glu Val Ile Asp
        115                 120                 125

Gly Arg Pro Gly Thr Met Val Ile Glu Ser Phe Val Val Asp Val Pro
    130                 135                 140

Asp Gly Asn Thr Arg Asp Glu Thr Cys Tyr Phe Val Glu Ala Leu Ile
145                 150                 155                 160
```

Arg Cys Asn Leu Ser Ser Leu Ala Asp Val Ser Glu Arg Met Ala Val
                165                 170                 175

Gln Gly Arg Thr Asn Pro Ile Asn His
            180                 185

<210> SEQ ID NO 101
<211> LENGTH: 178
<212> TYPE: PRT
<213> ORGANISM: Glycine max
<220> FEATURE:
<223> OTHER INFORMATION: soybean Glyma07g19120.1 protein

<400> SEQUENCE: 101

Met Ser Pro Asn Asn Pro Ser Thr Ile Val Ser Asp Ala Val Ala Arg
1               5                   10                  15

His His Thr His Val Val Ser Pro His Gln Cys Cys Ser Ala Val Val
                20                  25                  30

Gln Glu Ile Ala Ala Pro Val Ser Thr Val Trp Ser Val Val Arg Arg
            35                  40                  45

Phe Asp Asn Pro Gln Ala Tyr Lys His Phe Val Lys Ser Cys His Val
50                  55                  60

Ile Leu Gly Asp Gly Asp Val Gly Thr Leu Arg Glu Val Arg Val Ile
65                  70                  75                  80

Ser Gly Leu Pro Ala Ala Val Ser Thr Glu Arg Leu Asp Val Leu Asp
                85                  90                  95

Asp Glu Arg His Val Ile Gly Phe Ser Met Val Gly Gly Asp His Arg
                100                 105                 110

Leu Ser Asn Tyr Arg Ser Val Thr Ile Leu His Pro Arg Ser Ala Thr
            115                 120                 125

Asp Thr Val Val Val Glu Ser Tyr Val Val Asp Val Pro Ala Gly Asn
130                 135                 140

Thr Thr Glu Asp Thr Arg Val Phe Val Asp Thr Ile Leu Arg Cys Asn
145                 150                 155                 160

Leu Gln Ser Leu Ala Lys Phe Ala Glu Asn Leu Thr Asn Lys Leu His
                165                 170                 175

Gln Arg

<210> SEQ ID NO 102
<211> LENGTH: 246
<212> TYPE: PRT
<213> ORGANISM: Glycine max
<220> FEATURE:
<223> OTHER INFORMATION: soybean Glyma08g36770.1 protein

<400> SEQUENCE: 102

Met Ser Arg Ser His Asn Lys Arg Lys Pro Phe Ser Phe Ile Phe Lys
1               5                   10                  15

Ile Thr Leu Leu Glu Leu Leu Ser Ser Leu Leu Ser Ser Ser Leu Arg
                20                  25                  30

Phe Ala Met Asp Lys Thr His Ser Gly Glu Glu Gln Pro Asn Pro
            35                  40                  45

Thr His Pro Thr Arg Asn His Leu Asp Pro Pro Gly Leu Thr Pro
50                  55                  60

Glu Glu Phe Glu Asp Leu Lys Pro Ser Val Leu Glu His His Thr Tyr
65                  70                  75                  80

Ser Val Thr Pro Thr Arg Gln Cys Ser Ser Leu Leu Ala Gln Arg Ile
                85                  90                  95

```
His Ala Pro Pro His Thr Val Trp Thr Val Arg Cys Phe Asp Asn
            100                 105                 110

Pro Gln Ala Tyr Lys His Phe Ile Lys Ser Cys His Val Lys Glu Gly
        115                 120                 125

Phe Gln Leu Ala Val Gly Ser Thr Arg Asp Val His Val Ile Ser Gly
    130                 135                 140

Leu Pro Ala Ala Thr Ser Thr Glu Arg Leu Asp Leu Leu Asp Asp Asp
145                 150                 155                 160

Arg His Val Ile Gly Phe Thr Ile Val Gly Gly Asp His Arg Leu Arg
                165                 170                 175

Asn Tyr Arg Ser Val Thr Ser Val His Gly Phe Glu Arg Asp Gly Lys
            180                 185                 190

Ile Trp Thr Val Val Leu Glu Ser Tyr Val Val Asp Val Pro Glu Gly
            195                 200                 205

Asn Thr Glu Glu Asp Thr Arg Leu Phe Ala Asp Thr Val Val Lys Leu
            210                 215                 220

Asn Leu Gln Lys Leu Ala Ser Val Thr Glu Gly Met Cys Gly Asp Ser
225                 230                 235                 240

Asp Gly Lys Gly Asn Asn
                245

<210> SEQ ID NO 103
<211> LENGTH: 223
<212> TYPE: PRT
<213> ORGANISM: Glycine max
<220> FEATURE:
<223> OTHER INFORMATION: soybean Glyma09g33700.1 protein

<400> SEQUENCE: 103

Met Glu Lys Ala Glu Ser Ser Ala Ser Thr Ser Glu Pro Asp Ser Asp
  1               5                  10                  15

Asp Asn His His Arg His Pro Thr Asn His His Leu Asn Pro Pro Ser
                 20                  25                  30

Gly Leu Thr Pro Leu Glu Phe Ala Ser Leu Val Pro Ser Val Ala Glu
             35                  40                  45

His His Ser Tyr Leu Val Gly Pro Gly Gln Cys Ser Ser Leu Leu Ala
         50                  55                  60

Gln Arg Val His Ala Pro Pro Asp Ala Val Trp Ser Phe Val Arg Arg
 65                  70                  75                  80

Phe Asp Lys Pro Gln Thr Tyr Lys His Phe Ile Lys Ser Cys Ala Val
                 85                  90                  95

Lys Glu Pro Phe His Met Ala Val Gly Val Thr Arg Asp Val Asn Val
            100                 105                 110

Ile Ser Gly Leu Pro Ala Ala Thr Ser Thr Glu Arg Leu Asp Phe Leu
        115                 120                 125

Asp Asp Val Arg Arg Val Thr Gly Phe Ser Ile Ile Gly Gly Glu His
    130                 135                 140

Arg Leu Arg Asn Tyr Arg Ser Val Thr Thr Val His Ser Phe Asp Asp
145                 150                 155                 160

Asp Asn Ala Ser Ala Asp Gly Lys Ile Tyr Thr Val Leu Glu Ser
                165                 170                 175

Tyr Val Val Asp Val Pro Asp Gly Asn Thr Glu Glu Asp Thr Arg Leu
            180                 185                 190

Phe Ala Asp Thr Val Val Lys Leu Asn Leu Gln Lys Leu Ala Ser Val
        195                 200                 205
```

```
Thr Glu Gly Thr Asn Gly Asp Gly Asp Gly Lys Pro His Ser Arg
    210                 215                 220
```

<210> SEQ ID NO 104
<211> LENGTH: 229
<212> TYPE: PRT
<213> ORGANISM: Glycine max
<220> FEATURE:
<223> OTHER INFORMATION: soybean Glyma11g35670.1 protein

<400> SEQUENCE: 104

```
Met Pro Ser Ser Leu His Phe Asp Arg Phe Asn Pro Ile Thr His Ala
  1               5                  10                  15

Ala Thr Thr Val Ala Ile Ala Asn Gly Val Asn Cys Pro Lys Gln Pro
             20                  25                  30

Gln Ala Pro Pro Ser Ser Thr Ala Ala Arg Arg Leu Val Val Pro Ser
         35                  40                  45

Leu Ser Ser Gly Arg Gly Ile Ala Ala Pro Asp Thr Val Ala Leu His
 50                  55                  60

His Ala His Val Val Asp Pro Asn Gln Cys Cys Ser Ile Val Thr Gln
 65                  70                  75                  80

His Ile Asn Ala Pro Val Ser Ala Val Trp Ala Val Val Arg Arg Phe
                 85                  90                  95

Asp Asn Pro Gln Gly Tyr Lys Asn Phe Val Arg Ser Cys His Val Ile
            100                 105                 110

Thr Gly Asp Gly Ile Arg Val Gly Ala Val Arg Glu Val Arg Val Val
        115                 120                 125

Ser Gly Leu Pro Ala Glu Thr Ser Thr Glu Arg Leu Glu Ile Leu Asp
130                 135                 140

Asp Glu Arg His Val Ile Ser Phe Ser Met Val Gly Gly Asp His Arg
145                 150                 155                 160

Leu Arg Asn Tyr Gln Ser Val Thr Thr Leu His Ala Asn Gly Asn Gly
                165                 170                 175

Thr Leu Val Ile Glu Ser Tyr Val Val Asp Val Pro Gln Gly Asn Thr
            180                 185                 190

Lys Glu Glu Thr Cys Val Phe Val Asp Thr Ile Val Arg Cys Asn Leu
        195                 200                 205

Gln Ser Leu Ala Gln Ile Ala Glu Asn Arg Thr Asn Asn Cys Glu His
    210                 215                 220

Thr Ala Gln His Cys
225
```

<210> SEQ ID NO 105
<211> LENGTH: 191
<212> TYPE: PRT
<213> ORGANISM: Glycine max
<220> FEATURE:
<223> OTHER INFORMATION: soybean Glyma13g08120.1 protein

<400> SEQUENCE: 105

```
Met Asn Gly Ile Gly Asn Asp Gly Gly Gly Leu Ser Asn Val Glu
  1               5                  10                  15

Met Glu Tyr Ile Arg Arg His Arg His Glu Pro Gly Glu Asn Gln
             20                  25                  30

Cys Gly Ser Ala Leu Val Lys His Ile Arg Ala Pro Val Pro Gln Val
         35                  40                  45

Trp Ser Leu Val Arg Arg Phe Asp Gln Pro Gln Lys Tyr Lys Pro Phe
 50                  55                  60
```

Val Ser Arg Cys Val Val Arg Gly Asn Leu Glu Ile Gly Ser Leu Arg
65                  70                  75                  80

Glu Val Asp Val Lys Ser Gly Leu Pro Ala Thr Thr Ser Thr Glu Arg
                85                  90                  95

Leu Glu Leu Leu Asp Asp Asn Glu His Leu Leu Ser Ile Arg Ile Ile
            100                 105                 110

Gly Gly Asp His Arg Leu Arg Asn Tyr Ser Ser Ile Met Ser Leu His
        115                 120                 125

Pro Glu Ile Ile Asp Gly Arg Pro Gly Thr Leu Val Ile Glu Ser Phe
    130                 135                 140

Val Val Asp Val Pro Glu Gly Asn Thr Lys Asp Glu Thr Cys Tyr Phe
145                 150                 155                 160

Val Glu Ala Leu Ile Lys Cys Asn Leu Lys Ser Leu Ala Asp Val Ser
                165                 170                 175

Glu Gly Ile Ala Val Gln Asp Arg Thr Glu Pro Ile Asp Arg Ile
            180                 185                 190

<210> SEQ ID NO 106
<211> LENGTH: 169
<212> TYPE: PRT
<213> ORGANISM: Glycine max
<220> FEATURE:
<223> OTHER INFORMATION: soybean Glyma14g06100.1 protein

<400> SEQUENCE: 106

Met Val Ala Arg His His Ala His Ala Val Gly Pro Asn Gln Cys Cys
1               5                   10                  15

Ser Phe Val Ile Gln Ala Ile Asp Ala Pro Val Ser Ala Val Trp Pro
            20                  25                  30

Val Val Arg Arg Phe Asp Asn Pro Gln Ala Tyr Lys His Phe Val Lys
        35                  40                  45

Ser Cys His Val Val Ala Ala Gly Gly Ala Gly Asp Gly Ile
50                  55                  60

His Val Gly Ala Leu Arg Glu Val Arg Val Ser Gly Leu Pro Ala
65                  70                  75                  80

Val Ser Ser Thr Glu Arg Leu Glu Ile Leu Asp Asp Glu Arg His Val
                85                  90                  95

Met Ser Phe Ser Val Val Gly Gly Asp His Arg Leu Arg Asn Tyr Arg
            100                 105                 110

Ser Val Thr Thr Leu His Gly Asp Gly Ser Asn Gly Gly Thr Val Val
        115                 120                 125

Ile Glu Ser Tyr Val Val Asp Ile Pro Ala Gly Asn Thr Lys Glu Glu
    130                 135                 140

Thr Cys Val Phe Val Asp Thr Ile Val Arg Cys Asn Leu Gln Ser Leu
145                 150                 155                 160

Ala Gln Met Ala Glu Asn Met Gly Ser
                165

<210> SEQ ID NO 107
<211> LENGTH: 210
<212> TYPE: PRT
<213> ORGANISM: Glycine max
<220> FEATURE:
<223> OTHER INFORMATION: soybean Glyma14g10730.1 protein

<400> SEQUENCE: 107

Met Thr Ile Leu Pro His Ser Asn Asn Lys Ser Ser Asn His Lys Phe

```
        1               5                  10                 15
Ile Ala His Gln Asn Tyr Met Ala Ser Glu Thr His His Val Gln
                20                  25                  30
Gly Leu Thr Pro Glu Glu Leu Thr Lys Leu Glu Pro Ile Ile Lys Lys
                35                  40                  45
Tyr His Leu Phe Glu Gln Ser Pro Asn Thr Cys Phe Ser Ile Ile Thr
    50                  55                  60
Tyr Arg Ile Glu Ala Pro Ala Lys Ala Val Trp Pro Phe Val Arg Ser
65                  70                  75                  80
Phe Asp Asn Pro Gln Lys Tyr Lys His Phe Ile Lys Gly Cys Asn Met
                85                  90                  95
Arg Gly Asp Gly Gly Val Gly Ser Ile Arg Glu Val Thr Val Val Ser
                100                 105                 110
Gly Leu Pro Ala Ser Thr Ser Thr Glu Arg Leu Glu Ile Leu Asp Asp
                115                 120                 125
Asp Lys His Val Leu Ser Phe Arg Val Val Gly Gly Glu His Arg Leu
    130                 135                 140
Lys Asn Tyr Arg Ser Val Thr Ser Val Asn Glu Phe Asn Lys Glu Gly
145                 150                 155                 160
Lys Val Tyr Thr Ile Val Leu Glu Ser Tyr Ile Val Asp Ile Pro Glu
                165                 170                 175
Gly Asn Thr Glu Glu Asp Thr Lys Met Phe Val Asp Thr Val Val Lys
                180                 185                 190
Leu Asn Leu Gln Lys Leu Gly Val Val Ala Met Ala Ser Ser Met His
                195                 200                 205
Gly Gln
    210

<210> SEQ ID NO 108
<211> LENGTH: 193
<212> TYPE: PRT
<213> ORGANISM: Glycine max
<220> FEATURE:
<223> OTHER INFORMATION: soybean Glyma14g30260.1 protein

<400> SEQUENCE: 108

Met Asn Arg Ile Gly Asn Gly Gly Gly Gly Gly Gly Gly Leu Ser Asn
1               5                   10                  15
Val Glu Met Glu Tyr Ile Arg Arg His His Arg His Glu Pro Gly Glu
                20                  25                  30
Asn Gln Cys Gly Ser Ala Leu Val Lys His Ile Arg Ala Pro Val Pro
                35                  40                  45
Gln Val Trp Ser Leu Val Arg Arg Phe Asp Gln Pro Gln Lys Tyr Lys
    50                  55                  60
Pro Phe Ile Ser Arg Cys Val Val Arg Gly Asn Leu Glu Ile Gly Ser
65                  70                  75                  80
Leu Arg Glu Val Asp Val Lys Ser Gly Leu Pro Ala Thr Thr Ser Thr
                85                  90                  95
Glu Arg Leu Glu Leu Leu Asp Asp Asn Glu His Ile Leu Ser Ile Arg
                100                 105                 110
Ile Ile Gly Gly Asp His Arg Leu Arg Asn Tyr Ser Ser Ile Met Ser
                115                 120                 125
Leu His Pro Glu Ile Ile Asp Gly Arg Pro Gly Thr Leu Val Ile Glu
    130                 135                 140
Ser Phe Val Val Asp Val Pro Glu Gly Asn Thr Lys Asp Glu Thr Cys
```

```
                145                 150                 155                 160
Tyr Phe Val Glu Ala Leu Ile Lys Cys Asn Leu Lys Ser Leu Ala Asp
                165                 170                 175
Val Ser Glu Gly Leu Ala Val Gln Asp Cys Thr Glu Pro Ile Asp Arg
                180                 185                 190
Ile

<210> SEQ ID NO 109
<211> LENGTH: 188
<212> TYPE: PRT
<213> ORGANISM: Glycine max
<220> FEATURE:
<223> OTHER INFORMATION: soybean Glyma17g34800.1 protein

<400> SEQUENCE: 109

Met Ala Ser Glu Thr His His His Val Gln Gly Leu Thr Pro Glu Glu
  1               5                  10                  15

Leu Thr Gln Leu Glu Pro Ile Ile Lys Lys Tyr His Leu Phe Glu Ala
                 20                  25                  30

Ser Ser Asn Lys Cys Phe Ser Ile Ile Thr His Arg Ile Glu Ala Pro
             35                  40                  45

Ala Ser Ser Val Trp Pro Leu Val Arg Asn Phe Asp Asn Pro Gln Lys
         50                  55                  60

Tyr Lys His Phe Ile Lys Gly Cys Asn Met Lys Gly Asp Gly Ser Val
 65                  70                  75                  80

Gly Ser Ile Arg Glu Val Thr Val Ser Gly Leu Pro Ala Ser Thr
                 85                  90                  95

Ser Thr Glu Arg Leu Glu Ile Leu Asp Asp Asp Lys His Val Leu Ser
                100                 105                 110

Phe Arg Val Val Gly Gly Glu His Arg Leu Gln Asn Tyr Arg Ser Val
                115                 120                 125

Thr Ser Val Asn Glu Phe His Lys Gly Lys Val Tyr Thr Ile Val
                130                 135                 140

Leu Glu Ser Tyr Ile Val Asp Ile Pro Glu Gly Asn Thr Glu Glu Asp
145                 150                 155                 160

Thr Lys Met Phe Val Asp Thr Val Lys Leu Asn Leu Gln Lys Leu
                165                 170                 175

Gly Val Val Ala Met Ala Ser Ser Met Asn Gly Arg
                180                 185

<210> SEQ ID NO 110
<211> LENGTH: 177
<212> TYPE: PRT
<213> ORGANISM: Glycine max
<220> FEATURE:
<223> OTHER INFORMATION: soybean Glyma18g43680.1 protein

<400> SEQUENCE: 110

Met Leu Pro Asn Asn Pro Ser Thr Ile Val Pro Asp Ala Val Ala Arg
  1               5                  10                  15

His His Thr His Val Val Ser Pro Gln Gln Cys Cys Ser Ala Val Val
                 20                  25                  30

Gln Glu Ile Ala Ala Pro Val Ser Thr Val Trp Ser Val Arg Arg
             35                  40                  45

Phe Asp Asn Pro Gln Ala Tyr Lys His Phe Val Lys Ser Cys His Val
         50                  55                  60

Ile Leu Gly Asp Gly Asp Val Gly Thr Leu Arg Glu Val His Val Ile
```

```
                 65                  70                  75                  80
Ser Gly Leu Pro Ala Val Ser Thr Glu Arg Leu Asp Val Leu Asp
                 85                  90                  95

Asp Glu Arg His Val Ile Gly Phe Ser Met Val Gly Gly Asp His Arg
                100                 105                 110

Leu Phe Asn Tyr Arg Ser Val Thr Leu His Pro Arg Ser Ala Ala
                115                 120                 125

Gly Thr Val Val Glu Ser Tyr Val Val Asp Val Pro Pro Gly Asn
            130                 135                 140

Thr Thr Glu Asp Thr Arg Val Phe Val Asp Thr Ile Leu Arg Cys Asn
145                 150                 155                 160

Leu Gln Ser Leu Ala Lys Phe Ala Glu Asn Leu Thr Lys Leu His Gln
                165                 170                 175

Arg
```

<210> SEQ ID NO 111
<211> LENGTH: 185
<212> TYPE: PRT
<213> ORGANISM: Glycine max
<220> FEATURE:
<223> OTHER INFORMATION: soybean Glyma07g06270.2 protein

<400> SEQUENCE: 111

```
Met Asn Gly Gly Glu Ser Tyr Gly Ala Ile Glu Thr Gln Tyr Ile Arg
 1               5                  10                  15

Arg His His Lys His Glu Pro Arg Glu Asn Gln Cys Thr Ser Ala Leu
                20                  25                  30

Val Lys His Ile Arg Ala Pro Val His Leu Val Trp Ser Leu Val Arg
            35                  40                  45

Arg Phe Asp Gln Pro Gln Lys Tyr Lys Pro Phe Val Ser Arg Cys Ile
        50                  55                  60

Met Gln Gly Asp Leu Gly Ile Gly Ser Val Arg Glu Val Asn Val Lys
65                  70                  75                  80

Ser Gly Leu Pro Ala Thr Thr Ser Thr Glu Arg Leu Glu Gln Leu Asp
                85                  90                  95

Asp Glu Glu His Ile Leu Gly Ile Arg Ile Val Gly Gly Asp His Arg
                100                 105                 110

Leu Arg Asn Tyr Ser Ser Ile Ile Thr Val His Pro Glu Val Ile Asp
                115                 120                 125

Gly Arg Pro Gly Thr Met Val Ile Glu Ser Phe Val Val Asp Val Pro
            130                 135                 140

Asp Gly Asn Thr Arg Asp Glu Thr Cys Tyr Phe Val Glu Ala Leu Ile
145                 150                 155                 160

Arg Cys Asn Leu Ser Ser Leu Ala Asp Val Ser Glu Arg Met Ala Val
                165                 170                 175

Gln Gly Arg Thr Asn Pro Ile Asn His
            180                 185
```

<210> SEQ ID NO 112
<211> LENGTH: 191
<212> TYPE: PRT
<213> ORGANISM: Glycine max
<220> FEATURE:
<223> OTHER INFORMATION: soybean Glyma16g02910.1 protein

<400> SEQUENCE: 112

Met Gly Ile Thr Ile Gly Ile Gln Cys Leu Glu Ile Glu Glu Ile Ser

```
                    1               5               10              15
              Ile Cys Asp Gly Met Phe Cys Tyr Leu Val Asp Phe Val Asp Val Lys
                              20              25              30
              Glu Lys Met Asn Tyr Cys Leu Met Trp Phe Gly Tyr Phe Pro Ser Gln
                              35              40              45
              Val Trp Ser Leu Val Arg Arg Phe Asp Gln Pro Gln Lys Tyr Lys Pro
                      50              55              60
              Phe Val Ser Arg Cys Ile Met Gln Gly Asp Leu Gly Ile Gly Ser Val
               65             70              75              80
              Arg Glu Val Asn Val Lys Ser Gly Leu Pro Ala Thr Thr Ser Thr Glu
                              85              90              95
              Arg Leu Glu Gln Leu Asp Asp Glu Glu His Ile Leu Gly Ile Arg Ile
                              100             105             110
              Val Gly Gly Asp His Arg Leu Arg Asn Tyr Ser Ser Ile Ile Thr Val
                              115             120             125
              His Pro Glu Val Ile Asp Gly Arg Pro Ser Thr Met Val Ile Glu Ser
                              130             135             140
              Phe Val Asp Val Pro Asp Gly Asn Thr Arg Asp Glu Thr Cys Tyr
               145             150             155             160
              Phe Val Glu Ala Leu Ile Arg Cys Asn Leu Ser Ser Leu Ala Asp Val
                              165             170             175
              Ser Glu Arg Met Ala Val Gln Gly Arg Thr Asp Pro Ile Asn His
                              180             185             190

<210> SEQ ID NO 113
<211> LENGTH: 185
<212> TYPE: PRT
<213> ORGANISM: Artificial Sequence
<220> FEATURE:
<223> OTHER INFORMATION: synthetic PYR/PYL receptor protein

<400> SEQUENCE: 113

Met Asn Gly Gly Glu Ser Tyr Gly Ala Ile Glu Thr Gln Tyr Ile Arg
               1               5               10              15
              Arg His His Lys His Glu Pro Arg Glu Asn Gln Cys Thr Ser Ala Leu
                              20              25              30
              Val Lys His Ile Arg Ala Pro Val His Leu Val Trp Ser Leu Val Arg
                              35              40              45
              Arg Phe Asp Gln Pro Gln Lys Tyr Lys Pro Phe Val Ser Arg Cys Ile
                              50              55              60
              Met Gln Gly Asp Leu Gly Ile Gly Ser Val Arg Glu Val Asn Val Lys
               65              70              75              80
              Ser Gly Leu Pro Ala Thr Thr Ser Thr Glu Arg Leu Glu Gln Leu Asp
                              85              90              95
              Asp Glu Glu His Ile Leu Gly Ile Arg Ile Val Gly Gly Asp His Arg
                              100             105             110
              Leu Arg Asn Tyr Ser Ser Ile Ile Thr Val His Pro Glu Val Ile Asp
                              115             120             125
              Gly Arg Pro Ser Thr Met Val Ile Glu Ser Phe Val Val Asp Val Pro
                              130             135             140
              Asp Gly Asn Thr Arg Asp Glu Thr Cys Tyr Phe Val Glu Ala Leu Ile
               145             150             155             160
              Arg Cys Asn Leu Ser Ser Leu Ala Asp Val Ser Glu Arg Met Ala Val
                              165             170             175
              Gln Gly Arg Thr Asp Pro Ile Asn His
```

180                 185

<210> SEQ ID NO 114
<211> LENGTH: 204
<212> TYPE: PRT
<213> ORGANISM: Sorghum bicolor
<220> FEATURE:
<223> OTHER INFORMATION: sorghum Sb10g022200 protein

<400> SEQUENCE: 114

Met Glu Thr His Val Glu Arg Ala Leu Arg Ala Thr Leu Thr Glu Ala
1               5                   10                  15

Glu Val Arg Ala Leu Glu Pro Val Arg Glu His His Thr Phe Pro
            20                  25                  30

Ala Gly Arg Val Ala Ala Gly Thr Thr Thr Pro Thr Pro Thr Thr Cys
        35                  40                  45

Thr Ser Leu Val Ala Gln Arg Val Ser Ala Pro Val Arg Ala Val Trp
    50                  55                  60

Pro Ile Val Arg Ser Phe Gly Asn Pro Gln Arg Tyr Lys His Phe Val
65                  70                  75                  80

Arg Thr Cys Ala Leu Ala Ala Gly Asp Gly Ala Ser Val Gly Ser Val
                85                  90                  95

Arg Glu Val Thr Val Val Ser Gly Leu Pro Ala Ser Ser Thr Glu
            100                 105                 110

Arg Leu Glu Val Leu Asp Asp Arg His Ile Leu Ser Phe Arg Val
        115                 120                 125

Val Gly Gly Asp His Arg Leu Arg Asn Tyr Arg Ser Val Thr Ser Val
130                 135                 140

Thr Glu Phe Gln Pro Gly Pro Tyr Cys Val Val Glu Ser Tyr Ala
145                 150                 155                 160

Val Asp Val Pro Glu Gly Asn Thr Ala Glu Asp Thr Arg Met Phe Thr
                165                 170                 175

Asp Thr Val Val Arg Leu Asn Leu Gln Lys Leu Ala Ala Val Ala Glu
            180                 185                 190

Glu Ser Ala Ala Ala Ala Ala Gly Asn Arg Arg
        195                 200

<210> SEQ ID NO 115
<211> LENGTH: 204
<212> TYPE: PRT
<213> ORGANISM: Sorghum bicolor
<220> FEATURE:
<223> OTHER INFORMATION: sorghum Sb04g008040 protein

<400> SEQUENCE: 115

Met Glu Pro His Met Glu Thr Ala Leu Arg Gln Gly Gly Leu Ser Glu
1               5                   10                  15

Leu Glu Gln Arg Glu Leu Glu Pro Val Val Arg Ala His His Thr Phe
            20                  25                  30

Pro Gly Arg Ser Pro Gly Thr Thr Cys Thr Ser Leu Val Thr Gln Arg
        35                  40                  45

Val Asp Ala Pro Leu Ser Ala Val Trp Pro Ile Val Arg Gly Phe Ala
    50                  55                  60

Ala Pro Gln Arg Tyr Lys His Phe Ile Lys Ser Cys Asp Leu Arg Ser
65                  70                  75                  80

Gly Asp Gly Ala Thr Val Gly Ser Val Arg Glu Val Thr Val Val Ser
                85                  90                  95

```
Gly Leu Pro Ala Ser Thr Ser Thr Glu Arg Leu Glu Ile Leu Asp Asp
                100                 105                 110

Asp Arg His Ile Leu Ser Phe Arg Val Val Gly Gly Asp His Arg Leu
        115                 120                 125

Arg Asn Tyr Arg Ser Val Thr Ser Val Thr Glu Phe His His His His
    130                 135                 140

Gln Ala Ala Ala Gly Arg Pro Tyr Cys Val Val Glu Ser Tyr Val
145                 150                 155                 160

Val Asp Val Pro Glu Gly Asn Thr Glu Glu Asp Thr Arg Met Phe Thr
                165                 170                 175

Asp Thr Val Val Lys Leu Asn Leu Gln Lys Leu Ala Ala Ile Ala Thr
            180                 185                 190

Ser Ser Ala Ala Ala Ala Ser Asn Ser Ser Thr
            195                 200
```

```
<210> SEQ ID NO 116
<211> LENGTH: 258
<212> TYPE: PRT
<213> ORGANISM: Sorghum bicolor
<220> FEATURE:
<223> OTHER INFORMATION: sorghum Sb01g028330 protein

<400> SEQUENCE: 116

Met Val Glu Ser Pro Asn Pro Asn Ser Pro Ser Arg Pro Leu Cys Ile
1               5                   10                  15

Lys Tyr Thr Arg Ala Pro Ala Arg His Phe Ser Pro Pro Leu Pro Phe
            20                  25                  30

Ser Ser Leu Ile Ile Ser Ala Asn Pro Ile Glu Pro Lys Ala Met Asp
        35                  40                  45

Lys Gln Gly Ala Gly Gly Asp Val Glu Val Pro Ala Gly Leu Gly Leu
    50                  55                  60

Thr Ala Ala Glu Tyr Glu Gln Leu Arg Ser Thr Val Asp Ala His His
65                  70                  75                  80

Arg Tyr Ala Val Gly Glu Gly Gln Cys Ser Ser Leu Leu Ala Gln Arg
                85                  90                  95

Ile Gln Ala Pro Pro Ala Ala Val Trp Ala Ile Val Arg Arg Phe Asp
            100                 105                 110

Cys Pro Gln Val Tyr Lys His Phe Ile Arg Ser Cys Ala Leu Arg Pro
        115                 120                 125

Asp Pro Glu Ala Gly Asp Ala Leu Arg Pro Gly Arg Leu Arg Glu Val
    130                 135                 140

Ser Val Ile Ser Gly Leu Pro Ala Ser Thr Ser Thr Glu Arg Leu Asp
145                 150                 155                 160

Leu Leu Asp Asp Ala Ala Arg Val Phe Gly Phe Ser Ile Thr Gly Gly
                165                 170                 175

Glu His Arg Leu Arg Asn Tyr Arg Ser Val Thr Thr Val Ser Glu Leu
            180                 185                 190

Ala Asp Pro Gly Ile Cys Thr Val Leu Glu Ser Tyr Val Val Asp
        195                 200                 205

Val Pro Asp Gly Asn Thr Glu Asp Asp Thr Arg Leu Phe Ala Asp Thr
    210                 215                 220

Val Ile Arg Leu Asn Leu Gln Lys Leu Lys Ser Val Ala Glu Ala Asn
225                 230                 235                 240

Ala Ala Ala Ala Ala Ser Phe Val Ser Val Val Pro Pro Glu Pro
                245                 250                 255
```

Glu Glu

<210> SEQ ID NO 117
<211> LENGTH: 222
<212> TYPE: PRT
<213> ORGANISM: Sorghum bicolor
<220> FEATURE:
<223> OTHER INFORMATION: sorghum Sb01g038150 protein

<400> SEQUENCE: 117

Met Pro Cys Leu Gln Ala Ser Ser Pro Gly Ser Met Pro His Gln
1               5                   10                  15

His His Gly Arg Val Leu Ala Gly Val Gly Cys Ala Ala Glu Val Ala
            20                  25                  30

Ala Ala Ala Val Ala Ala Thr Ser Pro Ala Ala Gly Met Arg Cys Gly
        35                  40                  45

Ala His Asp Gly Glu Val Pro Ala Glu Ala Ala Arg His His Glu His
    50                  55                  60

Ala Ala Pro Gly Pro Gly Arg Cys Cys Ser Ala Val Val Gln His Val
65                  70                  75                  80

Ala Ala Pro Ala Ser Ala Val Trp Ser Val Val Arg Arg Phe Asp Gln
                85                  90                  95

Pro Gln Ala Tyr Lys Arg Phe Val Arg Ser Cys Ala Leu Leu Ala Gly
            100                 105                 110

Asp Gly Gly Val Gly Thr Leu Arg Glu Val Arg Val Val Ser Gly Leu
        115                 120                 125

Pro Ala Ala Ser Ser Arg Glu Arg Leu Glu Val Leu Asp Asp Glu Ser
    130                 135                 140

His Val Leu Ser Phe Arg Val Val Gly Gly Glu His Arg Leu Gln Asn
145                 150                 155                 160

Tyr Leu Ser Val Thr Thr Val His Pro Ser Pro Ala Ala Pro Asp Ala
                165                 170                 175

Ala Thr Val Val Val Glu Ser Tyr Val Val Asp Val Pro Pro Gly Asn
            180                 185                 190

Thr Pro Glu Asp Thr Arg Val Phe Val Asp Thr Ile Val Lys Cys Asn
        195                 200                 205

Leu Gln Ser Leu Ala Thr Thr Ala Glu Lys Leu Ala Ala Val
    210                 215                 220

<210> SEQ ID NO 118
<211> LENGTH: 211
<212> TYPE: PRT
<213> ORGANISM: Sorghum bicolor
<220> FEATURE:
<223> OTHER INFORMATION: sorghum Sb04g009280 protein

<400> SEQUENCE: 118

Met Val Glu Met Asp Gly Gly Val Gly Val Val Gly Gly Gly Gln Gln
1               5                   10                  15

Thr Pro Ala Pro Arg Arg Trp Arg Leu Ala Asp Glu Leu Arg Cys Asp
            20                  25                  30

Leu Arg Ala Met Glu Thr Asp Tyr Val Arg Arg Phe His Arg His Glu
        35                  40                  45

Pro Arg Asp His Gln Cys Ser Ser Ala Val Ala Lys His Ile Lys Ala
    50                  55                  60

Pro Val His Leu Val Trp Ser Leu Val Arg Arg Phe Asp Gln Pro Gln
65                  70                  75                  80

Leu Phe Lys Pro Phe Val Ser Arg Cys Glu Met Lys Gly Asn Ile Glu
                85                  90                  95

Ile Gly Ser Val Arg Glu Val Asn Val Lys Ser Gly Leu Pro Ala Thr
            100                 105                 110

Arg Ser Thr Glu Arg Leu Glu Leu Leu Asp Asp Asn Glu His Ile Leu
        115                 120                 125

Ser Val Lys Phe Val Gly Gly Asp His Arg Leu Gln Asn Tyr Ser Ser
    130                 135                 140

Ile Leu Thr Val His Pro Glu Val Ile Asp Gly Arg Pro Gly Thr Leu
145                 150                 155                 160

Val Ile Glu Ser Phe Val Val Asp Val Pro Asp Gly Asn Thr Lys Asp
                165                 170                 175

Glu Thr Cys Tyr Phe Val Glu Ala Leu Leu Lys Cys Asn Leu Lys Ser
            180                 185                 190

Leu Ala Glu Val Ser Glu Arg Gln Val Ile Lys Asp Gln Thr Glu Pro
        195                 200                 205

Leu Asp Arg
    210

<210> SEQ ID NO 119
<211> LENGTH: 216
<212> TYPE: PRT
<213> ORGANISM: Sorghum bicolor
<220> FEATURE:
<223> OTHER INFORMATION: sorghum Sb09g023180 protein

<400> SEQUENCE: 119

Met Pro Tyr Thr Ala Pro Arg Pro Ser Pro Gln Gln His Ser Arg Val
1               5                   10                  15

Thr Gly Gly Gly Ala Lys Ala Ala Ile Val Ala Ala Ser His Gly Ala
            20                  25                  30

Ser Cys Ala Ala Val Pro Ala Glu Val Ala Arg His His Glu His Ala
        35                  40                  45

Ala Arg Ala Gly Gln Cys Cys Ser Ala Val Val Gln Ala Ile Ala Ala
    50                  55                  60

Pro Val Gly Ala Val Trp Ser Val Val Arg Arg Phe Asp Arg Pro Gln
65                  70                  75                  80

Ala Tyr Lys His Phe Ile Arg Ser Cys Arg Leu Val Asp Asp Gly Gly
                85                  90                  95

Gly Gly Ala Gly Ala Gly Ala Gly Thr Val Ala Val Gly Ser Val
            100                 105                 110

Arg Glu Val Arg Val Val Ser Gly Leu Pro Ala Thr Ser Ser Arg Glu
        115                 120                 125

Arg Leu Glu Ile Leu Asp Asp Glu Arg Arg Val Leu Ser Phe Arg Val
    130                 135                 140

Val Gly Gly Glu His Arg Leu Ala Asn Tyr Arg Ser Val Thr Thr Val
145                 150                 155                 160

His Glu Ala Glu Ala Gly Ala Gly Gly Thr Val Val Val Glu Ser Tyr
                165                 170                 175

Val Val Asp Val Pro Pro Gly Asn Thr Ala Asp Glu Thr Arg Val Phe
            180                 185                 190

Val Asp Thr Ile Val Arg Cys Asn Leu Gln Ser Leu Ala Arg Thr Ala
        195                 200                 205

Glu Arg Leu Ala Leu Ala Leu Ala
    210                 215

<210> SEQ ID NO 120
<211> LENGTH: 20
<212> TYPE: DNA
<213> ORGANISM: Artificial Sequence
<220> FEATURE:
<223> OTHER INFORMATION: synthetic quantitative RT-PCR forward primer
      for Arabidopsis AT1G05100 MAPKKK18

<400> SEQUENCE: 120
aagcggcgcg tggagagaga                                          20

<210> SEQ ID NO 121
<211> LENGTH: 20
<212> TYPE: DNA
<213> ORGANISM: Artificial Sequence
<220> FEATURE:
<223> OTHER INFORMATION: synthetic quantitative RT-PCR reverse primer
      for Arabidopsis AT1G05100 MAPKKK18

<400> SEQUENCE: 121
gctgtccatc tctccgtcgc                                          20

<210> SEQ ID NO 122
<211> LENGTH: 21
<212> TYPE: DNA
<213> ORGANISM: Artificial Sequence
<220> FEATURE:
<223> OTHER INFORMATION: synthetic quantitative RT-PCR forward primer
      for Arabidopsis AT5G52310 RD29A

<400> SEQUENCE: 122
tgaagtgatc gatgcaccag g                                        21

<210> SEQ ID NO 123
<211> LENGTH: 22
<212> TYPE: DNA
<213> ORGANISM: Artificial Sequence
<220> FEATURE:
<223> OTHER INFORMATION: synthetic quantitative RT-PCR reverse primer
      for Arabidopsis AT5G52310 RD29A

<400> SEQUENCE: 123
gacacgacag gaaacacctt tg                                       22

<210> SEQ ID NO 124
<211> LENGTH: 25
<212> TYPE: DNA
<213> ORGANISM: Artificial Sequence
<220> FEATURE:
<223> OTHER INFORMATION: synthetic quantitative RT-PCR forward primer
      for Arabidopsis AT5G52300 RD29B

<400> SEQUENCE: 124
tatgaatcct ctgccgtgag aggtg                                    25

<210> SEQ ID NO 125
<211> LENGTH: 24
<212> TYPE: DNA
<213> ORGANISM: Artificial Sequence
<220> FEATURE:
<223> OTHER INFORMATION: synthetic quantitative RT-PCR reverse primer
      for Arabidopsis AT5G52300 RD29B

<400> SEQUENCE: 125
acaccactga gataatccga tcct                                     24

```
<210> SEQ ID NO 126
<211> LENGTH: 22
<212> TYPE: DNA
<213> ORGANISM: Artificial Sequence
<220> FEATURE:
<223> OTHER INFORMATION: synthetic quantitative RT-PCR forward primer
      for Arabidopsis AT4G34000 ABF3F

<400> SEQUENCE: 126
gttgatggtg tgagtgagca gc                                              22

<210> SEQ ID NO 127
<211> LENGTH: 23
<212> TYPE: DNA
<213> ORGANISM: Artificial Sequence
<220> FEATURE:
<223> OTHER INFORMATION: synthetic quantitative RT-PCR reverse primer
      for Arabidopsis AT4G34000 ABF3F

<400> SEQUENCE: 127
aacccattac tagctgtccc aag                                             23

<210> SEQ ID NO 128
<211> LENGTH: 22
<212> TYPE: DNA
<213> ORGANISM: Artificial Sequence
<220> FEATURE:
<223> OTHER INFORMATION: synthetic quantitative RT-PCR forward primer
      for Arabidopsis AT2G46270 GBF3

<400> SEQUENCE: 128
gacgcttttg agcatcgaca ct                                              22

<210> SEQ ID NO 129
<211> LENGTH: 23
<212> TYPE: DNA
<213> ORGANISM: Artificial Sequence
<220> FEATURE:
<223> OTHER INFORMATION: synthetic quantitative RT-PCR reverse primer
      for Arabidopsis AT2G46270 GBF3

<400> SEQUENCE: 129
actgtttcct tcgctcccgt ttc                                             23

<210> SEQ ID NO 130
<211> LENGTH: 19
<212> TYPE: DNA
<213> ORGANISM: Artificial Sequence
<220> FEATURE:
<223> OTHER INFORMATION: synthetic quantitative RT-PCR forward primer
      for Arabidopsis internal control ACT2

<400> SEQUENCE: 130
ctcatgaaga tccttacag                                                  19

<210> SEQ ID NO 131
<211> LENGTH: 20
<212> TYPE: DNA
<213> ORGANISM: Artificial Sequence
<220> FEATURE:
<223> OTHER INFORMATION: synthetic quantitative RT-PCR reverse primer
      for Arabidopsis internal control ACT2

<400> SEQUENCE: 131
ctttcaggtg gtgcaacgac                                                 20

<210> SEQ ID NO 132
```

```
<211> LENGTH: 20
<212> TYPE: DNA
<213> ORGANISM: Artificial Sequence
<220> FEATURE:
<223> OTHER INFORMATION: synthetic quantitative RT-PCR forward primer
      for soybean GmNAC4

<400> SEQUENCE: 132
acgtcagttc cgcaaaagat                                                   20

<210> SEQ ID NO 133
<211> LENGTH: 19
<212> TYPE: DNA
<213> ORGANISM: Artificial Sequence
<220> FEATURE:
<223> OTHER INFORMATION: synthetic quantitative RT-PCR reverse primer
      for soybean GmNAC4

<400> SEQUENCE: 133
ggacccgttg gtttctcac                                                    19

<210> SEQ ID NO 134
<211> LENGTH: 23
<212> TYPE: DNA
<213> ORGANISM: Artificial Sequence
<220> FEATURE:
<223> OTHER INFORMATION: synthetic quantitative RT-PCR forward primer
      for soybean GmbZIP1

<400> SEQUENCE: 134
gggaatggga atttgggtga gaa                                               23

<210> SEQ ID NO 135
<211> LENGTH: 21
<212> TYPE: DNA
<213> ORGANISM: Artificial Sequence
<220> FEATURE:
<223> OTHER INFORMATION: synthetic quantitative RT-PCR reverse primer
      for soybean GmbZIP1

<400> SEQUENCE: 135
ccttctgcca gggctagcat g                                                 21

<210> SEQ ID NO 136
<211> LENGTH: 23
<212> TYPE: DNA
<213> ORGANISM: Artificial Sequence
<220> FEATURE:
<223> OTHER INFORMATION: synthetic quantitative RT-PCR forward primer
      for soybean internal control Gm18S

<400> SEQUENCE: 136
cctgcggctt aatttgactc aac                                               23

<210> SEQ ID NO 137
<211> LENGTH: 19
<212> TYPE: DNA
<213> ORGANISM: Artificial Sequence
<220> FEATURE:
<223> OTHER INFORMATION: synthetic quantitative RT-PCR reverse primer
      for soybean internal control Gm18S

<400> SEQUENCE: 137
taagaacggc catgcacca                                                    19

<210> SEQ ID NO 138
<211> LENGTH: 19
```

```
<212> TYPE: DNA
<213> ORGANISM: Artificial Sequence
<220> FEATURE:
<223> OTHER INFORMATION: synthetic quantitative RT-PCR forward primer
      for barley HVA1

<400> SEQUENCE: 138
aacacgctgg gcatgggag                                                    19

<210> SEQ ID NO 139
<211> LENGTH: 22
<212> TYPE: DNA
<213> ORGANISM: Artificial Sequence
<220> FEATURE:
<223> OTHER INFORMATION: synthetic quantitative RT-PCR reverse primer
      for barley HVA1

<400> SEQUENCE: 139
cgaacgacca aacacgacta aa                                                22

<210> SEQ ID NO 140
<211> LENGTH: 20
<212> TYPE: DNA
<213> ORGANISM: Artificial Sequence
<220> FEATURE:
<223> OTHER INFORMATION: synthetic quantitative RT-PCR forward primer
      for barley HvDRF1

<400> SEQUENCE: 140
cgggcggcgc gattgcgagc                                                   20

<210> SEQ ID NO 141
<211> LENGTH: 20
<212> TYPE: DNA
<213> ORGANISM: Artificial Sequence
<220> FEATURE:
<223> OTHER INFORMATION: synthetic quantitative RT-PCR reverse primer
      for barley HvDRF1

<400> SEQUENCE: 141
acggaattag ggccatcacg                                                   20

<210> SEQ ID NO 142
<211> LENGTH: 20
<212> TYPE: DNA
<213> ORGANISM: Artificial Sequence
<220> FEATURE:
<223> OTHER INFORMATION: synthetic quantitative RT-PCR forward primer
      for barley internal control Hvtubulin2

<400> SEQUENCE: 142
tccatgatgg ccaagtgtga                                                   20

<210> SEQ ID NO 143
<211> LENGTH: 21
<212> TYPE: DNA
<213> ORGANISM: Artificial Sequence
<220> FEATURE:
<223> OTHER INFORMATION: synthetic quantitative RT-PCR reverse primer
      for barley internal control Hvtubulin2

<400> SEQUENCE: 143
gacatcccca cggtacatga g                                                 21

<210> SEQ ID NO 144
<211> LENGTH: 18
<212> TYPE: DNA
```

```
<213> ORGANISM: Artificial Sequence
<220> FEATURE:
<223> OTHER INFORMATION: synthetic quantitative RT-PCR forward primer
      for maize ZmLEA

<400> SEQUENCE: 144
gcagcaggca ggggagaa                                                   18

<210> SEQ ID NO 145
<211> LENGTH: 19
<212> TYPE: DNA
<213> ORGANISM: Artificial Sequence
<220> FEATURE:
<223> OTHER INFORMATION: synthetic quantitative RT-PCR reverse primer
      for maize ZmLEA

<400> SEQUENCE: 145
gccgagcgag ttcatcatc                                                  19

<210> SEQ ID NO 146
<211> LENGTH: 23
<212> TYPE: DNA
<213> ORGANISM: Artificial Sequence
<220> FEATURE:
<223> OTHER INFORMATION: synthetic quantitative RT-PCR forward primer
      for maize ZmRAB17

<400> SEQUENCE: 146
atgagtacgg tcagcagggg cag                                             23

<210> SEQ ID NO 147
<211> LENGTH: 21
<212> TYPE: DNA
<213> ORGANISM: Artificial Sequence
<220> FEATURE:
<223> OTHER INFORMATION: synthetic quantitative RT-PCR reverse primer
      for maize ZmRAB17

<400> SEQUENCE: 147
ctccctcgca ggctggaact g                                               21

<210> SEQ ID NO 148
<211> LENGTH: 27
<212> TYPE: DNA
<213> ORGANISM: Artificial Sequence
<220> FEATURE:
<223> OTHER INFORMATION: synthetic quantitative RT-PCR forward primer
      for maize internal control ZmUbi

<400> SEQUENCE: 148
tgccgatgtg cctgcgtcgt ctggtgc                                         27

<210> SEQ ID NO 149
<211> LENGTH: 26
<212> TYPE: DNA
<213> ORGANISM: Artificial Sequence
<220> FEATURE:
<223> OTHER INFORMATION: synthetic quantitative RT-PCR reverse primer
      for maize internal control ZmUbi

<400> SEQUENCE: 149
tgaaagacag aacataatga gcacag                                          26
```